United States Patent
Haining et al.

(10) Patent No.: US 10,927,410 B2
(45) Date of Patent: Feb. 23, 2021

(54) COMPOSITIONS AND METHODS FOR IDENTIFICATION, ASSESSMENT, PREVENTION, AND TREATMENT OF T-CELL EXHAUSTION USING CD39 BIOMARKERS AND MODULATORS

(71) Applicants: Dana-Farber Cancer Institute, Inc., Boston, MA (US); President and Fellows of Harvard College, Cambridge, MA (US)

(72) Inventors: William N. Haining, Newton, MA (US); Arlene H. Sharpe, Brookline, MA (US); Jernej Godec, Brookline, MA (US)

(73) Assignees: Dana-Farber Cancer Institute, Inc., Boston, MA (US); President and Fellows of Harvard College, Cambridge, MA (US)

( * ) Notice: Subject to any disclaimer, the term of this patent is extended or adjusted under 35 U.S.C. 154(b) by 125 days.

(21) Appl. No.: 15/518,860

(22) PCT Filed: Oct. 16, 2015

(86) PCT No.: PCT/US2015/055938
§ 371 (c)(1),
(2) Date: Apr. 13, 2017

(87) PCT Pub. No.: WO2016/061456
PCT Pub. Date: Apr. 21, 2016

(65) Prior Publication Data
US 2017/0233808 A1    Aug. 17, 2017

Related U.S. Application Data

(60) Provisional application No. 62/065,192, filed on Oct. 17, 2014.

(51) Int. Cl.
| | | |
|---|---|---|
| *C12N 5/02* | (2006.01) | |
| *C12Q 1/6881* | (2018.01) | |
| *G01N 33/569* | (2006.01) | |
| *C12Q 1/6883* | (2018.01) | |

(52) U.S. Cl.
CPC ......... *C12Q 1/6881* (2013.01); *C12Q 1/6883* (2013.01); *G01N 33/56972* (2013.01); *C12Q 2600/106* (2013.01); *C12Q 2600/158* (2013.01); *G01N 2333/70517* (2013.01); *G01N 2333/70596* (2013.01); *G01N 2800/52* (2013.01)

(58) Field of Classification Search
None
See application file for complete search history.

(56) References Cited

U.S. PATENT DOCUMENTS

2014/0044641 A1    2/2014    Toporik et al.

FOREIGN PATENT DOCUMENTS

| WO | WO-2006133396 A2 | 12/2006 |
|---|---|---|
| WO | WO-2010/133880 A1 | 11/2010 |
| WO | WO-2011/159877 A2 | 12/2011 |
| WO | WO-2013/006474 A2 | 1/2013 |
| WO | WO-2013/079945 A1 | 6/2013 |
| WO | WO-2013/090552 A1 | 6/2013 |
| WO | WO-2014/070874 A1 | 5/2014 |

OTHER PUBLICATIONS

Xu et al. Neuro-Oncology. 2013. 15(9):1160-1172. (Year: 2013).*
Pulte et al. ( Clinical Lymphoma, 2011, v.11, n.4 pp. 367-372.*
Antonioli et al., "CD39 and CD73 in Immunity and Inflammation," Trends Mol Med, 19(6): 355-367 (2013).
GenBank S73813.1 submitted by Maliszewski et al., "The CD39 lymphoid cell activation antigen. Molecular cloning and structural characterization," J. Immunol. 153:3574-3583 (1994).
International Search Report and Written Opinion for International Application No. PCT/US15/55938 dated Jun. 28, 2016.
Maliszewski et al., "The CD39 lymphoid cell activation antigen. Molecular cloning and structural characterization," J Immunol, 153(8): 3574-3583 (1994).
Toth et al., "Decreased frequency of CD73 CD8 T cells of HIV-infected patients correlates with immune activation and T cell exhaustion," J Leukocyte Biol, 94(4): 551-561 (2013).
Baitsch et al., "Exhaustion of tumor-specific CD8+ T cells in metastases from melanoma patients," J Clin Invest, 121(6):2350-2360 (2011).
Doering et al., "Network analysis reveals centrally connected genes and pathways involved in CD8+ T cell exhaustion versus memory," Immunity, 37(6):1130-1144 (2012).
Extended European Search Report issued by the European Patent Office in corresponding Application No. EP 15850572.7 dated Feb. 16, 2018.
Gupta et al., "CD39 expression identifies terminally exhausted CD8+ T cells," PLoSPathog, 11(10):e1005177 (2015).
Quigley et al., "Transcriptional analysis of HIC-specific CD8+ T cells shows that PD-1 inhibits T cell function by upregulating BATF," Nat Med, 16(10):1147-1151 (2010).
Wherry et al., Molecular Signature of CD8+ T Cell Exhaustion during Chronic Viral Infection, Immunity, 27(4):670-684 (2007).
Wherry, "T cell exhaustion," Nat Immunol, 12(6):492-499 (2011).

* cited by examiner

*Primary Examiner* — Michail A Belyavskyi
(74) *Attorney, Agent, or Firm* — Foley Hoag LLP

(57) ABSTRACT

The present invention is based on the identification, of compositions and methods for the identification, assessment, prevention, and treatment of T-cell exhaustion using CD39 biomarkers and modulators.

7 Claims, 15 Drawing Sheets
Specification includes a Sequence Listing.

Figure 9
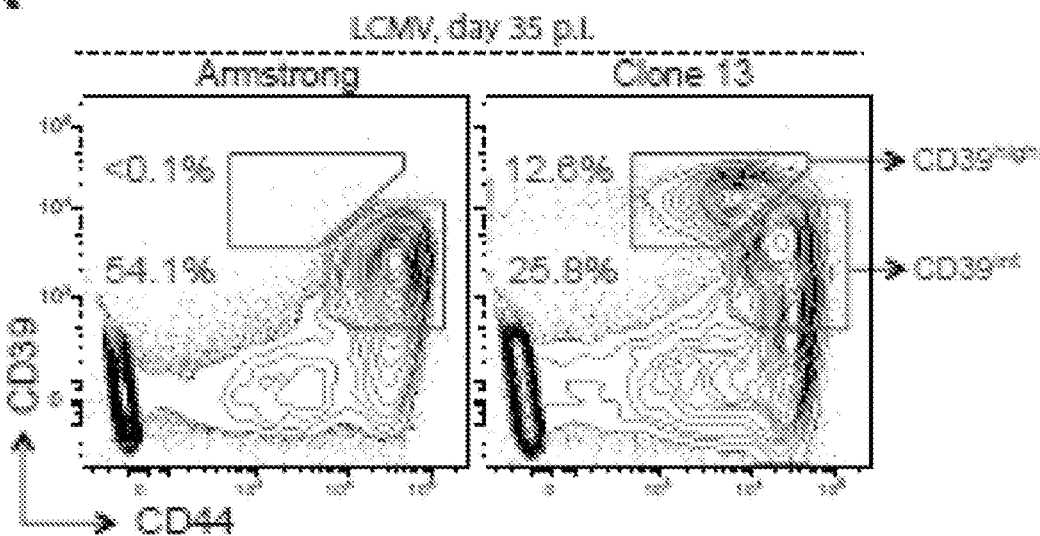
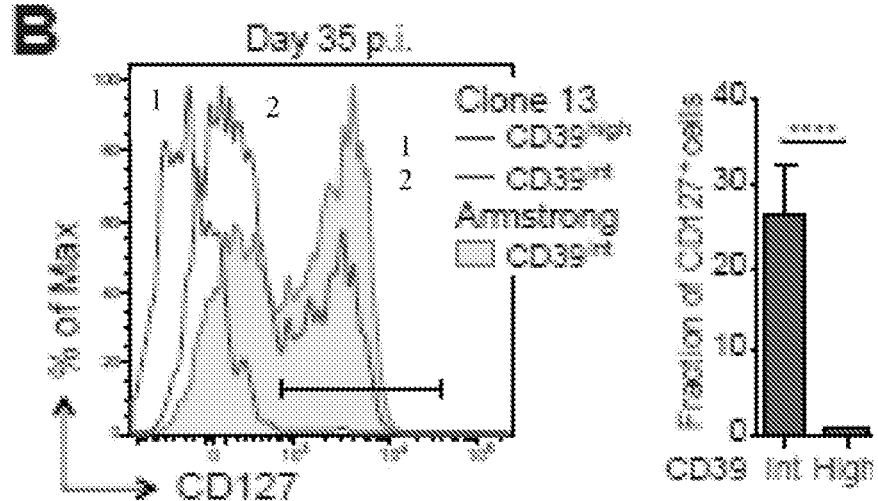
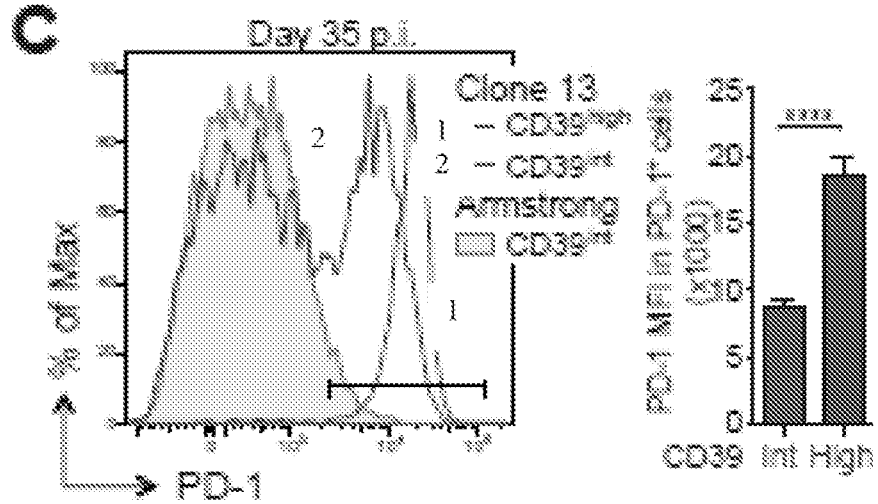

COMPOSITIONS AND METHODS FOR IDENTIFICATION, ASSESSMENT, PREVENTION, AND TREATMENT OF T-CELL EXHAUSTION USING CD39 BIOMARKERS AND MODULATORS

CROSS-REFERENCE TO RELATED APPLICATIONS

This application claims the benefit of U.S. Provisional Application No. 62/065,192, filed on 17 Oct. 2014; the entire contents of said application are incorporated herein in their entirety by this reference.

STATEMENT OF RIGHTS

This invention was made with government support under grant numbers 5U19 AI082630 and AI091493 awarded by The National Institutes of Health. The government has certain rights in the invention.

BACKGROUND OF THE INVENTION

In acute infections, antigen-specific T cells differentiate into activated effector cells and then into memory T cells which rapidly gain effector functions and re-expand on subsequent encounter with the same pathogen (Kaech and (2012) *Nat. Rev. Immunol.* 12:749-761). In contrast, during chronic infections, pathogen-specific T cells gradually lose effector function, fail to expand, and can eventually become physically deleted (Wherry (2011) *Nat. Immunol.* 12:492-499). These traits are collectively termed "T cell exhaustion" and have been described both in animal models of chronic viral infection, as well as in human infections with Hepatitis C virus (HCV) and Human immunodeficiency virus (HIV) (Wherry (2011) *Nat. Immunol.* 12:492-499; Day et al. (2006) *Nature* 443:350-354; Lechner et al. (2000) *J. Exp. Med.* 191:1499-1512).

Prolonged or high-level expression of multiple inhibitory receptors, such as PD-1, Lag3, and CD244 (2B4), is a cardinal feature of exhausted T cells in both animal models and human disease (Wherry et al. (2007) *Immunity* 27:670-684; Barber et al. (2006) *Nature* 439:682-687; Kroy et al. (2014) *Gastroenterol.* 146:550-561). Expression of PD-1 appears to be a particularly important feature of exhausted $CD8^+$ T cells, as the majority of exhausted cells in mouse models of chronic infection express this receptor, and blockade of the PD-1:PD-L1 axis can restore the function of exhausted $CD8^+$ T cells in humans and mouse models (Wherry (2011) *Nat. Immunol.* 12:492-499; Barber et al. (2006) *Nature* 439:682-687). However, in humans, many inhibitory receptors can also be expressed by a large fraction of fully functional memory $CD8^+$ T cells. PD-1, for instance, can be expressed by as much as 60% of memory $CD8^+$ T cells in healthy individuals, making it challenging to use this marker to identify exhausted $CD8^+$ T cells in humans, particularly when the antigen-specificity of potentially exhausted $CD8^+$ T cells is not known (Duraiswamy et al. (2011) *J. Immunol.* 186:4200-4212).

Studies in mice and humans suggest that exhausted $CD8^+$ T cells are not a homogeneous population, but instead include at least two subpopulations of T cells that differ in the expression of the transcription factors T-bet and Eomesodermin (Eomes) (Paley et al. (2012) *Science* 338:1220-1225; Buggert et al. (2014) *PLoS Pathgens* 10:e1004251). T-bet$^{high}$ $CD8^+$ T cells represent a progenitor subset with proliferative potential that give rise to Eomes$^{high}$ $CD8^+$ T cells, which are terminally differentiated and can no longer proliferate in response to antigen or be rescued by PD-1 blockade (Paley et al. (2012) *Science* 338:1220-1225; Blackburn et al. (2008) *Proc. Natl. Acad. Sci. U.S.A.* 105: 15016-15021). Both populations express PD-1, but Eomes$^{high}$ exhausted cells express the highest levels of PD-1. However, no specific markers of this terminally differentiated population of exhausted cells have thus far been identified.

The identification of exhausted T cells is important because such immune repertoire components mount ineffective responses against immunological targets. In particular, identifying reversible mechanisms of T cell exhaustion is a major goal in medicine. Moreover, these cell populations are dysfunctional in many important scenarios where mounting effective immune responses are desired to increase human health, such as in response to chronic immune disorders. However, neither biomarkers useful for identifying exhausted T cell populations, nor methods of use thereof to identify exhausted T cell populations or identify the mechanisms by which such cells are functionally impaired in immune disorders, such as in chronic infections, are known in the art. Accordingly, there is a great need in the art to identify such biomarkers, as well as diagnostic, prognostic, and therapeutic uses thereof.

SUMMARY OF THE INVENTION

The present invention is based, at least in part, on the discovery that the ectonucleotidase CD39 is a specific marker of exhausted T cells (e.g., CD8+ T cells) and that CD39-mediated production of adenosine tonically suppresses T cell effector function and inflammation in chronic immune disorders (e.g., viral infections like HIV and HCV). In contrast to $CD8^+$ T cells from healthy donors, antigen-specific $CD8^+$ T cells responding to chronic viral infection in humans and a mouse model express high levels of biochemically active CD39. $CD39^+$ $CD8^+$ T cells co-express PD-1 and are enriched for a gene signature of T cell exhaustion. Thus, CD8+ T cells that are specific for such chronic immune disorders express high levels of CD39, in contrast to T cells specific for acute immune disorders, such as influenza, or latent immune disorders, such as CMV infections, which do not. The ecto-enzyme is biochemically active and hydrolyzes ATP to adenosine, a known inhibitor of T cell activation. For example, cellular and transcriptional analysis of CD39+ CD8+ T cells in HCV and HIV infection showed that CD39 is co-expressed with PD-1, and CD39 expression correlates with viral load. In a mouse model of chronic immune infection, CD39 was selectively expressed by exhausted CD8+ T cells and identifies terminally exhausted Eomes(hi) CD8+ T cells. It has been determined herein that high CD39 expression identifies the most terminally exhausted T cells and can be used to distinguish between reversible versus irreversible T cell exhaustion, as well as to determine T cell function during chronic immune disorders, such as a chronic viral infection, in subjects prior to treatment, during treatment, and/or post-treatment. Animals lacking CD39 showed marked exacerbation of T cell activation and immunopathology during chronic viral infection. In addition, it is demonstrated herein that exhausted T cells are not only believed to be passive recipients of inhibitory signals, but contribute to the inhibitory microenvironment by increasing the local abundance of the soluble inhibitory mediator, adenosine. Thus, CD39 provides a specific, pathological marker of exhausted $CD8^+$ T cells in chronic viral infection in humans and mouse models of chronic viral infection and is particularly useful for determining T cell function because other markers, such as immune checkpoint receptors, are widely expressed and are thus not useful for discerning the functional status of a T cell.

In one aspect, a method of identifying exhausted CD8+ T cells, the method comprising a) determining the presence, copy number, amount, and/or activity of at least one biomarker listed in Table 1 in a biological sample comprising CD8+ T cells; b) determining the presence, copy number, amount, and/or activity of the at least one biomarker in a control; and c) comparing the presence, copy number, amount, and/or activity of said at least one biomarker detected in steps a) and b); wherein the presence or a significant increase in the copy number, amount, and/or activity of the at least one biomarker in the biological sample relative to the control indicates that the biological sample comprises exhausted CD8+ T cells, is provided. In one embodiment, the method further comprises determining the presence, copy number, amount, and/or activity of at least one T cell exhaustion biomarker in the biological sample; determining the presence, copy number, amount, and/or activity of the at least one T cell exhaustion biomarker in a control; and comparing the presence, copy number, amount, and/or activity of said at least one T cell exhaustion biomarker, wherein the presence or a significant increase in the copy number, amount, and/or activity of the at least one T cell exhaustion biomarker in the biological sample relative to the control indicates that the biological sample comprises exhausted CD8+ T cells. In another embodiment, the T cell exhaustion biomarker is selected from the group consisting of CD39, inhibitory receptors, eomesodermin, T-bet, and combinations thereof. In still another embodiment, the immune checkpoint inhibitor is selected from the group consisting of PD-1, PD-L1, PD-L2, LAG-3, TIM-1, CTLA-4, VISTA, B7-H2, B7-H3, B7-H4, B7-H6, 2B4, ICOS, HVEM, CD160, gp49B, PIR-B, KIR family receptors, TIM-1. TIM-4, BTLA, SIRPalpha (CD47), CD48, 284 (CD244), B7.1, B7.2, ILT-2, ILT-4, TIGIT, and A2aR. In yet another embodiment, the control is a sample comprising CD8+ T cells obtained from a subject not afflicted with a chronic immune condition. In another embodiment, the control is a copy number, amount, and/or activity value determined from a population of CD8+ T cells not afflicted with a chronic immune condition or obtained with a subject not afflicted with a chronic immune condition. In still another embodiment, the method further comprises determining responsiveness of the subject from which the biological samples was obtained to anti-chronic immune condition therapy measured by at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria.

In another aspect, a method of reducing CD8+ T cell exhaustion comprising contacting exhausted CD8+ T cells with an agent that inhibits CD39, is provided. In one embodiment, the method further comprises contacting the exhausted CD8+ T cells with one or more agents that inhibit an immune checkpoint inhibitor. In another embodiment, the immune checkpoint inhibitor is selected from the group consisting of PD-1, PD-L1, PD-L2, LAG-3, TIM-1, CTLA-4, VISTA, B7-H2, B7-H3, B7-H4, B7-H6, 2B4, ICOS, HVEM, CD160, gp49B, PIR-B, KIR family receptors, TIM-1, TIM-4, BTLA, SIRPalpha (CD47), CD48, 2B4 (CD244), B7.1, B7.2, ILT-2, ILT-4, TIGIT, and A2aR. In still another embodiment, the exhausted CD8+ T cells are contacted with the agent(s) in vitro, ex vivo, or in vivo. In yet another embodiment, the exhausted CD8+ T cells are contacted with the agent(s) in vivo. In another embodiment, the exhausted CD8+ T cells are contacted in vivo with a therapeutically effective amount of a pharmaceutical composition comprising the agent(s) in a subject in need thereof.

In still another aspect, a method of treating a subject afflicted with a chronic immune condition, comprising administering to the subject a therapeutically effective amount of a pharmaceutical composition comprising an agent that inhibits CD39 is provided. In one embodiment, the method further comprises administering to the subject a therapeutically effective amount of a pharmaceutical composition comprising one or more anti-chronic immune condition agents. In another embodiment, the one or more anti-chronic immune condition agents is one or more agents that inhibit an immune checkpoint inhibitor. In still another embodiment, the immune checkpoint inhibitor is selected from the group consisting of PD-1, PD-L1, PD-L2, LAG-3, TIM-1, CTLA-4, VISTA, B7-H2, B7-H3, B7-H4, B7-H6, 2B4, ICOS, HVEM, CD160, gp49B, PIR-B, KIR family receptors, TIM-1, TIM-4, BTLA, SIRPalpha (CD47), CD48, 2B4 (CD244), B7.1, B7.2, ILT-2, ILT-4, TIGIT, and A2aR.

In yet another aspect, a method of assessing the efficacy of an agent for reducing CD8+ T cell exhaustion, comprising a) detecting in a first sample comprising exhausted CD8+ T cells and maintained in the presence of the agent the presence, copy number, amount, and/or activity of at least one biomarker listed in Table 1; b) detecting the presence, copy number, amount, and/or activity of the at least one biomarker listed in Table 1 in a second sample comprising exhausted CD8+ T cells and maintained in the absence of the test agent; and c) comparing the presence, copy number, amount, and/or activity of the at least one biomarker listed in Table 1 from steps a) and b), wherein the presence or a significantly increased copy number, amount, and/or activity of the at least one biomarker listed in Table 1 in the first sample relative to the second sample, indicates that the agent reduces CD8+ T cell exhaustion, is provided. In one embodiment, the method further comprises determining the effect of the test agent on the copy number, level of expression, and/or level of activity of at least one immune checkpoint inhibitor in the first sample; determining the effect of the test agent on the copy number, level of expression, and/or level of activity of the at least one immune checkpoint inhibitor in the second sample; and comparing the differences in the copy number, level of expression, and/or level of activity of the at least one immune checkpoint inhibitor between the samples, wherein a significant decrease in the copy number, level of expression, and/or level of activity of the at least one immune checkpoint inhibitor in the first sample relative to the second sample further indicates that the agent reduces CD8+ T cell exhaustion. In another embodiment, the method further comprises determining T cell effector function of the CD8+ T cells in the first sample; determining T cell effector function of the CD8+ T cells in the second sample; and comparing the T cell effector function determinations, wherein a significant increase in the T cell effector function of the CD8+ T cells in the first sample relative to the second sample further indicates that the agent reduces CD8+ T cell exhaustion. In still another embodiment, one or both samples are obtained from a source selected from the group consisting of an animal model of a chronic immune disorder, a subject afflicted with a chronic immune disorder, and purified population of CD8+ T cells. In yet another embodiment, maintaining the cells of the sample in the presence or absence of the test agent occurs in vivo, ex vivo, or in vitro. In another embodiment, the method further comprises determining the ability of the test agent to bind to the at least one biomarker listed in Table 1 before or after determining the effect of the test agent on the copy number, level of expression, or level of activity of the at least one biomarker listed in Table 1.

In another aspect, a method of monitoring the progression of a chronic immune disorder in a subject, comprising a) detecting at a first point in time the presence, copy number, amount, and/or activity of at least one biomarker listed in Table 1 in CD8+ T cells from a subject sample; b) repeating step a) during at least one subsequent point in time after administration of a therapeutic agent; and c) comparing the presence, copy number, amount, and/or activity detected in steps a) and b), wherein the presence or a significantly increased copy number, amount, and/or activity of the at least one biomarker listed in Table 1 in the CD8+ T cells from the first subject sample relative to at least one subsequent subject sample, indicates that the agent treats the chronic immune disorder in the subject, is provided. In one embodiment, the method further comprises determining the copy number, level of expression, and/or level of activity of at least one immune checkpoint inhibitor in the CD8+ T cells from the first subject sample; determining the copy number, level of expression, and/or level of activity of the at least one immune checkpoint inhibitor in the CD8+ T cells from the at least one subsequent subject sample; and comparing the differences in the copy number, level of expression, and/or level of activity of the at least one immune checkpoint inhibitor between the samples, wherein a significant decrease in the copy number, level of expression, and/or level of activity of the at least one immune checkpoint inhibitor in the at least one subsequent subject sample relative to the first subject sample further indicates that the agent treats the chronic immune disorder in the subject. In another embodiment, the method further comprises determining T cell effector function of the CD8+ T cells in the first subject sample; determining T cell effector function of the CD8+ T cells in the at least one subsequent subject sample; and comparing the T cell effector function determinations, wherein a significant increase in the T cell effector function of the CD8+ T cells in the at least one subsequent subject sample relative to the first subject sample further indicates that the agent treats the chronic immune disorder in the subject. In still another embodiment, the subject has undergone treatment, completed treatment, and/or is in remission for the chronic immune disorder in between the first point in time and the subsequent point in time. In yet another embodiment, the subject has undergone anti-immune checkpoint inhibitor therapy in between the first point in time and the subsequent point in time. In another embodiment, the first and/or at least one subsequent sample is selected from the group consisting of ex vivo and in vivo samples. In still another embodiment, the first and/or at least one subsequent sample is obtained from an animal model of the chronic immune disorder. In yet another embodiment, the first and/or at least one subsequent sample is a portion of a single sample or pooled samples obtained from the subject.

Numerous embodiments are further provided that can be applied to any aspect of the present invention described herein. For example, in one embodiment, the sample is selected from the group consisting of cells, cell lines, histological slides, paraffin embedded tissue, fresh frozen tissue, fresh tissue, biopsies, blood, plasma, serum, buccal scrape, saliva, cerebrospinal fluid, urine, stool, mucus, bone marrow, and samples obtained from a subject. In another embodiment, the presence or copy number is assessed by whole exome sequencing, microarray, quantitative PCR (qPCR), high-throughput sequencing, comparative genomic hybridization (CGH), or fluorescent in situ hybridization (FISH). In still another embodiment, the amount of the at least one biomarker is assessed by detecting the presence in the samples of a polynucleotide molecule encoding the biomarker or a portion of said polynucleotide molecule. In yet another embodiment, the polynucleotide molecule is a mRNA, cDNA, or functional variants or fragments thereof. In another embodiment, the step of detecting further comprises amplifying the polynucleotide molecule. In still another embodiment, the amount of the at least one biomarker is assessed by annealing a nucleic acid probe with the sample of the polynucleotide encoding the one or more biomarkers or a portion of said polynucleotide molecule under stringent hybridization conditions. In yet another embodiment, the amount of the at least one biomarker is assessed by detecting the presence a polypeptide of the at least one biomarker. In another embodiment, the presence of said polypeptide is detected using a reagent which specifically binds with said polypeptide. In still another embodiment, the reagent is selected from the group consisting of an antibody, an antibody derivative, and an antibody fragment. In yet another embodiment, the activity of the at least one biomarker is assessed by determining the magnitude of enzymatic activity, cellular proliferation, cell death, or cytokine production. In another embodiment, the agent or therapy is selected from the group consisting of a blocking antibody, small molecule, antisense nucleic acid, interfering RNA, shRNA, siRNA, piwiRNA, aptamer, ribozyme, dominant-negative protein, and combinations thereof. In still another embodiment, the agent or anti-immune checkpoint inhibitor therapy is a blocking antibody of PD-1, PD-L1, PD-L2, LAG-3, TIM-1, CTLA-4, VISTA, B7-H2, B7-H3, B7-H4, B7-H6, 214, ICOS, HVEM, CD160, gp49B, PIR-B, KIR family receptors, TIM-1, TIM-4, BTLA, SIRPalpha (CD47), CD48, 2B4 (CD244), B7.1, B7.2, ILT-2, ILT-4, TIGIT, A2aR, and combinations thereof. In yet another embodiment, the agent or anti-immune checkpoint inhibitor therapy is selected from the group consisting of inhibitors of PD-L, PD-L1, PD-L2, CTLA-4, and combinations thereof. In another embodiment, the chronic immune disorder is a chronic infection or cancer. In still another embodiment, the infection is caused by an agent selected from the group consisting of human immunodeficiency virus (HIV), hepatitis C virus (HCV), hepatitis B virus (HBV), adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyoma virus BK, polyoma virus JC, measles virus, rubella virus, human T cell leukemia virus I, human T cell leukemia virus II, *Leishmania, Toxoplasma, Trypanosoma, Plasmodium. Schistosoma*, and *Encephalitozoon*. In yet another embodiment, the chronic infection is not a latent infection. In another embodiment, the cancer is a hematological cancer or a solid cancer. In still another embodiment, the solid cancer is selected from the group consisting of lung cancer, non-small cell lung cancer (NSCLC), skin cancer, melanoma, cervical cancer, uterine cancer, ovarian cancer, breast cancer, pancreatic cancer, stomach cancer, esophageal cancer, colorectal cancer, liver cancer, prostate cancer, kidney cancer, bladder cancer, head and neck cancer, sarcoma, lymphoma, and brain cancer. In yet another embodiment, the subject is a mammal, such as a human or an animal model of a chronic immune disorder.

Figure 1:
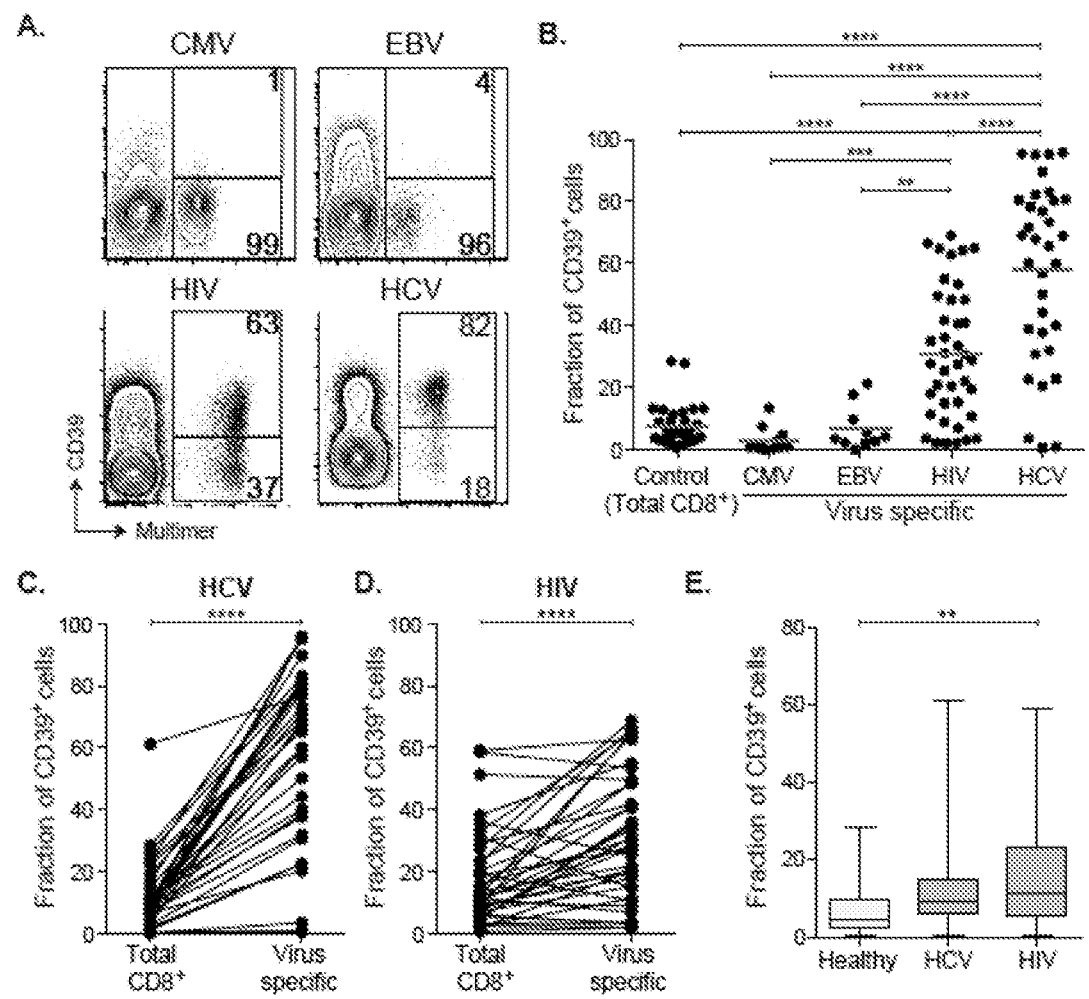
FIG. 1 includes 5 panels, identified as panels A, B, C, D, and E, which show that CD39 is highly expressed by viral-specific CD8$^+$ T cells in chronic viral infection. Panel A shows the expression of CD39 by virus-specific CD8$^+$ T cells. Plots are gated on CD8$^+$. Panel B shows the fraction of total or antigen-specific CD8$^+$ T cells expressing CD39. In Panels 1A-1B, 11 CMV and 10 EBV samples were tested. Panels 1C-1D show a comparison of CD39 protein expression by total CD8$^+$ T cells to virus-specific CD8$^+$ T cells from patients with HCV (Panel 1C) and HIV (Panel 1D) infections. Panel 1E shows the fraction of total CD8$^+$ T cells expressing CD39 in healthy, HIV, or HCV infected donors. Error bars represent the standard error of the mean (SEM). Statistical significance was assessed by one-way ANOVA (Panel 1A), paired (Panels 1C-1D), or unpaired (Panel 1E) Student's t-test. P<0.01, *P<0.001, ****P<0.0001.

For any figure showing a bar histogram, curve, or other data associated with a legend, the bars, curve, or other data presented from left to right for each indication correspond directly and in order to the boxes from top to bottom of the legend.

DETAILED DESCRIPTION OF THE INVENTION

The present invention is based, at least in part, on the discovery that CD39 is a specific marker of exhausted T cells (e.g., CD8+ T cells) and that CD39-mediated production of adenosine tonically suppresses T cell effector function and inflammation in chronic immune disorders (e.g., viral infections like HIV and HCV). In contrast to T cells specific for acute immune disorders or immune disorders in a latent phase (e.g., infections with influenza or cytomegalovirus, respectively), CD8+ T cells specific for chronic immune disorders express high levels of CD39. Such expression of the CD39 ectonucleotidase is demonstrated herein to be biochemically active in order to yield adenosine, an inhibitor of T cell activation. In addition, CD39 is co-expressed with immune checkpoint inhibitors, such as PD-1, and such co-expression correlates with chronic immune disorder status (e.g., viral load).

Accordingly, the present invention relates, in part, to methods for identifying exhausted T cells (e.g., CD8+ T cells) and diagnosing or prognosing chronic immune disorders associated with exhausted T cells based upon a determination and analysis of specific biomarkers described herein. In addition, such analyses can be used in order to identify and provide useful agents and treatment regimens for reducing exhaustion in exhausted T cells (e.g., CD8+ T cells) and for treating chronic immune disorders associated with exhausted T cells.

I. Definitions

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a chronic immune disorder sample, as compared to the expression level or copy number of the biomarker nucleic acid in a control sample. The term "altered amount" of a biomarker also includes an increased or decreased protein level of a biomarker protein in a sample. e.g., a chronic immune disorder sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternately, the amount of the biomarker in the subject can be considered "significantly" higher or lower than the normal amount if the amount is at least about two, and preferably at least about three, four, or five times, higher or lower, respectively, than the normal amount of the biomarker. Such "significance" can also be applied to any other measured parameter described herein, such as for expression, inhibition, cytotoxicity, cell growth, and the like.

The term "altered level of expression" of a biomarker refers to an expression level or copy number of the biomarker in a test sample, e.g., a sample derived from a patient suffering from a chronic immune disorder, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples.

The term "altered activity" of a biomarker refers to an activity of the biomarker which is increased or decreased in a disease state, e.g., in a chronic immune disorder sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide, fragment thereof, or biomarker metabolite). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VI-1, CL and CH1 domains; (ii) a F(ab')$_2$ fragment, a bivalent fragment comprising two Fab fragments linked by a disulfide bridge at the hinge region; (iii) a Fd fragment consisting of the VII and CH1 domains; (iv) a Fv fragment consisting of the VL and VII domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, *Nature Biotechnology* 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. U.S.A.* 90:6444-6448; Poljak et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybrkomas* 6:93-101) and use of a cysteine residue, biomarker peptide and a C-terminal polyhistidinc tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the invention bind specifically or substantially specifically to a biomarker polypeptide or fragment thereof. The terms "monoclonal antibodies" and "monoclonal antibody composition," as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vim), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the predictive score."

The term "biomarker" refers to a measurable entity of the present invention that has been determined to be associated with a chronic immune disorder. Biomarkers can include, without limitation, nucleic acids, proteins, and metabolites, particularly those shown in Table 1.

For example, "CD39" or "ectonucleoside triphosphate diphosphohydrolase I (ENTPDI)" molecules are biomarkers of the present invention and refer to a membrane-bound (transmembrane) ectonucleotidase that hydrolyzes pericellular adenosine triphosphate (ATP) to its nucleoside monophosphate AMP, which is then degraded to the nucleoside adenosine by the action of a membrane-bound or soluble ecto-5'-nucleotidase, CD73 (Junger (2011) Nat. Rev. Immunol. 11:201-212). Pericellular adenosine can modulate proinflammatory or proinhibitory signals in immune cells by binding various adenosine receptors (Ernst et al. (2010) J. Immunol. 185:1993-1998; Antonioli et al. (2013) Trends Mol. Med. 19:355-367; Parodi et al. (2013) Cancer Immunol. Immunother. 62:851-862; Boer et al. (2013) Eur. J. Immunol. 43:1925-1932; Xu et al. (2013) Neuro-Oncol. 15:1160-1172; U.S. Pat. Publ. 2013/0123345). For example, adenosine binds to A2A receptors expressed by lymphocytes causing accumulation of intracellular cAMP, preventing T cell activation and NK cytotoxicity (Zarek et al. (2008) Blood 111:251-259; Lokshin et al. (2006) Canc. Rev. 66:7758-7765). CD39 was originally identified as an activation marker on human lymphocytes, but has subsequently been shown to be a hallmark feature of regulatory T cells (Kansas et al. (1991) J. Immunol. 146:2235-2244; Deaglio et al. (2007) J. Exp. Med. 204:1257-1265; Borsellino et al. (2007) Blood 110:1225-1232). Loss of CD39 in Tregs markedly impairs their ability to suppress T cell activation, suggesting that the juxtacrine activity of CD39 serves to negatively regulate T cell function (Deaglio et al. (2007) J. Exp. Med. 204:1257-1265). However, $CD8^+$ T cells have generally been reported to be CD39 (Kansas et al. (1991) J. Immunol. 146:2235-2244; Moncrieffe et al. (2010) J. Immunol. 185:134-143; Pulte et al. (2011) Clin. Lymph. Myeloma Leuk. 11:367-372; Boer et al. (2013) Eur. J. Immunol. 43:1925-1932), and the expression of this marker on exhausted T cells has not been examined.

The structure-function relationship CD39 proteins is well known in the art (reviewed, for example, by Antonioli et al. (2013) Trend Mol. Med. 19:355-367; Wang and Guidotti (1996) J. Biol. Chem. 271:9898-9901; Kaczmarck et al. (1996) J. Biol. Chem. 271:33116-33122). For example, human CD39 is an approximately 500-amino acid protein with approximately seven potential N-linked glycosylation sites, eleven Cys residues, and two transmembrane regions (Maliszewski et al. (1994) J. Immunol. 153:3574-3583) organized in the form of two transmembrane domains, a small cytoplasmic domain comprising the N- and C-terminal segments, and a large extracellular hydrophobic domain consisting of five highly conserved domains, known as apyrase conserved regions (ACR) 1-5, which are required for the enzyme's catabolic activity (Heine et al. (2001) Eur. J. Biochem. 268:364-373). The amino acid sequences of ACR 1 and ACR 5 contain a phosphate-binding motif (DXG), which is important for stabilizing the interaction between the enzyme and its nucleotide substrate during phosphate cleavage. In addition, two ACR residues, Glu 174 in ACR 3 and Ser 218 of ACR 4 are also required for enzymatic activity (Heine et al. (2001) Eur. J. Biochem. 268:364-373: Smith et al. (1998) Biochim. Biophys. Acta 1386:65-78). Upon cell surface expression, CD39 becomes catalytically active (Smith et al. (1998) Biochim. Biophys. Acta 1386:65-78).

Representative human CD39 cDNA and protein sequences are well-known in the art and are publicly available from the National Center for Biotechnology Information (NCBI). For example, at least seven human CD39 transcript variants are known encoding six different human CD39 isororms. Human CD39 isoform 1 is available under accession numbers NM_001776.5 and NP_001767.3. The transcript variant represents the longest transcript and encodes isoform 1. Human CD39 isoform 2, available under accession numbers NM_001098175.1 and NP_001091645.1, uses an alternate 5' exon than transcript variant 1 that results in a distinct 5' untranslated region (UTR) and causes translation initiation at an alternate start codon leading to a longer and distinct N-terminus. Human CD39 isoform 3, available under accession numbers NM_001164178.1 and NP_001157650.1, uses an alternate 5' exon than transcript variant 1 that results in a distinct 5' UTR and causes translation initiation at an alternate start codon leading to a longer and distinct N-terminus. Human CD39 isoform 4, available under accession numbers NM_001164179.1 and NP_001157651.1, uses an alternate in-frame splice site as compared with transcript variant 1 resulting in a shorter isoform. Human CD39 isoform 5, available under accession numbers NM_001164181.1 and NP_001157653.1, uses an alternate exon in the 5' region that results in a distinct 5' UTR and translation initiation at a downstream start codon relative to transcript variant 1 resulting in a shorter isoform. Human CD39 isoform 6, available under accession numbers NM_001164182.1 and NP_001157654.1, lacks an alternate exon that results in a distinct 5' UTR and causes translation initiation at a downstream start codon relative to transcript variant 1 resulting in a shorter isoform. Human CD39 isoform 6 is also encoded by another transcript variant, available under accession numbers NM_001164183.1 and NP_001157655.1, which lacks two alternate internal exons that results in a distinct 5' UTR and causes translation initiation at a downstream start codon relative to transcript variant 1 resulting in a shorter isoform.

Nucleic acid and polypeptide sequences of CD39 orthologs in organisms other than humans are well known and include, for example, mouse CD39 (NM_009848.3 and NP_033978.1), rat CD39 (NM_022587.1 and NP_072109.1), cow CD39 (NM_174536.2 and NP_776961.1), frog CD39 (NM_001006795.1 and NP_001006796.1), and zebrafish CD39 (NM_001003545.1 and NP_001003545.1). Representative CD39 sequences are presented below in Table 1.

CD39 activity modulators are well known in the art. For example, 6-N,N-Diethyl-D-β-γ-dibromomethylene adenosine triphosphate (ARL 67156) (Levesque et al. (2007) *Br. J. Pharmacol.* 152:141-150; Crack et al. (1959) *Br. J. Pharmacol.* 114: 475-481; Kennedy et al. (1996) *Semin. Neurosci.* 8:195-199) and 8-thiobutyladenosine 5'-triphosphate (8-Bu-S-ATP) are small molecule CD39 inhibitors (Gendron et al. (2000) *J. Med. Chem.* 43:2239-2247). Other small molecule CD39 inhibitors, such as polyoxymetate-1 (POM-1) and a,b-methylene)diphosphate (APCP), are also well known in the art (see, at least, U.S. Pat. Publs. 2010/204182 and 2013/0123345; U.S. Pat. No. 6,617,439). In addition, nucleic acid and antibody inhibitors of CD39 are also well known in the art (see, at least, U.S. Pat. Publ. 2013/0273062, 2010/0303828; Nikolova ea al. (2011) *PLoS* DOI: 10.1371/journal.ppat.1002110; Hausler et al. (2014) *Am. J. Transl. Res.* 6:129-139. Other CD39 activity modulators are known to a person skilled in the art including, but not limited to, allelic variants, splice variants, derivative variants, substitution variants, deletion variants, and/or insertion variants, fusion polypeptides, orthologs, and interspecies homologs. For example, the extensive glycosylation of CD39 is associated with its cell surface expression and activity such that deletion of glycosylated residues or mutations to non-glycosylatable residues results in significantly reduced CD39 activity (see, for example, deletion or mutation of glycosylatable residues 73 at the N terminus, 333 in the middle, and/or 429 and/or 458 at the C terminus of rat CD39 or corresponding residues in orthologs thereof; Wu et al. (2005) *Mol. Biol. Cell.* 16:1661-1672). Similarly, mutations of conserved residues in the apyrase conserved region (ACR) of any one or more of ACRs 1-5 causes a reduction in CD39 activity (Schulte am Esch et al. (1999) *Biochem.* 38:2248-2258; Yang et al. (2001) *Biochem.* 40:3943-4940: Wang and Guidotti (1998) *J. Biol. Chem.* 273:11392-11399). Any combination of CD39 activity modulators is contemplated.

The modulation (e.g., decrease) in CD39 activity can be measured in any number of ways (e.g., according to measures described herein, including using controls, ratios, comparisons to baselines, and the like). For example, a CD39 activity modulator can decrease the catalytic activity of the ectonucleotidase or overall CD39 activity as compared to the level of such ectonucleotidase in the presence of a test agent. In one embodiment, CD39 activity is determined by analyzing the concentration of adenosine in a sample. The concentration can be assessed over time. In another embodiment, ATP is added in the sample tested and the concentration of AMP or adenosine is determined or assessed. A modulation in this context, such as a decrease, can mean a decrease of 1%, 5%, 10%>, 20%, 25%, 30%, 35%, 40%, 45%, 50%, 55%, 60%, 65%, 70%, 75%, 80%, 85%, 90%, 95%, 100%, 120%, 150%, 200%, 500%, 1000%, or more. In an embodiment, said increase is detected over time.

It is to be noted that the biomarkers described herein can be used to refer to any combination of features described herein regarding any individual or combination of such biomarkers. For example, any combination of sequence composition, percentage identity, sequence length, domain structure, functional activity, mutation status, etc. can be used to describe a biomarker molecule of the present invention.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluid that are normally not (e.g., bronchoalveolar lavage fluid, amniotic fluid, aqueous humor, bile, blood and blood plasma, cerebrospinal fluid, cerumen and earwax, cowper's fluid or pro-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. In some embodiments, such cells exhibit such characteristics in part or in full due to exhausted immune cells characterized by the expression of a biomarker described herein and, in some embodiments, the co-expression and activity of immune checkpoint inhibitors, such as PD-1, PD-L1, PD-L2, and/or CTLA-4. Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia), and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it as known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control chronic immune disorder patient (can be stored sample or previous sample measurement) with a known outcome; normal tissue or cells isolated from a subject, such as a normal patient or the chronic immune disorder patient, cultured primary cells/tissues isolated from a subject such as a normal subject or the chronic immune disorder patient, adjacent normal cells/tissues obtained from the same organ or body location of the chronic immune disorder patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care chronic immune disorder therapy). It will be understood by those of skill in the art that such control samples and reference standard expression product levels can be used in combination as controls in the methods of the present invention. In one embodiment, the control may comprise normal or non-chronic immune disordered cell/tissue sample. In another preferred embodiment, the control may comprise an expression level for a set of patients, such as a set of chronic immune disorder patients, or for a set of chronic immune disorder patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having a benign chronic immune disorder such as a benign cancer. In another embodiment, the control may also comprise a measured value for example, average level of expression of a particular gene in a population compared to the level of expression of a housekeeping gene in the same population. Such a population may comprise normal subjects, chronic immune disorder patients who have not undergone any treatment (i.e., treatment naive), chronic immune disorder patients undergoing standard of care therapy, or patients having benign chronic immune disorder such as a benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with a chronic immune disorder. In one embodiment a control expression product level is established wherein higher or lower levels of expression product relative to, for instance, a particular percentile, are used as the basis for predicting outcome. In another preferred embodiment, a control expression product level is established using expression product levels from chronic immune disorder control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid, protein, or metabolite is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with a chronic immune disorder, or from a corresponding non-chronic immune disordered tissue in the same subject who has a chronic immune disorder.

The term "determining a suitable treatment regimen for the subject" is taken to mean the determination of a treatment regimen (i.e., a single therapy or a combination of different therapies that are used for the prevention and/or treatment of the chronic immune disorder in the subject) for a subject that is started, modified and/or ended based or essentially based or at least partially based on the results of the analysis according to the present invention. One example is determining whether to provide targeted therapy against a chronic immune disorder to provide immunotherapy that generally increases immune responses against the chronic immune disorder (e.g., anti-CD39 therapy with or without anti-immune checkpoint inhibitor therapy). Another example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "expression signature" or "signature" refers to a group of two or more coordinately expressed biomarkers. For example, the genes, proteins, metabolites, and the like making up this signature may be expressed in a specific cell lineage, stage of differentiation, or during a particular biological response. The biomarkers can reflect biological aspects of the tumors in which they are expressed, such as the cell of origin of the chronic immune disorder, the nature of the non-chronic immune disordered cells in the biopsy, and the pathophysiological mechanisms responsible for the chronic immune disorder. Expression data and gene expression levels can be stored on computer readable media, e.g., the computer readable medium used in conjunction with a microarray or chip reading device. Such expression data can be manipulated to generate expression signatures.

As used herein, the terms "high," "low," "intermediate," and "negative" in connection with cellular biomarker expression refers to the amount of the biomarker expressed relative to the cellular expression of the biomarker by one or more reference cells. Biomarker expression can be determined according to any method described herein including, without limitation, an analysis of the cellular level, activity, structure, and the like, of one or more biomarker genomic nucleic acids, ribonucleic acids, and/or polypeptides. In one embodiment, the terms refer to a defined percentage of a population of cells expressing the biomarker at the highest, intermediate, or lowest levels, respectively. Such percentages can be defined as the top 0.1%, 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 11%, 12%, 13%, 14%, 15% or more, or any range in between, inclusive, of a population of cells that either highly express or weakly express the biomarker. The term "low" excludes cells that do not detectably express the biomarker, since such cells are "negative" for biomarker expression. The term "intermediate" includes cells that express the biomarker, but at levels lower than the population expressing it at the "high" level. In another embodiment, the terms can also refer to, or in the alternative refer to, cell populations of biomarker expression identified by qualitative or statistical plot regions. For example, cell populations sorted using flow cytometry can be discriminated on the basis of biomarker expression level by identifying distinct plots based on detectable moiety analysis, such as based on mean fluorescence intensities and the like, according to well-known methods in the art. Such plot regions can be refined according to number, shape, overlap, and the like based on well-known methods in the art for the biomarker of interest. In still another embodiment, the terms can also be determined according to the presence or absence of expression for additional biomarkers. For example, T-bet(low) cells can, in some embodiments, require the absence of Eomes expression. Similarly, CD39(high) cells can, in some embodiments, require the co-expression of PD-1.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "immune cell" refers to cells that play a role in the immune response. Immune cells are of hematopoietic origin, and include lymphocytes, such as B cells and T cells: natural killer cells; myeloid cells, such as monocytes, macrophages, eosinophils, mast cells, basophils, and granulocytes.

The term "immune checkpoint inhibitor" means a group of molecules on the cell surface of CD4+ and/or CD8+ T cells that fine-tune immune responses by down-modulating or inhibiting an anti-tumor immune response. Immune checkpoint inhibitor proteins are well known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). "Anti-immune checkpoint inhibitor therapy" refers to the use of agents that inhibit immune checkpoint inhibitors. Inhibition of one or more immune checkpoint inhibitors can block or otherwise neutralize inhibitory signaling to thereby upregulate an immune response in order to more efficaciously treat chronic immune disorder. Exemplary agents useful for inhibiting immune checkpoint inhibitors include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint inhibitor nucleic acids, or fragments thereof. Exemplary agents for upregulating an immune response include antibodies against one or more immune checkpoint inhibitor proteins block the interaction between the proteins and its natural receptor(s); a non-activating form of one or more immune checkpoint inhibitor proteins (e.g., a dominant negative polypeptide); small molecules or peptides that block the interaction between one or more immune checkpoint inhibitor proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint inhibitor nucleic acid transcription or translation; and the like. Such agents can directly block the interaction between the one or more immune checkpoint inhibitors and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and anti-CTLA-4 antibodies, either alone or in combination, are used to inhibit immune checkpoint inhibitors.

"PD-1" is an immune checkpoint inhibitor that refers to a member of the immunoglobulin gene superfamily that functions as a co-inhibitory receptor having PD-L1 and PD-L2 as known ligands. PD-1 was previously identified using a subtraction cloning based approach to select for proteins involved in apoptotic cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) Int. Immunol. 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) Int. Immunol. 8:773).

The nucleic acid and amino acid sequences of a representative human PD-1 biomarker is available to the public at the GenBank database under NM_005018.2 and NP_005009.2 (see also Ishida et al. (1992) 20 EMBO J 11:3887; Shinohara et al. (1994) Genomics 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) EMBO J. 11:3887; Shinohara et al. (1994) Genomics 23:704; and U.S. Pat. No. 5,698,520).

These features also define a larger family of polypeptides, called the immunoinhibitory receptors, which also includes gp49B, PIR-B, and the killer inhibitory receptors (KIRs) (Vivier and Dacron (1997) Immunol. Today 18:286). It is often assumed that the tyrosyl phosphorylated ITIM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al. (1999) Immunol. Today 20(6):285-8). Nucleic acid and polypeptide sequences of PD-1 orthologs in organisms other than humans are well known and include, for example, mouse PD-1 (NM_008798.2 and NP_032824.1), rat PD-1 (NM_001106927.1 and NP_001100397.1), dog PD-1 (XM_543338.3 and XP_543338.3), cow PD-1 (NM_001083506.1 and NP_001076975.1), and chicken PD-1 (XM_422723.3 and XP_422723.2).

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity" includes the ability of a PD-1 polypeptide to modulate an inhibitory signal in an activated immune cell, e.g., by engaging a natural PD-1 ligand on an antigen presenting cell. PD-1 transmits an inhibitory signal to an immune cell in a manner similar to CTLA4. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

The term "PD-1 ligand" refers to binding partners of the PD-1 receptor and includes both PD-L1 (Freeman et al. (2000) *J. Exp. Med.* 192:1027) and PD-L2 (Latchman et al. (2001) *Nat. Immunol.* 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) *J. Exp. Med.* 192:1027 for sequence data) and PD-L2 (See Latchman et al. (2001) *Nat. Immunol.* 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells, although PD-L1 expression is broader. For example, PD-L1 is known to be constitutively expressed and upregulated to higher levels on murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, macrophages, and bone marrow-derived mast cells (see, Butte et al. (2007) *Immunity* 27:111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1 (CD80), B7-2 (CD86), inducible costimulatory ligand (ICOS-L), B7-H3, B7-H4, VISTA, B7-H6, B7h (Swallow et al. (1999) *Immunity* 11:423), and/or PD-1 ligands (e.g., PD-L or PD-L2). For example, human B7-1 and B7-2 share approximately 26% amino acid sequence identity when compared using the BLAST program at NCBI with the default parameters (Blosum62 matrix with gap penalties set at existence 11 and extension 1 (see the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two β sheets, each consisting of anti-parallel β strands of 5-10 amino acids with a conserved disulfide bond between the two sheets in most, but not all, IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than IgC domains and contain an additional pair off strands.

The term "PD-L1" refers to a specific PD-1 ligand. Two forms of human PD-L1 molecules have been identified. One form is a naturally occurring PD-L1 soluble polypeptide, i.e., having a short hydrophilic domain at the COOH-terminal end and no transmembrane domain, and is referred to herein as PD-L1S. The second form is a cell-associated polypeptide, i.e., having a transmembrane and cytoplasmic domain, referred to herein as PD-L1M. The nucleic acid and amino acid sequences of representative human PD-L1 biomarkers regarding PD-L1M are also available to the public at the GenBank database under NM_014143.3 and NP_054862.1. PD-L1 proteins comprise a signal sequence, and an IgV domain and an IgC domain. The signal sequence is from about amino acid 1 to about amino acid 18. The signal sequence is from about amino acid 1 to about amino acid 18. The IgV domain is from about amino acid 19 to about amino acid 134 and the IgV domain is from about amino acid 19 to about amino acid 134. The IgC domain is from about amino acid 135 to about amino acid 227 and the IgC domain of SEQ ID NO: 6 is shown from about amino acid 135 to about amino acid 227. The hydrophilic tail of PD-L1 comprises a hydrophilic tail shown from about amino acid 228 to about amino acid 245. The PD-L1 polypeptide comprises a transmembrane domain shown from about amino acids 239 to about amino acid 259 and a cytoplasmic domain shown of about 30 amino acids from 260 to about amino acid 290. In addition, nucleic acid and polypeptide sequences of PD-L1 orthologs in organisms other than humans are well known and include, for example, mouse PD-L1 (NM_021893.3 and NP_068693.1), rat PD-L1 (NM_001191954.1 and NP_001178883.1), dog PD-L1 (XM_541302.3 and XP_541302.3), cow PD-L1 (NM_001163412.1 and NP_001156884.1), and chicken PD-L1 (XM_424811.3 and XP_424811.3).

The term "PD-L2" refers to another specific PD-ligand. PD-L2 is a B7 family member expressed on various APCs, including dendritic cells, macrophages and bone-marrow derived mast cells (Zhong et al. (2007) *Eur. J. Immunol.* 37:2405). APC-expressed PD-L2 is able to both inhibit T cell activation through ligation of PD-1 and costimulate T cell activation, through a PD-1 independent mechanism (Shin et al. (2005) *J. Exp. Med.* 201:1531). In addition, ligation of dendritic cell-expressed PD-L2 results in enhanced dendritic cell cytokine expression and survival (Radhakrishnan et al. (2003) *J. Immunol.* 37:1827; Nguyen et al. (2002) *J. Exp. Med.* 196:1393). The nucleic acid and amino acid sequences of representative human PD-L2 biomarkers are well known in the art and are also available to the public at the GenBank database under NM_025239.3 and NP_079515.2. PD-12 proteins are characterized by common structural elements. In some embodiments, PD-L2 proteins include at least one or more of the following domains: a signal peptide domain, a transmembrane domain, an IgV domain, an IgC domain, an extracellular domain, a transmembrane domain, and a cytoplasmic domain. For example, amino acids 1-19 comprise a signal sequence. As used herein, a "signal sequence" or "signal peptide" serves to direct a polypeptide containing such a sequence to a lipid bilayer, and is cleaved in secreted and membrane bound polypeptides and includes a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., valine, leucine, isoleucine or phenylalanine). In another embodiment, amino acid residues 220-243 of the native human PD-L2 polypeptide and amino acid residues 201-243 of the mature polypeptide comprise a transmembrane domain. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta et al. (1996) *Annu. Rev Neurosci.* 19: 235-263. In still another embodiment, amino acid residues 20-120 of the native human PD-L2 polypeptide and amino acid residues 1-101 of the mature polypeptide comprise an IgV domain. Amino acid residues 121-219 of the native human PD-L2 polypeptide and amino acid residues 102-200 of the mature polypeptide comprise an IgC domain. As used herein, IgV and IgC domains are recognized in the art as Ig superfamily member domains. These domains correspond to structural units that have distinct folding patterns called Ig folds. Ig folds are comprised of a sandwich of two β sheets, each consisting of antiparallel β strands of 5-10 amino acids with a conserved disulfide bond between the two sheets in most, but not all, domains. IgC domains of Ig, TCR, and MHC molecules share the same types of sequence patterns and are called the C1 set within the Ig superfamily. Other IgC domains fall within other sets. IgV domains also share sequence patterns and are called V set domains. IgV domains are longer than C-domains and form an additional pair of strands. In yet another embodiment, amino acid residues 1-219 of the native human PD-L2 polypeptide and amino acid residues 1-200 of the mature polypeptide comprise an extracellular domain. As used herein, the term "extracellular domain" represents the N-terminal amino acids which extend as a tail from the surface of a cell. An extracellular domain of the present invention includes an IgV domain and an IgC domain, and may include a signal peptide domain. In still another embodiment, amino acid residues 244-273 of the native human PD-L2 polypeptide and amino acid residues 225-273 of the mature polypeptide comprise a cytoplasmic domain. As used herein, the term "cytoplasmic domain" represents the C-terminal amino acids which extend as a tail into the cytoplasm of a cell. In addition, nucleic acid and polypeptide sequences of PD-L2 orthologs in organisms other than humans are well known and include, for example, mouse PD-L2 (NM_021396.2 and NP_067371.1), rat PD-L2 (NM_001107582.2 and NP_001101052.2), dog PD-L2 (XM_847012.2 and XP_852105.2), cow PD-L2 (XM_0.586846.5 and XP_586846.3), and chimpanzee PD-L2 (XM_001140776.2 and XP_001140776.1).

The term "PD-L2 activity," "biological activity of PD-L2," or "functional activity of PD-L2," refers to an activity exerted by a PD-L2 protein, polypeptide or nucleic acid molecule on a PD-L2-responsive cell or tissue, or on a PD-L2 polypeptide binding partner, as determined in vivo, or in vitro, according to standard techniques. In one embodiment, a PD-L2 activity is a direct activity, such as an association with a PD-L2 binding partner. As used herein, a "target molecule" or "binding partner" is a molecule with which a PD-L2 polypeptide binds or interacts in nature, such that PD-L2-mediated function is achieved. In an exemplary embodiment, a PD-L2 target molecule is the receptor RGMb. Alternatively, a PD-L2 activity is an indirect activity, such as a cellular signaling activity mediated by interaction of the PD-L2 polypeptide with its natural binding partner, e.g., RGMb. The biological activities of PD-L2 are described herein. For example, the PD-L2 polypeptides of the present invention can have one or more of the following activities: 1) bind to and/or modulate the activity of the receptor RGMb, PD-1, or other PD-L2 natural binding partners, 2) modulate intra- or intercellular signaling, 3) modulate activation of immune cells, e.g., T lymphocytes, and 4) modulate the immune response of an organism, e.g., a mouse or human organism.

The term "immune response" includes T cell-mediated and/or B cell-mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

The term "immune response" refers to a response by a cell of the immune system, such as a B cell, T cell (CD4 or CD8), regulatory T cell, antigen-presenting cell, dendritic cell, monocyte, macrophage, NKT cell, NK cell, basophil, eosinophil, or neutrophil, to a stimulus. In one embodiment, the response is specific for a particular antigen (an "antigen-specific response"), and refers to a response by a CD4 T cell, CD8+ T cell, or B cell via their antigen-specific receptor. In another embodiment, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response. In still another embodiment, an immune response is an effector T cell response, such as occurs when a cytotoxic CD8+ cell produces an antigen-specific response.

"Exhaustion" or "unresponsiveness" refers to a state of a cell where the cell does not perform its usual function or activity in response to normal input signals, and includes refractivity of immune cells to stimulation, such as stimulation via an activating receptor or a cytokine. Such a function or activity includes, but is not limited to, proliferation or cell division, entrance into the cell cycle, cytokine production, cytotoxicity, trafficking, phagocytotic activity, or any combination thereof. Normal input signals can include, but are not limited to, stimulation via a receptor (e.g., T cell receptor, B cell receptor, co-stimulatory receptor, and the like).

Exhausted immune cells can have a reduction of at least 10%, 15%, 20%, 25%, 30%, 35%, 40%, 45%, 50%, 55%, 60%, 65%, 70%, 75%, 80%, 85%, 90%, 95%, 99% or more in cytotoxic activity, cytokine production, proliferation, trafficking, phagocytotic activity, or any combination thereof, relative to a corresponding control immune cell of the same type. In one embodiment, a cell that is exhausted is a CD8+ T cell (e.g., an effector CD8+ T cell that is antigen-specific). CD8 cells normally proliferate (e.g., clonally expand) in response to T cell receptor and/or co-stimulatory receptor stimulation, as well as in response to cytokines such as IL-2. Thus, an exhausted CD8$^+$ T cell is one which does not proliferate and/or produce cytokines in response to normal input signals. It is well known that the exhaustion of effector functions can be delineated according to several stages, which eventually lead to terminal or full exhaustion and, ultimately, deletion (Yi et al. (2010) *Immmol.* 129:474-481; Wherry and Ahmed (2004) *J. Virol.* 78:5535-5545). In the first stage, functional T cells enter a "partial exhaustion I" phase characterized by the loss of a subset of effector functions, including loss of IL-2 production, reduced TNFα production, and reduced capacity for proliferation and/or ex vivo lysis ability. In the second stage, partially exhausted T cells enter a "partial exhaustion II" phase when both IL-2 and TNFα production ceases following antigenic stimulation and IFNγ production is reduced. "Full exhaustion" or "terminal exhaustion" occurs when CD8+ T cells lose all effector functions, including the lack of production of IL-2, TNFα, and IFNγ and loss of ex vivo lytic ability and proliferative potential, following antigenic stimulation. A fully exhausted CD8+ T cell is one which does not proliferate, does not lyse target cells (cytotoxicity), and/or does not produce appropriate cytokines, such as IL-2, TNFα, or IFNγ, in response to normal input signals. Such lack of effector functions can occur when the antigen load is high and/or CD4 help is low. This hierarchical loss of function is also associated with the expression of co-inhibitor immune receptors, such as PD-1. TIM-3, LAG-3, and the like (Day et al. (2006) *Nature* 443:350-4; Trautmann et al. (2006) *Nat. Med.* 12:1198-202; and Urbani et al. (2006) *J. Virol.* 80:1398-1403). Other molecular markers distinguish the hierarchical stages of immune cell exhaustion, such as high eomcsodermin (EOMES) and low TBET expression as a marker of terminally exhausted T cells (Paley et al. (2012) *Science* 338:1220-1225). Additional markers of exhausted T cells, such as the reduction of Bcl-b and the increased production of BLIMP-1 (Pdrm1).

The term "reducing exhaustion" or "reducing unresponsiveness" refers to a given treatment or set of conditions that leads to increased T cell activity, responsiveness, and/or ability or receptiveness, with regards to activation. Methods of measuring T cell activity are well known in the art. Modulation of one or more of any of the immune cell exhaustion parameters described above can be assayed. For example, T cell activity can be measured by contacting T cells with recall antigen, anti-CD3 in the absence of costimulation, and/or ionomycin. Also, proliferation of T cells can be measured in the presence of a relevant antigen assayed, e.g. by a $^3$H-thymidine incorporation assay or cell number. Markers of T cell activation after exposure to the relevant antigen can also be assayed, e.g. flow cytometry analysis of cell surface markers indicative of T cell activation (e.g., CD69, CD30, CD25, and HLA-DR) and/or T cell exhaustion. In some embodiments, the assays can be in vivo assays, such as through challenging immune cells with antigen in vive. For example, animal models expressing homogeneous populations of T cells from TCR transgenic and other transgenic mice can be transferred into hosts that constitutively express an antigen recognized by the transferred T cells, e.g., the H-Y antigen TCR transgenic; pigeon cytochrome C antigen TCR transgenic; or hemagglutinin (HA) TCR transgenic. In such models, T cells expressing the TCR specific for the antigen constitutively or inducibly expressed by the recipient mice typically undergo an immediate expansion and proliferative phase, followed by a period of unresponsiveness, which is reversed when the antigen is removed and/or antigen expression is inhibited. Accordingly, if the T cells proliferate or expand, show cytokine activity, etc. significantly more in an assay (e.g., with or without additional treatment of immunomodulatory agents) than control T cells, then T cell exhaustion is reduced. Such measurements of proliferation can occur in vivo using T cells labeled with BrDU, CFSE or another intravital dye that allows tracking of proliferation prior to transferring to a recipient animal expressing the antigen, or cytokine reporter T cells, or using ex vivo methods to analyze cellular proliferation and/or cytokine production, such as thymidine proliferation assays, ELISA, cytokine bead assays, and the like. Moreover, reduction of immune cell exhaustion can be assessed by examination of rumor infiltrating lymphocytes or T lymphocytes within lymph nodes that drain from an established tumor. Such T cells exhibit features of exhaustion through expression of cell surface molecules, such as immunoinhibitory receptors described above, for example, and decreased secretion of cytokines, such as those described above. Accordingly, if increased quantities and/or activities of T cells are observed with, for example, 1) antigen specificity for tumor associated antigens (e.g., as determined by major histocompatibility complex class I or class II tetramers which contain tumor associated peptides) and/or 2) that are capable of secreting high levels of appropriate cytokines and cytolytic effector molecules such as granzyme-B, then T cell exhaustion has been reduced.

The term "acute immune disorder" refers to conditions that can be resolved by an appropriate immune response that eradicates a targeted antigen and host comprising such a targeted antigen, such as a cancer or an infection agent like a virus, bacteria, parasite, mycoplasma, fungus, and the like. Such conditions are relatively brief and last on the order of a few days to a few weeks.

By contrast, the term "chronic immune disorders" refers to those conditions that are not effectively cleared or eliminated by the induction of a host immune response. In chronic immune disorders, a targeted antigen (and/or host comprising the targeted antigen), such as an infectious agent or cancer cell, and the immune response reach equilibrium such that the subject maintains the targeted antigen or host comprising the targeted antigen (e.g., remains infectious or afflicted with cancer) over a long period of time (i.e., a time period of months to years or even a lifetime) without necessarily expressing symptoms. Chronic immune disorders can involve stages of both silent and productive targeted antigen maintenance without rapidly killing or even producing excessive damage of the host cells.

Detection of the targeted antigen or host comprising the targeted antigen can be made according to any one of many well known methods in the art and described, for example, in U.S. Pat. Nos. 6,368,832, 6,579,854, and 6,808,710 and U.S. Patent Application Publication Nos. 20040137577, 20030232323, 20030166531, 20030064380, 20030044768, 20030039653, 20020164600, 20020160000, 20020110836, 20020107363, and 200201067. In some embodiments, chronic immune disorders are the result of infection, such as an infection with a virus including, but not limited to, human immunodeficiency viruses (HIV), hepatitis C viruses (HCV), T-cell leukemia viruses, Epstein-Barr virus, cytomegalovirus, herpesviruses, varicella-zoster virus, measles, papovaviruses, prions, hepatitis viruses, adenoviruses, parvoviruses, papillomaviruses, prions, and the like. Chronic immune disorders include, for example, chronic conditions and latent conditions. As used herein, chronic immune disorders can be limited to chronic conditions, latent conditions, or both.

In a "chronic condition," the targeted antigen can be detected in the subject at all times regardless of whether the signs and symptoms of the disease are present or absent, even for an extended period of time. Non-limiting examples of chronic conditions resulting from infection include hepatitis B (caused by hepatitis B virus (HBV)) and hepatitis C (caused by hepatitis C virus (HCV)) adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyoma virus BK, polyoma virus JC, measles virus, rubella virus, human immunodeficiency virus (HIV), human T cell leukemia virus I, and human T cell leukemia virus II. Parasitic persistent infections can arise as a result of infection by, for example, *Leishmania, Toxoplasma, Trypanosoma, Plasmodium, Schistosoma*, and *Encephalitozoon*.

A particular type of chronic condition involving infections is known as a "latent condition," where the infectious agent (such as a virus) is seemingly inactive and dormant such that the subject does not always exhibit signs or symptoms. In a latent viral infection, the virus remains in equilibrium with the host for long periods of time before symptoms again appear; however, the actual viruses cannot typically be detected until reactivation of the disease occurs. Infection latency is the ability of a pathogenic infection agent, such as a virus, to lie dormant within a cell. For example, a latent viral infection is a phase in the life cycle of certain viruses in which after initial infection, virus production ceases. However, the virus genome is not fully eradicated. The result of this is that the virus can reactivate and begin producing large amounts of viral progeny (the lytic part of the viral life cycle) without the host being infected by a new virus. The virus may stay within the host indefinitely. In one embodiment, virus latency is not identical to clinical latency, in which the virus is undergoing an incubation period but is not dormant. Non-limiting examples of latent infections include infections caused by herpes simplex virus (HSV)-1 (fever blisters), HSV-2 (genital herpes), and varicella zoster virus VZV (chickenpox-shingles).

The term "immunotherapeutic agent" can include any molecule, peptide, antibody or other agent which can stimulate a host immune system to generate an immune response against the chronic immune disorder in the subject. Various immunotherapeutic agents are useful in the compositions and methods described herein.

The term "inhibit" includes the decrease, limitation, or blockage, of, for example a particular action, function, or interaction. In some embodiments, a chronic immune disorder is "inhibited" if at least one symptom of the chronic immune disorder is alleviated, terminated, slowed, or prevented. As used herein, a chronic immune disorder is also "inhibited" if recurrence or metastasis of the chronic immune disorder is reduced, slowed, delayed, or prevented.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe or small molecule, fir specifically detecting and/or affecting the expression of a marker of the invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allow patients with large breast cancer to undergo breast-conserving surgery.

The "normal" level of expression of a biomarker is the level of expression of the biomarker in cells of a subject, e.g., a human patient, not afflicted with a chronic immune disorder. An "over-expression" or "significantly higher level of expression" of a biomarker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

The term "predictive" includes the use of a biomarker nucleic acid, protein, and/or metabolite status, e.g., over- or under-activity, emergence, expression, growth, remission, recurrence or resistance of tumors before, during or after therapy, for determining the likelihood of response of a chronic immune disorder to treatment, such as anti-CD39 therapy with or without anti-immune checkpoint inhibitor treatment (e.g., therapeutic antibodies against PD-1, PD-L1, PD-L2, and/or CTLA-4). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC) and/or biomarker metabolite, or increased or decreased activity (determined by, for example, modulation of biomarkers, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed relevant human chronic immune disorder types or samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with the chronic immune disorder; (3) its absolute or relatively modulated presence or absence in clinical subset of patients with the chronic immune disorder (e.g., those responding to a particular anti-CD39 therapy with or without anti-immune checkpoint inhibitor therapy or those developing resistance thereto).

The terms "prevent," "preventing." "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of chronic immune disorder or the likelihood of recovery from the disease. In some embodiments, the use of statistical algorithms provides a prognosis of a chronic immune disorder in an individual. For example, the prognosis can be surgery, development of a clinical subtype of cancer (e.g., solid tumors, such as lung cancer, melanoma, and renal cell carcinoma), development of one or more clinical factors, development of intestinal cancer, or recovery from the disease.

The term "response to therapy" relates to any response of a chronic immune disorder to therapy, such as anti-CD39 and/or anti-immune checkpoint inhibitor therapy, preferably to a change in symptoms such as reduced infection or viral load, tumor mass and/or volume after initiation of neoadjuvant or adjuvant chemotherapy, and the like. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a chronic immune disorder sample or a mammal to a chronic immune disorder therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same chronic immune disorder sample or mammal before the resistance is acquired, or by comparing with a different chronic immune disorder sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary chronic immune disorder therapy (e.g., anti-immune checkpoint inhibitor, chemotherapeutic, and/or radiation therapy) is able to produce a significant decrease in chronic immune disordered tissue at a level of statistical significance (e.g., $p<0.05$) when compared to chronic immune disordered tissue in the circumstance where the primary therapy alone is unable to produce a statistically significant decrease. For example, this generally applies to tumor volume measurements made at a time when the untreated tumor is growing log rhythmically.

The terms "response" or "responsiveness" refers to an anti-chronic immune disorder response, e.g. in the sense of reduction of tumor size or inhibiting tumor growth or a cancer or reduction of infectious agent load or number of affected cells. The terms can also refer to an improved prognosis, for example, as reflected by an increased time to recurrence, which is the period to first recurrence censoring for second primary chronic immune disorder as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the invention, or a fragment thereof, short interfering RNA (siRNA), and small molecules which interfere with or inhibit expression of a target biomarker nucleic acid by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn, G, and Cullen, B. (2002) *J. of Virology* 76(18):9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter chronic immune disordered cells such as cancer cells in a way that allows for more effective treatment of the associated chronic immune disorder with a therapy (e.g., anti-immune checkpoint inhibitor, chemotherapeutic, and/or radiation therapy). In some embodiments, normal cells are not affected to an extent that causes the normal cells to be unduly injured by the therapy. An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M. Shoemaker R H, Marsden J A. Dill P L. Baker J A. Moran E M, Cancer Res 1984; 94: 161-173; Weisenthal L M, Lippman M E, Cancer Treat Rep 1985; 69: 615-632; Weisenthal L M, In: Kaspers G J L, Picters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring chronic immune disorder symptom reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to cancer therapy.

The term "synergistic effect" refers to the combined effect of two or more chronic immune disorder, such as an anti-CD39 therapy and anti-immune checkpoint inhibitor therapy can be greater than the sum of the separate effects of the agents alone.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see. e.g., Stewart, et al. (2003) *RNA* April; 9(4):493-501 incorporated by reference herein).

RNA interfering agents, e.g., siRNA molecules, may be administered to a patient having or at risk for having a chronic immune disorder, to inhibit expression of a biomarker gene which is overexpressed in the chronic immune disorder and thereby treat, prevent, or inhibit the chronic immune disorder in the subject.

The term "subject" refers to any healthy animal, mammal or human, or any animal, mammal or human afflicted with a chronic immune disorder. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include chronic immune disorders such as cancer and infections). The length of said survival may be calculated by reference to a defined start point (e.g. time of diagnosis or start of treatment) and end point (e.g. death, recurrence or metastasis). In addition, criteria for efficacy of treatment can be expanded to include response to therapy, probability of survival, probability of metastasis within a given time period, and probability of tumor recurrence.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves a half-maximal effect, such as cytotoxic or cytostatic effect on cancer cells or inhibition of viral replication or load) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, an effect in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even (100% decrease in a malignancy or viral load can be achieved.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Table 1) are well known in the art and readily available on publicly available databases, such as the National Center for Biotechnology Information (NCBI). For example, exemplary nucleic acid and amino acid sequences derived from publicly available sequence databases are provided below.

TABLE 1

SEQ ID NO: 1 Human CD39 (transcript variant 1) cDNA sequence

```
  1 atggaagata caaaggagtc taacgtgaag acattttgct ccaagaatat cctagccatc
 61 cttggcttct cctctatcat agctgtgata gctttgcttg ctgtggggtt gacccagaac
121 aaagcattgc cagaaaacgt taagtatggg attgtgctgg atgcgggttc ttctcacaca
181 agtttataca tctataagtg gccagcagaa aaggagaatg acacaggcgt ggtgcatcaa
241 gtagaagaat gcagggttaa aggtcctgga atctcaaaat ttgttcagaa agtaaatgaa
```

TABLE 1-continued

```
 301 ataggcattt acctgactga ttgcatggaa agagctaggg aagtgattcc aaggtcccag
 361 caccaagaga cacccgttta cctgggagcc acggcaggca tgcggttgct caggatggaa
 421 agtgaagagt tggcagacag ggttctggat gtggtggaga ggagcctcag caactacccc
 481 tttgacttcc agggtgccag gatcattact ggccaagagg aaggtgccta tggctggatt
 541 actatcaact atctgctggg caaattcagt cagaaaacaa ggtggttcag catagtccca
 601 tatgaaacca taatcagga aacctttgga gctttggacc ttgggggagc ctctacacaa
 661 gtcacttttg taccccaaaa ccagactatc gagtccccag ataatgctct gcaatttcgc
 721 ctctatggca aggactacaa tgtctacaca catagcttct gtgctatgg aaggatcag
 781 gcactctggc agaaactggc caaggacatt caggttgcaa gtaatgaaat tctcagggac
 841 ccatgctttc atcctggata taagaaggta gtgaacgtaa gtgacctttg caagaccccc
 901 tgcaccaaga gatttgagat gactcttcca ttcgagcagt ttgaaatcca gggtattgga
 961 aactatcaac aatgccatca aagcatcctg gagctcttca caccagtta ctgcccttac
1021 tcccagtgtg ccttcaatgg gattttcttg ccaccactcc agggggattt tggggcattt
1081 tcagcttttt actttgtgat gaagtttta aacttgacat cagagaaagt ctctcaggaa
1141 aaggtgactg agatgatgaa aaagttctgt gctcagcctt gggaggagat aaaaacatct
1201 tacgctggag taaaggagaa gtacctgagt gaatactgct tttctggtac ctacattctc
1261 tccctccttc tgcaaggcta tcatttcaca gctgattcct gggagcacat ccatttcatt
1321 ggcaagatcc agggcagcga cgccggctgg actttgggct acatgctgaa cctgaccaac
1381 atgatcccag ctgagcaacc attgtccaca cctctctccc actccaccta tgtcttcctc
1441 atggttctat tctccctggt cctttttcaca gtgccatca taggcttgct tatctttcac
1501 aagccttcat atttctggaa agatatggta tag
```

SEQ ID NO: 2 Human CD39 (isoform 1) amino acid sequence

```
  1 medtkesnvk tfcsknilai igfssiiavi allavgltqn kalpenvkyg ivldagssht
 61 slyiykwpae kendtgvvhq veecrvkgpg iskfvqkvne igiyltdcme rareviprsq
121 hqetpvylga tagmrllrme seeladrvld vverslsnyp fdfqgariit gqeegaygwi
181 tinyllgkfs qktrwfsivp yetnnqetfg aldlggastq vtfvpqnqti espdnalqfr
241 lygkdynvyt hsflcygkdq alwqklakdl gvasneilrd pcfhpgykkv vnvsdlyktp
301 ctkrfemtlp fqqfeiqgig nyqqchqsil elfntsycpy sqcafngifl pplqgdfgaf
361 safyfvmkfl nltsekvsqe kvtemmkkfc aqpweeikts yagvkekyls eycfsgtyil
421 slllqgyhft adswehihfi gkiqgsdagw tlgymlnltn mipaeqplst plshstyvfl
481 mvlfslvlft vaiigllifh kpsyfwkdmv
```

SEQ ID NO: 3 Human CD39 (transcript variant 2) cDNA sequence

```
  1 atgaagggaa ccaaggacct gacaagccag cagaaggagt ctaacgtgaa gacattttgc
 61 tccaagaata tcctagccat ccttggcttc tcctctatca tagctgtgat agctttgctt
121 gctgtggggt tgacccagaa caaagcattg ccagaaaacg ttaagtatgg gattgtgctg
181 gatgcgggtt cttctcacac aagtttatac atctataagt ggccagcaga aaaggagaat
241 gacacaggcg tggtgcatca gtagaagaa tgcagggtta aggtcctgg aatctcaaaa
301 tttgttcaga agtaaatga ataggcatt tacctgactg attgcatgga agagctagg
361 gaagtgattc caaggtccca gcaccaagag acacccgttt acctgggagc cacggcaggc
421 atgcggttgc tcaggatgga aagtgaagag ttggcagaca gggttctgga tgtggtggag
```

TABLE 1-continued

```
 481 aggagcctca gcaactaccc ctttgacttc cagggtgcca ggatcattac tggccaagag
 541 gaaggtgcct atggctggat tactatcaac tatctgctgg gcaaattcag tcagaaaaca
 601 aggtggttca gcatagtccc atatgaaacc aataatcagg aaacctttgg agctttggac
 661 cttgggggag cctctacaca agtcactttt gtacccaaaa accagactat cgagtcccca
 721 gataatgctc tgcaatttcg cctctatggc aaggactaca atgtctacac acatagcttc
 781 ttgtgctatg gaaggatca ggcactctgg cagaaactgg ccaaggacat tcaggttgca
 841 agtaatgaaa ttctcaggga cccatgcttt catcctggat ataagaaggt agtgaacgta
 901 agtgaccttt acaagacccc ctgcaccaag agatttgaga tgactcttcc attccagcag
 961 tttgaaatcc agggtattgg aaactatcaa caatgccatc aaagcatcct ggagctcttc
1021 aacaccagtt actgcccctta ctcccagtgt gccttcaatg ggattttctt gccaccactc
1081 caggggatt ttggggcatt ttcagctttt tactttgtga tgaagttttt aaacttgaca
1141 tcagagaaag tctctcagga aaaggtgact gagatgatga aaaagttctg tgctcagcct
1201 tgggaggaga taaaaacatc ttacgctgga gtaaaggaga agtacctgag tgaatactgc
1261 ttttctggta cctacattct ctccctcctt ctgcaaggct atcatttcac agctgattcc
1321 tgggagcaca tccatttcat tggcaagatc cagggcagcg acgccggctg gactttgggc
1381 tacatgctga acctgaccaa catgatccca gctgagcaac cattgtccac acctctctcc
1441 cactccacct atgtcttcct catggttcta ttctccctgg tccttttcac agtggccatc
1501 ataggcttgc ttatctttca caagccttca tatttctgga agatatggt atag
```

SEQ ID NO: 4 Human CD39 (isoform 2) amino acid sequence

```
  1 mkgtkdltsq qkesnvktfc sknilailgf ssiiaviall avgltqnkal penvkygivl
 61 dagsshtsly iykwpaeken dtgvvhqvee crvkgpgisk fvqkvneigi yltdcmerar
121 eviprsqhqe tpvylgatag mrllrmesee ladrvldvve rslsnypfdf qgariitgqe
181 egaygwitin yllgkfsqkt rwfsivpyet nnqetfgald lggaatqvtf vpqnqtiesp
241 dnalqfrlyg kdynvythsf lcygkdqalw qklakdiqva sneilrdpcf hpgykkvvnv
301 sdlyktpctk rfemtlpfqq feiqgignyq qchqsilelf ntsycpysqc afngiflppl
361 qgdfgafsaf yfvmkflnlt sekvsqekvt emmkkfcaqp weeiktsyag vkekylseyc
421 fsgtyilsll lqgyhftads wehihfigki qgsdagwtlg ymlnltnmip aeqplstpls
481 hstyvflmvl fslvlftvai igllifhkps yfwkdmv
```

SEQ ID NO: 5 Human CD39 (transcript variant 3) cDNA sequence

```
  1 atggggaggg aagaactgtt cttgactttc agttttttcga gcgggtttca agagtctaac
 61 gtgaagacat tttgctccaa gaatatccta gccatccttg cttctcctc tatcatagct
121 gtgatagctt gccttgctgt ggggttgacc cagaacaaag cattgccaga aaacgttaag
181 tatgggattg tgctggatgc gggttcttct cacacaagtt atacatctta aagtggcca
241 gcagaaaagg agaatgacac aggcgtggtg catcaagtag aagaatgcag ggttaaaggt
301 cctggaatct caaatttgt tcagaaagta aatgaaatag catttacct gactgattgc
361 atggaaagag ctagggaagt gattccaagg tcccagcacc aagagacacc cgtttacctg
421 ggagccacgg caggcatgcg gttgctcagg atggaaagtg aagagttggc agacagggtt
481 ctggatgtgg tggagaggag cctcagcaac taccccttg acttcagggg tgccaggatc
541 attactggcc aagaggaagg tgcctatggc tggattacta tcaactatct gctgggcaaa
601 ttcagtcaga aaacaaggtg gttcagcata gtcccatatg aaaccaataa tcaggaaacc
```

TABLE 1-continued

```
 661 tttggagctt tggaccttgg gggagcctct acacaagtca cttttgtacc ccaaaaccag
 721 actatcgagt ccccagataa tgctctgcaa tttcgcctct atggcaagga ctacaatgtc
 781 tacacacata gcttcttgtg ctatgggaag gatcaggcac tctggcagaa actggccaag
 841 gacattcagg ttgcaagtaa tgaaattctc agggacccat gctttcatcc tggatataag
 901 aaggtagtga acgtaagtga cctttacaag accccctgca ccaagagatt tgagatgact
 961 cttccattcc agcagtttga aatcgagggt attggaaact atcaacaatg ccatcaaagc
1021 atcctggagc tcttcaacac cagttactgc ccttactccc agtgtgcctt caatgggatt
1081 ttcttgccac cactccaggg ggattttggg gcattttcag ctttttactt tgtgatgaag
1141 tttttaaact tgacatcaga gaaagtctct caggaaaagg tgactgagat gatgaaaaag
1201 ttctgtgctc agccttggga ggagataaaa acatcttacg ctggagtaaa ggagaagtac
1261 ctgagtgaat actgcttttc tggtacctac attctctccc tccttctgca aggctatcat
1321 ttcacagctg attcctggga gcacatccat ttcattggca agatccaggg cagcgacgcc
1381 ggctggactt tgggctacat gctgaacctg accaacatga tcccagctga gcaaccattg
1441 tccacacctc tctcccactc cacctatgtc ttcctcatgg ttctattctc cctggtcctt
1501 ttcacagtgg ccatcatagg cttgcttatc tttcacaagc cttcatattt ctggaaagat
1561 atggtatag
```

SEQ ID NO: 6 Human CD39 (isoform 3) amino acid sequence

```
  1 mgreelfltf sfssgfqesn vktfcsknil ailgfssiia viallavglt gnkalpenvk
 61 ygivldagss htslyiykwp aekendtgvv hqveecrvkg pgiskfvqkv neigiyltdc
121 merarevipr sqhqetpvyl gatagmrllr meseeladrv ldvverslsn ypfdfqgari
181 itgqeegayg witinyllgk fsqktrwfsi vpyetnnqet fgaldllggas tqvtfvpqnq
241 tiespdnalq frlygkdynv ythsflcygk dqalwqklak diqvasneil rdpcfhpgyk
301 kvvnvsdlyk tpctkrfemt lpfqqfeiqg ignyqqchqs ilelfntsyc pysqcafngi
361 flpplqgdfg afsafyfvmk flnltsekvs qekvtemmkk fcaqpweeik tsyagvkeky
421 lseycfsgty ilslllqgyh ftadswehih fiqkiqgsda gwtlgymlnl tnmipaeqpl
481 stplshstyv flmvlfslvl ftvaiiglli fhkpsyfwkd mv
```

SEQ ID NO: 7 Human CD39 (transcript variant 4) cDNA sequence

```
  1 atggaagata caaaggagtc taacgtgaag acatttttgct ccaagaatat cctagccatc
 61 cttggcttct ccctctatcat agctgtgata gctttgcttg ctgtggggtt gacccagaac
121 aaagcattgc cagaaaacgt taagtatggg attgtgctgg atgcgggttc ttctcacaca
181 agtttataca tctataagtg gccagcagaa aaggagaatg acacaggcgt ggtgcatcaa
241 gtagaagaat gcagggttaa aggtcctgga atctcaaaat ttgttcagaa agtaaatgaa
301 ataggcattt acctgactga ttgcatggaa agagctaggg aagtgattcc aaggtcccag
361 caccaagaga cacccgtttta cctgggagcc acggcaggca tgcggttgct caggatggaa
421 agtgaagagt tggcagacag ggttctggat gtggtggaga ggagcctcag caactacccc
481 tttgacttcc agggtgccag gatcattact ggccaagagg aaggtgccta ggctggatt
541 actatcaact atctgctggg caaattcagt cagaaaacaa ggtggttcag catagtccca
601 tatgaaacca ataatcagga aacctttgga gctttggacc ttgggggagc tctacacaa
661 gtcacttttg taccccaaaa ccagactatc gagtccccag ataatgctct gcaatttcgc
721 ctctatggca aggactacaa tgtctacaca catagcttct gtgctatgg gaaggatcag
```

TABLE 1-continued

```
 781 gcactctggc agaaactggc caaggacatt cagcagtttg aaatccaggg tattggaaac 841 tatcaacaat gccatcaaag catcctggag ctcttcaaca ccagttactg cccttactcc 901 cagtgtgcct tcaatgggat tttcttgcca ccactccagg gggattttgg ggcattttca 961 gcttttact ttgtgatgaa gtttttaaac ttgacatcag agaaagtctc tcaggaaaag 1021 gtgactgaga tgatgaaaaa gttctgtgct cagccttggg aggagataaa aacatcttac 1081 gctggagtaa aggagaagta cctgagtgaa tactgctttt ctggtaccta cattctctcc 1141 ctccttctgc aaggctatca tttcacagct gattcctggg agcacatcca tttcattggc 1201 aagatccagg gcagcgacgc cggctggact ttgggctaca tgctgaacct gaccaacatg 1261 atcccagctg agcaaccatt gtccacacct ctctcccact ccacctatgt cttcctcatg 1321 gttctattct ccctggtcct tttcacagtg gccatcatag gcttgcttat ctttcacaag 1381 ccttcatatt tctgga.aaga tatggtatag
```

SEQ ID NO: 8 Human CD39 (isoform 4) amino acid sequence

```
  1 medtkesnvk tfcsknilai lgfssiiavi allavgltqn kalpenvkyg ivldagssht 61 slyiykwpae kendtgvvhq veecrvkgpg iskfvqkvne igiyltdcme rareviprsq 121 hqetpvylga tagmrllrme seeladrvld vverslsnyp fdfqgariit gqeegaygwi 181 tinyllgkfs qktrwfsivp yetnnqetfg aldlggastq vtfvpqnqti espdnalqfr 241 lygkdynvyt hsflcygkdq alwqklakdi qqfeiqgign yqqchqsile lfntsycpys 301 qcafngiflp plqgdfgafs afyfvmkfln ltseksvsqek vtemmkkfca qpweeiktsy 361 agvkekylse ycfsgtyils liiqgyhfta dswehihfig kiqgsdagwt lgyminltnm 421 ipaeqplstp lshstyvflm vlfslvlftv aiigllifhk psyfwkdmv
```

SEQ ID NO: 9 Human CD39 (transcript variant 5) cDNA sequence

```
  1 atggaaagag ctagggaagt gattccaagg tcccagcacc aagagacacc cgtttacctg 61 ggagccacgg caggcatgcg gttgctcagg atggaaagtg aagagttggc agacagggtt 121 ctggatgtgg tggagaggag cctcagcaac taccccttg acttccaggg tgccaggatc 181 attactggcc aagaggaagg tgcctatggc tggattacta tcaactatct gctgggcaaa 241 ttcagtcaga aaacaaggtg gttcagcata gtcccatatg aaaccaataa tcaggaaacc 301 tttggagctt tggaccttgg gggagcctct acacaagtca cttttgtacc caaaaccag 361 actatcgagt ccccagataa tgctctgcaa tttcgcctct atggcaagga ctacaatgtc 421 tacacacata gcttcttgtg ctatgggaag atcaggcac tctggcagaa actggccaag 481 gacattcagg ttgcaagtaa tgaaattctc agggacccat gctttcatcc tggatataag 541 aaggtagtga acgtaagtga cctttacaag acccctgca ccaagagatt tgagatgact 601 cttccattcc agcagtttga aatccagggt attggaaact atcaacaatg ccatcaaagc 661 atcctggagc tcttcaacac cagttactgc ccttactccc agtgtgcctt caatggaatt 721 ttcttgccac cactccaggg ggattttggg gcattttcag cttttacttt gtgatgaag 781 ttttaaact tgacatcaga gaaagtctct caggaaaagg tgactgagat gatgaaaaag 841 ttctgtgctc agccttggga ggagataaaa acatcttacg ctggagtaaa ggagaagtac 901 ctgagtgaat actgctttc tggtacctac attctctccc tccttctgca aggctatcat 961 ttcacagctg attcctggga gcacatccat ttcattggca gatccagggg cagcgacgcc 1021 ggctggactt tgggctacat gctgaacctg accaacatga tcccagctga gcaaccattg 1081 tccacacctc tctcccactc cacctatgtc ttcctcatgg ttctattctc cctggtcctt
```

TABLE 1-continued

```
1141 ttcacagtgg ccatcatagg cttgcttatc tttcacaagc cttcatattt ctggaaagat
1201 atggtatag
```

SEQ ID NO: 10 Human CD39 (isoform 5) amino acid sequence

```
  1 merarevipr sqhqetpvyl gatagmrllr meseeladrv ldvverslsn ypfdfqgari
 61 itgqeegayg witinyllgk fsqktrwfsi vpyetnnqet fgaldlggas tqvtfvpqnq
121 tiespdnalq frlygkdynv ythsflcygk dqalwqklak diqvasneil rdpcfhpgyk
181 kvvnvsdlyk tpctkrfemt lpfqqfeiqg ignyqqchqs ilelfntsyc pysqcafngi
241 flpplqgdfg afsafyfvmk flnltsekvs qekvtemmkk fcaqpweeik tsyagvkeky
301 lseycfsgty ilslllqgyh ftadswehih figkiqgsda gwtlgymlnl tnmipaeqpl
361 stplshstyv flmvlfslvi ftvaiiglli fhkpsyfwkd mv
```

SEQ ID NO: 11 Human CD39 (transcript variant 6) cDNA sequence

```
  1 atggaaagtg aagagttggc agacagggtt ctggatgtgg tgagaggag cctcagcaac
 61 taccccttttg acttccaggg tgccaggatc attactggcc aagaggaagg tgcctatggc
121 tggattacta tcaactatct gctgggcaaa ttcagtcaga aaacaaggtg gttcagcata
181 gtcccatatg aaaccaataa tcaggaaacc tttggagctt ggaccttgg gggagcctct
241 acacaagtca cttttgtacc ccaaaaccag actatcgagt ccccagataa tgctctgcaa
301 tttcgcctct atggcaagga ctacaatgtc tacacacata gcttcttgtg ctatgggaag
361 gatcaggcac tctggcagaa actggccaag gacattcagg ttgcaagtaa tgaaattctc
421 agggacccat gctttcatcc tggatataag aaggtagtga acgtaagtga cctttacaag
481 accccctgca ccaagagatt tgagatgact cttccattcc agcagtttga aatccagggt
541 attggaaaact atcaacaatg ccatcaaagc atcctggagc tcttcaacac cagttactgc
601 ccttactccc agtgtgcctt caatgggatt ttcttgccac cactccaggg ggattttggg
661 gcattttcag ctttttactt tgtgatgaag ttttttaaact tgacatcaga aaagtctct
721 caggaaaagg tgactgagat gatgaaaaag ttctgtgctc agccttggga ggagataaaa
781 acatcttacg ctggagtaaa ggagaagtac ctgagtgaat actgcttttc tggtacctac
841 attctctccc tccttctgca aggctatcat ttcacagctg attcctggga gcacatccat
901 ttcattggca gatccagggg cagcgacgcc ggctggactt gggctacat gctgaacctg
961 accaacatga tcccagctga gcaaccattg tccacacctc tctcccactc cacctatgtc
1021 ttcctcatgg ttctattctc cctggtcctt ttcacagtgg ccatcatagg cttgcttatc
1081 tttcacaagc cttcatattt ctggaaagat atggtatag
```

SEQ ID NO: 12 Human CD39 (transcript variant 7) cDNA sequence

```
  1 atggaaagtg aagagttggc agacagggtt ctggatgtgg tgagaggag cctcagcaac
 61 taccccttttg acttccaggg tgccaggatc attactggcc aagaggaagg tgcctatggc
121 tggattacta tcaactatct gctgggcaaa ttcagtcaga aaacaaggtg gttcagcata
181 gtcccatatg aaaccaataa tcaggaaacc tttggagctt ggaccttgg gggagcctct
241 acacaagtca cttttgtacc ccaaaaccag actatcgagt ccccagataa tgctctgcaa
301 tttcgcctct atggcaagga ctacaatgtc tacacacata gcttgttgtg ctatgggaag
361 gatcaggcac tctggcagaa actggccaag gacattcagg ttgcaagtaa tgaaattctc
421 agggacccat gctttcatcc tggatataag aaggtagtga acgtaagtga cctttacaag
481 accccctgca ccaagagatt tgagatgact cttccattcc agcagtttga aatccagggt
```

TABLE 1-continued

```
 541 attggaaact atcaacaatg ccatcaaagc atcctggagc tcttgaacac cagttactgc 601 ccttactccc agtgtgcctt caatgggatt ttcttgccac cactgcaggg ggattttggg 661 gcattttcag cttttttactt tgtgatgaag ttttttaaact tgacatcaga gaaagtctct 721 caggaaaagg tgactgagat gatgaaaaag ttctgtgctc agccttggga ggagataaaa 781 acatcttacg ctggagtaaa ggagaagtac ctgagtgaat actgcttttc tggtacctac 841 attctctccc tccttctgca aggctatcat ttcacagctg attcctggga gcacatccat 901 ttcattggca agatccaggg cagcgacgcc ggctggactt tgggctacat gctgaacctg 961 accaacatga tcccagctga gcaaccattg tccacacctc tctcccactc cacctatgtc 1021 ttcctcatgg ttcattctc cctggtcctt ttcacagtgg ccatcatagg cttgcttatc 1081 tttcacaagc cttcatattt ctggaaagat atggtatag
```

SEQ ID NO: 13 Human CD39 (isoform 6/7) amino acid sequence

```
  1 meseeladrv ldvverslsn ypfdfggari itgqeegayg witinyllgk fsqktrwfsi 61 vpyatnnqet fgaldlggas tqvtfvpqnq tiespdnalq frlygkdynv ythsflcygk 121 dqalwqklak diqvasneil rdpcfhpgyk kvvnvsdlyk tpctkrfemt lpfqqfeiqg 181 ignyqqchqs ilelfntsyc pysqcafngi flpplqgdfg afsafyfvmk flnltsekvs 241 gekvtemmkk fcaqpweeik tsyagvkeky lseycfsgty ilslllqgyh ftadswehih 301 figkiwgsda gwtlgymlnl tnmipaeqpl stplshstyv flmvlfslvl ftvaiiglli 361 fhkpsyfwkd mv
```

SEQ ID NO: 14 Mouse CD39 cDNA sequence

```
  1 atggaagata taaaggattc taaggtgaag agattttgct ccaaaaatat tctgatcatc 61 cttggtttca cctctatctt ggctgtgata gctttgattg ctgtgggact gacccagaac 121 aaacctttgc cagaaaatgt taagtatggg attgtgttgg atgcggggtc atctcacagc 181 aacctgtaca tctacaagtg gccggccgag aaggagaatg cacagggggt ggtgcagcag 241 ttagaggaat gccaagtgaa aggtcctaga atctgaaaat atgctcagaa aacagatgaa 301 atcggtgcgt acctggccga atggatgaaa ctgtccaccg aactgatacc aacatccaag 361 catcaccaga ctcctgtcta cctgggagcc acagcaggca tgcgcttgct tagaatggaa 421 agcgaacaat cggcagacga ggtcctggct gcagtgtcaa caagccttaa gagctacccc 481 tttgacttcc agggtgccaa gatcatcact ggacaagagg aaggtgccta tgggtggatt 541 actattaact atctgctggg cagattcact caggaacaga gttggctaag cctcatctca 601 gacagtcaga acaggaaac ctttggcgct ttggatctcg ggggagcctc cacagagatc 661 accttcgtgc cccaaaacag cactatagag tccccagaaa actctctgca attccgtctc 721 tatggcgagg actatactgt gtacacacac agcttcctgt gctatgggaa ggatcaggct 781 ctctggcaga aactggccaa ggacattcag gtttcaagtg gtggcgtcct taaggaccca 841 tgctttaacc caggatacga gaaggttgtg aatgtaagtg agctctatgg cactccctgc 901 accaaaagat cgaaaagaa gctaccattt gatcagtttc gaatccaggg cactggagac 961 tacgaacagt gccaccagag catccttgag ctcttcaaca cagccactg cccttactcc 1021 cagtgtgcct tcaatggcgt cttccttgcca cctctccatg gggttttggg ggcgttttct 1081 gctttctact ttgtgatgga ttttttaag aaggtggcga aaacagtgt catctctcag 1141 gagaaaatga ccgagataac aaaaaatttt tgctcaaaat cttgggaaga cacaaagaca 1201 tcttatcctt cagtaaagga gaagtacctg agtgagtact gcttctcggg cgcctacatc
```

TABLE 1-continued

```
1261 ctctctctcc tgcaaggcta aacttcaca gacagctcct gggaacagat tcattttatg 1321 ggcaagatca aagacagcaa cgcggggtgg actttgggct acatgctgaa cttgaccaac 1381 atgatcccag ctgaacagcc gttgtccccg cctctccctc actccaccta catcggcctc 1441 atggttctct tctccctgct cttggttgct gtggccatca caggcctgtt catctatagc 1501 aagccttcat atttctggaa ggaggcagta tag
```

SEQ ID NO: 15 Mouse CD39 amino acid sequence

```
  1 medikdskvk rfcsknilii lgftsilavi aliavgltqn kplpenvkyg ivldagssht 61 nlyiykwpae kendtgvvqq leecqvkgpg iskyaqktde igaylaecme lsteliptsk 121 hhqtpvylga tagmrllrme seqsadevla avstslksyp fdfqgakiit gqeegaygwi 181 tinyllgrft geqswlslis dsqkqetfga ldlggastqi tfvpqnstie spenslqfrl 241 ygedytvyth sflcygkdqa lwwklakdiq vssggvlkdp cfnpgyekvv nvselygtpc 301 tkrfekklpf dqfriqgtgd yeqchqsile lfnnshcpys qcafngvflp plhgsfgafs 361 afyfvmdffk kvaknsvisq ekmteitknf csksweetkt sypsvkekyl seycfsgayi 421 lsliqgynft dssweqihfm gkikdsnagw tlgyminltn mipaeqplsp plphstyigl 481 mvlfslllva vaitglfiys kpsyfwkeav
```

SEQ ID NO: 16 Rat CD39 cDNA sequence

```
  1 atggaagata taaaggattc taaggtgaag agattttgct ccaaaaatat tctgatcatc 61 cttggttcct cctctgtctt ggctgtgata gctttgattg ctgtgggact gacccacaac 121 aaaccattgc cagaaaatgt taagtatggg attgtgctgg atgccgggtc gtctcacacc 181 aacctgtaca tctacaagtg gccggctgag aaggagaatg atacaggagt ggtgcagctg 241 ttagaagaat gccaagtgaa aggtcccgga atctcaaaat acgctcagaa aacagatgaa 301 atagctgcat atctggctga atgcatgaaa atgtccactg agcggatacc agcgtccaaa 361 cagcaccaga cacccgtgta cctggagcc accgcgggca tgcgcttgct cagaatggaa 421 agcaagcaat cggcagacga agtcctggct gcagtgtcta ggagcctgaa gagctacccc 481 tttgacttcc agggcgccaa gatcatcact gggcaggagg aaggggccta tgggtggatt 541 actattaact atctgctggg cagattcact caggaacaga gttggctaaa cttcatctca 601 gacagccaga acaggcaac ctttggcgct ttggatcttg gcggcagttc tacacaagtc 661 accttcgtgc ccctaaatca gactctagag gccccagaaa cctccctgca gttccgtctc 721 tacggcacgg actacaccgt gtacacacac agcttcctgt gctatgggaa ggatcaggca 781 ctctggcaga aactggccca ggacattcag gtttcaagtg gtgggattct caaggacccg 841 tgcttttacc caggatataa gaaggttgtg aatgtaagcg aactctatgg cactccctgc 901 accaagagat tgagaagaa ctaccgtttt aatcagtttc aagttcaggg cactggagat 961 tacgaacagt gccaccagag catcctcaag ttcttcaaca cagccactg ccttactcc 1021 cagtgtgcct tcaacggtgt ctttttacca cctctccagg ggagttttgg ggcatttct 1081 gctttctact ttgtgatgga ctttttaag aagatggcga acgacagtgt ctcctctcag 1141 gagaaaatga ctgagataac aaaaaacttt tgctcaaagc cttgggagga ggtaaaggca 1201 tcttatccta cagtaaagga gaagtacctg agtgaatact gttctcgggg acctacatc 1261 ctgtctctcc ttctgcaagg ctataacttc acgggaacct cctgggacca gattcatttt 1321 atgggcaaga tcaaagacag caacgcaggg tggactttgg gctacatgct gaacttgacc 1381 aacatgatcc cagctgaaca gccattatcc ccgcctctcc ctcactccac ctacatcagc
```

TABLE 1-continued

```
1441 ctcatggttc tcttctccct ggtcttggtc gccatggtca tcacagggct gttcatcttt
1501 agcaagcctt cgtatttctg gaaagaggca gtatag
```

SEQ ID NO: 17 Rat CD39 amino acid sequence

```
  1 medikdskvk rfcsknilii lgfssvlavi aliavglthn kplpenvkyg ivldagssht
 61 nlyiykwpae kendtgvvqi leecqvkgpg iskyagktde iaaylaecmk msteripask
121 qhqtpvylga tagmrllrme skqsadevla avsrslksyp fdfqgakiit gq.egaygwi
181 tinyllgrft qeqswlnfis dsqkqatfga ldlggsstqv tfvplnqtle apetslqfrl
241 ygtdytvyth sflcygkdqa lwqklaqdiq vasggilkdp cfypgykkvv nvselygtpc
301 tkrfekklpf nqfqvqgtgd yeqchqsilk ffnnshcpys qcafngvflp plqgsfgafs
361 afytvmdffk kmandsvssq ekmteitknf cskpweevka syptvkekyl seycfsgtyi
421 lslllqgynf tgtswdqihd mgkikdsnag wtlgymlnlt nmipaeqpls pplphstyis
481 lmvlfslvlv amvitglfif skpsyfwkea v
```

SEQ ID NO: 18 Cow CD39 cDNA sequence

```
   1 atggaagata aagggaatc tgaactgaag gtattttgct ctaaaaacat actgagcata
  61 cttggtttct cctgcatcat cgctgtgata gcattgctcg ctttggggct gacccagaac
 121 aaagcactgc cagaaaatgt taagtttggg attgtgctgg atgcgggctc ctctcatacg
 181 agtttgtaca tctatagatg gccggcagag aaggagaatg cacgggggt ggtgactcag
 241 atagaagaat cgaacgttaa aggtcccgga atctcaggct ttgctaaaaa agtaaatgaa
 301 atcaatgttt atctgacggc atgcatggaa agagcccaga agtgattcc gtcaatccag
 361 cacatggaaa cacctgtgta cctgggagcc acggccggca tgcggttgct ccggatggaa
 421 aataaacaga tggcagacaa gatcctggct gcagttgcaa gcagcatcag cgagtacccc
 481 tttgacttcc aaggtgccag aatcatcagt ggccaggagg aaggtgccta ggctggatt
 541 actgtcaact atttgctggg caaattcact cagaaattga gttggtttaa cctgaagcca
 601 agcaaagacg acactcagga aacctatgga gctttagacc ttggggagc ctctacacaa
 661 atcacttttg tgcccaaaa tgaaacgacc gagtctccaa acaacaacct gtacttccgc
 721 ctctatggca agaactacag tgtatacaca cacagcttcc tgtgctatgg gaaggaccaa
 781 gcacttttgc agaaactggc cctgggactt cagggtacaa atggaatcat ccatgagcca
 841 tgctttcact caagatacat gaggaaaata aagatgagcg tcttaaacga aggtttctgt
 901 accaagagac atgagttgaa ttcttcattt tatccactcg ttgacattga aatccgtggc
 961 gctggaaact ccaacgatg tcggcaaagc atcattcaac tctttaacac cagttactgc
1021 ccttactcca gttgctcctt caatgggggtt ttcttgccgc cactccatgg gcagtttggg
1081 gcattttcag ctttttacta tgtgatgag ttttttaaacc ttacatcaga ggaatcagta
1141 tctgtggaac agttgactga aagttggaa gagttctgcg cacagcgttg ggaagaggtg
1201 cagaagaatt ttggtgaagt gaaggagaaa tacctgagtg aatactgctt ttctggcacc
1261 tacatcctgg ttctcctcct gaatggctac cattttacag ctgagtcctg aaaaaatatt
1321 cacttcatga acaaggtccg gagcaccgac gttgggtgga ctttgggcta catgctgaac
1381 ctgaccaaca agattccagc tgaagagcca atgtccccac ccctccccca ctccacctat
1441 gtcttcctca tggtcctctt ctccctgatc ctgctcgcag tgatcatcgt aggcatagtt
1501 gtcttttcaca agccttcgta tttctggaaa gacatggtat ag
```

TABLE 1-continued

SEQ ID NO: 19 Cow CD39 amino acid sequence

```
  1 medrreselk vfcsknilsi lgfsciiavi allalgltqn kalpenvkfg ivldagssht
 61 slyiyrwpae kendtgvvtq ieesnvkgpg isgfakkvne invyltacme raqkvipsiq
121 hmetpvylga tagmrllrme nkgmadkila avassiseyp fdfggariis gqeegaygwi
181 tvnyllgkft qklswfnlkp skddtqetyg aldlggastq itfvpqnett espnnnlyfr
241 lygknysvyt hsflcygkdq allgklalgl qgtngiihep cfhsrymrki kmsvlnegfc
301 tkrhelnssf yplvdieirg agnfqrcrqs iiqlfntsyc pysscsfngv flpplhgqfg
361 afsafyyvme flnltseesv sveqltekle efcaqrweev qknfgevkek ylseycfsgt
421 yilvlllngy hftaeswkni hfmnkvrstd vgwtlgymln ltnkipaeep mspplphsty
481 vflmvlfsli llaviivgiv vfhkpsyfwk dmv
```

SEQ ID NO: 20 Frog CD39 cDNA sequence

```
   1 atggacgaac caaaggctgc aaaacagaag aagacatggc acaaaaaagt cataatcttc
  61 ctaggagctc tgtttgtctt gggtgttatc tctttagtcg caattgcagt agtgcagaat
 121 aaacctcttc caaagaatat taagtatggc attgtgctgg acgctggttc gtcccatacc
 181 agtgtgtata tatatgaatg gccggcagaa aaggaaaatg acaccggtgt tgtacagcag
 241 ataaacgagt gcaaagttga aggcaacggt atatccagtt atggccacga gccactgaag
 301 gccggtcttt ctctacagaa gtgtatgaat aaagcccgtc aggtcattcc tgagaagcag
 361 caaagggaga caccagttta tttaggggcc acagcaggaa tgcgtttgct caggctaact
 421 aatgcaacaa tggctgagga gtcctgtctt cagtggaaaa tacgctgcg ttcctttccg
 481 tttgattttc agggtgccag aataattaca ggacaagaag aaggcgctta tggatggatc
 541 acaattaatt atctgcttgg aaactttatc caggattcag gttggttcaa atatatacca
 601 aatttcaaac ccactgaaac ttccggtaca ctggatcttg gaggtgcttc aacacagatc
 661 acctttgagt ccaaaagaga gattgaatcc caagaaaatt ccttgcactt ccgcctttat
 721 ggtaaatcct atgatatcta tacacacagc tttctctgct atggaaagga ccaagctctg
 781 cgccttcaga tagctaatag tataaaggat gcaacagatt ccatccttt ggatccttgc
 841 tttaactcag gatatagaag gaacgcaagc accaatgacc tctacagtag tccctgcata
 901 tctaaactga ggataccaac agcacccagc accttagata ttagaggcac tggcaattat
 961 cagctatgca agagaaatgt ccaggcaatc ttcaacagaa cacattgtac ttactcacat
1021 tgctctttta atggggtttt tcaaccaagt ttggatggca catttggggc attctcagca
1081 tattattttg ttatgaattt tttaaacctt accaatgagc aaatgtctct tgacaaagta
1141 aaagagacgg tagaaagaca ctgctccaga ccatgggacg aggtaaaaaa agactttcca
1201 aaaattaaag aaaaatacct gagtgaatac tgttttttctg aacatatat attaaatctt
1261 cttgaatatg gatacggctt tagctctgaa aactggaacg atatcagatt tttaggcaag
1321 atcaaagaca gtgatgcagg atggacactt ggttatatgc tgaacctgac caatatgatc
1381 cctgcagagc tgccttattc tcctccgctg tcccacgctg gttacactgg acttatggtc
1441 ttcttctcca ttttgttagt ctgcattatt ttgacttgct ggctgagttt ccggaaacca
1501 aaatgtctac acaagggcat catctag
```

SEQ ID NO: 21 Frog CD39 amnino acid sequence

```
  1 mdepkaakqk ktwhkkviif lgalfvagvi slvaiavvqn kplpknikyg ivldagssht
 61 svyiyewpae kendtgvvqq ineckvegng issygheplk aglslqkcmn karqvipekq
```

TABLE 1-continued

```
121 qretpvylga tagmrllrlt natmaeevls sventlrsfp fdfqgariit ggeegaygwi
181 tinyllgnfi qdsgwfkyip nfkptetsga ldlggastqi tfeskreies qenslhfrly
241 gksydiyths flcygkdqal rlqiansikd atdsilldpc fnsgyrrnas tndlyssspci
301 sklriptaps tldirgtgny qlckrnvqai fnrthctysh csfngvfqps ldgtfgafsa
361 yyfvmnflnl tneqmsldkv ketverhcsr pwdevkkdfp kikekylsey cfsgtyilnl
421 leygygfsse nwndirflgk ikdsdagwtl gymlnltnmi paelpysppl shagytglmv
481 ffsillvcii ltcwlsfrkp kclhkgii
```

SEQ ID NO: 22 Zebrafish CD39 cDNA sequence

```
   1 atggaagtaa aagtcaaaaa cccatggcac aggccggttg tcatctttct gatggctgtt
  61 gttgccgtgg ggattgtcat catggtatcc atttctgttg tccagcacaa gcctttaccc
 121 caaaagtaca gtatggaat agtcctggat gccggctcct ctcacacctc tgtgtttatc
 181 tataaatggc cagcagagaa agagaacaac acaggcatgg tacagcagca tcacacgtgc
 241 aatgttaaag gcaaaggcat ctccagttac ttcgataaac cacatggggc tggtgcatct
 301 ctggaggagt gcatgaagga ggccaaggag aaaatacctg ctcacagaca cagcgaaacc
 361 cctgtctacc tgggagccac ggctggcatg agactgctca agatggagga tgaaatggcc
 421 tcagaaaaag tgcttacctc cgttgcacat tcactgaaga cgtaccccct ctcctatcag
 481 ggagctcgta tcctttcagg ccaagaggag ggagcttttg gtggattac agtcaactac
 541 cttagtgaaa acttgagaaa gcccgcaggc actcttggag ctctggacct tggtggagcc
 601 tctactcaaa taaccttcgt acctcagcag attattgaat catctgacaa ttcgattgac
 661 ttcagactgt atggaaatga ttatcatcta tacacccaca gctttctctg ttatgggaag
 721 gaccaagctc tcaagcttgc tatggctgag aaattgcgct caacacctga caagacagat
 781 gccattttgt taagggatcc ttgttttcat cctggatata caccaccaa gacgcttgaa
 841 agtgtcaata caccatgtat aaaaccactg aaaatgccaa aggagcagtt ctcccatgtg
 901 gagcttggaa attggtctca gtgccaagaa tcaatcagaa aggtttttaa tactagccat
 961 tgtccttatt caggctgctc attcaatggt gttttccaac ctactgttga aggaaaattt
1021 ggggcttttt ctgctttctt ttttgtaatg gacttttaa atctgaaaaa cgattcattg
1081 gacaaaacaa agcagaggct ggcaatgtac tgctctaccc catggcaaaa gattgtacaa
1141 gatcacccaa agtaaaaga gaagtaccct tctgaatact gcttctcagc aacatacatt
1201 ctcactctcc tggaacatgg atacaattc acctcagaca actggaacga catcaagttt
1261 atcaagaaga ttggagacag tgatgcaggc tggactttag gttacatgct taacctgacc
1321 aacatgattc cggctgaaga tccagacaag ccactgatgc ctcatggagg atacgtcaca
1381 tttatgatcc tcttctcact tttgatactc gtcctcatca ttatggccta catttatttc
1441 cgtcgcttta ctaaaacagc ccagaaagac attatttag
```

SEQ ID NO: 23 Zebrafish CD39 amino acid sequence

```
   1 mevkvknpwh rpvviflmav vavgivimvs isvvqhkplp qkykygivld agsshtsvfi
  61 ykwpaekenn tgmvqqhhtc nvkgkgissy fdkphgagas leecmkeake kipahrhset
 121 pvylgatagm rllkmedema sekvltsvah slktypfsyq garilsqqee gafgwitvny
 181 lsenlrkpag tlgaldlgga stqitfvpqq iiessdnsid frlygndyhl ythsflcygk
 241 dqalklamae klrstpdktd aillrdpcfh pgynttktle svntpcmkpl kmpkeqfshv
 301 glgnwsqcqe sirkvfntsh cpysgcsfng vfqptvegkf gafsafffvm dflnlkndsl
```

TABLE 1-continued

```
361 dktkgrlamy cstpwqkivq dhpkvkekyl seycfsatyi ltllehgynf tsdnwndikf 421 ikkigdsdag wtlgymlnlt nmipaedpdk plmphggyvt fmilfsllil vliimayiyf 481 rrftktaqkd ii
```

\* Included in Table 1 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein. Such nucleic acid molecules can also be allelic variants, splice variants, derivative variants, substitution variants, deletion variants, insertion variants, fusion polypeptides, orthologs, interspecies homologs, and the like that modulate (e.g., decrease CD39 activity) or encode a CD39 with modulated (e.g., reduced) activity relative to wild-type CD39.

Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein. Such polypeptides can also be allelic variants, derivative variants, substitution variants, deletion variants, insertion variants, fusion polypeptides, orthologs, interspecies homologs, and the like that modulate (e.g., decrease CD39 activity) activity relative to wild-type CD39.

\* In addition, any CD39 modulator, direct CD39 binding protein, or CD39 downstream adenosine receptor pathway component such as CD73, described herein is also included in Table 1. The nucleic acid and polypeptide descriptions provided above in the asterisked sections of Table 1 also apply.

\* Included in Table 1 are biomarker metabolites, including, without limitation, AMP and adenosine. Moreover, Table 1 includes additional markers of T cell terminal exhaustion, such as one or more immune checkpoint regulators, such as PD-1, or other biomarkers of exhausted T cells, particularly terminally exhausted T cells, are included. For example, combinations, such as $CD39^{hi}$ and PD-1; $CD39^{hi}$, PD-1, and 2B4; $CD39^{hi}$, PD-1, 2B4 and LAG-3; $CD39^{hi}Eomes^{hi}Tbet^{lo}$; and the like, are contemplated. The $CD39^{hi}$ $CD8^+$ T cells express multiple inhibitory receptors, high levels of Eomes and low levels of T-bet, identify the most terminally exhausted T cells (i.e., irreversible exhaustion).

II. Subjects

In one embodiment, the subject for whom exhausted CD8+ T cells are identified or for whom diagnosis, prognosis, or treatment of a chronic immune disorder is made, is a mammal (e.g., mouse, rat, primate, non-human mammal, domestic animal such as dog, cat, cow, horse), and is preferably a human. Chronic immune disorders are described herein and the methods of the present invention can be applied to any one or more of such disorders.

In another embodiment of the methods of the invention, the subject has not undergone treatment, such as chemotherapy, radiation therapy, targeted therapy, and/or anti-immune checkpoint inhibitor therapy. In still another embodiment, the subject has undergone treatment, such as chemotherapy, radiation therapy, targeted therapy, and/or anti-immune checkpoint inhibitor therapy.

In certain embodiments, the subject has had surgery to remove chronic immune disordered tissue, such as infected, cancerous, or precancerous tissue. In other embodiments, such tissue has not been removed, e.g., the cancerous tissue may be located in an inoperable region of the body, such as in a tissue that is essential for life, or in a region where a surgical procedure would cause considerable risk of harm to the patient.

III. Sample Collection, Preparation and Separation

In some embodiments, biomarker amount and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be selected for treatment, evaluate a response to a therapy (e.g., anti-CD39 therapy with or without anti-immune checkpoint inhibitor therapy), and/or evaluate a response to a combination of therapies. A pre-determined biomarker amount and/or activity measurement(s) may be determined in populations of patients with or without a chronic immune disorder. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., expression and/or activity of biomarkers to that of wild type biomarkers and expression and/or activity of a biomarker of interest normalized to that of a housekeeping gene).

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.5 fold, about 1.0 fold, about 1.5 fold, about 2.0 fold, about 2.5 fold, about 3.0 fold, about 3.5 fold, about 4.0 fold, about 4.5 fold, or about 5.0 fold or greater. In some embodiments, the fold change is less than about 1, less than about 5, less than about 10, less than about 20, less than about 30, less than about 40, or less than about 50. In other embodiments, the fold change in biomarker amount and/or activity measurement(s) compared to a predetermined level is more than about 1, more than about 5, more than about 10, more than about 20, more than about 30, more than about 40, or more than about 50.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., bronchoalevolar lavage fluid, amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermeable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIFF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

IV. Biomarker Nucleic Acids and Polypeptides

One aspect of the invention pertains to the use of isolated nucleic acid molecules that correspond to biomarker nucleic acids that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual,* 2nd ed., Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

Moreover, a nucleic acid molecule of the invention can comprise only a portion of a nucleic acid sequence, wherein the full length nucleic acid sequence comprises a marker of the invention or which encodes a polypeptide corresponding to a marker of the invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the invention or to a nucleic acid molecule encoding a protein corresponding to a marker of the invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue as required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from the naturally-occurring proteins which correspond to the markers of the invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanin, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

The present invention also contemplates the use of nucleic acids for modulating the expression and/or activity of target biomolecules. Generally, such nucleic acids may be nucleic acids themselves or encode a polypeptide, a naturally-occurring binding partner of a target of interest, an antibody against a target of interest, a combination of antibodies against a target of interest and antibodies against other immune-related targets, an agonist or antagonist of a target of interest, a peptidomimetic of a target of interest, a peptidomimetic of a target of interest, a small RNA directed against or a mimic of a target of interest, and the like. Such modulators are well known in the art and include, for example, an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule such as a Piwi RNA, triplex oligonucleotide, ribozyme, coding sequence for a target of interest Such agents modulate the expression and/or activity of target biomolecules, which includes any decrease in expression or activity of the target biomolecule of at least about 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more as compared to the expression or activity of the target biomolecule which has not been targeted by a modulating agent.

In one embodiment, nucleic acids are useful for overexpressing and/or enhancing the activity of a nucleic acid or protein of interest. For example, the nucleic acid may encode a protein or other molecule the expression of which is desired in the host cell. Such protein-encoding nucleic acid sequences are not particularly limited and are selected based on the desired exogenous perturbation desired. Thus, the nucleic acid includes any gene that the skilled practitioner desires to have integrated and/or expressed. For example, exogenous expression of proteins related to autoimmune, allergic, vaccination, immunotolerance, cancer immunotherapy, immune exhaustion, immunological memory, or immunological epitope responses may be used. The nucleic acid can encode a protein or be a nucleic acid that serves as a marker to identify cells of interest or transduced cells. The nucleic acid may encode a protein that modifies a physical characteristic of the transduced cell, such as a protein that modifies size, growth, or eventual tissue composition. In another example, the nucleic acid may encode a protein of commercial value that may be harvested. Generally, the nucleic acid is operatively linked to other sequences that are useful for obtaining the desired expression of the nucleic acid, such as transcriptional regulatory sequences like inducible promoters, as described further below.

In one embodiment, the nucleic acid is engineered to express the CRISPR-Cas system for precise editing of genomic nucleic acids (e.g., for creating null mutations). In such embodiments, the CRISPR guide RNA and/or the Cas enzyme may be expressed. For example, a vector containing only the guide RNA can be administered to an animal or cells transgenic for the Cas9 enzyme. Similar strategies may be used (e.g., designer zinc finger, transcription activator-like effectors (TALEs) or homing meganucleases). Such systems are well known in the art (see, for example, U.S. Pat. No. 8,697,359; Sander and Joung (2014) *Nat. Biotech.* 32:347-355; Hale et al. (2009) *Cell* 139:945-956; Karginov and Hannon (2010) *Mol. Cell* 37:7; U.S. Pat. Publ. 2014/0087426 and 2012/0178169; Boch et al. (2011) *Nat. Biotech.* 29:135-136; Boch et al. (2009) *Science* 326:1509-1512; Moscou and Bogdanove (2009) *Science* 326:1501; Weber et al. (2011) *PLoS One* 6:e19722; Li et al. (2011) *Nucl. Acids Res.* 39:6315-6325; Zhang et al. (2011) *Nat. Biotech.* 29:149-153; Miller et al. (2011) *Nat. Biotech.* 29:143-148; Lin et al. (2014) *Nucl. Acids Re.* 42:e47).

In another embodiment, the nucleic acid is useful for inhibiting the expression and/or activity of a nucleic acid or protein of interest. For example, target biomolecule expression and/or activity, such as an RNA coding region, may be reduced or inhibited using inhibitory RNAs. An "RNA coding region" is a nucleic acid that may serve as a template for the synthesis of an RNA molecule, such as an siRNA. "RNA interference (RNAi)" is an evolutionally conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see, for example, Coburn and Cullen (2002) *J. Virol.* 76:9225), thereby inhibiting expression of the target biomarker nucleic acid. In one embodiment, the RNA coding region is a DNA sequence. The ability to down-regulate a target gene has many therapeutic and research applications, including identifying the biological functions of particular genes. Moreover, such inhibition may be achieved in screening assays that take advantage of pooling techniques, whereby groups of 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more, or any number or range in between, of RNA inhibitory agents, either co-expressed from the same vector or more than one vector, are transduced into cells of interest. Suitable inhibitory RNAs include, but are not limited to siRNAs, shRNAs, miRNAs, Piwis, dicer-substrate 27-mer duplexes, single-stranded interfering RNA, and the like. In particular, the combination of RNA inhibitory technology and lentiviruses as a tool for a gene specific knock-down in animal models is well known in the art (see, for example, U.S. Pat. Publ. 2005/0251872; EP Pat. Publ. 2166107; PCT Pubis. WO 2004/022722 and 2007/109131; Tiscomia et al. (2003) *Proc. Natl. Acad. Sci. U.S.A.* 100:1844-1848; Rubinson et al. (2003) *Nat. Genet.* 33:401-406; and Dann er al. (2006) *Proc. Natl. Acad. Sci. U.S.A.* 103:11246-11251).

siRNAs typically refer to a double-stranded interfering RNA unless otherwise noted. In various embodiments, suitable siRNA molecules include double-stranded ribonucleic acid molecules comprising two nucleotide strands, each strand having about 19 to about 28 nucleotides (i.e. about 19, 20, 21, 22, 23, 24, 25, 26, 27, or 28 nucleotides). Thus, the phrase "interfering RNA having a length of 19 to 49 nucleotides" when referring to a double-stranded interfering RNA means that the antisense and sense strands independently have a length of about 19 to about 49 nucleotides, including interfering RNA molecules where the sense and antisense strands are connected by a linker molecule.

In addition to siRNA molecules, other interfering RNA molecules and RNA-like molecules may be used. Examples of other interfering RNA molecules that may to inhibit target biomolecules include, but are not limited to, short hairpin RNAs (shRNAs), single-stranded siRNAs, microRNAs (miRNAs), piwiRNA, dicer-substrate 27-mer duplexes, and variants thereof containing one or more chemically modified nucleotides, one or more non-nucleotides, one or more deoxyribonucleotides, and/or one or more non-phosphodiester linkages. Typically, all RNA or RNA-like molecules that may interact with transcripts RISC complexes and participate in RISC-related changes in gene expression may be referred to as "interfering RNAs" or "interfering RNA molecules."

Suitable interfering RNAs may readily be produced based on the well-known nucleotide sequences of target biomolecules. In various embodiments interfering RNAs that inhibit target biomolecules may comprise partially purified RNA, substantially pure RNA, synthetic RNA, recombinantly produced RNA, as well as altered RNA that differs from naturally-occurring RNA by the addition, deletion, substitution, and/or alteration of one or more nucleotides. Such alterations may include, for example, addition of non-nucleotide material, such as to the end(s) of the interfering RNAs or to one or more internal nucleotides of the interfering RNAs, including modifications that make the interfering RNAs resistant to nuclease digestion. Such alterations result in sequences that are generally at least about 80%, 81%, 82%, 83%, 84%, 85%, 86%, 87%, 88%, 89%, 90%, 91%, 92%, 93%, 94%, 95%, 96%, 97%, 98%, 99%, 99.5%, or more, or 100% identical to the sequence of the target biomolecule. When the gene to be down regulated is in a family of highly conserved genes, the sequence of the duplex region may be chosen with the aid of sequence comparison to target only the desired gene. On the other hand, if there is sufficient identity among a family of homologous genes within an organism, a duplex region may be designed that would down regulate a plurality of genes simultaneously.

In various embodiments one or both strands of the interfering RNAs may comprise a 3' overhang. As used herein, a "3' overhang" refers to at least one unpaired nucleotide extending from the 3'-end of an RNA strand. Thus in one embodiment, the interfering RNAs comprises at least one 3' overhang of from 1 to about 6 nucleotides (which includes ribonucleotides or deoxynucleotides) in length, from 1 to about 5 nucleotides in length, from 1 to about 4 nucleotides in length, or about 2 to about 4 nucleotides in length. In an illustrative embodiment in which both strands of the interfering RNAs molecule comprise a 3' overhang, wherein the length of the overhangs may be the same or different for each strand. In certain embodiments the 3' overhang is present on both strands of the interfering RNAs and is one, two, or three nucleotides in length. For example, each strand of the interfering RNAs may comprise 3' overhangs of dithymidylic acid ("TT") or diuridylic acid ("uu").

In order to enhance the stability of the interfering RNAs, the 3' overhangs may be also stabilized against degradation. In one embodiment, the overhangs are stabilized by including purine nucleotides, such as adenosine or guanosine nucleotides. In certain embodiments, substitution of pyrimidine nucleotides by modified analogues, e.g., substitution of uridine nucleotides in the 3' overhangs with 2'-deoxythymidine, is tolerated and does not affect the efficiency of RNA interference degradation. In particular, it is believed the absence of a 2' hydroxyl in the 2'-deoxythymidine may significantly enhance the nuclease resistance of the 3' overhang.

Interfering RNAs may be expressed from a vector described herein either as two separate, complementary RNA molecules, or as a single RNA molecule with two complementary regions. Selection of vectors suitable for expressing interfering RNAs, methods for inserting nucleic acid sequences for expressing the interfering RNAs into the vector, and methods of delivering the recombinant plasmid to the cells of interest are well known in the art (Tuschl (2002) *Nat. Biotechnol.* 20: 446-448; Brummelkamp et al. (2002) *Science* 296:550 553; Miyagishi et al. (2002) *Nat. Biotechnol.* 20:497-500; Paddison et al. (2002) *Genes Dev.* 16:948-958; Lee et al. (2002) *Nat. Biotechnol.* 20:500-505; and Paul et al. (2002) *Nat. Biotechnol.* 20:505-508).

In certain embodiments, the interfering RNAs may be delivered as a small hairpin RNA or short hairpin RNA (shRNA) (see, for example, U.S. Pat. Nos. 8,697,359 and 8,642,569). shRNA is a sequence of RNA that makes a tight hairpin turn that may be used to silence gene expression via RNA interference. In typical embodiments, shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA that is bound to it.

In certain embodiments, the sense sequence of the shRNA will be from about 19 to about 30, more nucleotides (e.g. about 19, 20, 21, 22, 23, 24, 25, 26, 27, 28, 29, or 30 nucleotides) in length, more typically from about 19 to about 22 nucleotides in length, the antisense sequence will be from about 19 to about 30, more typically from 19 to about 22 nucleotides (e.g. about 19, 20, 21 or 22 nucleotides), in length, and the loop region will be from about 3 to about 19 nucleotides (e.g., about 3, 4, 5, 6, 7, 8, 9, 10, 11, 12, 13, 14, 15, 16, 17, 18, and 19 nucleotides) in length. In some embodiments, the sense and antisense sequences are the same length, i.e. the shRNA will form a symmetrical hairpin, but this is not necessarily the case. In some cases, the sense or antisense strand may be shorter than its complementary strand, and an asymmetric hairpin is formed. Further, while in some instances the base pairing between the sense and antisense sequences is exact, this also need not be the case. Thus, some mismatch between the sequences may be tolerated, or even desired, e.g. to decrease the strength of the hydrogen bonding between the two strands. However, in one illustrative embodiment, the sense and antisense sequences are the same length, and the base pairing between the two is exact and does not contain any mismatches. The shRNA molecule may also comprise a 5'-terminal phosphate group that may be chemically modified. In addition, the loop portion of the shRNA molecule may comprise, for example, nucleotides, non-nucleotides, linker molecules, conjugate molecules, etc.

In certain embodiments, the PIWI RNA pathway is used to provide inhibition of target biomolecules. Piwi-interacting RNAs (piRNAs) were identified through association with Piwi proteins in mammalian testes (Aravin et al. (2006); Girard et al. (2006); Grivna et al. (2006); Lau et al. (2006). piRNAs and methods of making and using same to target and degrade nucleic acids are well known in the art (see, for example, U.S. Pat. Publ. 2011-0207625). These RNAs range from 26-30 nucleotides in length and are produced from discrete loci. Generally, genomic regions spanning 50-100 kB in length give rise to abundant piRNAs with profound strand asymmetry. Although the piRNAs themselves are not conserved, even between closely related species, the positions of piRNA loci in related genomes are conserved, with virtually all major piRNA-producing loci having syntenic counterparts in mice, rats and humans (Girard et al. (2006)). The loci and consequently the piRNAs themselves are relatively depleted of repeat and transposon sequences, with only 17% of human piRNAs corresponding to known repetitive elements as compared to a nearly 50% repeat content for the genome as a whole. In certain embodiments, methods are provided for inhibiting such targets in a cell, comprising administering an effective amount of a siRNA/shRNA/piwiRNA to the cell, such that target mRNA is degraded.

In some embodiments, the present invention further contemplates the use of anti-biomarker antisense nucleic acid molecules, i.e., molecules which are complementary to a sense nucleic acid of the invention, e.g., complementary to the coding strand of a double-stranded eDNA molecule corresponding to a marker of the invention or complementary to an mRNA sequence corresponding to a marker of the invention. Accordingly, an antisense nucleic acid molecule of the invention can hydrogen bond to (i.e. anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, qucosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a polypeptide corresponding to a selected marker of the invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pot 11 or pol 111 promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, Nucleic Acids Rev. 15:6625-6641). The antisense nucleic acid molecule can also comprise a 2'-o-methylribonucleotide (Inoue et al., 1987, Nucleic Acids Res. 15:6131-6148) or a chimeric RNA-DNA analogue (Inoue ei al., 1987, FEBS Lett. 215:327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, Nature 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the invention can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the invention can be used to select a catalytic RNA having a specific ribonuclease activity from a pool of RNA molecules (see, e.g., Bartcel and Szostak, 1993, Science 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) Anticancer Drug Des. 6(6):569-84; Helene (1992) Ann. N. Y. Acad. Sci. 660:27-36; and Maher (1992) Bioassays 14(12):807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, Bioorganic & Medicinal Chemistry 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) Proc. Natl. Acad. Sc. USA 93:14670-675.

PNAs can be used in therapeutic and diagnostic applications. For example, PNAs can be used as antisense or antigen agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., SI nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the invention are produced by recombinant DNA techniques. Alternative to recombinant expression, a polypeptide corresponding to a marker of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins corresponding to a biomarker protein. As used herein, a "chimeric protein" or "fusion protein" comprises all or part (preferably a biologically active part) of a polypeptide corresponding to a marker of the invention operably linked to a heterologous polypeptide (i.e., a polypeptide other than the polypeptide corresponding to the marker). Within the fusion protein, the term "operably linked" is intended to indicate that the polypeptide of the invention and the heterologous polypeptide are fused in-frame to each other. The heterologous polypeptide can be fused to the amino-terminus or the carboxyl-terminus of the polypeptide of the invention.

One useful fusion protein is a GST fusion protein in which a polypeptide corresponding to a marker of the invention is fused to the carboxyl terminus of GST sequences. Such fusion proteins can facilitate the purification of a recombinant polypeptide of the invention.

In another embodiment, the fusion protein contains a heterologous signal sequence, immunoglobulin fusion protein, toxin, or other useful protein sequence. Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel c al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198: 1056; Ike et al., 1983 *Nucleic Acid Res.* 1:477).

In addition, libraries of fragments of the coding sequence of a polypeptide corresponding to a marker of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, *Proc. Natl. Acad. Sci. USA* 89:7811-7815; Delgrave et al., 1993, *Protein Engineering* 6(3):327-331).

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors for use in the invention can be designed for expression of a polypeptide corresponding to a marker of the invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89. In *Gene Expression Technology: Methods in Enzymology* vol. 185, Academic Press, San Diego, Calif., 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in E. coli is to express the protein in a host bacterium with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in E. coli (Wada et al., 1992, *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast S. cerevisiae include pYcpSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Viroogy* 170:31-39).

In yet another embodiment, a nucleic acid of the invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, adenovirus 2, cytomegalovirus and Simian Virus 40. For other suitable expression systems for both prokaryotic and eukaryotic cells see chapters 16 and 17 of Sambrook et al, supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byme and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., E. coli) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like. In addition, analysis of biomarker activity can be performed according to a determination of metabolites resulting from biomarker enzymatic function.

a. Methods for Detection of Copy Number

Methods of evaluating the copy number of a biomarker nucleic acid are well known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. A copy number of at least 3, 4, 5, 6, 7, 8, 9, or 10 is predictive of poorer outcome of anti-immune checkpoint inhibitor treatment.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well known in the art (see, e.g., U.S. Pat. Nos. 6,335,167; 6,197,501; 5,830.645; and 5,665,549 and Albertson (1984) *EMBO J*. 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the an. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger. et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Rev* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner ei al. (1997) *Science* 278: 1481; Emmert-Buck et al. (1996) Science 274:998; Fend et al. (1999) Am. J. Path. 154: 61 and Murakami et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysacecharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies. Grand Island, N.Y.).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see. e.g., Wang ei al. (1989) PNAS 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)), and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section or a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well known in the art (see. e.g., U.S. Pat. Nos. 6,618,679; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to an anti-immune checkpoint inhibitor therapy. Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}$I or $^{35}$S, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker proteinantibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldchyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I), carbon ($^{14}$C), sulphur ($^{35}$S), tritium ($^{3}$H), indium ($^{112}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$M, $10^{-7}$M, $10^{-8}$, $10^{-9}$M, $10^{-10}$M, $10^{-11}$M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other protcases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab) 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397, Boss et al., European Patent No. 0,120,694 B1; Neubcrger, M. S. et. al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et. al., EP 0519596 A1. See also, Newman, R. et. al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify biomarkers.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080, and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) Proc. Natl. Acad. Sci. USA. 74:560 or Sanger (1977) Proc. Natl. Acad Sci. USA 74:5463. It is also contemplated that any of a variety of automated sequencing procedures can be utilized when performing the diagnostic assays (Naeve (1995) Biotechniques 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in a biomarker gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) Proc Vail. Acad. Sci USA 86:2766; see also Cotton (1993) Mutat. Rev. 285:125-144 and Hayashi (1992) Genet. Anal. Tech. Appl. 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trend Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163; Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

e. Methods for Detection of Biomarker Metabolite Expression

Biomarker metabolites, such as those shown in Table 1 or the Examples, can be detected in numerous ways according to well-known techniques. For example, such metabolites, as well as biomarker proteins, can be detected using mass spectrometry methods, such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), reverse phase high performance liquid chromatography (rpHPLC), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference.

Mass spectrometry methods are well known in the art and have been used to quantify and/or identify biomolecules, such as chemical metabolites and proteins (see, e.g., Li et al. (2000)) Tibtech 18, 151-160; Rowley at al. (2000) Methods 20, 383-397; Kuster and Mann (1998) Curr. Opin. Structural Biol. 8, 393-400)). Further, mass spectrometric techniques have been developed that permit at least partial de novo sequencing of isolated proteins (see, e.g., Chait et al. (1993) Science 262, 89-92; Keough et al. (1999) Proc. Natl. Acad. Sci. USA. 96, 7131-7136; reviewed in Bergman (2000) EXS 88, 133-44).

In certain embodiments, a gas phase ion spectrophotometer is used. In other embodiments, laser-desorption/ionization mass spectrometry is used to analyze the sample. Modem laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. However, MALDI has limitations as an analytical tool. It does not provide means for fractionating the sample, and the matrix material can interfere with detection, especially for low molecular weight analytes (see, e.g., Hellenkamp et al., U.S. Pat. No. 5,118,937 and Beavis and Chait. U.S. Pat. No. 5,045,694).

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied (see, e.g., Hutchens and Yip. U.S. Pat. No. 5,719,060 and Hutchens and Yip, WO 98/59361). The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition, Skoog, Saunders College Publishing, Philadelphia, 1985: and Kirk-Othmer Encyclopedia of Chemical Technology, 4.sup.th ed. Vol. 15 (John Wiley & Sons, New York 1995), pp. 1071-1094.

Detection of the presence of a marker or other substances will typically involve detection of signal intensity. For example, in certain embodiments, the signal strength of peak values from spectra of a first sample and a second sample can be compared (e.g., visually or by computer analysis) to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

Any person skilled in the art understands, any of the components of a mass spectrometer (e.g., desorption source, mass analyzer, detect, etc.) and varied sample preparations can be combined with other suitable components or preparations described herein, or to those known in the art. For example, in some embodiments a control sample may contain heavy atoms (e.g. $^{13}C$) thereby permitting the test sample to be mixed with the known control sample in the same mass spectrometry run. In some embodiments, internal controls, such as phenylalanine-d8 and/or valine-d8 can be run with the samples.

In one embodiment, a laser desorption time-of-flight (TOF) mass spectrometer is used. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio.

In some embodiments the relative amounts of one or more biomolecules present in a first or second sample is determined, in part, by executing an algorithm with a programmable digital computer. The algorithm identifies at least one peak value in the first mass spectrum and the second mass spectrum. The algorithm then compares the signal strength of the peak value of the first mass spectrum to the signal strength of the peak value of the second mass spectrum of the mass spectrum. The relative signal strengths are an indication of the amount of the biomolecule that is present in the first and second samples. A standard containing a known amount of a biomolecule can be analyzed as the second sample to provide better quantification of the amount of the biomolecule present in the first sample. In certain embodiments, the identity of the biomolecules in the first and second sample can also be determined.

Biomarker expression and activity can also be assessed according to functional assays described further below.

3. Anti-Chronic Immune Disorder Therapies and Combination Therapies

Anti-chronic immune disorder therapy according to the present invention is based on the use of anti-CD39 therapy with or without anti-immune checkpoint inhibitor therapy (e.g., anti-PD-1, anti-PD-L1, anti-PD-L2, and anti-CTLA4 therapies). In addition, other additional therapy can be combined, such as anti-infection therapy or anti-cancer therapy. Other combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with an anti-CD39 therapy with or without anti-immune checkpoint inhibitor therapy. In another embodiment, such therapies can be avoided once a subject is indicated as not being a likely responder (e.g., not having exhausted CD8+ T cells) and an alternative treatment regimen, such as targeted and/or untargeted anti-viral or anti-cancer therapies can be administered.

Useful agents for use in treating chronic immune disorders arising from infections are well known in the art. For example, antiviral agents (e.g., vidarabine, acyclovir, gancyclovir, valgancyclovir, nucleoside-analog reverse transcriptase inhibitor (NRTI) such as AZT (Zidovudine), ddl (Didanosine), ddC (Zalcitabine), d4T (Stavudine), or 3TC (Lainivudine), non-nucleoside reverse transcriptase inhibitor (NNRTI) such as nevirapine or delavirdine, protease inhibitors, such as saquinavir, ritonavir, indinavir, or nelfinavir, ribavirin, and interferon), an antibacterial compound, an antifungal compound, an antiparasitic compound, an anti-inflammatory compound, anti-neoplastic compounds or an analgesic, are contemplated.

The term "targeted therapy" refers to administration of agents that selectively interact with a chosen biomolecule to thereby treat cancer.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" reefers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, carboplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, pemetrcxed, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, e al. (2005) Nature 434:913-917; Farmer H, et al. (2005) *Nature* 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (1-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A: and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs: antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and at can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical-known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter-less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with anti-immune checkpoint inhibitor therapies may vary according to the particular anti-immune checkpoint inhibitor agent or combination thereof (e.g., Jak kinase stimulating agents in combination with inhibitors of PD-1, PD-L1, PD-L2, CTLA-4, and the like). An appropriate treatment time for a particular cancer therapeutic agent will be appreciated by the skilled artisan. The invention contemplates the continued assessment of optimal treatment schedules for each cancer therapeutic agent, where the phenotype of the cancer of the subject as determined by the methods of the invention is a factor in determining optimal treatment doses and schedules.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Feigner, et al., Ann NY Acad Sci 126-139, 1995). Formulation of DNA, e.g. with various lipid or liposome materials, may then be effected using known methods and materials and delivered to the recipient mammal. See, e.g., Canonico et al., Am J Respir Cell Mol Biol 10:24-29, 1994; Tsan et al., Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus). HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the $\alpha$- and $\beta$-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468. WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993: Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) *Science*. 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

4. Clinical Efficacy

Clinical efficacy can be measured by any method known in the art. For example, the response to a therapy, such as anti-CD39 therapy with or without anti-immune checkpoint inhibitor therapies, relates to any response of the chronic immune disorder, e.g., a tumor, to the therapy, preferably to a change in tumor mass and/or volume after initiation of neoadjuvant or adjuvant chemotherapy.

For example, clinical efficacy for treating chronic immune disorders caused by infectious agents can involve determining reductions in the infectious microbial (e.g., viral, bacterial, fungal, mycoplasm, or parasitic) load in the subject relative to such load in an untreated control. As compared with an equivalent untreated control, such reduction or degree of prevention is at least 5%, 10%, 20%, 40%, 50%, 60%, 80%, 90%, 95%, or 100% as measured by any standard technique. The infectious agent can be completely cleared as detected by any standard method known in the art. Diagnosis and monitoring may involve, for example, detecting the level of microbial load in a biological sample (e.g., tissue biopsy, blood test, or urine test), detecting the level of a biomarker surrogate marker of the infectious agent in a biological sample, detecting symptoms associated with the chronic immune disorder, or detecting immune cells involved in the immune response typical of the chronic immune disorder (e.g., detection of antigen-specific, exhausted CD8+ T cells).

Chronic immune disorders associated with cancers can also be assessed. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) Breast (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular anti-immune checkpoint inhibitor therapeutic regimen is at least 25%, 30%, 35%, 40%, 45%, 50%, 55%, 60%, 65%, 70%, 75%, 80%, 85%, or more.

Additional criteria for evaluating the response to anti-CD39 therapy with or without anti-immune checkpoint inhibitor therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-CD39 therapy with or without anti-immune checkpoint inhibitor therapeutic regimen can be administered to a population of subjects and the outcome can be correlated to biomarker measurements that were determined prior to administration of the therapy or any therapy. The outcome measurement may be pathologic response to therapy given in the neoadjuvant setting. Alternatively, outcome measures, such as overall survival and disease-free survival can be monitored over a period of time for subjects following anti-immune checkpoint inhibitor therapy for whom biomarker measurement values are known. In certain embodiments, the same doses of therapeutic agents are administered to each subject. In related embodiments, the doses administered are standard doses known in the art for such agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an CD39 therapy with or without anti-immune checkpoint inhibitor therapy can be determined using methods such as those described in the Examples section.

5. Further Uses and Methods of the Present Invention

The compositions described herein can be used in a variety of diagnostic, prognostic, and therapeutic applications.

a. Screening Methods

One aspect of the present invention relates to screening assays, including non-cell based assays. In one embodiment, the assays provide a method for identifying exhausted CD8+ T cells. In another embodiment, the assays provide a method for determining whether a chronic immune disorder is likely to respond to anti-CD39 therapy with or without anti-immune checkpoint inhibitor therapy. In still another embodiment, the assays provide a method for determining whether an agent can reduce exhaustion in exhausted CD8+ T cells with or without anti-immune checkpoint inhibitor therapy. For any method described herein, the presence, copy number, level of expression, and/or level of activity of CD39 or other biomarker described herein can be assessed. In addition, the presence, copy number, level of expression, and/or level of activity of one or more biomarkers of exhausted T cells can be analyzed (e.g., an immune checkpoint inhibitor).

In one embodiment, the invention relates to assays for screening test agents which bind to, or modulate the biological activity of, at least one biomarker listed in Table 1. In one embodiment, a method for identifying such an agent entails determining the ability of the agent to modulate, e.g. inhibit, the at least one biomarker listed in Table 1.

In one embodiment, an assay is a cell-free or cell-based assay, comprising contacting at least one biomarker listed in Table 1, with a test agent, and determining the ability of the test agent to modulate (e.g. inhibit) the enzymatic activity of the biomarker, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}I$, $^{35}S$, $^{14}C$, or $^{3}H$, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies of the present invention can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and a substrate or a biomarker metabolite and its natural binding partner can be accomplished by determining the ability of the test agent to modulate the activity of a polypeptide or other product that functions downstream or upstream of its position within the pathway (e.g., feedback loops).

The present invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

In some embodiments, the assay is based on the capability of a test agent to modulate the ability of CD39 to bind a substrate or hydrolyzes the substrate. The term "substrate" refers to adenosine triphosphate (ATP) or an analog that can be bound by CD39 and hydrolyzed by CD39. A test agent is contacted or reacted with a suitable reaction mixture comprising CD39 polypeptide and a substrate. The reaction is carried out under conditions and for a time sufficient to allow any substrate hydrolysis to be detected. Subsequently, the presence or absence of hydrolyzed substrate in the substrate may be determined by standard methods known in the art as described above for autophophorylation assays. Further, the assay may comprise a step, wherein the level of substrate hydrolysis in the presence of a test substance is compared to that in the absence of said test substance. If the level of substrate hydrolysis is decreased as compared to the control (no test substance present), the test substance is an inhibitor of CD39 enzymatic activity. Performing the assay using CD39 expressed on a biological membrane, such as on a cell, can be used to confirm that the CD39 enzymatic activity is also ectonucleotidase activity.

CD39 modulators can also be screened, identified, and characterized by employing calorimetric methods such as differential scanning calorimetry or fluorimetry, or isothermal titration calorimetry or fluorimetry, where the binding of the modulator is analysed with respect to a change in the kinetic properties of CD39. Such methods are known to a person skilled in the art and include measurement of surface plasmon resonance or spectrocopical methods including fluorescence, UV/visible light, CD, NMR based methods and microscopy methods including atom force microscopy, as well as crystallography.

In cell-based assays, cells can be used that express the specified biomarker of interest on the cell surface. Furthermore, infectious agent load, replication, cytokine production, colony formation, cellular mobility, proliferation, or other cellular functions can be used as a readout for the assays. In one embodiment, the expression of at least one immune checkpoint inhibitor is analyzed (e.g., PD-1 and/or LAG-3 expression).

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the amount and/or activity level of a biomarker listed in Table 1 in the context of a biological sample (e.g., blood, serum, cells, or tissue) to thereby identify the presence of exhausted CD8+ T cells and/or the status of an individual afflicted with a chronic immune disorder. Such assays can be used for prognostic or predictive purpose to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers listed in Table 1.

Another aspect of the present invention pertains to monitoring the influence of agents (e.g., drugs, compounds, and small nucleic acid-based molecules) on the expression or activity of a biomarker listed in Table 1. These and other agents are described in further detail in the following sections.

The skilled artisan will also appreciated that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the present invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample contains exhausted CD8+ T cells and/or is associated with a chronic immune disorder. In some embodiments, the present invention is useful for classifying such a sample using a statistical algorithm and/or empirical data (e.g., the amount or activity of a biomarker listed in Table 1).

An exemplary method involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely anti-immune checkpoint inhibitor therapy responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a chronic immune disorder or exhausted T CD8+ T cells), a biological sample from the subject during remission, or a biological sample from the subject during treatment for the chronic immune disorder.

d. Prognostic Assays

The diagnostic methods described herein can furthermore be utilized to identify subjects having or at risk of developing a chronic immune disorder or for identifying the subjects having a chronic immune disorder who will benefit from anti-CD39 therapy with or without anti-immune checkpoint inhibitor therapy. The assays described herein, such as the preceding diagnostic assays or the following assays, can be utilized to identify a subject having or at risk of developing a disorder associated with a misregulation of the amount or activity of at least one biomarker described in Table 1, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

The compositions described herein (including dual binding antibodies and derivatives and conjugates thereof) can be used in a variety of in vitro and in vivo therapeutic applications using the formulations and/or combinations described herein. In one embodiment, anti-CD39 inhibitor is used. In another embodiment, the anti-CD39 inhibitor is used in combination with one or more additional anti-immune disorder agents. In still another embodiment, at least one of the one or more additional anti-immune disorder agents is an anti-immune checkpoint inhibitor. For example, antibodies that block the interaction between PD-L1, PD-L2, and/or CTLA-4 and their receptors (e.g., PD-L1 binding to PD-1, PD-L2 binding to PD-1, and the like) can be used as anti-immune checkpoint inhibitors.

6. Pharmaceutical Compositions

In another aspect, the present invention provides pharmaceutically acceptable compositions which comprise a therapeutically-effective amount of an agent that modulates biomarker expression and/or activity (e.g., decreases CD39 activity and/or decreases the activity of CD39 activators), one or more anti-immune checkpoint inhibitors, or a combination thereof, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates biomarker expression and/or activity, or expression and/or activity of the complex, or composition comprising an agent that modulates biomarker expression and/or activity, or expression and/or activity of the complex, which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water, (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates biomarker expression and/or activity, or expression and/or activity of the complex encompassed by the invention. These salts can be prepared in situ during the final isolation and purification of the agents, or by separately reacting a purified agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates biomarker expression and/or activity, or expression and/or activity of the complex. These salts can likewise be prepared in situ during the final isolation and purification of the agents, or by separately reacting the purified agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates biomarker expression and/or activity, with the carrier and, optionally, one or more accessory ingredients. In general, the formulations are prepared by uniformly and intimately bringing into association a agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release prolific, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions, which are compatible with body tissue.

When the agents of the present invention are administered as pharmaceuticals, to humans and animals, they can be given per sc or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g. control biological samples or metabolite standards). A kit may additionally include buffers and other reagents recognized for use in a method of the disclosed invention. Non-limiting examples include agents to reduce non-specific binding, such as a carrier protein or a detergent.

Other embodiments of the present invention are described in the following Examples. The present invention is further illustrated by the following examples which should not be construed as further limiting.

EXAMPLES

Example 1: Materials and Methods for Examples 2-8 a. Human Subjects

Healthy human donors were recruited at the Kraft family Blood Donor Center, Dana-Farber Cancer Institute (DFCI) with written informed consent following approval by Partners Institutional Review Board. All human subjects with HCV infection were recruited at the Gastrointestinal Unit and the Department of Surgery of the Massachusetts General Hospital (Boston, Mass.) with written consent in accordance with Institutional Review Board approval from the Partners HealthCare. HCV chronics (n=27) were defined by positive anti-HCV antibody and detectable viral load. HCV resolvers (n=14) were defined by positive anti-HCV antibody but an undetectable viral load for at least 6 months. All HCV patients were treatment naive and obtained between 5.9 and 237.3 weeks post infection. HCV RNA levels were determined using the VERSANT HCV RNA 3.0 (bDNA 3.0) assay (Bayer Diagnostics).

All HIV infected cohorts were recruited after written informed consent from the Ragon Institute at the Massachusetts General Hospital (Boston, USA) and the Peter Medawar Building for Pathogen Research (Oxford, UK) where ethics approval was given by the Oxford Research Committee. HIV controllers included elite controllers (n=5) defined as having HIV RNA below the level of detection (<75 viral copies per ml); viremic controllers (n=7) with HIV RNA levels <2,000 viral copies per ml. HIV chronic progressors (n=28) were defined as having >2,000 viral copies per ml. All subjects were off therapy. Viral load in chronic infection was measured using the Roche Amplicor® version 1.5 assay.

b. HLA Class I Tetramers

Major histocompatibility complex (MHC) class I HIV Gag-specific tetramers were produced as described in Leisner et al. (2008) *PloS One* 3:e1678 or obtained from Proimmune. CMV- and EBV-specific MHC class I dextramers conjugated with FITC and APC were purchased from Immudex. Mouse MHC class I tetramers of H-2D$^b$ complexed with LCMV GP$_{276-286}$ as described in Wherry et al. (2003) *J. Virol.* 77:4911-4927 and Murali-Krishna et al. (1998) *Immunity* 8:177-187. Biotinylated complexes were tetramerized using allophycocyanin-conjugated streptavidin (Molecular Probes). The complete list of multimers can be found in Table 2.

TABLE 2

| Virustype | Multimer | HLA | Peptide used | Antigen derived from | Person | Supplier |
|---|---|---|---|---|---|---|
| HCV | Pentamer | A*02:01 | GIDPNIRTGV | HCV NS3 1273-1082 | David Wolski | Proimmune |
| HCV | Pentamer | A*02:01 | KLVALGINAV | HCV NS3 1406-1415 | David Wolski | Proimmune |
| HCV | Pentamer | A*01:01 | ATDALMTGY | HCV NS3 1435-1443 | David Wolski | Proimmune |
| HCV | Pentamer | B*40:01 | REISVPAEIL | HCV NS5a 2266-2275 | David Wolski | Proimmune |
| HCV | Pentamer | B*07:02 | GPRLGVRAT | HCV core 41-49 | David Wolski | Proimmune |
| HCV | Pentamer | A*02:01 | VLSDFKTWL | HCV NS5a 1987-1996 | David Wolski | Proimmune |
| HCV | Pentamer | A*02:01 | YPYRLWHYPC | HCV E2 610-619 | David Wolski | Proimmune |

TABLE 2-continued

| Multimer Virustype | HLA | Peptide used | Antigen derived from | Person | Supplier |
|---|---|---|---|---|---|
| HCV Pentamer | B*27:01 | ARMILMTHF | HCV core 470-478 | David Wolski | Proimmune |
| HCV Pentamer | A*02:01 | CINGVCWTV | HCV NS3 1073-1081 | David Wolski | Proimmune |
| CMV Dextramer | A*02:01 | NLVPMVATC | HCMV pp65 | Kash Gupta | Immudex |
| EBV Dextramer | A*02:01 | GLCTLVAML | EBV BMLF-1 | Kash Gupta | Immudex |
| HIV Tetramer | A*24:02 | RYPLTFGW | Nef RW8 | Emily Adland | Custom made |
| HIV Tetramer | B*57:01 | KAFSPEVIPMF | Gag KF11 | Emily Adland | Custom made |
| HIV Tetramer | B*14:02 | DRFYKTLRA | Gag DA9 | Emily Adland | Custom made |
| HIV Tetramer | B*35:01 | HPVHAGPIA | Gag HA9 | Emily Adland | Custom made |
| HIV Tetramer | B*14:02 | DRFYKTLRA | Gag DA9 | Emily Adland | Custom made |
| HIV Dextramer | A*02:01 | SLYNTVATL | Gag SL9 | Cormac Cosgrove | Immudex |
| HIV Pentamer | B*07:02 | TPQDLNTML | Gag TL9 | Cormac Cosgrove | Proimmune |
| HIV Dextramer | A*02:01 | SLYNTVATL | Gag SL9 | Cormac Cosgrove | Immudex |
| HIV Dextramer | B*57:01 | KAFSPEVIPMF | Gag KF11 | Cormac Cosgrove | Immudex |
| HIV Tetramer | B*08:01 | EIYKRWII | Gag EI8 | Cormac Cosgrove | Custom made |
| HIV Tetramer | B*35:01 | VPLRPMTY | Naf VY8 | Cormac Cosgrove | Beckman |
| HIV Dextramer | B*07:02 | GPGHKARVL | Gag GL9 | Cormac Cosgrove | Immudex |
| LCMV Tetramer | H-2Db | SGVENPGGYCL | GP276-286 | Jernej Godec | Dr. E. John Wherry | c. Antibodies and Flow Cytometry

The following anti-human (anti-hu) and anti-mouse (anti-m) fluorochromne-conjugated antibodies were used for flow cytometry: huCD8α (RPA-T8), huCD4 (OKT4), huCD3 (OKT3), huCD39 (A1), huPD-1 (EG12.2H7), huCD25 (BC96), huCCR7 (G043H7), huCD45RA (H100), huT-bet (4B10), mCD8☐ (53-6.7), mCD4 (GK1.5), mCD3 (145-2C211), mCD244.2 (m2B4 (B6)458.1), mPD-1 (RMP1-30), mLag3 (C9B7W), mCD44 (IM7), mCD127 (A7R34) (all from Biolegend), mT-bet (04-46; BD Pharmingen), mCD39 (24DMS1), huEomes (WD1928) and mEomes (Dan11mag) (eBioscience). Intracellular staining was performed following surface stains and fixed and permeabilized using the FoxP3/Transcription Factor Staining Buffer Set (eBioscience). Cells were sorted by BD FACS ARIA® II and all other analyses were performed on BD LSR II and BD LSR Fortessa® flow cytometers equipped with FACSDiva® v6.1. Gates were set using Full Minus One (FMO) controls. Data were analyzed using FlowJo software (Treestar).

d. Mice and Infections

All mice were used according to the Harvard Medical School Standing Committee on Animals and National Institutes of Animal Healthcare Guidelines. Wildtype C57BL/6J mice were purchased from The Jackson Laboratory. Female mice (6-8 weeks old) were infected with $2 \times 10^5$ plaque forming units (p.f.u.) of LCMV-Armstrong intraperitoneally or $4 \times 10^6$ p.f.u. of LCMV-Clone 13 intravenously and analyzed at indicated time points by homogenizing the spleen into a single-cell suspension, ACK lysis of red blood cells, followed by antibody staining. Viruses were propagated as described in Wherry et al. (2003) *J. Virol.* 77:4911-4927, Murali-Krishna et al. (1998) *Immunity* 8:177-187, and Ahmed et al. (1984) *J. Exp. Med.* 160:521-540.

e. HPLC Analysis of ATP Levels

The concentration of ATP hydrolyzed by CD8$^+$ T cells from subjects with HCV infection (n=6) was assessed by high performance liquid chromatography (HPLC) as described in Lazarowski et al. (2004) *J. Biol. Chem.* 279: 36855-36864. Briefly, 10,000 CD39$^+$ CD8$^+$ T cells were sorted and placed on ice to minimize ATP production by cells. Twenty μM of ATP was added and incubated for 1 h. at 37° C. in 5% CO2 to allow for cellular activity to increase and CD39-mediated ATP hydrolysis to occur. Samples were then placed in an ice bath for 10 min. to halt enzymatic activity, collected, and centrifuged for 10 min at 380×g rpm and 0° C. Cells were discarded and supernatant centrifuged again to remove remaining cells (2350×g rpm, 5 min, 0° C.). The resulting RPMI samples (160 μl) were treated with 10 μl of an 8 M perchloric acid solution (Sigma-Aldrich) and centrifuged at 15,900×g for 10 min. at 0° C. to precipitate proteins. In order to neutralize the pH of the resulting solutions and to remove lipids, supernatants (80 μl) were treated with 4 M K$_2$HPO$_4$ (8 μl) and tri-N-octylamine (50 μl). These samples were mixed with 50 μl of 1,1,2-trichlorotrifluoroethane and centrifuged (15,900×g, 10 min., 0° C.) and this last lipid extraction step was repeated once. The resulting supernatants were subjected to the following procedure to generate fluorescent etheno-adenine products: 150 μl supernatant (or nucleotide standard solution) was incubated at 72° C. for 30 min. with 250 mM Na$_2$HPO$_4$ (20 μl)

and 1 M chloroacetaldehyde (30 μl; Sigma-Aldrich) in a final reaction volume of 200 μl resulting in the formation of 1,N6-etheno derivatives as described in Lazarowski et al. (2004) *J. Biol. Chem.* 279:36855-36864. Samples were placed on ice, alkalinized with 0.5 M $NH_4HCO_3$ (50 μl), filtered with 1 ml syringe and 0.45 μm filter and analyzed using a Waters HPLC system and Supelcosil 3 μM LC-18T reverse phase column (Sigma) consisting of a gradient system described previously, a Waters autosampler, and a Waters 474 fluorescence detector (Chen et al. (2006) *Science* 314:1792-1795). Empower2 software was used for the analysis of data and all samples were compared with water and ATP standard controls as well as a sample with no cells to determine background degradation of ATP.

f. Microarray Data Acquisition and Analysis $CD8^+$ T cells from subjects with HCV infection were sorted and pelleted and re-suspended in TRzol (Invitrogen). RNA extraction was performed using the RNAdvance Tissue Isolation kit (Agencourt). Concentrations of total RNA were determined with a Nanodrop spectrophotometer or Ribogreen RNA quantification kits (Molecular Probes/Invitrogen). RNA purity was determined by Bioanalyzer 2100 traces (Agilent Technologies). Total RNA was amplified with the WT-Ovation Pico RNA Amplification system (NuGEN) according to the manufacturer's instructions. After fragmentation and biotinylation, cDNA was hybridized to Affymetrix HG-U133A 2.0 microarrays.

Prior to analysis, microarray data were pre-processed and normalized using robust multichip averaging, as described in Haining et al. (2008) *J. Immunol.* 181:1859-1868. Differentially gene expression and consensus clustering was performed using Gene-E software (available on the World Wide Web at broadinstitute.org/cancer/software/GENE-E/), and gene set enrichment analysis was performed as described using gene sets from MSigDB (Liberzon (2014) *Methods Mol. Biol.* 1150:153-160) or published resources (Doering et al. (2012) *Immunity* 37:1130-1144; Subramanian et al. (2005) *Proc. Natl. Acad. U.S.A.* 102:15545-15550). EnrichmentMap analysis of GSEA results was performed as described in Merico et al. (2010) *PloS One* 5:e13984.

g. $CD8^+$ T Cell Cytokyine Assays

Ly5.1+ (CD45.1+) P14 TCR transgenic cells were isolated from peripheral blood, and 500 P14 cells were transferred intravenously (i.v.) into 5-6 week old wild-type female mice one day prior to infection. Mice were infected with $4 \times 10$ p.f.u. of LCMV-Clone 13 intravenously and analyzed 36 days following infection by homogenizing the spleen into a single-cell suspension. $2 \times 10^6$ splenocytes were cultured in the presence of $GP_{33-41}$ peptide (0.2 μg/ml) (sequence KAVYNFATM), brefeldin A (BD), and monensin (BD) for 4.5 hours at 37° C. Following staining for surface antigens CD8, CD44, CD45.1, and CD45.2 in order to distinguish transferred CD45.1+P14 CD8+ T cells from endogenous CD45.2+CD8+ T cells, cells were permeabilized and stained for intracellular cytokines IFNγ and TNFα with the BD Cytofix/Cytoperm™ kit according to the manufacturer's instructions (BD Biosciences).

h. $CD8^+$ T Cell Tumor Assays

C57BL/6 wild type mice were injected subcutaneously in the flank with 1 million B16 melanoma cells or MC38 colorectal cancer cells. Mice were analyzed when tumors reached 1,000 $mm^3$, which generally occurred about 3 weeks post-injection. The tumor draining inguinal lymph node, as well as the tumor, were excised and homogenized into single cell suspensions. The tumor was further digested using collagenase and $CD8^+$ T cells were enriched using an OptiPrep™ gradient. Lymphocytes from the tumor and lymph node were stained with antibodies to CD45, CD8b, CD44, PD-1, CD39, Tim-3, Lag-3, CD244, T-bet, Eomes, Tox, IL-2, TNFα, and IFNγ. For cytokine analysis, the $CD8^+$ T cells were stimulated in vitro with phorbol 12-myristate 13-acetate (50 ng/mL) and ionomycin (500 ng/mL) in the presence of brefeldin A (BD) for 4 hours at 37° C. After stimulation, the cells were permeabilized and stained for the intracellular cytokines IL-2, IFNγ, and TNFα with the Foxp3 Fix/Perm® kit (eBioscience). For analysis of the transcription factors, Eomes, Tox, and T-bet, the cells were permeabilized and stained for the intracellular transcription factors Eomes, Tox, and T-bet with the Foxp3 Fix/Perm® kit (eBioscience).

Example 2: CD39 is Expressed by $CD8^+$ T Cells Responding to Chronic Infection

Figure 2:
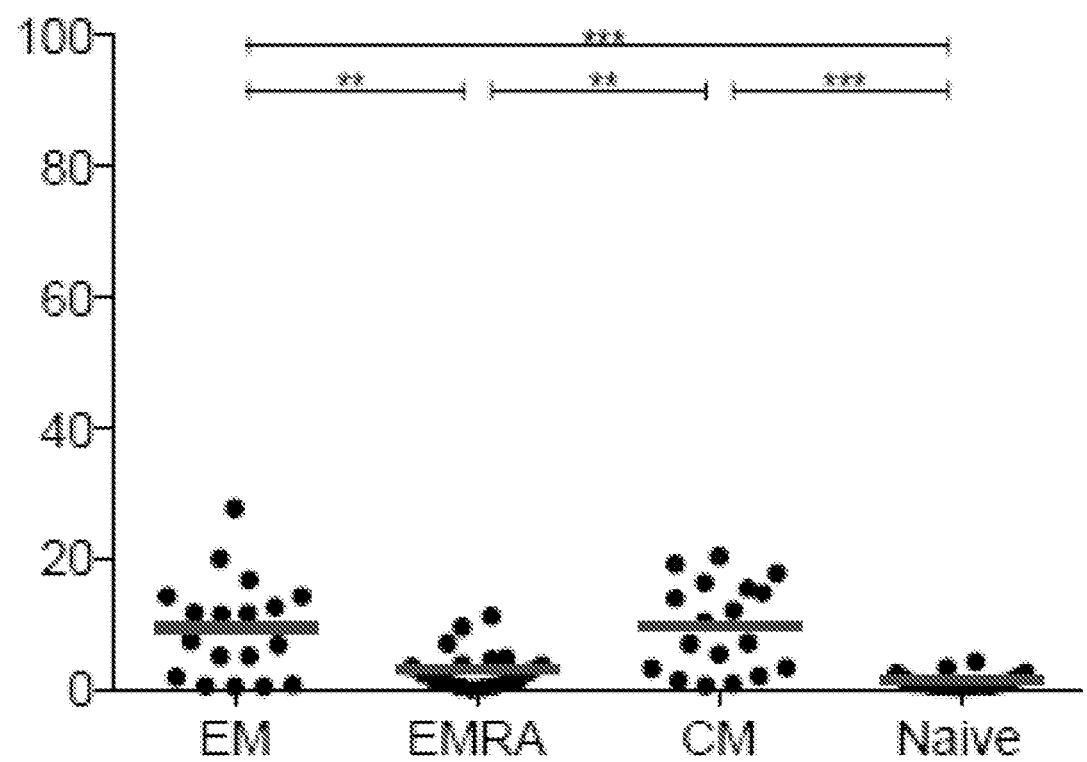
FIG. 2 shows that CD39 is expressed by few CD8$^+$ T cells in health donors. The fraction of CD39$^+$ cells in naïve CD8$^+$ T and central memory (CM), effector memory (EM) and effector memory RA$^+$ (EMRA) subpopulations of CD8$^+$ T cells from 18 healthy donors is shown. Error bars represent SEM. Statistical significance was assessed by one-way ANOVA. P<0.01, *P<0.001.

The expression of CD39 by $CD8^+$ T cells from healthy adult subjects without chronic viral infection was analyzed. Consistent with previous reports, it was found that only a small fraction (mean 7%) of $CD8^+$ T cells in healthy individuals expressed CD39 (FIG. 1A) (Kansas et al. (1991) *J. Immunol.* 146:2235-2244; Moncrieffe et al. (2010) *J. Immunol.* 185:134-143; Pulte et al. (2011) *Clin. Lymph. Myeloma Leuk.* 11:367-372; Boer et al. (2013) *Eur. J. Immunol.* 43:1925-1932). This small population of $CD39^+$ $CD8^+$ T cells in healthy donors was primarily found in the effector memory compartment while virtually no naive $CD8^+$ T cells expressed CD39 (FIG. 2). CD39 expression by antigen-specific $CD8^+$ T cells specific for latent viruses in healthy subjects was also analyzed. It was found that only a very small fraction of CMV- or EBV-specific $CD8^+$ T cells expressed CD39 (FIG. 1A) (mean 3% and 7% respectively).

In order to analyze CD39 expression by T cells specific for chronic, rather than latent, viruses, peripheral blood samples of individuals with either HCV or HIV infection were analyzed. CD39 expression was measured in 34 subjects, including acute HCV infections (13 with acute resolving infection and 21 with chronically evolving infection), and in 40 subjects with HIV infection (28 chronic progressors and 12 controllers of infection) (clinical characteristics of the subjects are summarized in Table 3). It was found that a mean of 58% of HCV-specific $CD8^+$ T cells and 31% of HIV-specific $CD8^+$ T cells expressed CD39, a number significantly higher than $CD8^+$ T cells specific for EBV or CMV, or in total $CD8^+$ T cell populations from healthy individuals (FIGS. 1A-1B). A significantly greater fraction of virus-specific $CD8^+$ T cells from HCV-infected subjects expressed CD39 than did those from HIV-infected subjects.

In subjects with chronic infection, the frequency of CD39-expressing cells in the virus-specific population was significantly higher than in the total CD8 T cell population (FIG. 1C-1D). However, the fraction of $CD8^+$ T cells expressing CD39 in the $CD8^+$ T cell compartment of individuals with chronic infection was slightly increased compared to healthy controls (FIG. 1E), consistent with the presence of other, unmeasured virus-specific $CD8^+$ T cells that were also CD39 in the tetramer fraction of $CD8^+$ T cells. Thus, CD39 is expressed infrequently by $CD8^+$ T cells in healthy donors, but marks a large fraction of pathogen-specific cells $CD8^+$ T cells in patients with chronic infection.

TABLE 3

| Patient ID | Gender | Chronic/Resolver | Viral Load/iu/L | Virus Genotype | ALT/iu/L |
|---|---|---|---|---|---|
| 00-23 P11 C63B | F | Chronic | <300 | 1a | 18 |
| 00-23 P27 C63B | F | Chronic | | 1b | 24 |
| 06-42 P3 | F | Chronic | 632972 | 1a | 280 |
| 06-42 P5 143D | F | Chronic | <615 | 1a | |
| 06K P3 143D | F | Resolver | <600 | 1a | 124 |
| 06K P6 143D | F | Resolver | undetected | 1a | |
| 06L | M | Resolver | | 3 | |
| 06L P7 4H | M | Resolver | undetected | 3 | 82 |
| 07-32 P2 4H | M | Chronic | | 2b | 585 |
| 07-32 P5 4H | M | Chronic | 89200 | 2b | 263 |
| 07-39 P18 | M | Chronic | 1170 | 1a | 33 |
| 07IP3 | M | Chronic | 1162 | 4a | 34 |
| 07P P4 | M | Chronic | | 1a | 1379 |
| 08-024 P1250A | F | Chronic | >700000 | 1 | 411 |
| 08-024 P14 A3Pool | F | Chronic | <43 | 1 | 11 |
| 08-024 P4 250A | F | Chronic | 7540000 | 1 | 259 |
| 08-024 P5 A3Pool | F | Chronic | <600 | 1 | 35 |
| 08-024 P6 A3Pool | F | Chronic | | 1 | 11 |
| 08-027 P1A2-198 | M | Chronic | 3838 | no test | 58 |
| 08-027 P5 A2-198 | M | Chronic | 1021 | no test | 75 |
| 08-23 P13 | M | Resolver | | 1 | |
| 08-27 P2 | M | Resolver | | no test | |
| 09-31 P3 | M | Chronic | detected | 1a | 128 |
| 09-33 P3 | F | Resolver | | 1a | 20 |
| 09-33 P5 143D | F | Resolver | undetected | 1a | 15 |
| 09-37 P3 c63b | M | Chronic | <600 | 1a | 32 |
| 09B P1 143D | M | Chronic | 217000 | 1a | 354 |
| 09B P5 | M | Chronic | 223000 | 1a | 73 |
| 10-048 P2 143D | F | Chronic | | 1a | 179 |
| 10-054 P1 143D | F | Chronic | 1130 | 1a | 209 |
| 10-078 P1 A2 226D | M | Chronic | 89200 | 3a | 875 |
| 10-19 P3 | F | Resolver | <615 | | 19 |
| 11-014 P1 143D | M | Resolver | 3150 | 2a | 129 |
| 11-017 P4 140G/259F | F | Chronic | 25431 | 1a | 481 |
| 12-043 P2 143D | M | Resolver | 81602 | | 692 |
| 12-103 P14H | F | Chronic | 432 | 3a | 44 |
| 12-181 P14H | F | Chronic | | 3a | |
| 13-024 P1 140G | M | Chronic | 147 | 1a | 205 |
| BR-3000 P12 A2 Mix2 | M | Resolver | undetected | 1a | 24 |
| BR-3000 P2 A2 Mix2 | M | Resolver | 47272 | 1a | 36 |
| BR-554 P13 C63B | F | Chronic | 2038 | 1a | 9 |
| BR-554 P17 C63B | F | Chronic | 6483017 | 1a | 45 |
| BR-554 P3 C63B | F | Chronic | 64497 | 1a | 39 |
| BR1036 P13 C63B | F | Resolver | <1000 | undetectable | 28 |
| BR1036 P9 C63B | F | Resolver | <1000 | undetectable | 4 |
| BR1144 P10 C63B | F | Resolver | <1000 | undetectable | 13 |
| BR1144 P5 C63B | F | Resolver | <1000 | undetectable | 2 |
| BR554 P13 C63B | F | Chronic | 2038 | 1a | 9 |
| BR554 P17 C63B | F | Chronic | 6483017 | 1a | 45 |
| BR949 P5 C63B | F | Chronic | 70047 | 1 | 36 |
| CR54 P2 4H | F | Chronic | detected | 1 | 237 |
| CR54 P3 4H | F | Chronic | detected | 1 | 103 |

Total = 32 (22 chronics and 10 resolvers)

| Patient ID | Gender | Progressor/Controller | ON/OFF Rx | Viral Load/cpm | CD4 Count | HLA A | HLA B | HLA C |
|---|---|---|---|---|---|---|---|---|
| 254567 | M | Chronic | OFF | 1823 | 606 | 0101 0201 | 0801 1501 | 0303 0701 |
| 350103 | F | Chronic | OFF | 431 | 625 | 0201 0301 | 1501 5701 | 0401 0602 |
| 350534 | M | Chronic | OFF | 24500 | 154 | 0101 0201 | 4402 5301 | 0602 0602 |
| 359260 | M | Chronic | OFF | 10322 | 541 | 0101 0101 | 0801 1302 | 0602 0701 |
| 384682 | M | Chronic | ON | 147 | 510 | 1101 7411 | 1508 3801 | 0210 0401 |
| 387879 | M | Chronic | OFF | 14600 | 677 | 2902 3002 | 0702 3901 | 0401 1505 |
| 403996 | F | Chronic | OFF | 2100 | 877 | 0101 0201 | 4402 5701 | 0602 1203 |
| 128019 | M | Viraamic Controllers | OFF | unknown | unknown | 2402 6901 | 3801 5701 | 0602 1203 |
| 186089 | M | Viraamic Controllers | OFF | 52 | 740 | 0101 0201 | 4001 5201 | 0304 1202 |
| 237983 | F | Viraamic Controllers | OFF | 189 | 1232 | 3201 3201 | 2705 4402 | 0102 0601 |
| 270245 | M | Viraamic Controllers | OFF | 15 | unknown | 0201 0301 | 0801 4405 | 0202 0701 |
| 302226 | M | Viraamic Controllers | OFF | 65 | 484 | 0101 2801 | 4501 9701 | 0802 0602 |
| 711960 | M | Viraamic Controllers | OFF | 300 | 700 | 0201 0205 | 5201 5801 | 0701 1202 |
| 732751 | M | Viraamic Controllers | OFF | 1860 | 1550 | 0301 3002 | 2705 4201 | 0202 17 |
| 255875 | M | Elite Controllers | OFF | 103 | 963 | 0201 0201 | 2705 5701 | 0102 0602 |
| 289198 | M | Elite Controllers | OFF | unknown | unknown | 0101 2402 | 3801 5701 | 0602 1203 |
| 285297 | F | Elite Controllers | OFF | 118 | 1246 | 0101 0201 | 5101 5701 | 0602 1502 |
| 321797 | M | Elite Controllers | OFF | unknown | unknown | 2402 2601 | 2705 5701 | 0102 0602 |
| 831969 | F | Elite Controllers | OFF | unknown | unknown | 0301 2601 | 4801 9701 | 0602 0602 |
| R060 | M | Chronic | OFF | 117934 | 480 | 0101 2402 | 0702 3501 | 0808 0702 |
| R086 | M | Chronic | OFF | 172886 | 410 | 0101 2402 | 1801 1801 | 0708 1203 |
| R089 | M | Chronic | OFF | 44000 | 680 | 0301 2402 | 0702 3701 | 0602 0702 |

TABLE 3-continued

| R048 | M | Chronic | OFF | 28445 | 910 | 0101 0201 | 4402 5701 | 0601 0602 |
| R050 | M | Chronic | OFF | 20210 | 440 | 0101 0101 | 0702 5701 | 0602 0702 |
| R041 | M | Chronic | OFF | 8435 | 320 | 0101 2402 | 0801 1402 | 0701 0802 |
| R017 | M | Chronic | OFF | 172886 | 410 | 2402 8001 | 0702 5801 | 0202 0302 |
| N034 | M | Chronic | OFF | 44000 | 680 | 2402 3101 | 4408 4901 | 0701 1601 |
| R134 | M | Chronic | OFF | 500000 | 430 | 0201 2402 | 0801 3501 | 0401 0701 |
| N012 | M | Chronic | OFF | 36695 | 7 | 0101 2402 | 0702 0801 | 0701 0702 |
| N090 | F | Chronic | OFF | 3362 | 490 | 0201 2402 | 4001 4001 | 0804 0304 |
| N104 | M | Chronic | OFF | 4533 | 390 | 1101 2402 | 0702 5501 | 0808 0702 |
| OX019 | F | Chronic | OFF | 42912 | 740 | 0101 2402 | 0801 3906 | 0701 0702 |
| R051 | M | Chronic | OFF | 500000 | 560 | 0101 3002 | 1801 3501 | 0401 0501 |
| R069 | M | Chronic | OFF | 63257 | 450 | 0201 0201 | 0702 3501 | 0401 0702 |
| N004 | M | Chronic | OFF | 500000 | 430 | 6802 6802 | 3501 3501 | 0401 0401 |
| N093 | F | Chronic | OFF | 2216 | 700 | 3001 3402 | 1510 3501 | 0304 0401 |
| OX034 | M | Chronic | OFF | 124153 | 430 | 0201 1101 | 0702 3501 | 0401 0702 |
| H005 | M | Chronic | OFF | 747 | 640 | 3004 7401 | 3501 5802 | 0401 0602 |
| H033 | M | Chronic | OFF | 8036 | 430 | 3601 7401 | 3501 5301 | 0401 0401 |
| R103 | F | Chronic | OFF | 8435 | 320 | 2301 3303 | 1402 5301 | 0401 0802 |

Example 3: CD39 Expressed by CD8$^+$ T Cells Hydrolyzes ATP

CD39 expressed by regulatory T cells catalyzes the hydrolysis of ADP to 5'-AMP (Kansas et al. (1991) *J. Immunol.* 146:2235-2244; Deaglio et al. (2007) *J. Exp. Med.* 204: 1257-1265; Borsellino et al. (2007) *Blood* 110:1225-1232). Therefore, the enzymatic function of CD39 expressed by CD8$^+$ T cells from patients infected with chronic HCV using ATP hydrolysis as a surrogate marker of CD39 activity was tested. CD39$^+$ and CD39$^+$ CD8$^+$ T cells were sorted from six HCV-infected individuals (four with chronic infection and two with resolved infection) and equal numbers of cells were incubated in the presence of extracellular ATP (eATP). The remaining levels of eATP were measured in the supernatant by HPLC. As control, ATP hydrolysis by CD4$^+$ CD25$^+$ CD39$^+$ regulatory T cells (Tregs) sorted from the same individuals was assessed.

Figure 3:
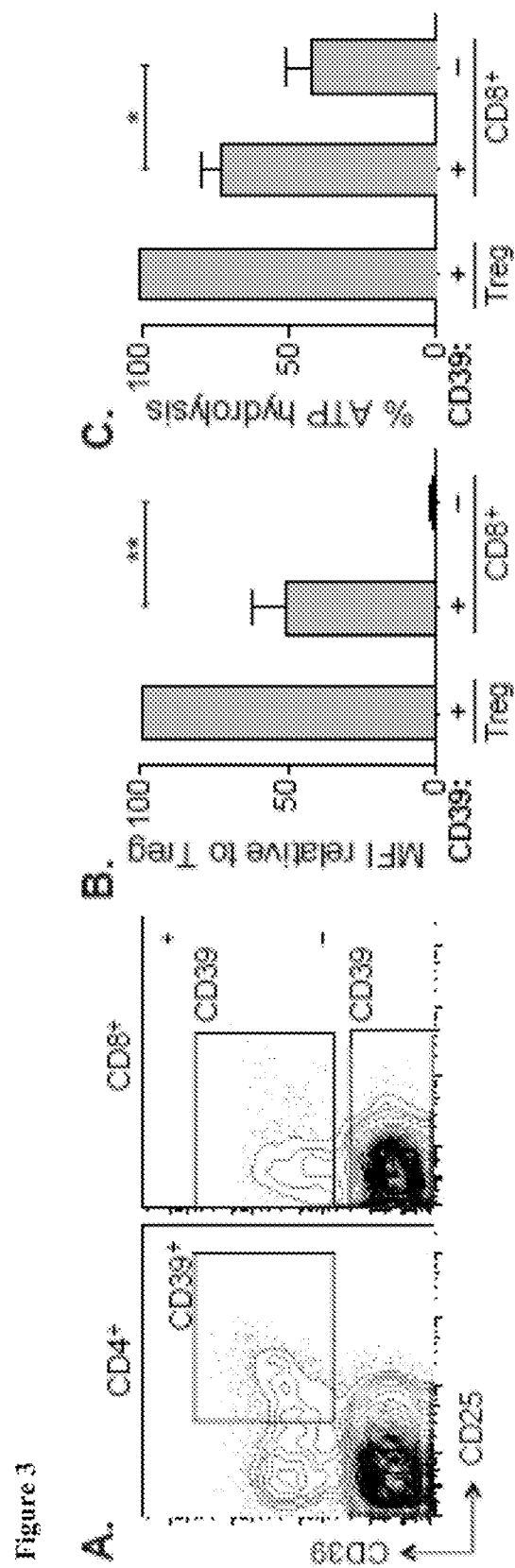
FIG. 3 includes 3 panels, identified as panels A, B, and C, which show that CD39 on CD8$^+$ T cells in HCV infection is enzymatically active. Panel A shows the results of flow cytometry sorting gates of CD39$^+$ and CD39$^-$ CD8$^+$ T cells and CD39$^+$ CD25$^+$ CD4$^+$ Tregs used for reverse-phase high performance liquid chromatography (rpHPLC) analysis of CD39 activity. Panel B shows a summary of CD39 expression level from cells in Panel A relative to Tregs in the same subjects. Panel C shows the results of ATP hydrolysis by CD8$^+$ T cell populations relative to Tregs. Data represent 6 patients with chronic evolving HCV infection. Error bars represent SEM. Statistical significance was assessed by paired Student's t-test (Panels B-C). *P<0.05, **P<0.01.
Figure 4:
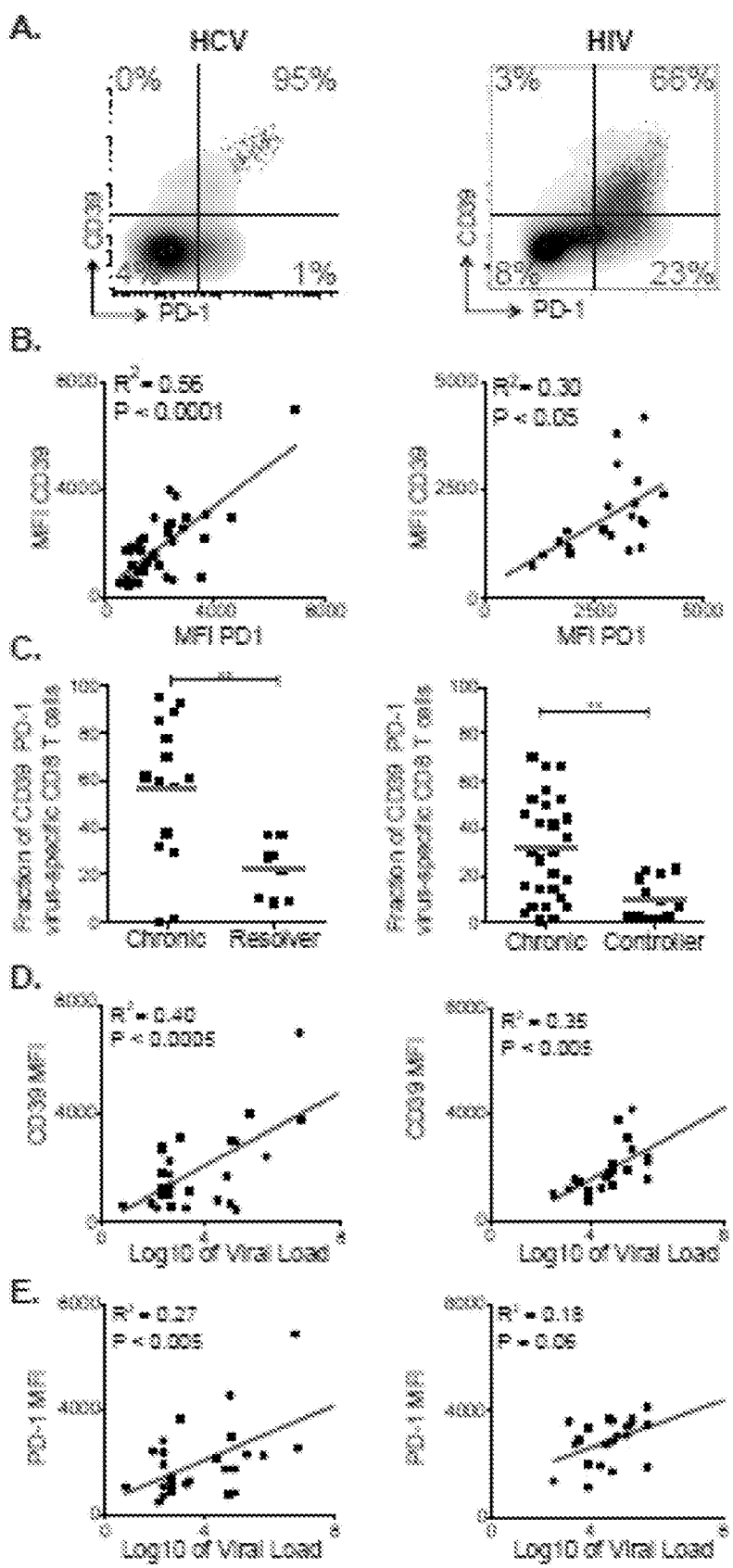
FIG. 4 includes 5 panels, identified as panels A, B, C, D, and E, which show that CD39 is a marker of CD8$^+$ T cell exhaustion in chronic viral infection and correlates with clinical parameters. Panel A shows the results of CD39 and PD-1 expression in chronic HCV (left) and HIV infections (right). Representative plots demonstrate total (gray) and virus-specific CD8$^+$ T cells. Panel B shows the correlation between CD39 and PD-1 expression of HCV- (left) and HIV-specific (right) CD8$^+$ T cells. Forty samples with HIV (21 chronic progressors, 7 viraemic controllers, and 5 elite controllers) and 39 patients with HCV (21 chronically infected and 13 resolvers) infection were tested. Panel C shows the fraction of CD39$^+$ PD-1$^+$ virus-specific CD8$^-$ T cells in HCV (left) or HIV (right) infection. Panel D shows the correlation between CD39 expression by virus-specific CD8$^+$ T cells and viral load count in HCV (left) or HIV (right) infection. Data are from 28 chronic HCV and 21 progressor HIV infection samples. Panel E shows the correlation between PD-1 expression by virus-specific CD8$^+$ T cells and viral load count in HCV (left) or HIV (right) infection from Panel D. Statistical significance was assessed by linear regression (Panels B, D, and E) or unpaired Student's t-test (Panel C). **P<0.01. MFI; mean fluorescence intensity.

Within the CD39$^+$ CD8$^+$ T cell population, the level of CD39 expression was lower than in Tregs (FIGS. 3A-3B). However, ATP hydrolysis by CD39$^+$ CD8$^+$ T cells was significantly greater than that of CD39$^-$ cells (FIG. 4C). Consistent with reduced CD39 expression relative to Tregs (FIG. 3A-3B), ATP hydrolysis by CD39$^+$ CD8$^+$ T cells was less than that by Tregs (FIG. 3C). These data indicate that CD39 expressed by CD8$^+$ T cells in HCV infection is enzymatically active and capable of hydrolyzing ATP.

Figure 5:
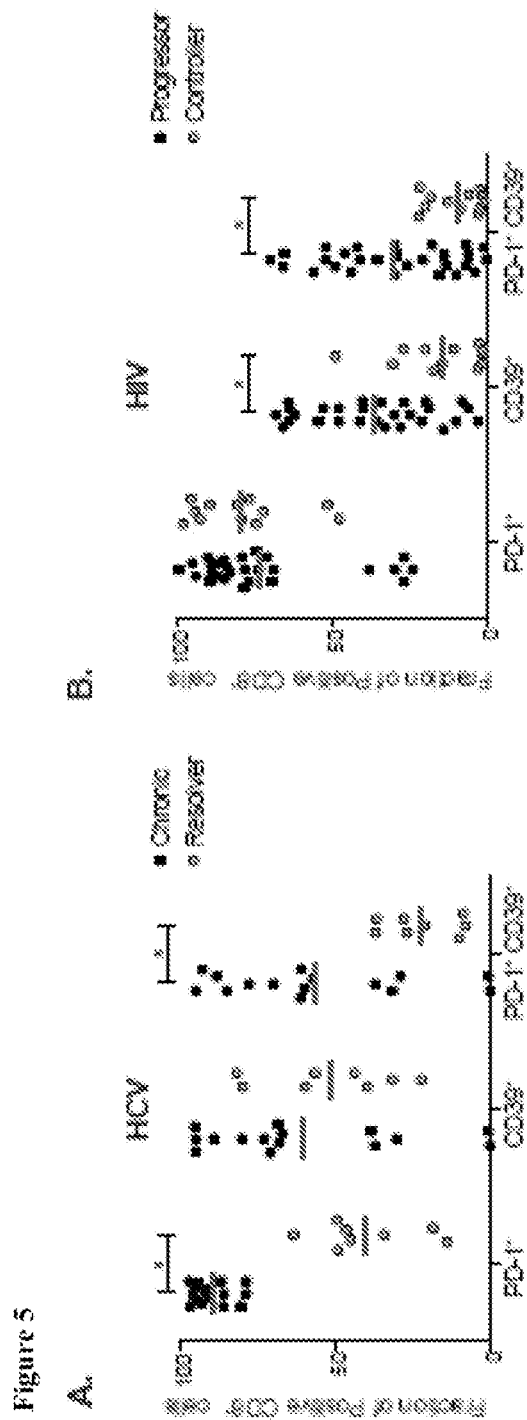
FIG. 5 includes 2 panels, identified as panels A and B, which show the results of CD39 and PD-1 co-expression in HCV and HIV. The fraction of HCV (Panel A) or HIV (Panel B) virus-specific CD8+ T cells expressing PD-1, CD39, or both, in patients with chronic disease (black) or patients that resolve virus (grey) are shown. Statistical significance was assessed by one-way ANOVA. *P<0.05.

Example 4: CD39 is Co-Expressed with PD-1 on Virus-Specific CD8$^+$ T Cells and Correlates with Viral Load in Both HCV and HIV Infection CD8$^+$ T cells specific for chronic viruses, such as HCV and HIV, express increased levels of PD-1 (Day et al. (2006) *Nature* 443:350-354; Kasprowicz et al. (2008) *J Virol.* 82:3154-3160). Thus, the relationship between CD39 and PD-1 expression by virus specific CD8$^+$ T cells in 40 patients infected with HIV (21 chronic progressors, 7 viremic controllers and 5 elite controllers) and 39 patients with HCV (21 chronically infected and 13 resolvers) was examined. In both diseases, a significant association between the level of expression (mean fluorescence intensity, MFI) of CD39 and PD-1 on antigen-specific CD8$^+$ T cells both in subjects with HCV and with HIV ($R^2$=0.56, P<0.0001 and $R^2$=0.3, P<0.05, respectively) was identified (FIGS. 4A-4B and FIG. 5).

It was next asked whether CD39 expression on viral-specific CD8$^+$ T cells in chronic viral infection could differentiate between patients with varying disease severity. Higher levels of PD-1 expression have been associated with surrogates of poor clinical outcome in HIV although the relationship is less clear for HCV (Day et al. (2006) *Nature* 443:350-354; Kasprowicz et al. (2008) *J. Virol.* 82:3154-3160; Urbani et al. (2006) *J. Virol.* 80:11398-11403). In HCV, it was found that the fraction of CD8$^+$ T cells expressing both CD39 and PD-1 was significantly higher in subjects with chronic infection, compared to those who with resolved infection (FIG. 4C, left panel). Similarly in HIV, it was found that the fraction of CD39$^+$ PD-1$^+$ virus-specific CD8$^+$ T cells was significantly higher in patients with chronic disease than in controllers (FIG. 4C, right panel).

The relationship between CD39 and PD-1 expression and viral load in HCV and HIV infection was also analyzed. It was found that both the HCV and HIV subject groups demonstrated a significant positive correlation between viral load and the level of CD39 expression on viral-specific CD8$^+$ T cells (FIG. 4D, left panel). The association between viral load and CD39 expression by HCV-specific CD8$^+$ T cells was slightly stronger than in HIV-specific CD8$^+$ T cells (FIG. 4D). Consistent with previous reports, PD-1 expression also correlated with the viral load in HIV-infected patients (FIG. 4E) (Day et al. (2006) *Nature* 443:350-354; Kasprowicz et al. (2008) *J. Virol.* 82:3154-3160). These data indicate that increased the antigen burden and inflammatory environment present in chronic HIV and chronic HCV infection is associated with increased expression of CD39 by virus-specific CD8$^+$ T cells.

Figure 6:
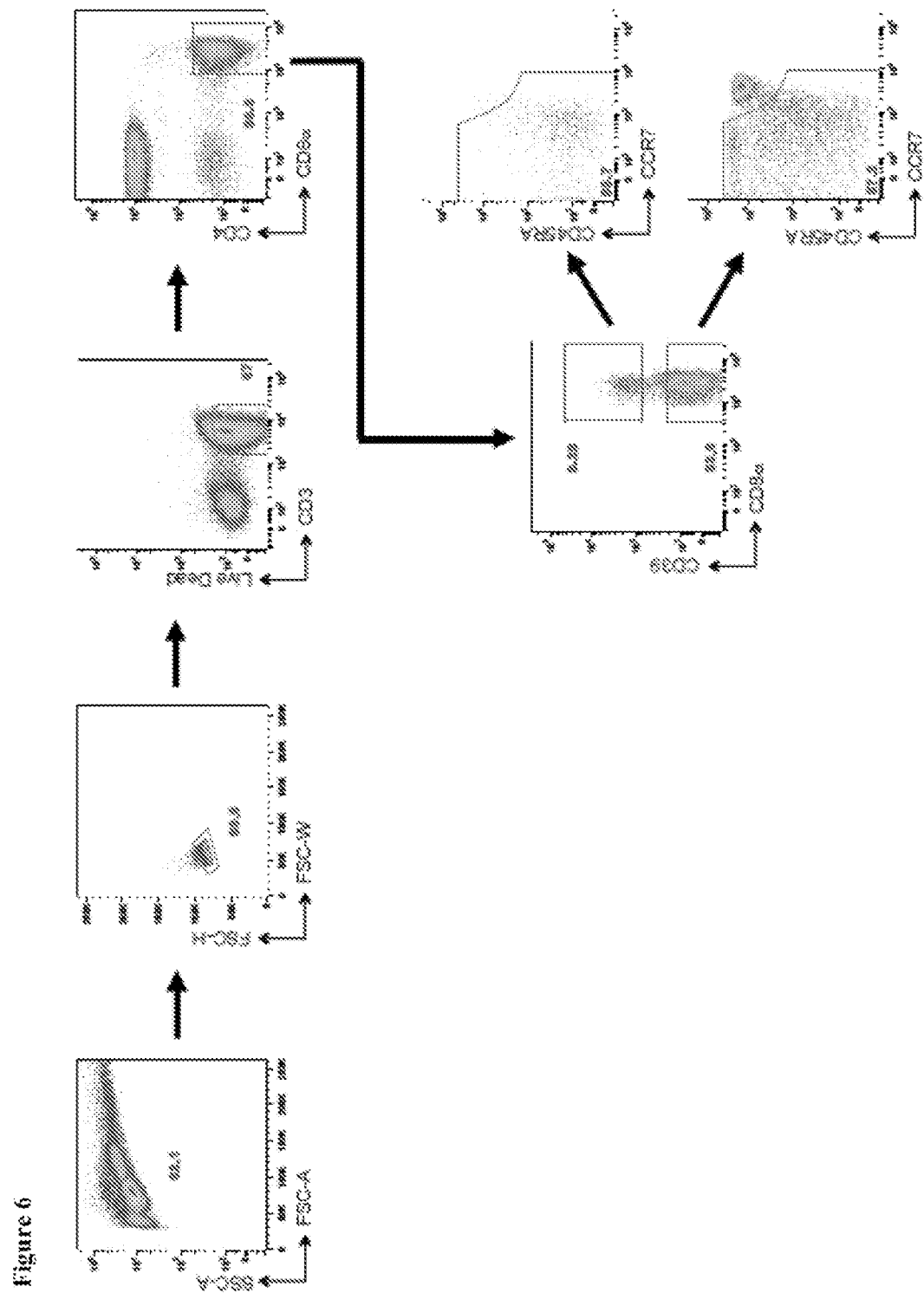
FIG. 6 shows the cell sorting strategy for the microarray experiment. The gating strategy for CD39$^+$ and CD39$^-$ live non-naïve CD8$^+$ T cells from HCV-infected patients is shown.

Example 5: Transcriptional Analysis of CD39$^+$ CD8$^+$ T Cells in HCV Infection In order to characterize more broadly the phenotype of CD39$^+$ CD8$^+$ T cells from individuals with chronic infection, the global gene expression profiles of sorted CD39$^+$ and CD39$^-$ CD8$^+$ T cells from 8 HCV-infected subjects (3 with acute resolving infection and 5 with chronically evolving infection) was compared. Clinical characteristics and information on cell sorting and cDNA quantification can be found in Table 4 and FIG. 6. Limited numbers of cells precluded the comparison of CD39$^+$ and CD39$^-$ CD8$^+$ T cells within HCV-specific cells, leading to a focus on the total CD8 population of antigen-experienced CD8$^+$ T cells (Table 4). Because naive CD8$^+$ T cells express little CD39 (FIG. 2), this population was excluded from the sorted cells (FIG. 6) in order to enable direct comparison of antigen-experienced CD39$^+$ and CD39$^-$ CD8$^+$ T cells. Unsupervised analysis of gene expression profiles using consensus hierarchical clustering (FIG. 7A) showed two distinct clusters of samples which corresponded almost exactly to CD39$^+$ and CD39$^-$ populations, indicating that that CD39 expression demarcates two types of CD8$^+$ T cells with markedly different patterns of gene expression. Supervised analysis of differential gene expression identified 619 genes differentially expressed (FDR<0.15) between CD39$^+$ and CD39$^-$ CD8$^+$ T cells (Table 4). Inspection of the list of differentially expressed genes revealed many with known roles in CD8$^+$ T cell biology including increased expression of the inhibitory receptors PD-1 and CTLA-4 in CD39$^+$ CD8$^+$ T cells.

TABLE 4

| Gene | Affymetrix ProbeSet Number | Signal to Noise | Rank | p-value | FDR(BH) | Fold Change |
| --- | --- | --- | --- | --- | --- | --- |
| ENTPD1 | 228585_at | 1.6166 | 3 | 0.001865 | 0.1043 | 5.7818 |
| CTLA4 | 236341_at | 1.5189 | 8 | 0.0006215 | 0.08198 | 3.8931 |
| BCAT1 | 226517_at | 0.8707 | 338 | 0.00404 | 0.1192 | 3.7141 |
| CHN1 | 212624_s_at | 1.3749 | 19 | 0.0009324 | 0.0867 | 3.6246 |
| TOP2A | 237469_at | 0.9373 | 245 | 0.00404 | 0.1192 | 3.4747 |
| PASK | 216945_x_at | 1.0923 | 103 | 0.002176 | 0.1073 | 3.0861 |
| HLA-DRA | 210982_s_at | 0.9644 | 212 | 0.00404 | 0.1192 | 2.5181 |
| SPRY1 | 230212_at | 0.9938 | 184 | 0.004662 | 0.1285 | 2.5022 |
| TNFRSF25 | 219423_x_at | 1.1711 | 71 | 0.001554 | 0.1014 | 2.4302 |
| TIAM1 | 313135_at | 1.2308 | 48 | 0.001243 | 0.09507 | 2.339 |
| CCNE1 | 242105_at | 0.9869 | 188 | 0.003108 | 0.1141 | 2.2869 |
| POU2AF1 | 205267_at | 1.0855 | 110 | 0.001243 | 0.09507 | 2.2527 |
| TRIB1 | 239818_x_at | 1.2677 | 41 | 0.0006216 | 0.08198 | 2.2411 |
| NGFRAP1 | 217963_s_at | 1.1219 | 90 | 0.0006216 | 0.08198 | 2.2196 |
| SNED1 | 213493_at | 1.4009 | 13 | 0.0003108 | 0.07173 | 2.1733 |
| AKAP5 | 230846_at | 0.7793 | 535 | 0.005594 | 0.1372 | 2.1278 |
| RCAN3 | 229064_s_at | 1.7913 | 1 | 0.0003108 | 0.07173 | 2.1042 |
| ICOS | 210439_at | 0.9978 | 180 | 0.00373 | 0.1192 | 2.0859 |
| MYB | 215152_at | 0.9375 | 244 | 0.003419 | 0.1181 | 2.084 |
| PHEX | 239229_at | 0.9058 | 283 | 0.00404 | 0.1192 | 2.061 |
| CC2D2B | 243534_at | 1.277 | 37 | 0.0006216 | 0.08198 | 2.0535 |
| AIF1 | 215051_x_at | 0.9386 | 242 | 0.00404 | 0.1192 | 2.0438 |
| CXCL13 | 205242_at | 0.7096 | 772 | 0.002797 | 0.1126 | 2.0253 |
| CCR4 | 208376_at | 0.9371 | 246 | 0.003419 | 0.1181 | 2.0074 |
| JAG1 | 231183_s_at | 0.8535 | 361 | 0.001554 | 0.1014 | 2.0002 |
| MEOX1 | 205619_s_at | 0.8474 | 374 | 0.007148 | 0.1493 | 1.9779 |
| ESPN | 234281_at | 1.057 | 127 | 0.002176 | 0.1073 | 1.9585 |
| ZC2HC1A | 241808_at | 1.0797 | 114 | 0.0009324 | 0.0867 | 1.952 |
| BUB1 | 216277_at | 1.2001 | 62 | 0.0003108 | 0.07173 | 1.9324 |
| MIRI1204 | 222087_at | 1.029 | 152 | 0.003108 | 0.1141 | 1.8742 |
| USP36 | 227093_at | 0.9968 | 181 | 0.0003108 | 0.07173 | 1.8693 |
| TACC3 | 218308_at | 1.0244 | 157 | 0.003419 | 0.1181 | 1.8655 |
| CD28 | 211861_x_at | 1.1224 | 88 | 0.001243 | 0.09507 | 1.8519 |
| FKBP5 | 224856_at | 0.8617 | 352 | 0.005905 | 0.1406 | 1.8418 |
| FAM134B | 218532_s_at | 0.8621 | 350 | 0.006838 | 0.1475 | 1.7984 |
| ITM2A | 202747_s_at | 0.9947 | 183 | 0.002176 | 0.1073 | 1.7762 |
| CCDC64 | 228320_x_at | 1.01 | 172 | 0.002176 | 1.1073 | 1.7529 |
| CAMK4 | 241871_at | 1.1362 | 81 | 0.001554 | 0.1014 | 1.6948 |
| LMCD1 | 227317_at | 1.2828 | 34 | 0.0009324 | 0.0867 | 1.6858 |
| MFGE8 | 210605_s_at | 0.9448 | 237 | 0.00373 | 0.1192 | 1.6769 |
| HLA-DOA | 226878_at | 1.0575 | 126 | 0.001554 | 0.1014 | 1.672 |
| MID1IP1 | 218251_at | 1.0447 | 134 | 0.001554 | 0.1014 | 1.654 |
| POLR1E | 231041_at | 1.238 | 47 | 0.001243 | 0.09507 | 1.6397 |
| FLJ13224 | 220211_at | 1.1922 | 66 | 0.001243 | 0.09507 | 1.6371 |
| ASAP1-IT1 | 220694_at | 0.8612 | 355 | 0.005284 | 0.1352 | 1.6268 |
| INTS1 | 212212_s_at | 1.581 | 5 | 0.0003108 | 0.07173 | 1.6224 |
| SYNJ2 | 240257_at | 1.1955 | 64 | 0.0009324 | 0.0867 | 1.6214 |
| CD7 | 214551_s_at | 0.9165 | 270 | 0.004662 | 0.1285 | 1.6204 |
| CD74 | 209619_at | 1.317 | 29 | 0.001243 | 0.09507 | 1.6103 |
| GNA15 | 205349_at | 1.0357 | 143 | 0.003108 | 0.1141 | 1.6005 |
| SHMT2 | 214437_s_at | 0.9797 | 198 | 0.0009324 | 0.0867 | 1.5858 |
| UX51 | 225583_at | 1.0347 | 147 | 0.001243 | 0.09507 | 1.5698 |
| LIMD2 | 218600_at | 1.0731 | 117 | 0.001554 | 0.1014 | 1.5658 |
| CD79A | 205049_s_at | 1.2543 | 44 | 0.0003108 | 0.07173 | 1.5641 |
| UBE2S | 202779_s_at | 1.1038 | 96 | 0.0006216 | 0.08198 | 1.5641 |
| PRKAR1B | 212559_at | 1.2049 | 59 | 0.0009324 | 0.0867 | 1.5641 |
| CENPO | 226118_at | 1.0167 | 163 | 0.002176 | 0.1073 | 1.5639 |
| ZEB1 | 239952_at | 1.1401 | 80 | 0.0006216 | 0.08198 | 1.5586 |
| GYPC | 202947_s_at | 1.3787 | 16 | 0.0009324 | 0.0867 | 1.5515 |
| TBXA2R | 336_at | 1.0191 | 160 | 0.002797 | 0.1126 | 1.5346 |
| ZNF335 | 78330_at | 0.9035 | 290 | 0.006838 | 0.1475 | 1.5271 |
| MCM5 | 216237_s_at | 0.7582 | 603 | 0.003108 | 0.1141 | 1.5265 |
| PBK | 219148_at | 0.9477 | 234 | 0.004662 | 0.1285 | 1.5127 |
| ADRBK2 | 228771_at | 0.9401 | 240 | 0.002486 | 0.1089 | 1.5054 |
| MLLT1 | 224993_at | 1.2092 | 57 | 0.0009324 | 0.0867 | 1.5011 |
| C17orf48 | 223401_at | 0.9041 | 288 | 0.006216 | 0.1445 | 1.5007 |
| C16orf45 | 212736_at | 0.8615 | 353 | 0.005594 | 0.1372 | 1.497 |
| LINC00312 | 240306_at | 0.8172 | 444 | 0.007148 | 0.1493 | 1.4928 |

TABLE 4-continued

| Gene | Affymetrix ProbeSet Number | Signal to Noise | Rank | p-value | FDR(BH) | Fold Change |
|---|---|---|---|---|---|---|
| PRRG4 | 238513_at | 1.0034 | 177 | 0.003108 | 0.1141 | 1.4913 |
| LGALS2 | 208450_at | 0.8456 | 377 | 0.007148 | 0.1493 | 1.49 |
| LOC441666 | 216469_at | 0.9687 | 208 | 0.001865 | 0.1043 | 1.4797 |
| CNOT3 | 229143_at | 1.1635 | 74 | 0.002176 | 0.1073 | 1.479 |
| SLC19A1 | 229639_s_at | 0.9586 | 218 | 0.0009324 | 0.0867 | 1.4771 |
| SEC14L2 | 240024_at | 0.9212 | 264 | 0.00373 | 0.1192 | 1.4728 |
| E2F8 | 219990_at | 0.7759 | 542 | 0.003108 | 0.1141 | 1.4676 |
| PDIA5 | 203857_s_at | 1.059 | 125 | 0.002486 | 0.1089 | 1.4642 |
| C19orf6 | 230089_s_at | 1.2051 | 58 | 0.0009324 | 0.0867 | 1.4635 |
| ADRBK1 | 38447_at | 1.0157 | 164 | 0.0009324 | 0.0867 | 1.4631 |
| MYO98 | 217297_s_at | 1.2785 | 35 | 0.0009324 | 0.0867 | 1.4598 |
| ADCY3 | 209321_s_at | 1.0122 | 167 | 0.001243 | 0.09507 | 1.4586 |
| MED15 | 222175_s_at | 1.0916 | 104 | 0.0006216 | 0.08198 | 1.4552 |
| COL6A3 | 201438_at | 0.9549 | 222 | 0.002176 | 0.1073 | 1.4518 |
| HSF1 | 213756_s_at | 1.5899 | 4 | 0.0003108 | 0.07173 | 1.4454 |
| CHMP7 | 212313_at | 0.8836 | 320 | 0.006527 | 0.1462 | 1.4306 |
| RAD54L | 204558_at | 0.9647 | 211 | 0.0009324 | 0.0867 | 1.4297 |
| FAM108B1 | 228872_at | 0.9388 | 241 | 0.004662 | 0.1285 | 1.4267 |
| ZBTB48 | 205025_at | 0.9019 | 292 | 0.006216 | 0.1445 | 1.4256 |
| ETV1 | 221911_at | 1.1624 | 75 | 0.001554 | 0.1014 | 1.4196 |
| ECE1 | 201750_s_at | 0.7817 | 530 | 0.007148 | 0.1493 | 1.4194 |
| MECP2 | 241924_at | 0.8589 | 357 | 0.006216 | 0.1445 | 1.4147 |
| CCDC94 | 204335_at | 1.0401 | 138 | 0.0009324 | 0.0867 | 1.4143 |
| CYP4F11 | 206153_at | 1.0791 | 115 | 0.003108 | 0.1141 | 1.4053 |
| PDCD1 | 207634_at | 1.0186 | 162 | 0.002486 | 0.1089 | 1.3992 |
| AGPAT3 | 225440_at | 1.2296 | 50 | 0.0009324 | 0.0867 | 1.3958 |
| EPB41 | 225051_at | 1.0982 | 97 | 0.001554 | 0.1014 | 1.3944 |
| DTX2 | 215732_s_at | 0.984 | 190 | 0.003108 | 0.1141 | 1.3941 |
| ARHGDIA | 213606_s_at | 0.8844 | 319 | 0.00404 | 0.1192 | 1.39 |
| KLF13 | 225390_s_at | 0.978 | 201 | 0.003108 | 0.1141 | 1.3877 |
| AURKAIP1 | 228800_x_at | 0.8636 | 347 | 0.005594 | 0.1372 | 1.3874 |
| TCEB3 | 213604_at | 1.2999 | 31 | 0.0009324 | 0.0867 | 1.386 |
| PPP1R7 | 213465_s_at | 0.8799 | 328 | 0.006838 | 0.1475 | 1.3831 |
| CDC37 | 209953_s_at | 0.9299 | 253 | 0.004662 | 0.1285 | 1.3827 |
| EIF3A | 200597_at | 0.8531 | 363 | 0.002797 | 0.1126 | 1.3818 |
| ASNA1 | 202024_at | 1.1055 | 95 | 0.001865 | 0.1043 | 1.374 |
| BTBD2 | 207722_s_at | 0.883 | 324 | 0.002797 | 0.1126 | 1.3731 |
| AP3D1 | 210974_s_at | 1.1529 | 78 | 0.001554 | 0.1014 | 1.3716 |
| OGDH | 201282_at | 1.0981 | 98 | 0.002486 | 0.1089 | 1.3711 |
| NR2F2 | 229092_at | 1.0777 | 116 | 0.0006216 | 0.08198 | 1.3708 |
| POLR2E | 217854_s_at | 0.7512 | 627 | 0.004351 | 0.1241 | 1.3702 |
| NAB2 | 216017_s_at | 1.1187 | 91 | 0.0006216 | 0.08198 | 1.37 |
| TLR8 | 229560_at | 1.3757 | 18 | 0.001554 | 0.1014 | 1.3698 |
| R3HDM4 | 55705_at | 0.9036 | 289 | 0.005284 | 0.1352 | 1.3674 |
| SMOX | 217074_at | 0.8996 | 297 | 0.003419 | 0.1181 | 1.3654 |
| OTUB1 | 38710_at | 0.8949 | 302 | 0.006527 | 0.1462 | 1.3654 |
| RBFOX2 | 216215_s_at | 0.9073 | 282 | 0.003419 | 0.1181 | 1.3649 |
| DNMT3L | 220139_at | 1.3772 | 17 | 0.0006216 | 0.08198 | 1.362 |
| BAI3 | 211568_at | 1.3393 | 27 | 0.0003108 | 0.07173 | 1.3617 |
| MYO7B | 235383_at | 1.2227 | 53 | 0.0006216 | 0.08198 | 1.3584 |
| RFX2 | 226872_at | 1.1614 | 76 | 0.002797 | 0.1126 | 1.358 |
| CHAF1A | 229808_at | 0.8502 | 367 | 0.006527 | 0.1462 | 1.3576 |
| CSF3R | 203591_s_at | 0.9518 | 225 | 0.004351 | 0.1241 | 1.3572 |
| LMNB2 | 216952_s_at | 1.0084 | 173 | 0.0009324 | 0.0867 | 1.3568 |
| SRM | 201516_at | 0.9723 | 204 | 0.002486 | 0.1089 | 1.3561 |
| ASCL2 | 229215_at | 0.8975 | 300 | 0.003419 | 0.1181 | 1.3546 |
| F3 | 204363_at | 1.1498 | 79 | 0.0003108 | 0.07173 | 1.3511 |
| TBXAS1 | 236345_at | 0.9024 | 291 | 0.007148 | 0.1493 | 1.3498 |
| MRPL12 | 229165_at | 0.965 | 210 | 0.0006216 | 0.08198 | 1.3494 |
| CLPB | 224510_s_at | 1.0053 | 175 | 0.0009324 | 0.0867 | 1.3478 |
| RAB9BP1 | 208245_at | 0.8935 | 305 | 0.004662 | 0.1285 | 1.3454 |
| MICALL1 | 55081_at | 0.8136 | 448 | 0.005284 | 0.1352 | 1.3435 |
| RFX1 | 226786_at | 1.0357 | 144 | 0.002176 | 0.1073 | 1.3427 |
| USE1 | 221706_s_at | 1.0559 | 129 | 0.002797 | 0.1126 | 1.3419 |
| NFRKB | 237210_at | 0.8421 | 384 | 0.005905 | 0.1406 | 1.3413 |
| CCNL2 | 232274_at | 1.0409 | 137 | 0.001243 | 0.09507 | 1.3391 |
| HAPLN2 | 220142_at | 1.2256 | 52 | 0.0003108 | 0.07173 | 1.3387 |
| LMTK2 | 235307_at | 1.1306 | 82 | 0.002486 | 0.1089 | 1.3387 |
| CLK3 | 238072_at | 1.0569 | 128 | 0.0006216 | 0.08198 | 1.3383 |
| WIF1 | 204712_at | 0.9548 | 223 | 0.004973 | 0.1317 | 1.3382 |
| DEAF1 | 230059_at | 1.2261 | 51 | 0.0009324 | 0.0867 | 1.3357 |
| CLN6 | 222539_at | 0.8746 | 332 | 0.005284 | 0.1352 | 1.3338 |
| BSG | 208677_s_at | 0.8824 | 325 | 0.004351 | 0.1241 | 1.3327 |
| PARD6A | 205245_at | 1.0353 | 145 | 0.001243 | 0.09507 | 1.332 |
| POU3F2 | 242455_at | 1.5791 | 6 | 0.0006216 | 0.08198 | 1.3309 |
| MLNR | 221365_at | 0.8848 | 317 | 0.003419 | 0.1181 | 1.3299 |

TABLE 4-continued

| Gene | Affymetrix ProbeSet Number | Signal to Noise | Rank | p-value | FDR(BH) | Fold Change |
|---|---|---|---|---|---|---|
| LYL1 | 210044_s_at | 1.0671 | 121 | 0.001865 | 1.1043 | 1.3297 |
| RBM47 | 229440_at | 1.0046 | 176 | 0.003108 | 0.1141 | 1.3296 |
| POLDIP3 | 243411_at | 0.9099 | 276 | 0.005594 | 0.1372 | 1.3296 |
| AKT2 | 236664_at | 0.8991 | 298 | 0.005594 | 0.1372 | 1.3288 |
| EDAR | 220048_at | 0.9075 | 281 | 0.006216 | 0.1445 | 1.3232 |
| SPANXA1 | 224032_x_at | 1.1266 | 85 | 0.0009324 | 0.0867 | 1.3228 |
| PPP4C | 208932_at | 0.8189 | 439 | 0.005594 | 0.1372 | 1.3227 |
| LRRC61 | 218907_s_at | 0.8183 | 442 | 0.004973 | 0.1317 | 1.3211 |
| ANKRD2 | 221232_s_at | 1.0629 | 124 | 0.001243 | 0.09507 | 1.3197 |
| GTPBP10 | 239773_at | 1.256 | 43 | 0.0009324 | 0.0867 | 1.3162 |
| PITX3 | 208277_at | 1.2969 | 32 | 0.0009324 | 0.0867 | 1.316 |
| STMN3 | 222557_at | 0.8746 | 333 | 0.006527 | 0.1462 | 1.3154 |
| MED8 | 213696_s_at | 0.9005 | 295 | 0.003419 | 0.1181 | 1.3126 |
| GREB1 | 210855_at | 1.089 | 107 | 0.001243 | 0.09507 | 1.3115 |
| MAP2K2 | 213490_s_at | 1.129 | 83 | 0.001243 | 0.09507 | 1.3106 |
| FOLR2 | 229619_at | 1.2393 | 46 | 0.0006216 | 0.08198 | 1.3092 |
| OR7A17 | 208509_s_at | 0.973 | 203 | 0.00373 | 0.1192 | 1.3091 |
| MGAT4B | 224598_at | 0.9225 | 262 | 0.005284 | 0.1352 | 1.3074 |
| C9orf53 | 220505_at | 1.0879 | 108 | 0.001865 | 0.1043 | 1.3055 |
| PRODH2 | 243614_s_at | 1.3045 | 30 | 0.0006216 | 0.08198 | 1.3053 |
| SEC13 | 207707_s_at | 1.2138 | 55 | 0.001865 | 0.1043 | 1.3041 |
| RRP1B | 212846_at | 1.164 | 73 | 0.0003108 | 0.07173 | 1.3039 |
| CPNE7 | 219707_at | 1.043 | 136 | 0.001243 | 0.09507 | 1.3022 |
| RFPL2 | 207227_x_at | 1.0473 | 131 | 0.0009324 | 0.0867 | 1.3008 |
| INPP5K | 202782_s_at | 0.8269 | 412 | 0.007148 | 0.1493 | 1.2989 |
| GYG2 | 215695_s_at | 1.5733 | 7 | 0.0003108 | 0.07173 | 1.2974 |
| CCR3 | 208304_at | 0.7616 | 589 | 0.002176 | 0.1073 | 1.2971 |
| DNAJB12 | 214338_at | 0.8124 | 449 | 0.006838 | 0.1475 | 1.2967 |
| ATXN7 | 243259_at | 0.924 | 260 | 0.00373 | 0.1192 | 1.2966 |
| KRT18 | 201596_x_at | 1.0322 | 149 | 0.002486 | 0.1089 | 1.296 |
| SH3GL1 | 201851_at | 1.2892 | 33 | 0.0003108 | 0.07173 | 1.29 |
| CHST15 | 244874_at | 0.8217 | 431 | 0.006838 | 0.1475 | 1.2886 |
| CD4 | 216424_at | 0.8471 | 375 | 0.006527 | 0.1462 | 1.2885 |
| FSD1 | 219170_at | 0.9858 | 189 | 0.003108 | 0.1141 | 1.2877 |
| NOS2 | 210037_s_at | 1.0802 | 113 | 0.002176 | 0.1073 | 1.2863 |
| HOXD3 | 217076_s_at | 1.0828 | 112 | 0.003108 | 0.1141 | 1.285 |
| SOX14 | 208574_at | 0.8207 | 435 | 0.001865 | 0.1043 | 1.2838 |
| FMO3 | 40665_at | 0.9275 | 256 | 0.00373 | 0.1192 | 1.2835 |
| GADD45GIP1 | 225495_x_at | 1.0705 | 119 | 0.0003108 | 0.07173 | 1.2829 |
| RHBG | 220510_at | 1.3928 | 14 | 0.0003108 | 0.07173 | 1.2811 |
| NOX1 | 210808_s_at | 1.1696 | 72 | 0.001865 | 0.1043 | 1.2805 |
| AKAP6 | 217669_s_at | 1.0721 | 118 | 0.001554 | 0.1014 | 1.2803 |
| PNPLA3 | 233030_at | 0.8261 | 415 | 0.004973 | 0.1317 | 1.2792 |
| RS1 | 216937_s_at | 0.8467 | 376 | 0.006838 | 0.1475 | 1.2789 |
| EHMT1 | 225461_at | 0.9574 | 220 | 0.001554 | 0.1014 | 1.2788 |
| BRD4 | 240360_at | 1.0326 | 148 | 0.00404 | 0.1192 | 1.2785 |
| ZNRF4 | 215461_at | 1.4331 | 11 | 0.0006216 | 0.08198 | 1.278 |
| SPIB | 232739_at | 0.8114 | 451 | 0.005284 | 0.1352 | 1.2771 |
| DLGAP1 | 235527_at | 0.8623 | 348 | 0.006216 | 0.1445 | 1.277 |
| PSMD8 | 200820_at | 0.8306 | 407 | 0.007148 | 0.1493 | 1.2759 |
| SLC22A14 | 207408_at | 1.1229 | 86 | 0.002176 | 0.1073 | 1.2741 |
| FLG | 215704_at | 1.1062 | 94 | 0.0006216 | 0.08198 | 1.274 |
| CDX1 | 206430_at | 1.0453 | 133 | 0.001554 | 0.1014 | 1.2712 |
| LPAR1 | 204038_s_at | 1.2036 | 60 | 0.0003108 | 0.07173 | 1.2707 |
| PEG3 | 209243_s_at | 0.8924 | 306 | 0.006216 | 0.1445 | 1.2696 |
| C7orf26 | 47083_at | 1.2783 | 36 | 0.0006216 | 0.08198 | 1.2691 |
| HLX | 214438_at | 1.1812 | 69 | 0.002176 | 0.1073 | 1.2676 |
| PCSK2 | 204870_s_at | 1.1988 | 63 | 0.0006216 | 0.08198 | 1.2676 |
| LOC284244 | 214162_at | 1.0118 | 168 | 0.00404 | 0.1192 | 1.2667 |
| RPS6KB1 | 226660_at | 0.9169 | 268 | 0.003108 | 0.1141 | 1.2664 |
| PAX3 | 231666_at | 1.0641 | 122 | 0.002486 | 0.1089 | 1.2659 |
| AMFR | 202204_s_at | 0.9452 | 236 | 0.004973 | 0.1317 | 1.2653 |
| DGCR6 | 208024_s_at | 0.9507 | 229 | 0.002797 | 0.1126 | 1.265 |
| TRIM29 | 211002_s_at | 0.9618 | 214 | 0.002486 | 0.1089 | 1.2643 |
| FKBP6 | 206763_at | 1.0112 | 169 | 0.00373 | 0.1192 | 1.2632 |
| PTPN13 | 243792_x_at | 0.7114 | 762 | 0.003419 | 0.1181 | 1.263 |
| RANBP9 | 243108_at | 0.8144 | 446 | 0.006216 | 0.1445 | 1.2622 |
| CCIN | 210642_at | 1.3469 | 26 | 0.0006216 | 0.08198 | 1.2621 |
| ALOXE3 | 222383_s_at | 0.8484 | 372 | 0.006527 | 0.1462 | 1.2621 |
| TNNT1 | 213201_s_at | 1.1787 | 70 | 0.0006216 | 0.08198 | 1.262 |
| CX3CL1 | 823_at | 1.3554 | 24 | 0.0003108 | 0.07173 | 1.2618 |
| GIF | 207033_at | 0.9502 | 230 | 0.001865 | 0.1043 | 1.2618 |
| CSF1 | 211839_s_at | 1.0351 | 146 | 0.002176 | 0.1073 | 1.2618 |
| MAGEB1 | 207534_at | 1.0278 | 153 | 0.002176 | 0.1073 | 1.2611 |
| FOXL1 | 243409_at | 0.96 | 216 | 0.003419 | 0.1181 | 1.2611 |
| TM4SF5 | 206242_at | 0.9805 | 196 | 0.002486 | 0.1089 | 1.2603 |

TABLE 4-continued

| Gene | Affymetrix ProbeSet Number | Signal to Noise | Rank | p-value | FDR(BH) | Fold Change |
|---|---|---|---|---|---|---|
| MSX1 | 228473_at | 0.9326 | 251 | 0.001865 | 0.1043 | 1.26 |
| GDF10 | 206159_at | 1.0383 | 140 | 0.002486 | 0.1089 | 1.2596 |
| MYCNOS | 216188_at | 0.8742 | 334 | 0.006527 | 0.1462 | 1.2588 |
| DDAH1 | 243711_at | 0.8767 | 330 | 0.005905 | 0.1406 | 1.2569 |
| CGB | 205387_s_at | 1.3582 | 23 | 0.0003108 | 0.07173 | 1.2567 |
| SRGAP3 | 232869_at | 0.8534 | 362 | 0.0003108 | 0.07173 | 1.2567 |
| MCHR1 | 230498_at | 0.9018 | 293 | 0.005594 | 0.1372 | 1.2567 |
| GPRC5A | 235563_at | 1.037 | 142 | 0.0009324 | 0.0867 | 1.2553 |
| DKKL1 | 220284_at | 0.8683 | 340 | 0.006527 | 0.1462 | 1.2551 |
| AKAP8L | 240554_at | 0.8915 | 307 | 0.007148 | 0.1493 | 1.2535 |
| EIF3C | 236700_at | 0.9721 | 205 | 0.00404 | 0.1192 | 1.2533 |
| EHD2 | 45297_at | 0.86 | 356 | 0.0009324 | 0.0867 | 1.2525 |
| WNT88 | 207612_at | 1.4476 | 10 | 0.0003108 | 0.07173 | 1.2508 |
| CORO2B | 209789_at | 0.8521 | 365 | 0.007148 | 0.1493 | 1.2505 |
| PFDN6 | 242048_at | 0.8061 | 469 | 0.007148 | 0.1493 | 1.2493 |
| ACTR3B | 218868_at | 0.7666 | 574 | 0.006527 | 0.1462 | 1.2486 |
| OBSL1 | 238776_x_at | 1.1151 | 93 | 0.002486 | 0.1089 | 1.2483 |
| CDK5RAP2 | 243153_at | 0.981 | 195 | 0.004351 | 0.1241 | 1.2477 |
| ATXN3L | 216539_at | 1.0379 | 141 | 0.001243 | 0.09507 | 1.2475 |
| ZNF592 | 227507_at | 0.9194 | 265 | 0.002797 | 0.1126 | 1.2472 |
| PPP2R1A | 200695_at | 0.976 | 202 | 0.00373 | 0.1192 | 1.2463 |
| SERPINA3 | 202376_at | 0.9299 | 254 | 0.00404 | 0.1192 | 1.2458 |
| HAO1 | 220224_at | 0.852 | 366 | 0.006527 | 0.1462 | 1.2452 |
| CNTLN | 241696_at | 0.9138 | 272 | 0.005284 | 0.1352 | 1.2451 |
| CNN1 | 203951_at | 0.9698 | 207 | 0.003419 | 0.1181 | 1.2449 |
| FGF3 | 214571_at | 1.0251 | 156 | 0.002176 | 0.1073 | 1.2446 |
| A4GALT | 219488_at | 1.091 | 105 | 0.001243 | 0.09507 | 1.2427 |
| CNN2 | 201605_x_at | 0.9295 | 255 | 0.004351 | 0.1241 | 1.2425 |
| GNB1L | 223564_s_at | 0.949 | 231 | 0.005594 | 0.1372 | 1.2421 |
| RALY | 201271_s_at | 0.8502 | 368 | 0.006527 | 0.1462 | 1.2415 |
| HTR5A | 221362_at | 0.996 | 182 | 0.001243 | 0.09507 | 1.2411 |
| DLG1 | 230229_at | 1.1583 | 77 | 0.001865 | 0.1043 | 1.2407 |
| CFHR5 | 208088_s_at | 0.9088 | 278 | 0.006527 | 0.1462 | 1.24 |
| LILRB4 | 210152_at | 1.0689 | 120 | 0.002176 | 0.1073 | 1.2383 |
| NAT9 | 204382_at | 0.8804 | 327 | 0.005594 | 0.1372 | 1.2376 |
| AZGP1P1 | 217013_at | 1.2577 | 42 | 0.0009324 | 0.0867 | 1.2371 |
| BEST2 | 207432_at | 0.7508 | 628 | 0.001865 | 0.1043 | 1.2365 |
| CATSPERG | 234353_at | 0.9482 | 233 | 0.00404 | 0.1192 | 1.2364 |
| SFSWAP | 240078_at | 0.7262 | 709 | 0.00404 | 0.1192 | 1.2359 |
| SPOCK3 | 235342_at | 1.2757 | 38 | 0.0009324 | 0.0867 | 1.2352 |
| GAST | 208138_at | 1.095 | 102 | 0.002176 | 0.1073 | 1.235 |
| GABRA2 | 216039_at | 1.4211 | 12 | 0.0003108 | 0.07173 | 1.2344 |
| KHSRP | 227555_s_at | 0.7978 | 489 | 0.003419 | 0.1181 | 1.2341 |
| FAM176B | 229998_x_at | 0.8229 | 427 | 0.007148 | 0.1493 | 1.2334 |
| MYO1E | 203072_at | 0.8573 | 359 | 0.006838 | 0.1475 | 1.2328 |
| TWF2 | 202009_at | 0.9091 | 277 | 0.003108 | 0.1141 | 1.2327 |
| OSGIN1 | 219475_at | 0.964 | 213 | 0.00404 | 0.1192 | 1.2327 |
| P2RX1 | 210401_at | 0.9597 | 217 | 0.002176 | 0.1073 | 1.2307 |
| MRC1 | 204438_at | 0.8948 | 303 | 0.00404 | 0.1192 | 1.2301 |
| PRAME | 204086_at | 0.9011 | 294 | 0.004662 | 0.1285 | 1.2288 |
| UBXN1 | 210623_at | 1.0217 | 158 | 0.001865 | 0.1043 | 1.2283 |
| GEMIN7 | 222821_s_at | 0.9356 | 248 | 0.004351 | 0.1241 | 1.2278 |
| UGT2A1 | 207958_at | 0.7546 | 619 | 0.005284 | 0.1352 | 1.2275 |
| SLITRK5 | 214930_at | 1.2308 | 49 | 0.001243 | 0.09507 | 1.2273 |
| EFNA3 | 210132_at | 0.8646 | 346 | 0.00404 | 0.1192 | 1.2264 |
| FGF4 | 206783_at | 0.8114 | 452 | 0.006838 | 0.1475 | 1.2259 |
| FBRS | 242217_s_at | 0.9899 | 186 | 0.002486 | 0.1089 | 1.2252 |
| SBNO2 | 215760_s_at | 1.1859 | 67 | 0.0006216 | 0.08198 | 1.2249 |
| NYX | 234496_x_at | 0.8357 | 393 | 0.004662 | 0.1285 | 1.2242 |
| CCDC40 | 239254_at | 1.0436 | 135 | 0.002797 | 0.1126 | 1.2232 |
| NTRK2 | 236095_at | 0.8266 | 414 | 0.006216 | 0.1445 | 1.223 |
| IL23A | 234865_at | 0.8877 | 311 | 0.00404 | 0.1192 | 1.2228 |
| AAK1 | 238100_at | 0.8322 | 400 | 0.005594 | 0.1372 | 1.2225 |
| PA2G4 | 214794_at | 0.956 | 221 | 0.00404 | 0.1192 | 1.2223 |
| AP2M1 | 200613_at | 1.3502 | 25 | 0.0009324 | 0.0867 | 1.221 |
| CNTFR | 205723_at | 1.1227 | 87 | 0.001554 | 0.1014 | 1.2208 |
| NR1I2 | 207203_s_at | 0.9916 | 185 | 0.004662 | 0.1285 | 1.2197 |
| CWH43 | 220724_at | 0.922 | 263 | 0.006527 | 0.1462 | 1.2196 |
| ACOT1 | 202982_s_at | 0.918 | 267 | 0.004662 | 0.1285 | 1.2194 |
| IL13 | 207844_at | 0.9513 | 226 | 0.005594 | 0.1372 | 1.2194 |
| TBX4 | 220634_at | 0.9603 | 215 | 0.002486 | 0.1089 | 1.2191 |
| CHAC1 | 219270_at | 0.9782 | 200 | 0.002176 | 0.1073 | 1.2186 |
| CSPG5 | 39966_at | 0.888 | 310 | 0.004351 | 0.1241 | 1.2179 |
| PDZRN3 | 238165_at | 0.9897 | 187 | 0.002797 | 0.1126 | 1.2172 |
| PNMA2 | 209598_at | 0.9384 | 243 | 0.003108 | 0.1141 | 1.2169 |
| TEX11 | 234296_s_at | 0.7109 | 765 | 0.002176 | 0.1073 | 1.2166 |

TABLE 4-continued

| Gene | Affymetrix ProbeSet Number | Signal to Noise | Rank | p-value | FDR(BH) | Fold Change |
|---|---|---|---|---|---|---|
| HIST1H4G | 208551_at | 0.7939 | 495 | 0.006527 | 0.1462 | 1.2163 |
| ETV4 | 211603_s_at | 0.8911 | 308 | 0.004973 | 0.1317 | 1.2162 |
| MYH6 | 214468_at | 0.9332 | 250 | 0.005284 | 0.1352 | 1.2161 |
| ADRA1D | 210961_s_at | 1.2113 | 56 | 0.001554 | 0.1014 | 1.216 |
| RBFOX1 | 235070_at | 0.9576 | 219 | 0.0006216 | 0.08198 | 1.2159 |
| DLGAP2 | 216916_s_at | 1.1925 | 65 | 0.0003108 | 0.07173 | 1.2154 |
| PYY | 211253_x_at | 1.0067 | 174 | 0.00373 | 0.1192 | 1.2152 |
| BMP15 | 221332_at | 0.7255 | 713 | 0.00404 | 0.1192 | 1.2145 |
| ADAMTS13 | 223844_at | 0.9169 | 269 | 0.004662 | 0.1285 | 1.2145 |
| DIO3 | 207154_at | 1.0903 | 106 | 0.002797 | 0.1126 | 1.2144 |
| IL20RA | 222829_s_at | 1.0189 | 161 | 0.002797 | 0.1126 | 1.2137 |
| GJB5 | 206156_at | 1.379 | 15 | 0.0003108 | 0.07173 | 1.2133 |
| GRIK2 | 215655_at | 0.9041 | 287 | 0.005594 | 0.1372 | 1.2133 |
| NRXN3 | 229649_at | 0.8723 | 336 | 0.005905 | 0.1406 | 1.2132 |
| KRT15 | 204734_at | 0.8683 | 341 | 0.006838 | 0.1475 | 1.213 |
| TRAF3IP1 | 238494_at | 1.098 | 100 | 0.002797 | 0.1126 | 1.2112 |
| CDKN2B | 236313_at | 0.8313 | 403 | 0.006838 | 0.1475 | 1.2109 |
| GUCA2B | 207502_at | 0.8325 | 399 | 0.006838 | 0.1475 | 1.2098 |
| JUP | 212236_x_at | 0.8215 | 432 | 0.003419 | 0.1181 | 1.208 |
| GUCY1A2 | 242342_at | 1.064 | 123 | 0.003419 | 0.1181 | 1.2075 |
| SLC6A14 | 219795_at | 1.2723 | 40 | 0.0003108 | 0.07173 | 1.2065 |
| PXDC1 | 212923_s_at | 0.9352 | 249 | 0.004973 | 0.1317 | 1.2061 |
| SIRPA | 202897_at | 0.8401 | 387 | 0.007148 | 0.1493 | 1.2055 |
| B3GNT3 | 204856_at | 1.0254 | 155 | 0.002797 | 0.1126 | 1.2043 |
| DNASE1L3 | 205554_s_at | 1.4971 | 9 | 0.0003108 | 0.07173 | 1.204 |
| PNPLA6 | 203718_at | 0.9118 | 275 | 0.006838 | 0.1475 | 1.204 |
| SCNN1A | 217264_s_at | 0.9811 | 194 | 0.002797 | 0.1126 | 1.2033 |
| HDHD3 | 221256_s_at | 0.7338 | 678 | 0.006838 | 0.1475 | 1.2031 |
| C16orf59 | 219556_at | 0.8107 | 453 | 0.004973 | 0.1317 | 1.2029 |
| AGPAT2 | 32837_at | 1.2154 | 54 | 0.0006216 | 0.08198 | 1.2025 |
| MRAS | 225185_at | 1.2478 | 45 | 0.001554 | 0.1014 | 1.2022 |
| FAM1988 | 223204_at | 0.8873 | 312 | 0.006216 | 0.1445 | 1.2013 |
| DSG3 | 235075_at | 1.3706 | 20 | 0.0006216 | 0.08198 | 1.2011 |
| SLC15A1 | 211349_at | 1.0307 | 150 | 0.001865 | 0.1043 | 1.201 |
| OR2J2 | 216818_s_at | 0.876 | 331 | 0.004351 | 0.1241 | 1.2009 |
| ADAM5P | 217003_s_at | 1.0197 | 159 | 0.002176 | 0.1073 | 1.1995 |
| VAV2 | 226063_at | 0.8658 | 345 | 0.002176 | 0.1073 | 1.1995 |
| FABP4 | 235978_at | 1.2746 | 39 | 0.0009324 | 0.0867 | 1.1985 |
| ADTRP | 229070_at | 0.8452 | 379 | 0.003108 | 0.1141 | 1.1975 |
| GDNF | 230090_at | 0.8731 | 335 | 0.003419 | 0.1181 | 1.1968 |
| MIR3917 | 217714_x_at | 0.9512 | 227 | 0.004351 | 0.1241 | 1.1955 |
| KCNJ16 | 222901_s_at | 1.098 | 99 | 0.0009324 | 0.0867 | 1.1944 |
| EDF1 | 209059_s_at | 1.039 | 139 | 0.00404 | 0.1192 | 1.1932 |
| CSF3 | 207442_at | 0.7837 | 526 | 0.004351 | 0.1241 | 1.1928 |
| CDKN1C | 219534_x_at | 1.1186 | 92 | 0.001865 | 0.1043 | 1.1926 |
| DHRS9 | 224009_x_at | 0.8851 | 316 | 0.0009324 | 0.0867 | 1.192 |
| CDH7 | 220679_s_at | 1.122 | 89 | 0.003108 | 0.1141 | 1.1919 |
| SLC25A6 | 212826_s_at | 0.9357 | 247 | 0.004351 | 0.1241 | 1.1914 |
| GPR88 | 220313_at | 1.0131 | 166 | 0.001554 | 0.1014 | 1.1913 |
| TRPV6 | 206827_s_at | 1.2019 | 61 | 0.001554 | 0.1014 | 1.1896 |
| SART1 | 231998_at | 0.7947 | 494 | 0.005905 | 0.1406 | 1.1888 |
| EPCAM | 201839_s_at | 1.3614 | 22 | 0.0003108 | 0.07173 | 1.1867 |
| MOBP | 242765_at | 1.1274 | 84 | 0.001554 | 0.1014 | 1.1854 |
| CYP2A13 | 208327_at | 1.7671 | 2 | 0.0003108 | 0.07173 | 1.186 |
| ABO | 21692_x_at | 0.9686 | 209 | 0.002176 | 0.1073 | 1.186 |
| HOXD9 | 205605_at | 0.9821 | 193 | 0.00404 | 0.1192 | 1.1854 |
| TSSK2 | 217275_at | 0.8103 | 455 | 0.005905 | 0.1406 | 1.1851 |
| SLC6A1 | 205152_at | 0.9404 | 239 | 0.004973 | 0.1317 | 1.1848 |
| HGC6.3 | 211111_at | 0.9832 | 191 | 0.00373 | 0.1192 | 1.1836 |
| IQSEC3 | 242694_at | 1.0976 | 101 | 0.0009324 | 0.0867 | 1.1835 |
| GPR85 | 234303_s_at | 0.8696 | 339 | 0.003419 | 0.1181 | 1.1834 |
| KRT20 | 213953_at | 1.0261 | 154 | 0.002176 | 0.1073 | 1.1827 |
| KRT6A | 214580_x_at | 0.899 | 299 | 0.005284 | 0.1357 | 1.1826 |
| HNF4A | 230914_at | 0.9141 | 271 | 0.00373 | 0.1192 | 1.1812 |
| TFDP3 | 207385_at | 0.8832 | 323 | 0.003419 | 0.1181 | 1.1783 |
| GPR162 | 205056_s_at | 0.943 | 238 | 0.002797 | 0.1126 | 1.178 |
| NR1H4 | 243800_at | 0.7533 | 621 | 0.005594 | 0.1372 | 1.1772 |
| PHOX2B | 207009_at | 0.9238 | 261 | 0.002797 | 0.1126 | 1.1766 |
| DCLK1 | 230962_at | 0.9531 | 224 | 0.00373 | 0.1192 | 1.1766 |
| CCNJL | 219227_at | 0.8708 | 337 | 0.003108 | 0.1141 | 1.1757 |
| TRPC4 | 224220_x_at | 0.9186 | 266 | 0.001865 | 0.1043 | 1.1755 |
| PKDREJ | 220548_at | 0.9458 | 235 | 0.006216 | 0.1445 | 1.1755 |
| MMP7 | 204259_at | 0.9002 | 296 | 0.002176 | 0.1073 | 1.1748 |
| HSPB3 | 206375_s_at | 1.0851 | 111 | 0.001554 | 0.1014 | 1.1716 |
| MMP26 | 220541_at | 1.0863 | 109 | 0.004662 | 0.1285 | 1.1701 |
| PON3 | 213695_at | 0.9047 | 286 | 0.001865 | 0.1043 | 1.169 |

TABLE 4-continued

| Gene | Affymetrix ProbeSet Number | Signal to Noise | Rank | p-value | FDR(BH) | Fold Change |
|---|---|---|---|---|---|---|
| ARNT2 | 2.02986_at | 1.0455 | 132 | 0.0003108 | 0.07173 | 1.1687 |
| MYF5 | 207424_at | 0.9508 | 228 | 0.0009324 | 0.0867 | 1.1658 |
| HRH1 | 205580_s_at | 0.8662 | 344 | 0.00404 | 0.1192 | 1.1649 |
| NDST4 | 208334_at | 0.9123 | 273 | 0.007148 | 0.1493 | 1.1649 |
| LMF2 | 31837_at | 1.0135 | 165 | 0.002486 | 0.1089 | 1.1616 |
| PFKL | 211065_x_at | 1.011 | 170 | 0.001554 | 0.1014 | 1.16 |
| SCGN | 205697_at | 0.8806 | 326 | 0.00404 | 0.1192 | 1.158 |
| C1QL1 | 214346_at | 0.9824 | 192 | 0.00404 | 0.1192 | 1.1573 |
| MAPK10 | 237413_at | 0.8441 | 380 | 0.003108 | 0.1141 | 1.1572 |
| TNNT2 | 215389_s_at | 0.8289 | 410 | 0.005284 | 0.1352 | 1.1563 |
| OR1A1 | 221388_at | 0.8208 | 434 | 0.004662 | 0.1285 | 1.1556 |
| GCKR | 206867_at | 0.8889 | 309 | 0.003419 | 0.1181 | 1.1514 |
| LOC100131392 | 221154_at | 0.9486 | 232 | 0.002797 | 0.1126 | 1.1511 |
| GATA4 | 243692_at | 0.867 | 342 | 0.005284 | 0.1352 | 1.1507 |
| LPPR4 | 213496_at | 0.8855 | 315 | 0.004351 | 0.1241 | 1.1492 |
| RPL4 | 211710_x_at | 1.0497 | 130 | 0.003108 | 0.1141 | 1.1454 |
| PIK3CA | 235980_at | 0.8455 | 378 | 0.005905 | 0.1406 | 1.1449 |
| CYP1A1 | 205749_at | 1.0302 | 151 | 0.001865 | 0.1043 | 1.1418 |
| EEF2 | 204102_s_at | 0.9253 | 257 | 0.002486 | 0.1089 | 1.1396 |
| HMHA1 | 212873_at | 0.8269 | 413 | 0.007148 | 0.1493 | 1.1395 |
| BST1 | 205715_at | 1.0023 | 178 | 0.0009324 | 0.0867 | 1.1376 |
| LGR5 | 213880_at | 0.8229 | 429 | 0.004973 | 0.1317 | 1.1369 |
| DSC2 | 226817_at | 1.1826 | 68 | 0.002176 | 0.1073 | 1.1357 |
| SLC13A3 | 230687_at | 0.9324 | 252 | 0.00404 | 0.1192 | 1.1351 |
| SLC17A2 | 207097_s_at | 0.9699 | 206 | 0.00404 | 0.1192 | 1.1347 |
| PPP2R4 | 216105_x_at | 0.7654 | 578 | 0.006838 | 0.1475 | 1.1347 |
| NKX6-1 | 221366_at | 0.7555 | 614 | 0.006838 | 0.1475 | 1.1286 |
| LRRC49 | 219338_s_at | 0.8218 | 430 | 0.005594 | 0.1372 | 1.1279 |
| KL | 205978_at | 0.7996 | 486 | 0.007148 | 0.1493 | 1.1271 |
| SERPINA7 | 206386_at | 0.9993 | 179 | 0.002176 | 0.1073 | 1.1228 |
| HMGCS2 | 240110_at | 0.8836 | 321 | 0.006216 | 0.1445 | 1.1126 |
| NPM1 | 221923_s_at | 1.3622 | 21 | 0.0003108 | 0.07171 | 1.1079 |
| PTGER1 | 231201_at | 0.8039 | 476 | 0.005594 | 0.1372 | 1.107 |
| GH1 | 211151_x_at | 1.3316 | 28 | 0.0006216 | 0.08198 | 1.1055 |
| AMELX | 208410_x_at | 0.7807 | 534 | 0.004973 | 0.1317 | 1.1023 |
| RPL8 | 200936_at | 0.9799 | 197 | 0.00404 | 0.1192 | 1.1011 |
| HRH3 | 221663_x_at | 0.7727 | 555 | 0.001243 | 0.09507 | 1.0914 |
| RPL7 | 239493_at | −0.8186 | 12696 | 0.002486 | 0.1089 | −1.0672 |
| RPS6 | 211690_at | −1.0334 | 12844 | 0.001243 | 0.09507 | −1.0821 |
| RPL27 | 200025_s_at | −0.8594 | 12734 | 0.005905 | 0.1406 | −1.1147 |
| RPS27A | 244624_at | −1.0319 | 12843 | 0.002797 | 0.1126 | −1.1217 |
| CAMK2B | 34646_at | −1.0289 | 12841 | 0.001865 | 0.1043 | −1.1364 |
| CCL5 | 204655_at | −1.009 | 12830 | 0.00373 | 0.1192 | −1.1487 |
| NONO | 210470_x_at | −0.9772 | 12816 | 0.002797 | 0.1126 | −1.1576 |
| HNRNPA3 | 211933_s_at | −0.821 | 12697 | 0.00404 | 0.1192 | −1.1585 |
| YTHDF2 | 222430_s_at | −1.1362 | 12875 | 0.002486 | 0.1089 | −1.1723 |
| EEF1B2 | 200705_s_at | −0.9744 | 12811 | 0.001554 | 0.1014 | −1.1756 |
| SEC22B | 209207_s_at | −1.0085 | 12829 | 0.003108 | 0.1141 | −1.1817 |
| LOC100506732 | 200627_at | −1.2372 | 12896 | 0.0006216 | 0.08198 | −1.1827 |
| KDM3B | 210878_s_at | −1.1015 | 12868 | 0.002176 | 0.1073 | −1.191 |
| FLJ11292 | 220828_s_at | −0.93 | 12784 | 0.004973 | 0.1317 | −1.204 |
| TRIM3 | 213885_at | −0.8459 | 12723 | 0.005905 | 0.1406 | −1.2204 |
| CALR | 214316_x_at | −0.9771 | 12815 | 0.003419 | 0.1181 | −1.2227 |
| CUTC | 218970_s_at | −0.767 | 12631 | 0.005284 | 0.1352 | −1.2251 |
| PTP4A2 | 216988_at | −1.9067 | 12924 | 0.0001 | 0 | −1.2278 |
| GGNBP2 | 233937_at | −0.8231 | 12702 | 0.005784 | 0.1352 | −1.2297 |
| MSN | 200600_at | −0.7682 | 12632 | 0.004973 | 0.1317 | −1.2308 |
| SAR1A | 210790_s_at | −0.7685 | 12633 | 0.006527 | 0.1462 | −1.2319 |
| KIF1B | 228657_at | −0.8909 | 12753 | 0.004662 | 0.1285 | −1.2349 |
| UBP1 | 218082_s_at | −0.9056 | 12766 | 0.004351 | 0.1241 | −1.2424 |
| MGEA5 | 235868_at | −0.9597 | 12802 | 0.004662 | 0.1285 | −1.2435 |
| TMEM59 | 241018_at | −1.3999 | 12915 | 0.0001 | 0 | −1.2436 |
| DMTF1 | 203301_s_at | −1.1502 | 12880 | 0.0003108 | 0.07173 | −1.2465 |
| ABI1 | 209028_s_at | −1.0074 | 12828 | 0.003419 | 0.1181 | −1.2485 |
| DICER1 | 216281_at | −1.0285 | 12840 | 0.002486 | 0.1089 | −1.2502 |
| ZNF358 | 226260_x_at | −0.9047 | 12763 | 0.003108 | 0.1141 | −1.2506 |
| ROCK1 | 235854_x_at | −0.9852 | 12820 | 0.00373 | 0.1192 | −1.251 |
| MAPK1 | 229847_at | −1.0021 | 12827 | 0.007148 | 0.1493 | −1.2513 |
| DSTNP2 | 211325_x_at | −0.8463 | 12724 | 0.0009325 | 0.0867 | −1.2528 |
| PRPF38B | 230270_at | −0.977 | 12814 | 0.00373 | 0.1192 | −1.2534 |
| HNRNPU | 235603_at | −1.0436 | 12849 | 0.0009325 | 0.0867 | −1.2573 |
| RAP2B | 238622_at | −0.9754 | 12812 | 0.007148 | 0.1493 | −1.2612 |
| WWP2 | 210200_at | −0.8035 | 12679 | 0.006838 | 0.1475 | −1.2622 |
| SMAP1 | 218137_s_at | −0.8588 | 12733 | 0.00404 | 0.1192 | −1.2642 |
| SLTM | 217828_at | −1.0985 | 12867 | 0.002486 | 0.1089 | −1.2656 |
| PSMD7 | 201705_at | −1.0548 | 12852 | 0.002486 | 0.1089 | −1.2665 |

TABLE 4-continued

| Gene | Affymetrix ProbeSet Number | Signal to Noise | Rank | p-value | FDR(BH) | Fold Change |
|---|---|---|---|---|---|---|
| DDR1 | 210749_x_at | −0.9248 | 12779 | 0.002797 | 0.1126 | −1.2692 |
| CTAGE5 | 235790_at | −0.933 | 12786 | 0.005594 | 0.1372 | −1.2702 |
| RFC5 | 213734_at | −1.0312 | 12842 | 0.002797 | 0.1126 | −1.2716 |
| VDAC3 | 208846_s_at | −1.3 | 12907 | 0.0006216 | 0.08198 | −1.2718 |
| C6orf62 | 213875_x_at | −1.3338 | 12912 | 0.0001 | 0 | −1.2748 |
| PPP1R11 | 201500_s_at | −1.0625 | 12855 | 0.002797 | 0.1126 | −1.2753 |
| YWHAZ | 214848_at | −1.1418 | 12877 | 0.001865 | 0.1043 | −1.2776 |
| PPID | 228469_at | −0.8815 | 12748 | 0.005284 | 0.1352 | −1.2824 |
| FAM65A | 45749_at | −0.9054 | 12765 | 0.002486 | 0.1089 | −1.2839 |
| DCUN1D1 | 240781_x_at | −0.9546 | 12795 | 0.003419 | 0.1181 | −1.2839 |
| SAP30 | 213963_s_at | −0.7529 | 12600 | 0.007148 | 0.1493 | −1.2844 |
| CRBN | 222533_at | −1.0508 | 12851 | 0.001865 | 0.1043 | −1.2858 |
| GATAD2A | 238324_at | −1.1395 | 12876 | 0.0006216 | 0.08198 | −1.2893 |
| RAB6A | 210406_s_at | −1.1114 | 12871 | 0.0003108 | 0.07173 | −1.2912 |
| ARF6 | 224788_at | −1.0124 | 12833 | 0.002176 | 0.1073 | −1.2949 |
| WDR44 | 235485_at | −0.8795 | 12746 | 0.005594 | 0.1372 | −1.2969 |
| PXN | 211823_s_at | −0.9265 | 12781 | 0.004662 | 0.1285 | −1.3009 |
| EPS15 | 217887_s_at | −0.9554 | 12797 | 0.00373 | 0.1192 | −1.3043 |
| LOC100506060 | 237464_at | −0.7397 | 12572 | 0.00373 | 0.1192 | −1.3067 |
| UBE2G1 | 226005_at | −0.8641 | 12736 | 0.005905 | 0.1406 | −1.3074 |
| ADAM8 | 205180_s_at | −0.8771 | 12744 | 0.00404 | 0.1192 | −1.3077 |
| CD164 | 208654_s_at | −1.0194 | 12838 | 0.001865 | 0.1043 | −1.3125 |
| OTUD3 | 213216_at | −1.0795 | 12859 | 0.001554 | 0.1014 | −1.3159 |
| TMED9 | 208757_at | −0.9255 | 12780 | 0.001243 | 0.09507 | −1.3187 |
| FBXO9 | 238472_at | −0.9448 | 12791 | 0.001865 | 0.1043 | −1.3228 |
| MYL12B | 221474_at | −1.2719 | 12903 | 0.0001 | 0 | −1.3278 |
| KDM2A | 208989_s_at | −0.9059 | 12768 | 0.005594 | 0.1372 | −1.3309 |
| FYCO1 | 218204_s_at | −0.8949 | 12757 | 0.004973 | 0.1317 | −1.3311 |
| DNAJA3 | 205963_s_at | −0.7026 | 12496 | 0.006838 | 0.1475 | −1.3327 |
| PPP2R5E | 229322_at | −0.9132 | 12772 | 0.002797 | 0.1126 | −1.3329 |
| CDK8 | 204831_at | −0.9187 | 12774 | 0.004973 | 0.1317 | −1.3357 |
| TOMM70A | 201519_at | −1.0354 | 12846 | 0.0003108 | 0.07173 | −1.3367 |
| KIAA0494 | 229524_at | −1.1918 | 12890 | 0.0009325 | 0.0867 | −1.3387 |
| VPS13C | 235023_at | −0.9027 | 12761 | 0.006838 | 0.1475 | −1.3402 |
| TM75E3 | 226478_at | −0.9943 | 12822 | 0.001554 | 0.1014 | −1.3436 |
| HIPK1 | 212293_at | −0.9311 | 12785 | 0.00404 | 0.1192 | −1.3468 |
| UFM1 | 242669_at | −1.0119 | 12831 | 0.001554 | 0.1014 | −1.347 |
| LTN1 | 23381_s_at | −0.8846 | 12751 | 0.005905 | 0.1406 | −1.3471 |
| PIGF | 205078_at | −0.8521 | 12728 | 0.004973 | 0.1317 | −1.3481 |
| RCOR3 | 241433_at | −0.9298 | 12783 | 0.00404 | 0.1192 | −1.3502 |
| VP54B | 218171_at | −0.8774 | 12745 | 0.006216 | 0.1445 | −1.3531 |
| ATP6AP2 | 201444_s_at | −1.2974 | 12905 | 0.0009325 | 0.0867 | −1.3542 |
| ZNF562 | 219163_at | −1.0021 | 12826 | 0.002486 | 0.1089 | −1.359 |
| TGOLN2 | 212043_at | −1.2854 | 12904 | 0.0003108 | 0.07173 | −1.3608 |
| AP5M1 | 222531_s_at | −0.8456 | 12722 | 0.006838 | 0.1475 | −1.3615 |
| KIAA0485 | 214295_at | −1.3268 | 12910 | 0.001243 | 0.09507 | −1.3652 |
| EIF4E | 242674_at | −1.0221 | 12839 | 0.002486 | 0.1089 | −1.3652 |
| RAP1A | 228548_at | −0.9502 | 12793 | 0.00404 | 0.1192 | −1.3669 |
| CYP3A5 | 243015_at | −0.863 | 12735 | 0.005594 | 0.1372 | −1.367 |
| TAF7 | 201023_at | −0.9073 | 12769 | 0.001865 | 0.1043 | −1.3675 |
| C17orf101 | 64438_at | −0.8429 | 12719 | 0.006527 | 0.1462 | −1.3705 |
| ARAP2 | 242402_x_at | −1.199 | 12891 | 0.0006216 | 0.08198 | −1.3739 |
| WSB2 | 201760_s_at | −1.5008 | 12922 | 0.0003108 | 0.07173 | −1.3756 |
| C14orf169 | 219526_at | −1.1472 | 12879 | 0.001243 | 0.09507 | −1.3764 |
| SRP9 | 201273_s_at | −0.9278 | 12782 | 0.001243 | 0.09507 | −1.3765 |
| PRICKLE4 | 223516_s_at | −0.9609 | 12804 | 0.001865 | 0.1043 | −1.3859 |
| HUS1 | 217618_x_at | −0.9728 | 12809 | 0.002486 | 0.1089 | −1.3909 |
| ZBTB11 | 242433_at | −0.7887 | 12662 | 0.006838 | 0.1475 | −1.3935 |
| C1orf56 | 230468_s_at | −0.7572 | 12609 | 0.006216 | 0.1445 | −1.3958 |
| DNAJB14 | 226399_at | −0.7533 | 12602 | 0.00404 | 0.1192 | −1.4024 |
| TMED10 | 238886_at | −0.827 | 12704 | 0.001865 | 0.1043 | −1.4075 |
| TBKBP1 | 205424_at | −0.7733 | 12638 | 0.004973 | 0.1317 | −1.4075 |
| RBM26 | 229433_at | −0.9556 | 12798 | 0.001865 | 0.1043 | −1.4086 |
| VPS26A | 243316_x_at | −0.8539 | 12730 | 0.006527 | 0.1467 | −1.4133 |
| SLK | 206875_s_at | −1.2644 | 12902 | 0.0006216 | 0.08198 | −1.4204 |
| GNAZ | 204993_at | −0.8741 | 12742 | 0.003108 | 0.1141 | −1.4217 |
| PDE4DIP | 232509_at | −0.8921 | 12754 | 0.00404 | 0.1192 | −1.4221 |
| TPP1 | 214196_s_at | −0.8765 | 12743 | 0.00404 | 0.1192 | −1.4228 |
| RNF5 | 216018_at | −1.1707 | 12884 | 0.0006216 | 0.08198 | −1.4264 |
| PDS5B | 242302_at | −0.8955 | 12758 | 0.001243 | 0.09507 | −1.4323 |
| MED4 | 222438_at | −0.9381 | 12788 | 0.006527 | 0.1462 | −1.4327 |
| BCL2L13 | 226798_at | −0.9 | 12759 | 0.005284 | 0.1352 | −1.434 |
| ERB82IP | 232896_at | −1.1207 | 12873 | 0.0009325 | 0.0867 | −1.4399 |
| PCNP | 237577_at | −1.0766 | 12858 | 0.003108 | 0.1141 | −1.4412 |
| FAM18B1 | 218446_s_at | −0.9766 | 12813 | 0.001865 | 0.1043 | −1.4417 |
| ELF4 | 31845_at | −1.1764 | 12885 | 0.0001 | 0 | −1.4442 |

TABLE 4-continued

| Gene | Affymetrix ProbeSet Number | Signal to Noise | Rank | p-value | FDR(BH) | Fold Change |
|---|---|---|---|---|---|---|
| ADCY7 | 203741_s_at | −0.9049 | 12764 | 0.006838 | 0.1475 | −1.4457 |
| VPS13A | 231585_at | −1.0576 | 12854 | 0.0006216 | 0.08198 | −1.4501 |
| MEAF6 | 228517_at | −1.4912 | 12921 | 0.0001 | 0 | −1.4765 |
| SRSF11 | 236948_x_at | −1.0158 | 12835 | 0.003419 | 0.1181 | −1.4789 |
| FUBP3 | 239193_at | −0.9538 | 12794 | 0.00373 | 0.1192 | −1.4808 |
| RAB9A | 221808_at | −1.0957 | 12866 | 0.001243 | 0.09507 | −1.4902 |
| RP2 | 205191_at | −0.8496 | 12725 | 0.005905 | 0.1406 | −1.4911 |
| FAM8A1 | 203420_at | −0.9731 | 12810 | 0.004973 | 0.1317 | −1.4963 |
| BICD2 | 213154_s_at | −0.9685 | 12808 | 0.005594 | 0.1372 | −1.5019 |
| ANKRD49 | 219069_at | −1.0451 | 12850 | 0.002486 | 0.1089 | −1.5034 |
| ATF2 | 212984_at | −1.2594 | 12899 | 0.0003108 | 0.07173 | −1.5058 |
| UBQLN2 | 215884_s_at | −0.957 | 12800 | 0.002486 | 0.1089 | −1.5065 |
| AGL | 203566_s_at | −1.2146 | 12893 | 0.0001 | 0 | −1.515 |
| CASP8 | 213373_s_at | −0.9334 | 12787 | 0.003108 | 0.1141 | −1.5232 |
| DZANK1 | 219951_s_at | −0.9801 | 12817 | 0.00404 | 0.1192 | −1.5514 |
| UEVLD | 220775_s_at | −0.8363 | 12712 | 0.00373 | 0.1192 | −1.5562 |
| C1D | 200056_s_at | −1.4076 | 12916 | 0.001865 | 0.1043 | −1.5637 |
| QKI | 241938_at | −1.332 | 12911 | 0.0003108 | 0.07173 | −1.5651 |
| BCL10 | 205263_at | −0.8137 | 12690 | 0.005284 | 0.1352 | −1.5731 |
| DSTN | 230933_at | −0.9564 | 12799 | 0.002486 | 0.1089 | −1.5771 |
| MAP4K5 | 211081_s_at | −1.1676 | 12883 | 0.003108 | 0.1141 | −1.5815 |
| ARL5A | 243176_at | −1.0387 | 12847 | 0.001243 | 0.09507 | −1.5866 |
| NKG7 | 213915_at | −0.9405 | 12789 | 0.00373 | 0.1192 | −1.5884 |
| CA11 | 209726_at | −0.7067 | 12507 | 0.007148 | 0.1493 | −1.5954 |
| SPINLW1 | 206319_s_at | −1.3118 | 12909 | 0.001243 | 0.09507 | −1.5986 |
| RAP1GAP2 | 213280_at | −0.9187 | 12775 | 0.004973 | 0.1317 | −1.603 |
| PANK3 | 221751_at | −1.0948 | 12865 | 0.0006216 | 0.08198 | −1.6069 |
| TMA16 | 218513_at | −0.8647 | 12737 | 0.005905 | 0.1406 | −1.6161 |
| MST4 | 224407_s_at | −1.4622 | 12919 | 0.0001 | 0 | −1.6189 |
| XPNPEP2 | 216910_at | −0.9975 | 12825 | 0.006527 | 0.1462 | −1.621 |
| MICB | 206247_at | −0.8585 | 12731 | 0.007148 | 0.1493 | −1.622 |
| NPTN | 202228_s_at | −1.4245 | 12918 | 0.0001 | 0 | −1.6221 |
| S1PR5 | 233743_x_at | −1.1848 | 12889 | 0.0006216 | 0.08198 | −1.6397 |
| CACNB3 | 34726_at | −1.3554 | 12914 | 0.0006216 | 0.08198 | −1.6523 |
| SLC20A1 | 230494_at | −1.4102 | 12917 | 0.0003108 | 0.07173 | −1.659 |
| TDRD7 | 213361_at | −1.0745 | 12857 | 0.0003108 | 0.07173 | −1.6619 |
| FAM3C | 240062_at | −0.9075 | 12770 | 0.001243 | 0.09507 | −1.6633 |
| CHSY1 | 203044_at | −0.9212 | 12776 | 0.005905 | 0.1406 | −1.6708 |
| LOC100509751 | 228019_s_at | −0.9648 | 12807 | 0.002486 | 0.1089 | −1.6933 |
| SPRYD7 | 230151_at | −1.1444 | 12878 | 0.0006216 | 0.08198 | −1.6958 |
| PAK6 | 219461_at | −0.9418 | 12790 | 0.00373 | 0.1192 | −1.697 |
| CLCF1 | 219500_at | −0.9969 | 12824 | 0.003108 | 0.1141 | −1.7058 |
| SSX2IP | 210871_x_at | −1.1155 | 12872 | 0.001865 | 0.1043 | −1.7475 |
| GOLGA8IP | 213737_x_at | −1.0709 | 12856 | 0.002486 | 0.1089 | −1.752 |
| IFNGR1 | 242903_at | −0.9212 | 12777 | 0.001554 | 0.1014 | −1.7701 |
| RHOC | 235742_at | −1.0559 | 12853 | 0.003108 | 0.1141 | −1.7934 |
| CPEB3 | 243651_at | −1.221 | 12894 | 0.0003108 | 0.07173 | −1.7952 |
| TGFBR3 | 226625_at | −0.9961 | 12823 | 0.003108 | 0.1141 | −1.7999 |
| PPP3CA | 202457_s_at | −1.0337 | 12845 | 0.002176 | 0.1073 | −1.8039 |
| GALNT10 | 230906_at | −1.0852 | 12862 | 0.005594 | 0.1372 | −1.8054 |
| ZNF137P | 207394_at | −1.3036 | 12908 | 0.0006216 | 0.08198 | −1.8262 |
| RAB11FIP5 | 210879_s_at | −1.0158 | 12836 | 0.003108 | 0.1141 | −1.8307 |
| SNX24 | 239739_at | −0.9861 | 12821 | 0.00373 | 0.1192 | −1.8719 |
| RCAN1 | 215254_at | −0.8229 | 12701 | 0.00373 | 0.1192 | −1.8819 |
| XBP1 | 242021_at | −1.1825 | 12887 | 0.001554 | 0.1014 | −1.9028 |
| NAA40 | 222369_at | −1.2516 | 12898 | 0.0006216 | 0.08198 | −1.9045 |
| DPY19L1 | 215433_at | −0.8661 | 12739 | 0.00404 | 0.1192 | −1.9074 |
| PPP2R2B | 213849_s_at | −0.894 | 12756 | 0.006838 | 0.1475 | −1.9443 |
| MCTP2 | 243109_at | −0.9057 | 12767 | 0.006527 | 0.1462 | −1.9686 |
| HERC5 | 219863_at | −0.8798 | 12747 | 0.004351 | 0.1241 | −1.9733 |
| GNPTAB | 240106_at | −1.1841 | 12888 | 0.0003108 | 0.07173 | −1.9914 |
| IGF2R | 201393_s_at | −1.2358 | 12895 | 0.0003108 | 0.07173 | −2.0166 |
| SLC35G2 | 219569_s_at | −0.9607 | 12803 | 0.004973 | 0.1317 | −2.0201 |
| TTC38 | 218272_at | −1.0917 | 12863 | 0.002486 | 0.1089 | −2.0559 |
| LPAL2 | 210909_x_at | −0.9117 | 12771 | 0.005905 | 0.1406 | −2.0607 |
| MAF | 209348_s_at | −1.0125 | 12834 | 0.002797 | 0.1126 | −2.0716 |
| UBE2E3 | 210024_s_at | −1.3387 | 12913 | 0.0001 | 0 | −2.0872 |
| BMI1 | 202265_at | −1.2995 | 12906 | 0.0003108 | 0.07173 | −2.0904 |
| ARHGEF12 | 234544_at | −1.21 | 12892 | 0.0006216 | 0.08198 | −2.1042 |
| MAN1A1 | 221760_at | −0.9571 | 12801 | 0.00404 | 0.1192 | −2.1058 |
| GBE1 | 203282_at | −1.2602 | 12900 | 0.0001 | 0 | −2.1332 |
| B3GAT1 | 219521_at | −0.9029 | 12762 | 0.006527 | 0.1462 | −2.1587 |
| ENPP4 | 204161_s_at | −1.0943 | 12864 | 0.001865 | 0.1043 | −2.1683 |
| VAV3 | 224221_s_at | −1.0424 | 12848 | 0.002797 | 0.1126 | −2.187 |
| SOX13 | 38918_at | −0.9633 | 12805 | 0.005594 | 0.1372 | −2.2081 |
| SETBP1 | 227478_at | −0.9643 | 12806 | 0.00373 | 0.1192 | −2.2191 |

TABLE 4-continued

| Gene | Affymetrix ProbeSet Number | Signal to Noise | Rank | p-value | FDR(BH) | Fold Change |
|---|---|---|---|---|---|---|
| EFHD2 | 222483_at | −1.135 | 12874 | 0.001554 | 0.1014 | −2.2398 |
| FAM49A | 230276_at | −1.0164 | 12837 | 0.001865 | 0.1043 | −2.3099 |
| SESN1 | 218346_s_at | −1.0119 | 12832 | 0.002176 | 0.1073 | −2.314 |
| GZMH | 210321_at | −0.9823 | 12818 | 0.00373 | 0.1192 | −2.4241 |
| ZEB2 | 235593_at | −1.0848 | 12861 | 0.0006216 | 0.08198 | −2.4852 |
| KLRG1 | 210288_at | −0.9548 | 12796 | 0.00404 | 0.1192 | −2.5442 |
| SLCO4C1 | 222071_s_at | −1.4875 | 12920 | 0.0003108 | 0.07173 | −2.6663 |
| KLRAP1 | 207229_at | −1.1575 | 12882 | 0.0001 | 0 | −2.9092 |
| ADRB2 | 206170_at | −1.2637 | 12901 | 0.0009325 | 0.0867 | −3.1899 |
| KLRD1 | 210606_x_at | −1.103 | 12869 | 0.002486 | 0.1089 | −3.2576 |
| PSTPIP2 | 219938_s_at | −1.1531 | 12881 | 0.0003108 | 0.07173 | −3.3844 |
| SLC4A4 | 211494_s_at | −1.0845 | 12860 | 0.001865 | 0.1043 | −3.5152 |
| FGR | 208438_s_at | −1.1813 | 12886 | 0.001554 | 0.1014 | −3.8525 |
| GPR56 | 212070_at | −1.2429 | 12897 | 0.001243 | 0.09507 | −4.074 |
| CACNA2D2 | 204811_s_at | −1.6569 | 12923 | 0.0009325 | 0.0867 | −4.4381 |
| PRSS23 | 229441_at | −1.1073 | 12870 | 0.002486 | 0.1089 | −4.6908 |
| KLRF1 | 220646_s_at | −0.9015 | 12760 | 0.004351 | 0.1241 | −4.9476 |
| PTCH1 | 209816_at | −0.9827 | 12819 | 0.003108 | 0.1141 | −5.1609 |
| CX3CR1 | 205898_at | −0.9172 | 12773 | 0.005905 | 0.1406 | −5.8299 |

In order to identify biological processes that were differentially active in CD39+ vs. CD39− cells, gene set enrichment analysis using the Gene Ontology collection of gene sets (Ashburner et al. (2000) Nat. Genet. 25:25-29) was performed. No significant enrichment of GO terms in the CD39− CD8+ subset was identified. By contrast, 21 gene sets significantly enriched (FDR<0.1) in the CD39+ population, almost all of which were related to mitosis and cell cycle related genes or cytoskeleton organization (FIG. 7B), were identified. These results indicate that CD39+ CD8+ T cells show coordinate up-regulation of genes related to proliferation.

Figure 7:
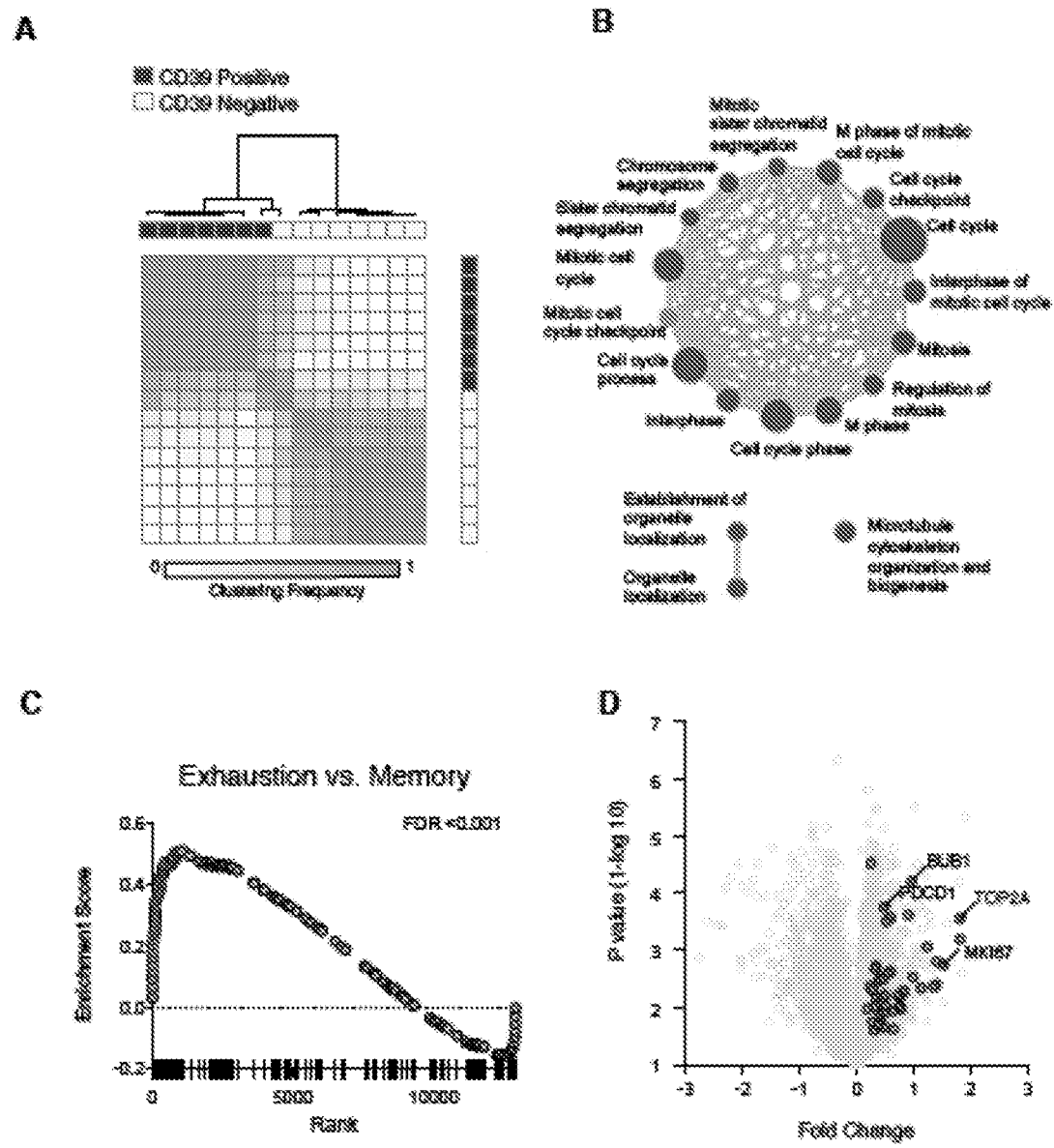
FIG. 7 includes 4 panels, identified as panels A, B, C, and D, which show the results of transcriptional analysis of CD39$^-$ and CD39$^-$ CD8$^+$ T cells in HCV infection. Panel A shows a consensus hierarchical clustering of expression profiles from CD39$^+$ (black) and CD39$^-$ (grey) CD8$^+$ T cells from 8 HCV infected patients. Clustering is based on the top 10% of genes by variance across the dataset. Sample similarity (1-Pearson correlation coefficient) is annotated with color from low (white) to high (dark). Panel B shows a gene set enrichment map displaying Gene Ontology gene sets enriched (FDR<0.1) in CD39$^+$ CD8$^+$ T cells from Panel A. Nodes are sized in proportion to gene set size and the connecting line thickness represents extent of gene member overlap between gene sets. Panel C shows the results of gene set enrichment analysis of a signature of 200 genes up-regulated in exhausted CD8$^+$ T cells from the mouse model of chronic viral infection versus acute infection (day 30 post infection) in the ranked list of genes differentially expressed in CD39$^+$ vs. CD39$^-$ CD8$^+$ T cells. Leading edge genes are indicated by symbols. Panel D shows a volcano plot of all genes (grey) or exhausted leading edge genes (dark).

CD39 is expressed by CD8+ T cells in chronic, but not acute/latent infection, indicating that it may be a marker of T cell exhaustion. It was tested whether the profile of CD39+ CD8+ T cells was enriched for genes expressed by exhausted CD8+ cells. Previous studies of gene expression in CD8+ T cells in the mouse model of chronic viral infection with the Clone 13 strain of LCMV have identified global signatures of T cell exhaustion that are conserved in exhausted CD8+ T cells in humans (Doering et al. (2012) Immunity 37:1130-1144; Quigley et al. (2010) Nat. Med. 16:1147-1151; Baitsch et al. (2011) J. Clin. Invest. 121:2350-2360). Thus, a signature of 200 genes up-regulated by exhausted CD8+ T cells responding to chronic infection relative to functional memory CD8+ T cells generated by acute infection (LCMV Armstrong strain) was curated. The exhausted CD8+ T cell signature from LCMV model was found to be significantly enriched in CD39+ vs. CD39 CD8+ T cells in subjects with HCV infection (FIG. 7C). The "leading edge" genes contributing most to the enrichment (Subranmanian et al. (2005) Proc. Natl. Acad. U.S.A. 102:15545-15550), which correspond to genes up-regulated both in the mouse exhausted signature and in the human CD39+ profile, were focused upon. As expected, the leading edge genes included PD-1 (PDCD1), a feature of both human CD39+ CD8+ T cells and of exhausted CD8+ T cells in the mouse model (FIG. 7D). In addition, it was found that up-regulation of many genes associated with proliferation, including BUB1, TOP2A and MKI67, was common to mouse exhausted CD8+ T cells and human CD39+ CD8+ T cells. Thus, CD39+ CD8+ T cells in HCV infection share transcriptional features with exhausted CD8+ T cells in a mouse model of chronic infection that are predominantly related to pathways representing proliferation.

Figure 8:
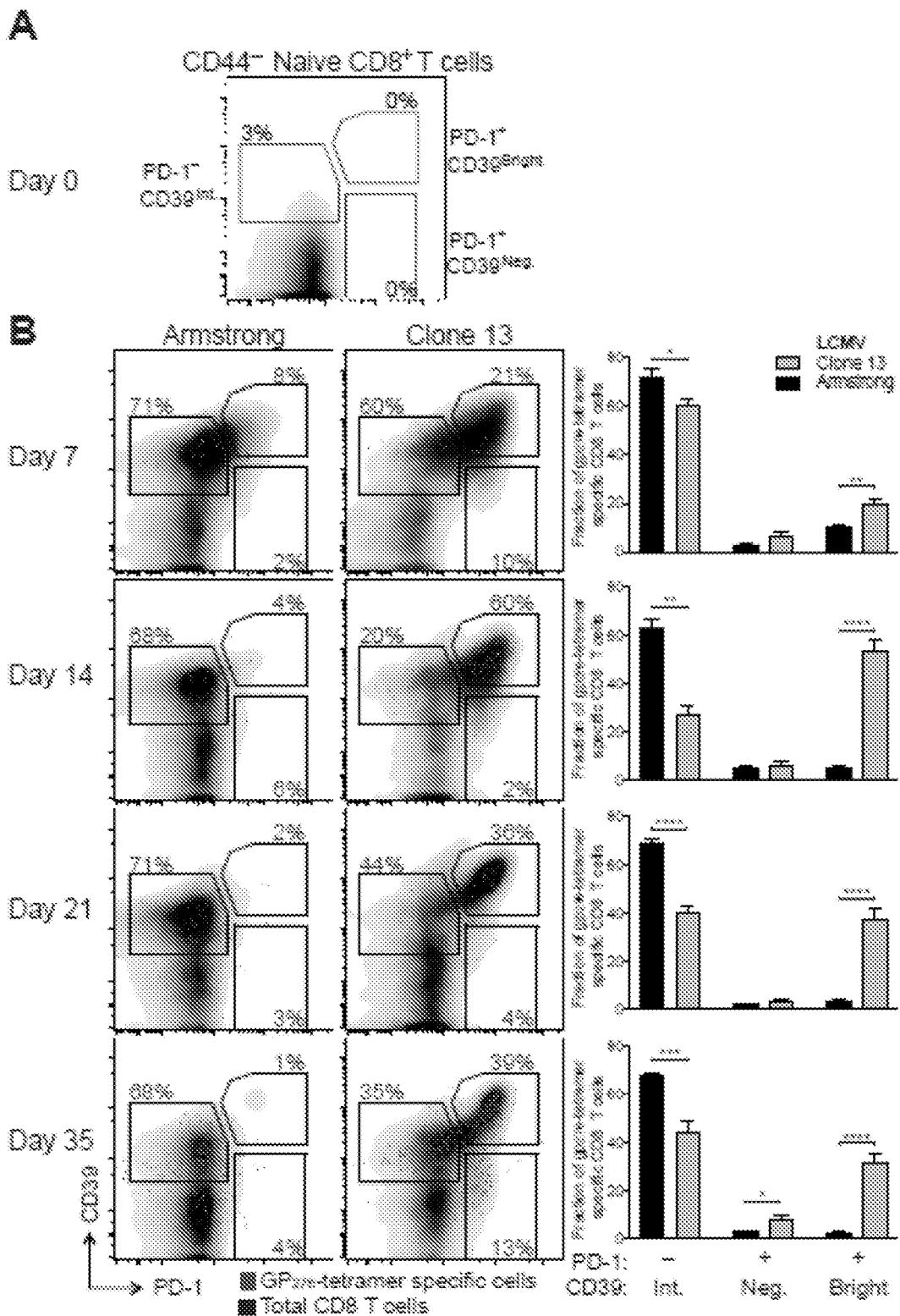
FIG. 8 includes 2 panels, identified as panels A and B, which show that CD39 is highly upregulated by exhausted CD8$^+$ T cells in a mouse model of chronic infection. The expression of CD39 and PD-1 on CD44$^-$ naive CD8$^+$ T cells (Panel A) and in CD8$^+$ T cells at indicated times following LCMV Armstrong (acute) or Clone 13 (chronic) infection (Panel B) is shown. Representative plots show total (black) and H-2Db GP$_{276-286}$ tetramer-specific CD8$^+$ T cells. Summary of results in 5 mice per group is shown in bar-graphs on the right. Statistical significance was assessed with unpaired student's t-test. *P<0.5, P<0.01, *P<0.001, ****P<0.0001.

Example 6: CD39 is Increased in Exhausted CD8+ T Cells in the Mouse Model of Chronic Viral Infection Since the mouse signature of CD8+ T cell exhaustion was significantly enriched in the transcriptional prolife of CD39+ CD8+ T cells in HCV-infected patients, it was next asked whether CD39 was up-regulated by CD8+ T cells in the mouse model of chronic viral infection. To address this question, two well-described mouse models of viral infection using two strains of Lymphocytic choriomenigitis virus (LCMV), LCMV Armstrong that causes acute infection that is resolved in up to 8 days and LCMV Clone 13 that persists in mice for up to 3 months and leads to T cell exhaustion, were compared. CD39 expression was measured and the levels were compared to PD-1 expression levels (Wherry et al. (2007) Immunity 27:670-684; Barber et al. (2006) Nature 439:682-687) in CD8+ T cells responding to each infection. While naive CD8+ T cells expressed neither CD39 nor PD-1 (FIG. 8A), both were rapidly up-regulated in antigen-experienced cells following either infection (day 7 post infection [d7 p.i.]) (FIG. 8B). However, in acute infection, the fraction of CD39 bright PD-1+ population decreased with time. In contrast, high expression of CD39 and PD-1 was maintained in Clone 13 infection. While there was a trend in accumulation of CD39 bright PD-1+ cells among total CD8+ population, this was most apparent in the H-2D$^b$ GP$_{276-286}$ tetramer-specific CD8+ T cells (FIG. 8B).

Thus, after chronic viral infection, exhausted antigen-specific CD8+ T cells can be identified by both high CD39 and PD-1 expression. This difference in expression of both markers between chronic and acute infection is noticeable as early as d7 p.i., but becomes even more pronounced as the infection progresses.

Figure 9:
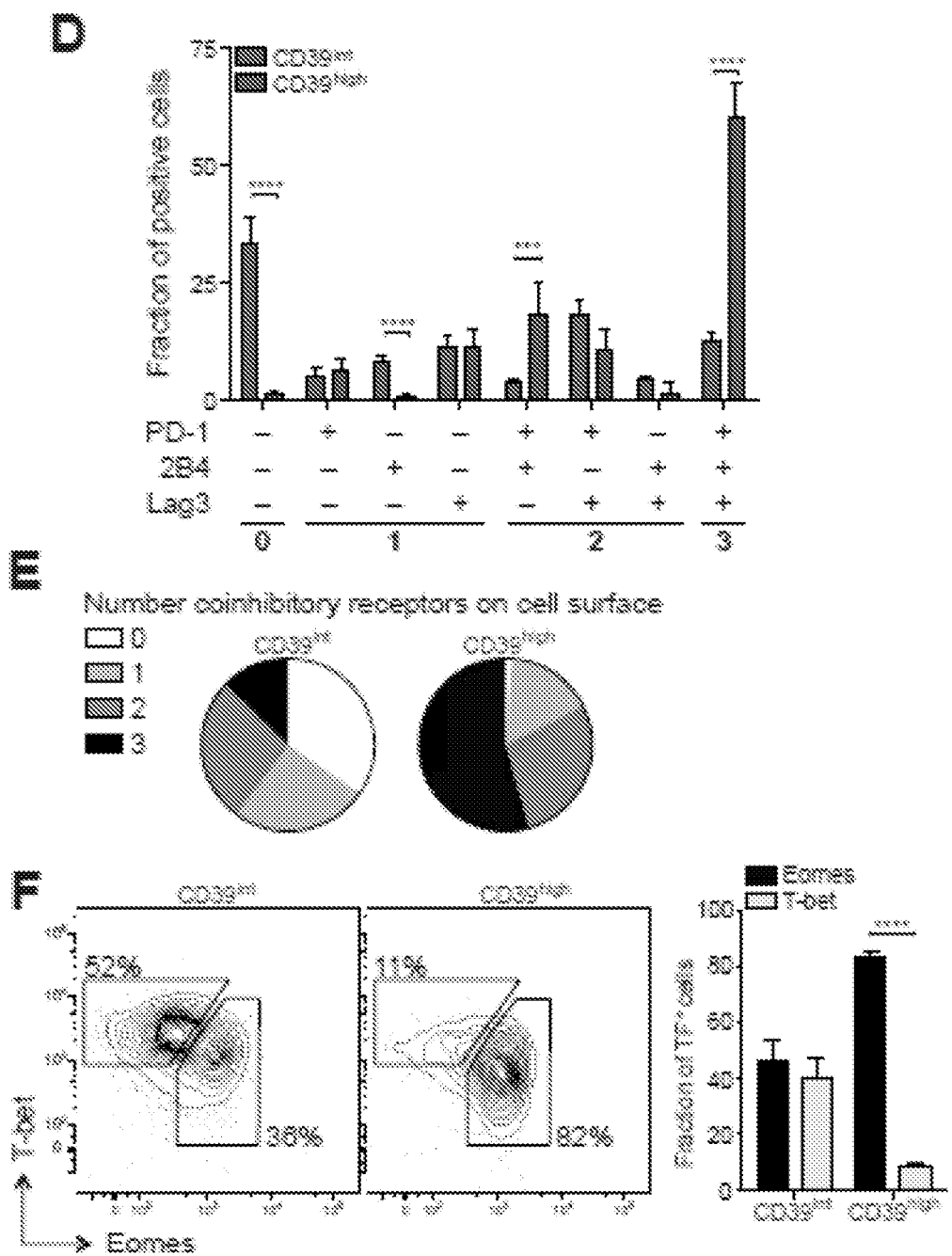
FIG. 9 includes 6 panels, identified as panels A, B, C, D, E, and F, which show that CD39 identifies terminally exhausted CD8$^+$ T cells in a mouse model of chronic infection. Panel A shows the expression of CD39 on CD44$^+$ CD8$^+$ T cells in spleens of mice 30-35 days following LCMV Armstrong (left) or Clone 13 (right) infection. Representative histograms (left) of CD127 (Panel B) and PD-1 (Panel C) expression by CD39$^{high}$ and CD39$^{int}$ CD8$^+$ T cells from Clone 13 and CD39$^+$ from Armstrong (filled gray) infected mice on d35 p.i. (left) are shown. The fraction of CD127$^+$ (Panel B) and MFI of PD-1 in PD-1$^+$ cells (Panel C) is shown on the right. Results are from 5 mice. Panel D shows the fraction of CD39$^{high}$ and CD39$^{int}$ CD44$^+$ CD8$^+$ T cells expressing different combinations of co-inhibitory receptors PD-1, 2B4, and Lag3. Panel E shows the average number of co-inhibitory receptors expressed by CD39$^{int}$ (left) or CD39$^{high}$ (right) CD8$^+$ T cells at d35 p.i. following LCMV Clone 13 infection. Panel F shows representative plots of T-bet and Eomes expression in CD39$^{int}$ (left) and CD39$^{high}$ (right) cells as in Panel A. A summary of results is shown on the right. The data are representative of three experiments of 5 mice per group. Statistical significance was assessed with Student's t-test (Panels B-C and F) with Holm-Sidak multiple comparison correction (Panel D). P<0.01, **P<0.0001.

Example 7: CD39 Identifies Terminally Exhausted CD8+ T Cells in Humans and in a Mouse Model Having determined that high, persistent expression of CD39 is a feature of LCMV-specific CD8+ T cells in mouse chronic infection models, it was next sought to further characterize the phenotype of CD39⁺ CD8+ T cells during Clone 13 infection. CD39 expression in antigen-experienced, CD44⁺ CD8⁺ T cells and found that mice infected with Clone 13 developed a population of cells with high expression of CD39 (CD39$^{high}$) was analyzed. This population was entirely absent in mice infected with the acute LCMV Armstrong strain, which only exhibited the presence of intermediate levels of CD39 staining (CD39$^{int}$) (FIG. 9A). Further characterization of the two sub-populations in Clone 13 infected mice revealed that the CD39$^{high}$ cells showed down-regulated CD127 (FIG. 9B) and expressed significantly higher levels of PD-1 (FIG. 9C) than did the CD39$^{int}$ population.

Figure 10:
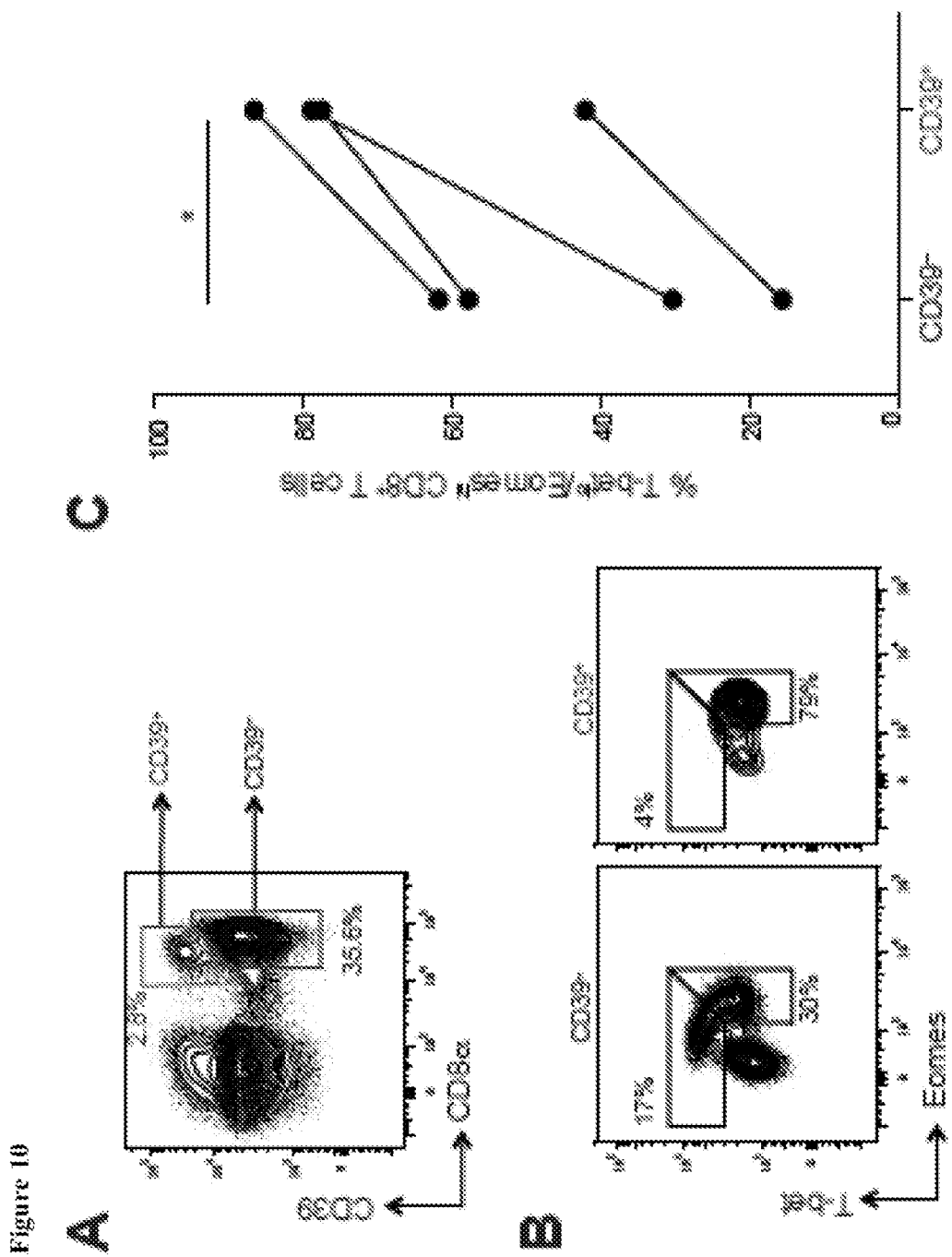
FIG. 10 includes 3 panels, identified as panels A, B, and C, which show a comparison of T-bet and Eomes expression by CD39$^+$ and CD39 CD8$^+$ T cells in HIV infection. Panel A shows the expression of CD39 in CD8$^+$ T cells in patients infected with HIV. Panel B shows the expression of transcription factors T-bet and Eomes on CD39 and CD39$^+$ populations identified in Panel A. Panel C shows a summary of the frequency of Eomces$^{hi}$/T-bet$^{lo}$ T cells in CD39$^-$ and CD39$^+$ CD8$^+$ T cells in HIV infection. Statistical significance was assessed with paired Student's t-test. *P<0.05.

Because the highest levels of PD-1 are characteristic of terminally exhausted CD8 T cells in chronic infection (Blackburn et al. (2008) Proc. Natl. Acad. Sci. U.S.A. 105:15016-15021; Blackburn et al. (2009) Nat. Immunol. 10:29-37), it was determined whether CD39$^{high}$ T cells in chronic infection showed other phenotypic characteristics of terminal exhaustion. Analysis of expression of two additional co-inhibitory receptors, CD244 (2B4) and Lag3, showed that a significantly higher fraction of CD39$^{high}$ cells co-expressed multiple receptors, consistent with terminal exhaustion. By contrast, CD39$^{int}$ CD8⁺ T cells were generally negative for all three receptors analyzed (FIGS. 9D-9E). The expression of transcription factors, T-bet and Eomes, were also analyzed. It was found that the CD39$^{high}$ subset of CD8⁺ T cells was comprised primarily of the Eomes$^{high}$ T-bet$^{low}$ terminally exhausted phenotype, while the CD39$^{int}$ CD8⁺ T cells showed an equal distribution of both (FIG. 9F). Similarly, it was found that in CD8⁺ T cells from subjects with HIV infection, a significantly higher fraction of CD39⁺ CD8⁺ T cells were Eomes$^{high}$ T-bet$^{low}$ compared to CD39⁻ CD8⁺ T cells (FIG. 10). Thus, in both humans and mice with chronic viral infection, CD39⁺ CD8⁺ T cells show a phenotype of terminal exhaustion.

Figure 11:
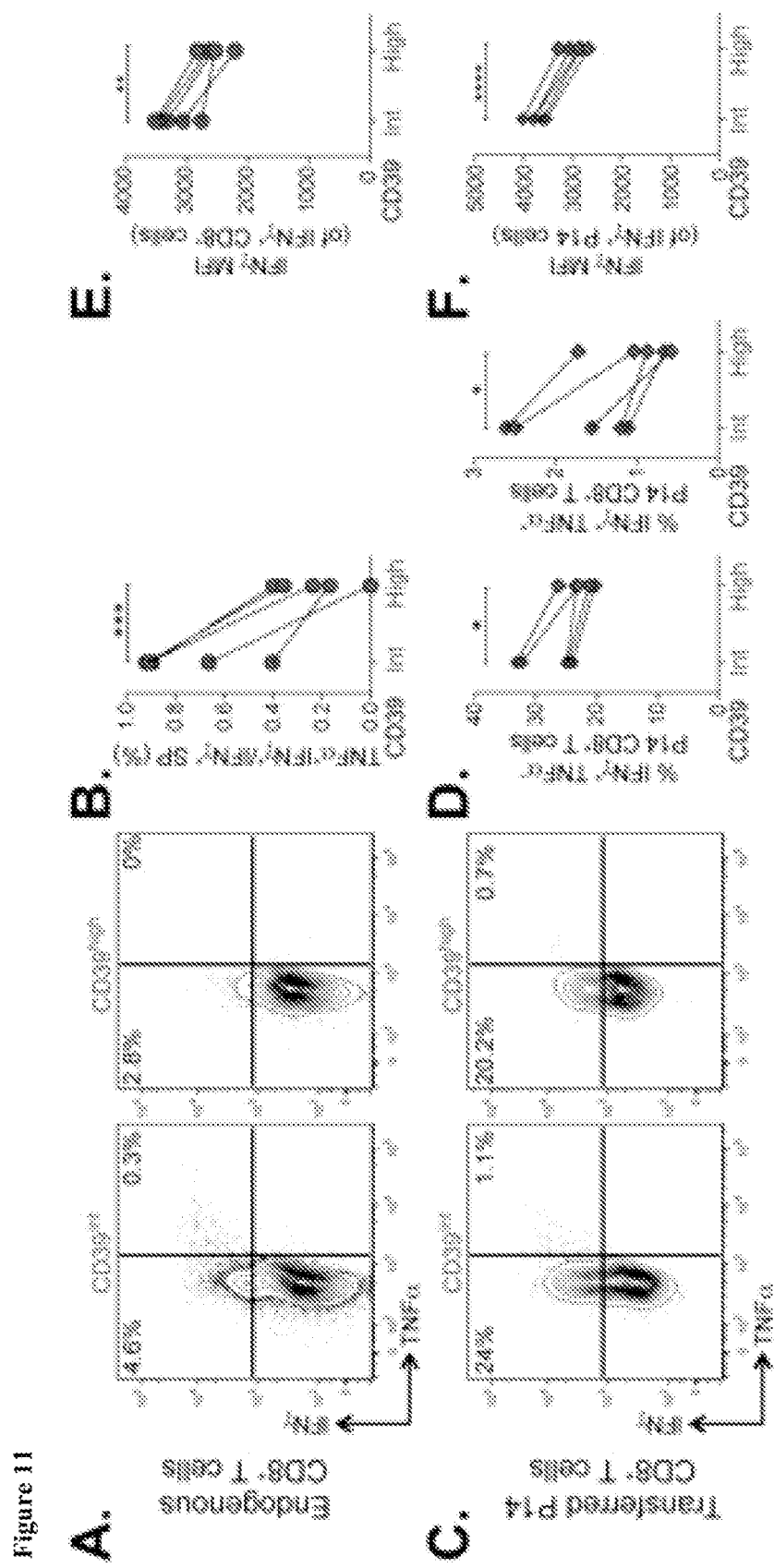
FIG. 11 includes 6 panels, identified as panels A, B, C, D, E, and F, which show that terminally exhausted CD8$^+$ T cells marked by high levels of CD39 are most impaired in their effector function. Panel A shows representative plots showing the production of IFN-γ and TNFα in CD39$^{int}$ or CD39$^{high}$ CD8$^+$ T cells 36 days following LCMV Clone 13 infection. Panel B shows quantification of cells in panel A that produce both TNFα and IFN-γ relative to IFN-γ only. Panels C and D show cytokine production by P14 cells (panel C) gated from an infection as in panel A and summary of IFN-γ and TNFα producing cells (panel D). Panels E and F show the mean fluorescence intensity (MFI) of IFN-γ in IFN-γ positive endogenous (panel E) and transferred P14 cells (panel F). Statistical significance was assessed with paired Student's t-test. *P<0.05. P<0.01, *P<0.001. ****P<0.0001.

The identification of CD39 as a marker of terminally exhausted CD8⁺ T cells in humans and in a mouse model was further confirmed based on analyzing the function of such T cells. FIG. 11 shows that the CD39$^{high}$ cells in the context of chronic viral infection produce the least amount of proinflammatory cytokines in a ex vivo reactivation challenge with viral antigen. FIG. 11 shows that both the fraction of cytokine production and the amount of cytokine by the positive cells is lower in the CD8⁺ CD39$^{high}$ T cell population as compared to CD8⁺ T cells expressing intermediate CD39 (CD39$^{int}$).

Figure 12:
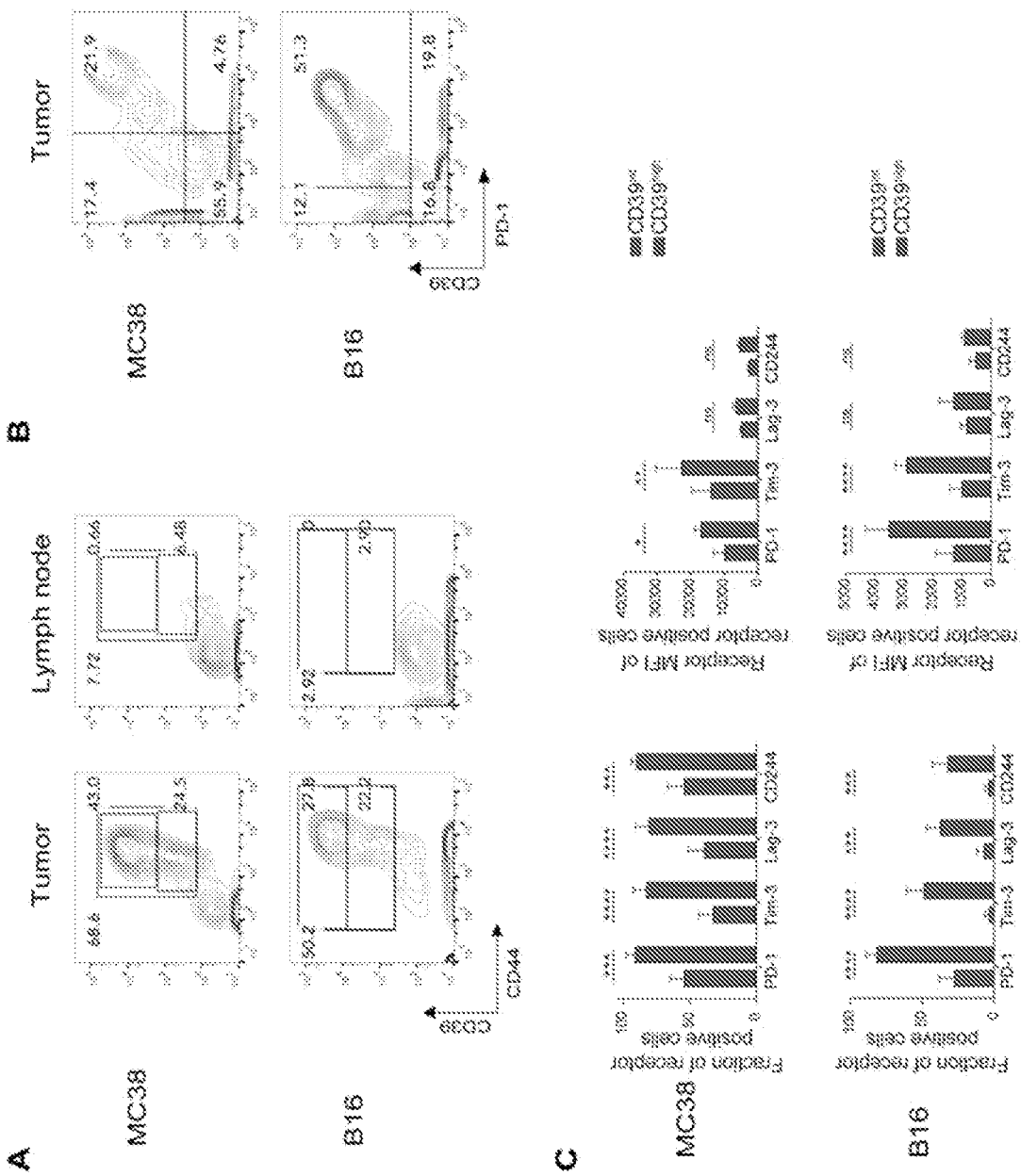
FIG. 12 includes 5 panels, identified as panels A, B, C, D and E, which show that CD39 is highly expressed by dysfunctional tumor infiltrating lymphocytes (TILs). Panel A shows representative plots showing the presence of CD39$^{int}$ and CD39$^{high}$ CD8$^+$ T cells in MC38 and B16 tumors 21 days following tumor inoculation. Panel B shows overlap of CD39$^{hi}$ and PD-1$^{hi}$ staining on CD8$^+$ T cells in the MC38 and B16 tumor models. Panel C shows a quantification of % receptor positive (left) and mean fluorescence intensity (right) of the coinhibitory receptors PD-1, Tim-3, Lag-3, and CD244 on CD8$^+$ T cells as in panel A from MC38 and B16 tumors. Panel D shows a quantification of T-bet, Tox, and Eomes positivity in CD8$^+$ CD44$^+$ cells, CD8$^+$ CD44$^+$ CD39$^+$ cells, CD8$^+$ CD44$^+$ CD39$^{hi}$ cells, and CD8$^+$ CD44$^+$ CD39$^+$ cells in MC38 tumors 21 days following tumor inoculation. Panel E shows quantification of cells as in panel A that produce the cytokine TNFα (left panel), TNFα and IFNγ (middle panel), and IL-2 (right panel) in MC38 tumors 21 days following tumor inoculation. MFI refers to the mean fluorescence intensity. Statistical significance was assessed with a two-way ANOVA. *P<0.05, P<0.01, *P<0.001, ****P<0.0001.
Figure 12:
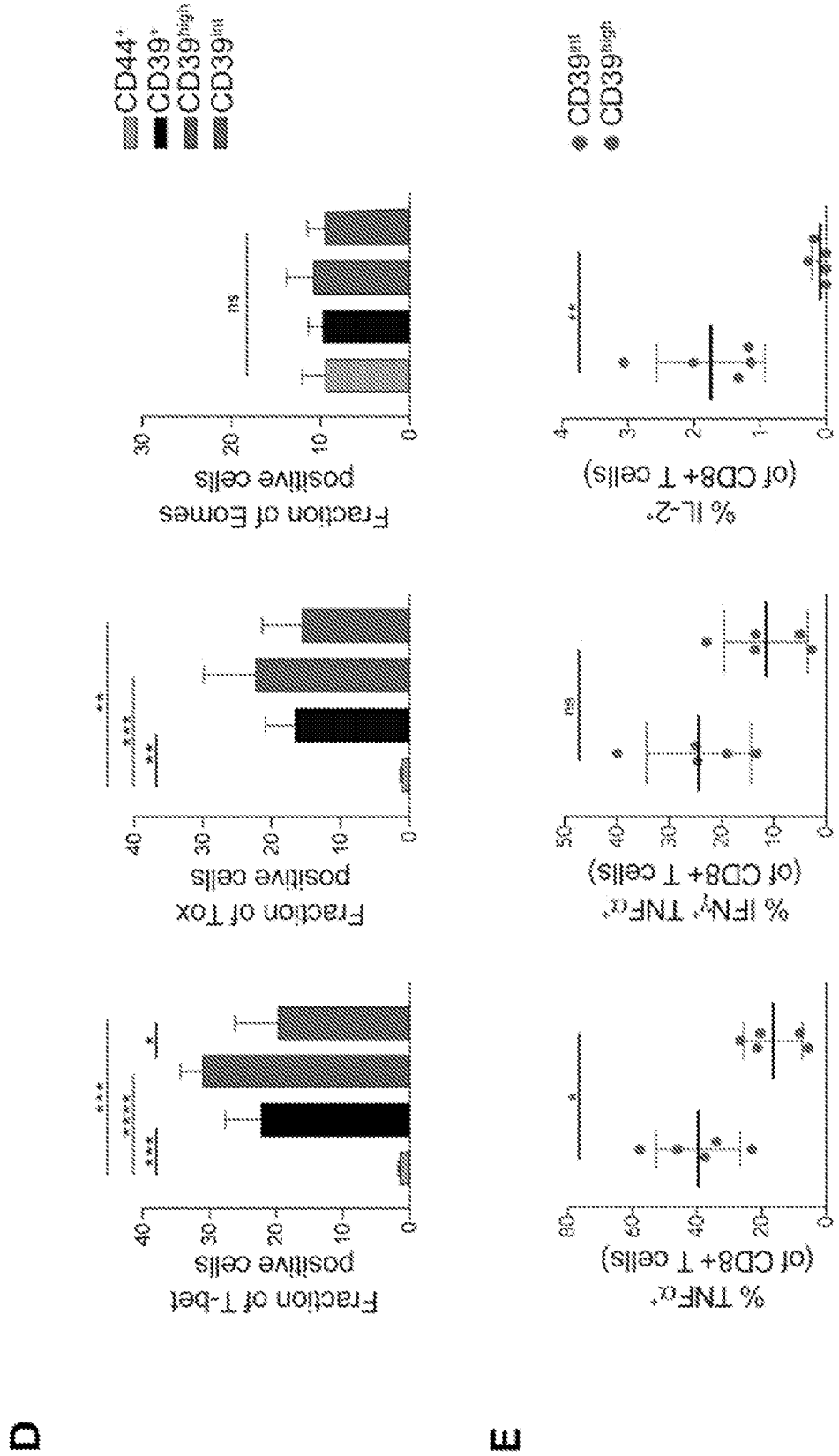
Figure 13:
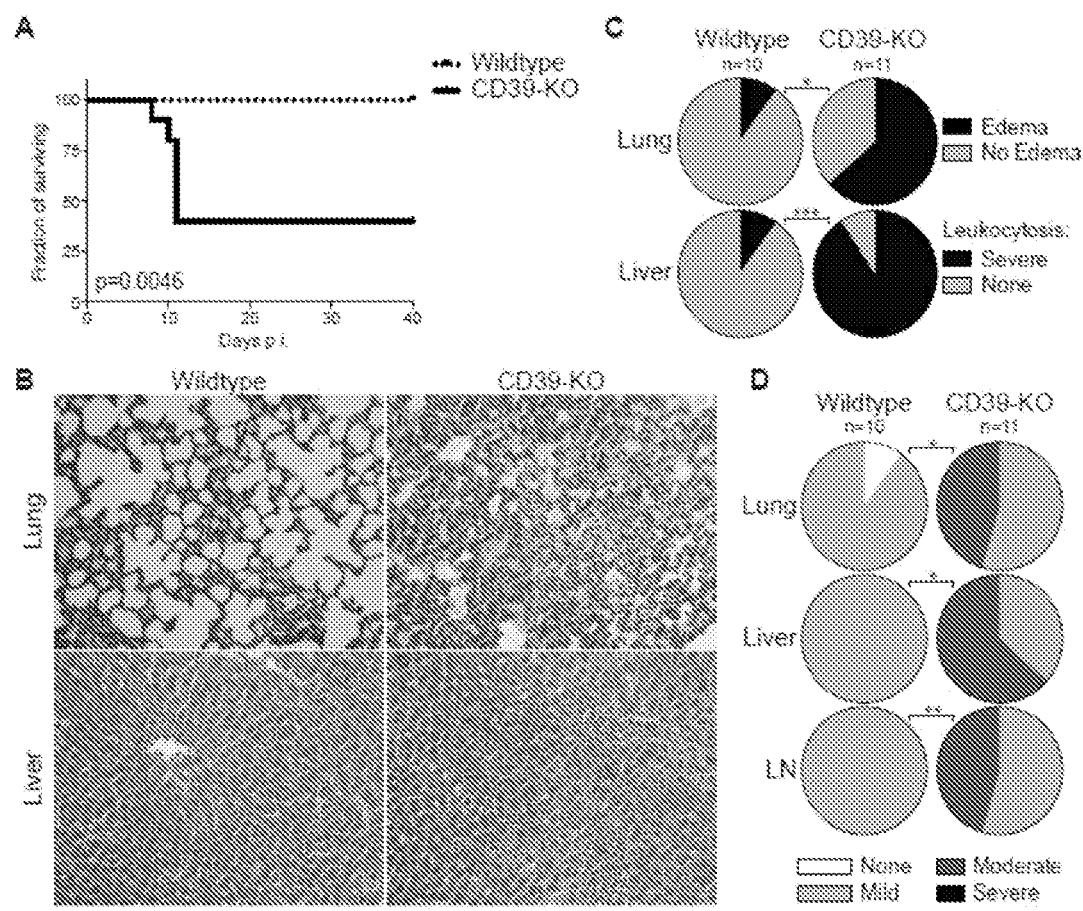
FIG. 13 includes 4 panels, identified as panels A, B, C, and D, which show that CD39 deficient mice exhibit increased mortality to LCMV-Clone 13 due to exacerbated immune response in target organs. Panel A shows the results of mortality of CD39 knockout and wild-type mice following LCMV Clone 13 infection and indicate that a significant proportion of knockout animals succumb to LCMV-Clone 13 infection in the first 10 days of infection. Panels B-D show histopathological analyses (H&E) of target organs 8-9 days following LCMV-Clone 13 infection. Panel B shows representative lung (top) and liver (bottom) images with quantification of lung edema (Panel C, top) and liver leukocytosis (Panel C, bottom). Panel D shows the severity of leukocyte infiltration in lung (top) and liver (middle) and monocytic infiltration in the lymph nodes (bottom). Statistical analysis was done using Mantel-Cox test (Panel A), Chi-square test (Panel C), or Mann Whitney test (Panel D), * P<0.05  P<0.01, * P<0.001. Data are representative of two independent experiments with 4-6 mice per group.

Similarly, FIG. 12 shows that CD39$^{high}$ cells are present in cancer (e.g., mouse melanoma and colorectal tumors) and the CD39 expression status indicates significant dysfunction (e.g., CD39$^{high}$ cells were the most dysfunctional).

Example 8: CD39-Deficient Mice Exhibit Increased Immune Responses and Mortality

Moreover, CD39 deficient mice exhibit increased mortality to LCMV-Clone 13 due to exacerbated immune response in target organs. Severely increased immunopathology in different organs in CD39 knock-out animals as compared to wild-type animals following LCMV-Clone 13 infection was observed (FIGS. 13A-13D).

The state of CD8⁺ T cell exhaustion is characterized by widespread changes in gene expression relative to functional memory CD8⁺ T cells (Wherry et al. (2007) Immunity 27:670-684). However, in humans, identifying specific markers of T cell exhaustion that are not shared by more functional CD8⁺ T cell populations has been challenging (Duraiswamy et al. (2011) J. Immunol. 186:4200-4212). It is demonstrated herein that high-level expression of the ecto-nucleotidase CD39 is characteristic of CD8⁺ T cells specific for chronic viral infections in humans and mice, but is otherwise rare in the CD8⁺ T cell compartment of healthy donors. Persistent, high-level expression is also seen in the mouse model of chronic viral infection, and CD39$^{High}$ CD8⁺ T cells express the highest levels of PD-1, co-express multiple inhibitory receptors, and are Tbet$^{lo}$/Eomes$^{hi}$. These data indicate that CD39 expression by CD8⁺ T cells in humans is a pathological finding and demarcates terminal exhaustion.

The fact that peripheral blood CD8⁺ T cells in humans can express CD39 is surprising. Previous data have shown that CD39 expression is restricted to CD4⁺ regulatory T cells, Th17 cells, and small populations of regulatory-like CD8⁺ T cells (Kansas et al. (1991) J. Immunol. 146:2235-2244; Moncrieffe et al. (2010) J. Immunol. 185:134-143; Pulte et al. (2011) Clin. Lymph. Myeloma Leuk. 11:367-372; Boer et al. (2013) Eur. J. Immunol. 43:1925-1932). Indeed, it was found herein that in the bulk population of CD8⁺ T cells in healthy donors, only a small minority of CD8⁺ T cells expresses CD39. However, CD39 is abundantly expressed by virus-specific CD8⁺ T cells in two human chronic infections (HIV and HCV). This helps explain why CD39⁺ CD8⁺ T cells have not been appreciated in earlier studies that have focused on healthy individuals, and indicates that, in steady-state conditions, the expression of CD39 by CD8⁺ T cells is a pathological occurrence related to the development of T cell exhaustion.

Several features of CD39-expressing CD8⁺ T cells described herein indicate that it is a marker of T cell exhaustion. First, in both human and mouse CD8⁺ T cells responding to chronic infection, CD39 is co-expressed with PD-1, which is an inhibitory receptor expressed by the majority of exhausted T cells (Wherry et al. (2007) Immunity 27:670-684; Barber et al. (2006) Nature 439:682-687). Second, CD39 expression correlates with viral load in subjects with HIV and HCV infection, indicating that the conditions of high levels of inflammation and antigen load that lead to exhaustion also increase CD39 expression in the virus-specific pool of CD8⁺ T cells, as has been observed for PD-1 (Day et al. (2006) Nature 443:350-354; Trautmann et al. (2006) Nat. Med. 12:1198-1202). The fact that a larger fraction of HCV-specific CD8⁺ T cells express CD39 than do HIV-specific CD8⁺ T cells is believed to be related to differences in the timing of blood sampling during the course of infection, or due to differences in the extent of antigen-load and inflammation in the two infections. Third, gene signatures characteristic of exhausted mouse CD8⁺ T cells are enriched in CD39⁺ cells relative to CD39⁻ CD8⁺ T cells in subjects with HCV infection, underscoring the association between CD39 expression and T cell exhaustion.

The expression of molecules that inhibit T cell function has been used to identify exhausted CD8⁺ T cells in several studies of human chronic infection and cancer (Wherry (2011) Nat. Immunol. 12:492-499). However, there are important distinctions between the pattern of CD39 expression and that of inhibitory receptors. Many inhibitory receptors, such as PD-1 (Day et al. (2006) Nature 443:350-354; Duraiswamy et al. (2011), J. Immunol. 186:4200-4212; Petrovas et al. (2006) J. Exp. Med. 203:2281-2292) and CD244 (Pita-Lopez et al. (2009) Immun. Ageing 6:11; Rey et al. (2006) Eur. J. Immunol. 36:2359-2366) are also expressed by a substantial fraction of CD8⁺ T cells in healthy donors that are not exhausted. In contrast, CD39 expression is found only in a very small minority of CD8+ T cells from healthy donors. This indicates that CD39 expression, particularly in combination with PD-1, is useful as a specific phenotype of exhausted CD8+ T cells, at least in HCV and HIV infection. Moreover, CD39 provides a useful marker to isolate exhausted CD8+ T cells in settings such as tumor-specific responses where very few reagents are available to identify antigen-specific T cells. Importantly, while CD39 is rare in the CD8 compartment in healthy donors, it is expressed by CD4+ Tregs (as is PD-1) making it relatively more difficult to distinguish between exhausted CD4+ T cells and Tregs alone.

Analysis of global expression profiles of CD39+ versus CD39− CD8+ T cells in HCV infection showed that the CD39+ fraction was strongly enriched for genes related to proliferation. This may at first seem counterintuitive, given the functional defects that have been described in exhausted CD8+ T cells (Wherry (2011) *Nat. Immunol.* 12:492-499; Wherry et al. (2007) *Immunity* 27:670-684). However, data from the mouse model of chronic infection indicate that, unlike memory CD8+ T cells, exhausted CD8+ T cells are dependent on continuous exposure to viral antigen to ensure their survival and undergo extensive cell division at a rate higher than that seen in physiological homeostatic proliferation of the memory CD8+ T cell pool (Shin et al. (2009) *Immunity* 31:309-320). Exhausted CD8+ T cells therefore have a paradoxical increase in their proliferation history but reduced proliferative potential (Migueles et al. (2002) *Nat. Immunol.* 3:1061-1068) explaining the increased expression of proliferation-associated genes in CD39+ CD8+ T cells in HCV infection and in mouse exhausted CD8+ T cells (Paley e al. (2012) *Science* 338:1220-1225; Shin et al. (2007) *J. Exp. Med.* 204:941-949).

Recent studies of exhausted CD8+ T cells have revealed that two distinct states of virus-specific CD8+ T cells exist in chronically infected mice and humans (Paley et al. (2012) *Science* 338:1220-1225). Differential expression of the T-box transcription factors T-bet and Eomes characterize two populations, which form a progenitor-progeny relationship. T-bet$^{high}$ cells display low intrinsic turnover but are capable of proliferation in response to persisting antigen, giving rise to Eomes$^{high}$ terminal progeny. In contrast, Eomes$^{high}$ CD8+ T cells responding to chronic infection had reduced capacity to undergo additional proliferation in vive. Indeed, in HCV, virus-specific CD8+ T cells from individuals with chronic infection show a higher level of Eomes than do resolvers (Buggert ei al. (2014) *PLoS Pathogens* 10:e1004251), consistent with the difference we found in CD39 expression (FIGS. 4C and 10). The data described herein demonstrate that in the mouse model of chronic infection and in HIV infection, the CD39$^{high}$ subset of CD8+ T cells demarcates terminally exhausted Eomes$^{high}$/Tbet$^{low}$ cells. Consistent with this, CD39+ CD8+ T cells in the mouse model express the highest levels of PD-1 and co-express multiple inhibitory receptors. These findings indicate that CD39 is a marker not only of the exhausted state, but specifically of the most terminally exhausted cells. The ability to distinguish between "reversible" and "irreversible" T cell exhaustion on the basis of surface expression of CD39 provides an effective correlate of T cell function in chronic viral infection, and a useful tool for studying this population ex vivo.

It is further believed that expression of CD39 contributes to the dysfunction of exhausted T cells. For instance, the expression of CD39 is believed to enable CD8+ T cells to provide negative regulation in an autocrine or juxtacrine fashion via adenosine in the same manner as Tregs (Deaglio et al. (2007) *J. Exp. Med.* 204:1257-1265). The fact that CD39 requires both a substrate (ATP) and a downstream enzyme (CD73) to generate adenosine could provide a mechanism to ensure that this negative signaling occurred only in certain contexts, such as in inflamed, damaged tissues, where the extracellular concentrations of ATP are high and CD73-expressing cells are present. Moreover, CD39-expressing CD8+ T cells may contribute to the general inhibitory milieu by contributing to the inhibition of activated T cells that express the adenosine receptor but are not yet exhausted.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of detecting terminally exhausted CD8+ T cells, the method comprising detecting the presence or a significant increase in the copy number, amount, and/or activity of CD39 in Eomesodermin+ CD8+ T cells in a biological sample comprising CD8+ T cells relative to a control, optionally wherein
   i) the biological sample is selected from the group consisting of cells, cell lines, histological slides, paraffin embedded tissue, fresh frozen tissue, fresh tissue, biopsies, blood, plasma, serum, buccal scrape, saliva, cerebrospinal fluid, urine, stool, mucus, bone marrow, and samples obtained from a subject;
   ii) the presence of CD39 or copy number of CD39 is assessed by whole exome sequencing, microarray, quantitative PCR (qPCR), high-throughput sequencing, comparative genomic hybridization (CGH), or fluorescent in situ hybridization (FISH);
   iii) the amount of CD39 is assessed by detecting the presence of a polynucleotide molecule encoding the biomarker or a portion of said polynucleotide molecule;
   iv) the amount of CD39 is assessed by annealing a nucleic acid probe of the polynucleotide encoding CD39 or a portion of said polynucleotide molecule under stringent hybridization conditions;
   v) the amount of CD39 is assessed by detecting the presence of CD39 polypeptide;
   vi) the activity of CD39 is assessed by determining the magnitude of enzymatic activity, cellular proliferation, cell death, or cytokine production;
   vii) the control is a sample comprising CD8+ T cells obtained from a subject not afflicted with a chronic immune condition; and/or
   viii) the control is a copy number, amount, and/or activity value determined from a population of CD8+ T cells not afflicted with a chronic immune condition or obtained with a subject not afflicted with a chronic immune condition.

2. The method of claim 1, further comprising
   i) detecting the presence or a significant increase in the copy number, amount, and/or activity of at least one T cell exhaustion biomarker in the CD8+ T cells in the biological sample comprising CD8+ T cells relative to a control; and/or
   ii) determining responsiveness of the subject from which the biological samples was obtained to anti-chronic immune condition therapy measured by at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria.

3. The method of claim 2, wherein the T cell exhaustion biomarker is selected from the group consisting of inhibitory receptors, T-bet, and combinations thereof.

4. The method of claim 1, wherein
a) the polynucleotide molecule in iii) is a mRNA, cDNA, or functional variants or fragments thereof;
b) the method further comprises amplifying the polynucleotide molecule;
c) the presence of CD39 polypeptide is detected using a reagent which specifically binds with said polypeptide, optionally wherein the reagent is selected from the group consisting of an antibody, an antibody derivative, and an antibody fragment; and/or
d) the subject is mammal, preferably a chronic immune disorder animal model or a human.

5. The method of claim 4, wherein
i) the reagent in c) is selected from the group consisting of an antibody, an antibody derivative, and an antibody fragment; and/or
ii) the chronic immune disorder in d) is a chronic infection or cancer.

6. The method of claim 5, wherein
a) the chronic infection in ii) is caused by an agent selected from the group consisting of human immunodeficiency virus (HIV), hepatitis C virus (HCV), hepatitis B virus (HBV), adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyoma virus BK, polyoma virus JC, measles virus, rubella virus, human T cell leukemia virus I, human T cell leukemia virus II, *Leishmania, Toxoplasma, Trypanosoma, Plasmodium, Schistosoma*, and *Encephalitozoon;*
b) the chronic infection in ii) is not a latent infection; and/or
c) the cancer in ii) is a hematological cancer or a solid cancer.

7. The method of claim 6, wherein the solid cancer in c) is selected from the group consisting of lung cancer, non-small cell lung cancer (NSCLC), skin cancer, melanoma, cervical cancer, uterine cancer, ovarian cancer, breast cancer, pancreatic cancer, stomach cancer, esophageal cancer, colorectal cancer, liver cancer, prostate cancer, kidney cancer, bladder cancer, head and neck cancer, sarcoma, lymphoma, and brain cancer.

* * * * *

SEQUENCE LISTING

```
<160> NUMBER OF SEQ ID NOS: 47

<210> SEQ ID NO 1
<211> LENGTH: 1533
<212> TYPE: DNA
<213> ORGANISM: Homo sapiens

<400> SEQUENCE: 1
atggaagata caaaggagtc taacgtgaag acattttgct ccaagaatat cctagccatc      60
cttggcttct cctctatcat agctgtgata gctttgcttg ctgtggggtt gacccagaac     120
```

```
aaagcattgc cagaaaacgt taagtatggg attgtgctgg atgcgggttc ttctcacaca      180
agtttataca tctataagtg gccagcagaa aaggagaatg cacaggcgt ggtgcatcaa        240 gtagaagaat gcagggttaa aggtcctgga atctcaaaat ttgttcagaa agtaaatgaa      300
ataggcattt acctgactga ttgcatggaa agagctaggg aagtgattcc aaggtcccag      360
caccaagaga cacccgttta cctgggagcc acggcaggca tgcggttgct caggatggaa      420
agtgaagagt tggcagacag ggttctggat gtggtggaga ggagcctcag caactacccc      480
tttgacttcc agggtgccag gatcattact ggccaagagg aaggtgccta tggctggatt      540
actatcaact atctgctggg caaattcagt cagaaaacaa ggtggttcag catagtccca      600
tatgaaacca ataatcagga aacctttgga gctttggacc ttggggggagc ctctacacaa      660 gtcacttttg taccccaaaa ccagactatc gagtccccag ataatgctct gcaatttcgc      720
ctctatggca aggactacaa tgtctacaca catagcttct tgtgctatgg aaggatcag       780 gcactctggc agaaactggc caaggacatt caggttgcaa gtaatgaaat tctcagggac      840
ccatgctttc atcctggata taagaaggta gtgaacgtaa gtgaccttta caagaccccc      900
tgcaccaaga gatttgagat gactcttcca ttccagcagt ttgaaatcca gggtattgga      960
aactatcaac aatgccatca aagcatcctg gagctcttca acaccagtta ctgcccttac     1020
tcccagtgtg ccttcaatgg gattttcttg ccaccactcc agggggattt tggggcattt     1080 tcagctttttt actttgtgat gaagtttttta aacttgacat cagagaaagt ctctcaggaa     1140
aaggtgactg agatgatgaa aaagttctgt gctcagcctt gggaggagat aaaaacatct     1200
tacgctggag taaaggagaa gtacctgagt gaatactgct tttctggtac ctacattctc     1260 tccctcctc tgcaaggcta tcattcaca gctgattcct gggagcacat ccatttcatt     1320
ggcaagatcc agggcagcga cgccggctgg actttgggct acatgctgaa cctgaccaac     1380
atgatcccag ctgagcaacc attgtccaca cctctctccc actccaccta tgtcttcctc     1440
atggttctat tctccctggt cctttttcaca gtggccatca taggcttgct tatctttcac     1500
aagccttcat atttctggaa agatatggta tag                                    1533
```

<210> SEQ ID NO 2
<211> LENGTH: 510
<212> TYPE: PRT
<213> ORGANISM: Homo sapiens

<400> SEQUENCE: 2

```
Met Glu Asp Thr Lys Glu Ser Asn Val Lys Thr Phe Cys Ser Lys Asn
1               5                   10                  15

Ile Leu Ala Ile Leu Gly Phe Ser Ser Ile Ala Val Ile Ala Leu
            20                  25                  30

Leu Ala Val Gly Leu Thr Gln Asn Lys Ala Leu Pro Glu Asn Val Lys
        35                  40                  45

Tyr Gly Ile Val Leu Asp Ala Gly Ser Ser His Thr Ser Leu Tyr Ile
    50                  55                  60

Tyr Lys Trp Pro Ala Glu Lys Glu Asn Asp Thr Gly Val Val His Gln
65                  70                  75                  80

Val Glu Glu Cys Arg Val Lys Gly Pro Gly Ile Ser Lys Phe Val Gln
                85                  90                  95

Lys Val Asn Glu Ile Gly Ile Tyr Leu Thr Asp Cys Met Glu Arg Ala
            100                 105                 110

Arg Glu Val Ile Pro Arg Ser Gln His Gln Glu Thr Pro Val Tyr Leu
        115                 120                 125
```

Gly Ala Thr Ala Gly Met Arg Leu Leu Arg Met Glu Ser Glu Glu Leu
130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
                180                 185                 190

Thr Arg Trp Phe Ser Ile Val Pro Tyr Glu Thr Asn Asn Gln Glu Thr
                195                 200                 205

Phe Gly Ala Leu Asp Leu Gly Gly Ala Ser Thr Gln Val Thr Phe Val
210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255

Gly Lys Asp Gln Ala Leu Trp Gln Lys Leu Ala Lys Asp Ile Gln Val
                260                 265                 270

Ala Ser Asn Glu Ile Leu Arg Asp Pro Cys Phe His Pro Gly Tyr Lys
                275                 280                 285

Lys Val Val Asn Val Ser Asp Leu Tyr Lys Thr Pro Cys Thr Lys Arg
290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
                340                 345                 350

Leu Gln Gly Asp Phe Gly Ala Phe Ser Ala Phe Tyr Phe Val Met Lys
                355                 360                 365

Phe Leu Asn Leu Thr Ser Glu Lys Val Ser Gln Glu Lys Val Thr Glu
370                 375                 380

Met Met Lys Lys Phe Cys Ala Gln Pro Trp Glu Glu Ile Lys Thr Ser
385                 390                 395                 400

Tyr Ala Gly Val Lys Glu Lys Tyr Leu Ser Glu Tyr Cys Phe Ser Gly
                405                 410                 415

Thr Tyr Ile Leu Ser Leu Leu Leu Gln Gly Tyr His Phe Thr Ala Asp
                420                 425                 430

Ser Trp Glu His Ile His Phe Ile Gly Lys Ile Gln Gly Ser Asp Ala
                435                 440                 445

Gly Trp Thr Leu Gly Tyr Met Leu Asn Leu Thr Asn Met Ile Pro Ala
450                 455                 460

Glu Gln Pro Leu Ser Thr Pro Leu Ser His Ser Thr Tyr Val Phe Leu
465                 470                 475                 480

Met Val Leu Phe Ser Leu Val Leu Phe Thr Val Ala Ile Ile Gly Leu
                485                 490                 495

Leu Ile Phe His Lys Pro Ser Tyr Phe Trp Lys Asp Met Val
                500                 505                 510

<210> SEQ ID NO 3
<211> LENGTH: 1554
<212> TYPE: DNA
<213> ORGANISM: Homo sapiens

<400> SEQUENCE: 3

```
atgaaggaa ccaaggacct gacaagccag cagaaggagt ctaacgtgaa gacattttgc    60
tccaagaata tcctagccat ccttggcttc tcctctatca tagctgtgat agctttgctt   120
gctgtgggt tgacccagaa caaagcattg ccagaaaacg ttaagtatgg gattgtgctg   180
gatgcggtt cttctcacac aagtttatac atctataagt ggccagcaga aaaggagaat   240
gacacaggcg tggtgcatca agtagaagaa tgcagggtta aggtcctgg aatctcaaaa   300
tttgttcaga aagtaaatga aataggcatt tacctgactg attgcatgga agagctagg   360
gaagtgattc caaggtccca gcaccaagag acacccgttt acctgggagc acggcaggc   420
atgcggttgc tcaggatgga aagtgaagag ttggcagaca gggttctgga tgtggtggag   480
aggagcctca gcaactaccc ctttgacttc cagggtgcca ggatcattac tggccaagag   540
gaaggtgcct atggctggat tactatcaac tatctgctgg gcaaattcag tcagaaaaca   600
aggtggttca gcatagtccc atatgaaacc aataatcagg aaaccttttg agcttttggac  660
cttggggag cctctacaca agtcactttt gtaccccaaa accagactat cgagtcccca   720
gataatgctc tgcaatttcg cctctatggc aaggactaca atgtctacac acatagcttc   780
ttgtgctatg gaaggatca ggcactctgg cagaaactgg ccaaggacat tcaggttgca   840
agtaatgaaa ttctcaggga cccatgcttt catcctggat ataagaaggt agtgaacgta   900
agtgaccttt acaagccccc ctgcaccaag agatttgaga tgactcttcc attccagcag   960
tttgaaatcc agggtattgg aaactatcaa caatgccatc aaagcatcct ggagctcttc  1020
aacaccagtt actgccctta ctcccagtgt gccttcaatg ggatttttctt gccaccactc  1080
cagggggatt ttgggcatt ttcagctttt tactttgtga tgaagttttt aaacttgaca   1140
tcagagaaag tctctcagga aaaggtgact gagatgatga aaaagttctg tgctcagcct  1200
tgggaggaga taaaaacatc ttacgctgga gtaaaggaga agtacctgag tgaatactgc  1260
tttctggta cctacattct ctccctcctt ctgcaaggct atcatttcac agctgattcc  1320
tgggagcaca tccatttcat tggcaagatc cagggcagcg acgccggctg gactttgggc  1380
tacatgctga acctgaccaa catgatccca gctgagcaac cattgtccac acctctctcc  1440
cactccacct atgtcttcct catggttcta ttctccctgg tccttttcac agtggccatc  1500
ataggcttgc ttatctttca caagccttca tatttctgga agatatggt atag          1554
```

<210> SEQ ID NO 4
<211> LENGTH: 517
<212> TYPE: PRT
<213> ORGANISM: Homo sapiens

<400> SEQUENCE: 4

```
Met Lys Gly Thr Lys Asp Leu Thr Ser Gln Gln Lys Glu Ser Asn Val
1               5                   10                  15

Lys Thr Phe Cys Ser Lys Asn Ile Leu Ala Ile Leu Gly Phe Ser Ser
            20                  25                  30

Ile Ile Ala Val Ile Ala Leu Leu Ala Val Gly Leu Thr Gln Asn Lys
        35                  40                  45

Ala Leu Pro Glu Asn Val Lys Tyr Gly Ile Val Leu Asp Ala Gly Ser
    50                  55                  60

Ser His Thr Ser Leu Tyr Ile Tyr Lys Trp Pro Ala Glu Lys Glu Asn
65                  70                  75                  80

Asp Thr Gly Val Val His Gln Val Glu Glu Cys Arg Val Lys Gly Pro
                85                  90                  95
```

```
Gly Ile Ser Lys Phe Val Gln Lys Val Asn Glu Ile Gly Ile Tyr Leu
            100                 105                 110

Thr Asp Cys Met Glu Arg Ala Arg Glu Val Ile Pro Arg Ser Gln His
            115                 120                 125

Gln Glu Thr Pro Val Tyr Leu Gly Ala Thr Ala Gly Met Arg Leu Leu
        130                 135                 140

Arg Met Glu Ser Glu Glu Leu Ala Asp Arg Val Leu Asp Val Val Glu
145                 150                 155                 160

Arg Ser Leu Ser Asn Tyr Pro Phe Asp Phe Gln Gly Ala Arg Ile Ile
                165                 170                 175

Thr Gly Gln Glu Glu Gly Ala Tyr Gly Trp Ile Thr Ile Asn Tyr Leu
        180                 185                 190

Leu Gly Lys Phe Ser Gln Lys Thr Arg Trp Phe Ser Ile Val Pro Tyr
        195                 200                 205

Glu Thr Asn Asn Gln Glu Thr Phe Gly Ala Leu Asp Leu Gly Gly Ala
        210                 215                 220

Ser Thr Gln Val Thr Phe Val Pro Gln Asn Gln Thr Ile Glu Ser Pro
225                 230                 235                 240

Asp Asn Ala Leu Gln Phe Arg Leu Tyr Gly Lys Asp Tyr Asn Val Tyr
                245                 250                 255

Thr His Ser Phe Leu Cys Tyr Gly Lys Asp Gln Ala Leu Trp Gln Lys
        260                 265                 270

Leu Ala Lys Asp Ile Gln Val Ala Ser Asn Glu Ile Leu Arg Asp Pro
        275                 280                 285

Cys Phe His Pro Gly Tyr Lys Lys Val Val Asn Val Ser Asp Leu Tyr
        290                 295                 300

Lys Thr Pro Cys Thr Lys Arg Phe Glu Met Thr Leu Pro Phe Gln Gln
305                 310                 315                 320

Phe Glu Ile Gln Gly Ile Gly Asn Tyr Gln Gln Cys His Gln Ser Ile
                325                 330                 335

Leu Glu Leu Phe Asn Thr Ser Tyr Cys Pro Tyr Ser Gln Cys Ala Phe
                340                 345                 350

Asn Gly Ile Phe Leu Pro Pro Leu Gln Gly Asp Phe Gly Ala Phe Ser
            355                 360                 365

Ala Phe Tyr Phe Val Met Lys Phe Leu Asn Leu Thr Ser Glu Lys Val
        370                 375                 380

Ser Gln Glu Lys Val Thr Glu Met Met Lys Lys Phe Cys Ala Gln Pro
385                 390                 395                 400

Trp Glu Glu Ile Lys Thr Ser Tyr Ala Gly Val Lys Glu Lys Tyr Leu
                405                 410                 415

Ser Glu Tyr Cys Phe Ser Gly Thr Tyr Ile Leu Ser Leu Leu Leu Gln
            420                 425                 430

Gly Tyr His Phe Thr Ala Asp Ser Trp Glu His Ile His Phe Ile Gly
        435                 440                 445

Lys Ile Gln Gly Ser Asp Ala Gly Trp Thr Leu Gly Tyr Met Leu Asn
        450                 455                 460

Leu Thr Asn Met Ile Pro Ala Glu Gln Pro Leu Ser Thr Pro Leu Ser
465                 470                 475                 480

His Ser Thr Tyr Val Phe Leu Met Val Leu Phe Ser Leu Val Leu Phe
                485                 490                 495

Thr Val Ala Ile Ile Gly Leu Leu Ile Phe His Lys Pro Ser Tyr Phe
            500                 505                 510
```

Trp Lys Asp Met Val
        515

<210> SEQ ID NO 5
<211> LENGTH: 1569
<212> TYPE: DNA
<213> ORGANISM: Homo sapiens

<400> SEQUENCE: 5

| | |
|---|---:|
| atggggaggg aagaactgtt cttgactttc agtttttcga gcgggtttca agagtctaac | 60 |
| gtgaagacat tttgctccaa gaatatccta gccatccttg gcttctcctc tatcatagct | 120 |
| gtgatagctt tgcttgctgt ggggttgacc cagaacaaag cattgccaga aaacgttaag | 180 |
| tatgggattg tgctggatgc gggttcttct cacacaagtt tatacatcta taagtggcca | 240 |
| gcagaaaagg agaatgacac aggcgtggtg catcaagtag aagaatgcag ggttaaaggt | 300 |
| cctggaatct caaaatttgt tcagaaagta aatgaaatag gcatttacct gactgattgc | 360 |
| atggaaagag ctagggaagt gattccaagg tcccagcacc aagagacacc cgtttacctg | 420 |
| ggagccacgg caggcatgcg gttgctcagg atggaaagtg aagagttggc agacagggtt | 480 |
| ctggatgtgg tggagaggag cctcagcaac tacccctttg acttccaggg tgccaggatc | 540 |
| attactggcc aagaggaagg tgcctatggc tggattacta tcaactatct gctgggcaaa | 600 |
| ttcagtcaga aaacaaggtg gttcagcata gtcccatatg aaaccaataa tcaggaaacc | 660 |
| tttggagctt tggaccttgg gggagcctct acacaagtca cttttgtacc ccaaaaccag | 720 |
| actatcgagt ccccagataa tgctctgcaa tttcgcctct atggcaagga ctacaatgtc | 780 |
| tacacacata gcttcttgtg ctatgggaag gatcaggcac tctggcagaa actggccaag | 840 |
| gacattcagg ttgcaagtaa tgaaattctc agggacccat gctttcatcc tggatataag | 900 |
| aaggtagtga acgtaagtga cctttacaag acccctgca ccaagagatt tgagatgact | 960 |
| cttccattcc agcagtttga aatccagggt attggaaact atcaacaatg ccatcaaagc | 1020 |
| atcctggagc tcttcaacac cagttactgc ccttactccc agtgtgcctt caatgggatt | 1080 |
| ttcttgccac cactccaggg ggattttggg gcattttcag cttttttactt tgtgatgaag | 1140 |
| tttttaaact tgacatcaga gaaagtctct caggaaaagg tgactgagat gatgaaaaag | 1200 |
| ttctgtgctc agccttggga ggagataaaa acatcttacg ctggagtaaa ggagaagtac | 1260 |
| ctgagtgaat actgcttttc tggtacctac attctctccc tccttctgca aggctatcat | 1320 |
| ttcacagctg attcctggga gcacatccat tcattggca agatccaggg cagcgacgcc | 1380 |
| ggctggactt tgggctacat gctgaacctg accaacatga tcccagctga gcaaccattg | 1440 |
| tccacacctc tctcccactc cacctatgtc ttcctcatgg ttctattctc cctggtcctt | 1500 |
| ttcacagtgg ccatcatagg cttgcttatc tttcacaagc cttcatattt ctggaaagat | 1560 |
| atggtatag | 1569 |

<210> SEQ ID NO 6
<211> LENGTH: 522
<212> TYPE: PRT
<213> ORGANISM: Homo sapiens

<400> SEQUENCE: 6

Met Gly Arg Glu Glu Leu Phe Leu Thr Phe Ser Phe Ser Ser Gly Phe
1               5                   10                  15

Gln Glu Ser Asn Val Lys Thr Phe Cys Ser Lys Asn Ile Leu Ala Ile
            20                  25                  30

```
Leu Gly Phe Ser Ser Ile Ile Ala Val Ile Ala Leu Ala Val Gly
             35                  40                  45
Leu Thr Gln Asn Lys Ala Leu Pro Glu Asn Val Lys Tyr Gly Ile Val
 50                  55                  60
Leu Asp Ala Gly Ser Ser His Thr Ser Leu Tyr Ile Tyr Lys Trp Pro
 65                  70                  75                  80
Ala Glu Lys Glu Asn Asp Thr Gly Val Val His Gln Val Glu Glu Cys
                 85                  90                  95
Arg Val Lys Gly Pro Gly Ile Ser Lys Phe Val Gln Lys Val Asn Glu
                100                 105                 110
Ile Gly Ile Tyr Leu Thr Asp Cys Met Glu Arg Ala Arg Glu Val Ile
                115                 120                 125
Pro Arg Ser Gln His Gln Glu Thr Pro Val Tyr Leu Gly Ala Thr Ala
130                 135                 140
Gly Met Arg Leu Leu Arg Met Glu Ser Glu Glu Leu Ala Asp Arg Val
145                 150                 155                 160
Leu Asp Val Val Glu Arg Ser Leu Ser Asn Tyr Pro Phe Asp Phe Gln
                165                 170                 175
Gly Ala Arg Ile Ile Thr Gly Gln Glu Glu Gly Ala Tyr Gly Trp Ile
                180                 185                 190
Thr Ile Asn Tyr Leu Leu Gly Lys Phe Ser Gln Lys Thr Arg Trp Phe
                195                 200                 205
Ser Ile Val Pro Tyr Glu Thr Asn Asn Gln Glu Thr Phe Gly Ala Leu
                210                 215                 220
Asp Leu Gly Gly Ala Ser Thr Gln Val Thr Phe Val Pro Gln Asn Gln
225                 230                 235                 240
Thr Ile Glu Ser Pro Asp Asn Ala Leu Gln Phe Arg Leu Tyr Gly Lys
                245                 250                 255
Asp Tyr Asn Val Tyr Thr His Ser Phe Leu Cys Tyr Gly Lys Asp Gln
                260                 265                 270
Ala Leu Trp Gln Lys Leu Ala Lys Asp Ile Gln Val Ala Ser Asn Glu
                275                 280                 285
Ile Leu Arg Asp Pro Cys Phe His Pro Gly Tyr Lys Lys Val Val Asn
                290                 295                 300
Val Ser Asp Leu Tyr Lys Thr Pro Cys Thr Lys Arg Phe Glu Met Thr
305                 310                 315                 320
Leu Pro Phe Gln Gln Phe Glu Ile Gln Gly Ile Gly Asn Tyr Gln Gln
                325                 330                 335
Cys His Gln Ser Ile Leu Glu Leu Phe Asn Thr Ser Tyr Cys Pro Tyr
                340                 345                 350
Ser Gln Cys Ala Phe Asn Gly Ile Phe Leu Pro Pro Leu Gln Gly Asp
                355                 360                 365
Phe Gly Ala Phe Ser Ala Phe Tyr Phe Val Met Lys Phe Leu Asn Leu
                370                 375                 380
Thr Ser Glu Lys Val Ser Gln Glu Lys Val Thr Glu Met Met Lys Lys
385                 390                 395                 400
Phe Cys Ala Gln Pro Trp Glu Glu Ile Lys Thr Ser Tyr Ala Gly Val
                405                 410                 415
Lys Glu Lys Tyr Leu Ser Glu Tyr Cys Phe Ser Gly Thr Tyr Ile Leu
                420                 425                 430
Ser Leu Leu Leu Gln Gly Tyr His Phe Thr Ala Asp Ser Trp Glu His
                435                 440                 445
Ile His Phe Ile Gly Lys Ile Gln Gly Ser Asp Ala Gly Trp Thr Leu
```

```
                450              455              460
Gly Tyr Met Leu Asn Leu Thr Asn Met Ile Pro Ala Glu Gln Pro Leu
465                 470                 475                 480

Ser Thr Pro Leu Ser His Ser Thr Tyr Val Phe Leu Met Val Leu Phe
                485                 490                 495

Ser Leu Val Leu Phe Thr Val Ala Ile Ile Gly Leu Leu Ile Phe His
                500                 505                 510

Lys Pro Ser Tyr Phe Trp Lys Asp Met Val
                515                 520

<210> SEQ ID NO 7
<211> LENGTH: 1410
<212> TYPE: DNA
<213> ORGANISM: Homo sapiens

<400> SEQUENCE: 7
atggaagata caaaggagtc taacgtgaag acattttgct ccaagaatat cctagccatc      60
cttggcttct cctctatcat agctgtgata gctttgcttg ctgtggggtt gacccagaac     120
aaagcattgc cagaaaacgt taagtatggg attgtgctgg atgcgggttc ttctcacaca     180
agtttataca tctataagtg gccagcagaa aaggagaatg cacaggcgt ggtgcatcaa      240 gtagaagaat gcagggttaa aggtcctgga atctcaaaat tgttcagaa agtaaatgaa      300 ataggcattt acctgactga ttgcatggaa agagctaggg aagtgattcc aaggtcccag     360
caccaagaga cacccgttta cctgggagcc acggcaggca tgcggttgct caggatggaa     420
agtgaagagt tggcagacag ggttctggat gtggtggaga ggagcctcag caactacccc     480
tttgacttcc agggtgccag gatcattact ggccaagagg aaggtgccta tgctggatt     540 actatcaact atctgctggg caaattcagt cagaaaacaa ggtggttcag catagtccca     600
tatgaaacca ataatcagga aacctttgga gctttggacc ttgggggagc ctctacacaa     660 gtcactttg taccccaaaa ccagactatc gagtccccag ataatgctct gcaatttcgc     720
ctctatggca aggactacaa tgtctacaca catagcttct tgtgctatgg aaggatcag     780 gcactctggc agaaactggc caaggacatt cagcagtttg aaatccaggg tattggaaac     840
tatcaacaat gccatcaaag catcctggag ctcttcaaca ccagttactg cccttactcc     900
cagtgtgcct tcaatgggat tttcttgcca ccactccagg gggattttgg ggcattttca     960
gctttttact tgtgatgaa gttttaaac ttgacatcag agaaagtctc tcaggaaaag      1020
gtgactgaga tgatgaaaaa gttctgtgct cagccttggg aggagataaa aacatcttac     1080
gctggagtaa aggagaagta cctgagtgaa tactgctttt ctggtaccta cattctctcc     1140
ctccttctgc aaggctatca tttcacagct gattcctggg agcacatcca tttcattggc     1200
aagatccagg gcagcgacgc cggctggact ttgggctaca tgctgaacct gaccaacatg     1260
atcccagctg agcaaccatt gtccacacct ctctcccact ccacctatgt cttcctcatg     1320
gttctattct ccctggtcct tttcacagtg gccatcatag gcttgcttat ctttcacaag     1380
ccttcatatt tctggaaaga tatggtatag                                     1410

<210> SEQ ID NO 8
<211> LENGTH: 469
<212> TYPE: PRT
<213> ORGANISM: Homo sapiens

<400> SEQUENCE: 8

Met Glu Asp Thr Lys Glu Ser Asn Val Lys Thr Phe Cys Ser Lys Asn
```

-continued

```
1               5                   10                  15
Ile Leu Ala Ile Leu Gly Phe Ser Ser Ile Ala Val Ile Ala Leu
            20                  25                  30
Leu Ala Val Gly Leu Thr Gln Asn Lys Ala Leu Pro Glu Asn Val Lys
            35                  40                  45
Tyr Gly Ile Val Leu Asp Ala Gly Ser Ser His Thr Ser Leu Tyr Ile
 50                  55                  60
Tyr Lys Trp Pro Ala Glu Lys Asn Asp Thr Gly Val Val His Gln
 65                  70                  75                  80
Val Glu Glu Cys Arg Val Lys Gly Pro Gly Ile Ser Lys Phe Val Gln
                85                  90                  95
Lys Val Asn Glu Ile Gly Ile Tyr Leu Thr Asp Cys Met Glu Arg Ala
                100                 105                 110
Arg Glu Val Ile Pro Arg Ser Gln His Gln Glu Thr Pro Val Tyr Leu
                115                 120                 125
Gly Ala Thr Ala Gly Met Arg Leu Leu Arg Met Glu Ser Glu Glu Leu
            130                 135                 140
Ala Asp Arg Val Leu Asp Val Val Glu Arg Ser Leu Ser Asn Tyr Pro
145                 150                 155                 160
Phe Asp Phe Gln Gly Ala Arg Ile Ile Thr Gly Gln Glu Glu Gly Ala
                165                 170                 175
Tyr Gly Trp Ile Thr Ile Asn Tyr Leu Leu Gly Lys Phe Ser Gln Lys
            180                 185                 190
Thr Arg Trp Phe Ser Ile Val Pro Tyr Glu Thr Asn Asn Gln Glu Thr
            195                 200                 205
Phe Gly Ala Leu Asp Leu Gly Gly Ala Ser Thr Gln Val Thr Phe Val
 210                 215                 220
Pro Gln Asn Gln Thr Ile Glu Ser Pro Asp Asn Ala Leu Gln Phe Arg
225                 230                 235                 240
Leu Tyr Gly Lys Asp Tyr Asn Val Tyr Thr His Ser Phe Leu Cys Tyr
                245                 250                 255
Gly Lys Asp Gln Ala Leu Trp Gln Lys Leu Ala Lys Asp Ile Gln Gln
                260                 265                 270
Phe Glu Ile Gln Gly Ile Gly Asn Tyr Gln Gln Cys His Gln Ser Ile
            275                 280                 285
Leu Glu Leu Phe Asn Thr Ser Tyr Cys Pro Tyr Ser Gln Cys Ala Phe
 290                 295                 300
Asn Gly Ile Phe Leu Pro Pro Leu Gln Gly Asp Phe Gly Ala Phe Ser
305                 310                 315                 320
Ala Phe Tyr Phe Val Met Lys Phe Leu Asn Leu Thr Ser Glu Lys Val
                325                 330                 335
Ser Gln Glu Lys Val Thr Glu Met Met Lys Lys Phe Cys Ala Gln Pro
                340                 345                 350
Trp Glu Glu Ile Lys Thr Ser Tyr Ala Gly Val Lys Glu Lys Tyr Leu
            355                 360                 365
Ser Glu Tyr Cys Phe Ser Gly Thr Tyr Ile Leu Ser Leu Leu Leu Gln
 370                 375                 380
Gly Tyr His Phe Thr Ala Asp Ser Trp Glu His Ile His Phe Ile Gly
385                 390                 395                 400
Lys Ile Gln Gly Ser Asp Ala Gly Trp Thr Leu Gly Tyr Met Leu Asn
                405                 410                 415
Leu Thr Asn Met Ile Pro Ala Glu Gln Pro Leu Ser Thr Pro Leu Ser
                420                 425                 430
```

His Ser Thr Tyr Val Phe Leu Met Val Leu Phe Ser Leu Val Leu Phe
        435                 440                 445

Thr Val Ala Ile Ile Gly Leu Leu Ile Phe His Lys Pro Ser Tyr Phe
    450                 455                 460

Trp Lys Asp Met Val
465

<210> SEQ ID NO 9
<211> LENGTH: 1209
<212> TYPE: DNA
<213> ORGANISM: Homo sapiens

<400> SEQUENCE: 9

```
atggaaagag ctagggaagt gattccaagg tcccagcacc aagagacacc cgtttacctg      60
ggagccacgg caggcatgcg gttgctcagg atggaaagtg aagagttggc agacagggtt     120
ctggatgtgg tggagaggag cctcagcaac tacccctttg acttccaggg tgccaggatc     180
attactggcc aagaggaagg tgcctatggc tggattacta tcaactatct gctgggcaaa     240
ttcagtcaga aaacaaggtg gttcagcata gtcccatatg aaaccaataa tcaggaaacc     300
tttggagctt tggaccttgg gggagcctct acacaagtca cttttgtacc ccaaaaccag     360
actatcgagt ccccagataa tgctctgcaa tttcgcctct atggcaagga ctacaatgtc     420
tacacacata gcttcttgtg ctatgggaag atcaggcac tctggcagaa actggccaag     480
gacattcagg ttgcaagtaa tgaaattctc agggacccat gctttcatcc tggatataag     540
aaggtagtga acgtaagtga cctttacaag accccctgca ccaagagatt tgagatgact     600
cttccattcc agcagtttga atccagggt attggaaact atcaacaatg ccatcaaagc     660
atcctggagc tcttcaacac cagttactgc ccttactccc agtgtgcctt caatgggatt     720
ttcttgccac cactccaggg ggattttggg gcattttcag cttttttactt tgtgatgaag     780
ttttaaaact tgacatcaga gaaagtctct caggaaaagg tgactgagat gatgaaaaag     840
ttctgtgctc agccttggga ggagataaaa acatcttacg ctggagtaaa ggagaagtac     900
ctgagtgaat actgcttttc tggtacctac attctctccc tccttctgca aggctatcat     960
ttcacagctg attcctggga gcacatccat tcattggca agatccaggg cagcgacgcc    1020
ggctggactt tgggctacat gctgaacctg accaacatga tcccagctga gcaaccattg    1080
tccacacctc tctcccactc cacctatgtc ttcctcatgg ttctattctc cctggtcctt    1140
ttcacagtgg ccatcatagg cttgcttatc tttcacaagc cttcatattt ctggaaagat    1200
atggtatag                                                            1209
```

<210> SEQ ID NO 10
<211> LENGTH: 402
<212> TYPE: PRT
<213> ORGANISM: Homo sapiens

<400> SEQUENCE: 10

Met Glu Arg Ala Arg Glu Val Ile Pro Arg Ser Gln His Gln Glu Thr
1               5                   10                  15

Pro Val Tyr Leu Gly Ala Thr Ala Gly Met Arg Leu Leu Arg Met Glu
            20                  25                  30

Ser Glu Glu Leu Ala Asp Arg Val Leu Asp Val Val Glu Arg Ser Leu
        35                  40                  45

Ser Asn Tyr Pro Phe Asp Phe Gln Gly Ala Arg Ile Ile Thr Gly Gln
    50                  55                  60

```
Glu Glu Gly Ala Tyr Gly Trp Ile Thr Ile Asn Tyr Leu Leu Gly Lys
 65                  70                  75                  80

Phe Ser Gln Lys Thr Arg Trp Phe Ser Ile Val Pro Tyr Glu Thr Asn
             85                  90                  95

Asn Gln Glu Thr Phe Gly Ala Leu Asp Leu Gly Gly Ala Ser Thr Gln
            100                 105                 110

Val Thr Phe Val Pro Gln Asn Gln Thr Ile Glu Ser Pro Asp Asn Ala
        115                 120                 125

Leu Gln Phe Arg Leu Tyr Gly Lys Asp Tyr Asn Val Tyr Thr His Ser
    130                 135                 140

Phe Leu Cys Tyr Gly Lys Asp Gln Ala Leu Trp Gln Lys Leu Ala Lys
145                 150                 155                 160

Asp Ile Gln Val Ala Ser Asn Glu Ile Leu Arg Asp Pro Cys Phe His
                165                 170                 175

Pro Gly Tyr Lys Lys Val Val Asn Val Ser Asp Leu Tyr Lys Thr Pro
            180                 185                 190

Cys Thr Lys Arg Phe Glu Met Thr Leu Pro Phe Gln Gln Phe Glu Ile
        195                 200                 205

Gln Gly Ile Gly Asn Tyr Gln Gln Cys His Gln Ser Ile Leu Glu Leu
    210                 215                 220

Phe Asn Thr Ser Tyr Cys Pro Tyr Ser Gln Cys Ala Phe Asn Gly Ile
225                 230                 235                 240

Phe Leu Pro Pro Leu Gln Gly Asp Phe Gly Ala Phe Ser Ala Phe Tyr
                245                 250                 255

Phe Val Met Lys Phe Leu Asn Leu Thr Ser Glu Lys Val Ser Gln Glu
            260                 265                 270

Lys Val Thr Glu Met Met Lys Lys Phe Cys Ala Gln Pro Trp Glu Glu
        275                 280                 285

Ile Lys Thr Ser Tyr Ala Gly Val Lys Glu Lys Tyr Leu Ser Glu Tyr
    290                 295                 300

Cys Phe Ser Gly Thr Tyr Ile Leu Ser Leu Leu Leu Gln Gly Tyr His
305                 310                 315                 320

Phe Thr Ala Asp Ser Trp Glu His Ile His Phe Ile Gly Lys Ile Gln
                325                 330                 335

Gly Ser Asp Ala Gly Trp Thr Leu Gly Tyr Met Leu Asn Leu Thr Asn
            340                 345                 350

Met Ile Pro Ala Glu Gln Pro Leu Ser Thr Pro Leu Ser His Ser Thr
        355                 360                 365

Tyr Val Phe Leu Met Val Leu Phe Ser Leu Val Leu Phe Thr Val Ala
    370                 375                 380

Ile Ile Gly Leu Leu Ile Phe His Lys Pro Ser Tyr Phe Trp Lys Asp
385                 390                 395                 400

Met Val

<210> SEQ ID NO 11
<211> LENGTH: 1119
<212> TYPE: DNA
<213> ORGANISM: Homo sapiens

<400> SEQUENCE: 11
atggaaagtg aagagttggc agacagggtt ctggatgtgg tggagaggag cctcagcaac      60
tacccctttg acttccaggg tgccaggatc attactggcc aagaggaagg tgcctatggc     120
tggattacta tcaactatct gctgggcaaa ttcagtcaga aaacaaggtg gttcagcata     180
```

```
gtcccatatg aaaccaataa tcaggaaacc tttggagctt tggaccttgg gggagcctct    240
acacaagtca cttttgtacc ccaaaaccag actatcgagt ccccagataa tgctctgcaa    300
tttcgcctct atggcaagga ctacaatgtc tacacacata gcttcttgtg ctatgggaag    360
gatcaggcac tctggcagaa actggccaag gacattcagg ttgcaagtaa tgaaattctc    420
agggacccat gctttcatcc tggatataag aaggtagtga acgtaagtga cctttacaag    480
accccctgca ccaagagatt tgagatgact cttccattcc agcagtttga aatccagggt    540
attggaaact atcaacaatg ccatcaaagc atcctggagc tcttcaacac cagttactgc    600
ccttactccc agtgtgcctt caatgggatt tccttgccac cactccaggg ggattttggg    660
gcattttcag cttttactt tgtgatgaag ttttaaact tgacatcaga gaaagtctct    720
caggaaaagg tgactgagat gatgaaaaag ttctgtgctc agccttggga ggagataaaa    780
acatcttacg ctggagtaaa ggagaagtac ctgagtgaat actgcttttc tggtacctac    840
attctctccc tccttctgca aggctatcat tcacagctg attcctggga gcacatccat    900
ttcattggca agatccaggg cagcgacgcc ggctggactt tgggctacat gctgaacctg    960
accaacatga tcccagctga gcaaccattg tccacacctc tctcccactc cacctatgtc   1020
ttcctcatgg ttctattctc cctggtcctt ttcacagtgg ccatcatagg cttgcttatc   1080
tttcacaagc cttcatattt ctggaaagat atggtatag                          1119

<210> SEQ ID NO 12
<211> LENGTH: 1119
<212> TYPE: DNA
<213> ORGANISM: Homo sapiens

<400> SEQUENCE: 12
atggaaagtg aagagttggc agacagggtt ctggatgtgg tggagaggag cctcagcaac     60 taccccttg acttccaggg tgccaggatc attactggcc aagaggaagg tgcctatggc    120
tggattacta tcaactatct gctgggcaaa ttcagtcaga aaacaaggtg gttcagcata    180
gtcccatatg aaaccaataa tcaggaaacc tttggagctt tggaccttgg gggagcctct    240
acacaagtca cttttgtacc ccaaaaccag actatcgagt ccccagataa tgctctgcaa    300
tttcgcctct atggcaagga ctacaatgtc tacacacata gcttcttgtg ctatgggaag    360
gatcaggcac tctggcagaa actggccaag gacattcagg ttgcaagtaa tgaaattctc    420
agggacccat gctttcatcc tggatataag aaggtagtga acgtaagtga cctttacaag    480
accccctgca ccaagagatt tgagatgact cttccattcc agcagtttga aatccagggt    540
attggaaact atcaacaatg ccatcaaagc atcctggagc tcttcaacac cagttactgc    600
ccttactccc agtgtgcctt caatgggatt tccttgccac cactccaggg ggattttggg    660
gcattttcag cttttactt tgtgatgaag ttttaaact tgacatcaga gaaagtctct    720
caggaaaagg tgactgagat gatgaaaaag ttctgtgctc agccttggga ggagataaaa    780
acatcttacg ctggagtaaa ggagaagtac ctgagtgaat actgcttttc tggtacctac    840
attctctccc tccttctgca aggctatcat tcacagctg attcctggga gcacatccat    900
ttcattggca agatccaggg cagcgacgcc ggctggactt tgggctacat gctgaacctg    960
accaacatga tcccagctga gcaaccattg tccacacctc tctcccactc cacctatgtc   1020
ttcctcatgg ttctattctc cctggtcctt ttcacagtgg ccatcatagg cttgcttatc   1080
tttcacaagc cttcatattt ctggaaagat atggtatag                          1119
```

```
<210> SEQ ID NO 13
<211> LENGTH: 372
<212> TYPE: PRT
<213> ORGANISM: Homo sapiens

<400> SEQUENCE: 13

Met Glu Ser Glu Glu Leu Ala Asp Arg Val Leu Asp Val Val Glu Arg
1               5                   10                  15

Ser Leu Ser Asn Tyr Pro Phe Asp Phe Gln Gly Ala Arg Ile Ile Thr
            20                  25                  30

Gly Gln Glu Glu Gly Ala Tyr Gly Trp Ile Thr Ile Asn Tyr Leu Leu
        35                  40                  45

Gly Lys Phe Ser Gln Lys Thr Arg Trp Phe Ser Ile Val Pro Tyr Glu
    50                  55                  60

Thr Asn Asn Gln Glu Thr Phe Gly Ala Leu Asp Leu Gly Gly Ala Ser
65                  70                  75                  80

Thr Gln Val Thr Phe Val Pro Gln Asn Gln Thr Ile Glu Ser Pro Asp
                85                  90                  95

Asn Ala Leu Gln Phe Arg Leu Tyr Gly Lys Asp Tyr Asn Val Tyr Thr
            100                 105                 110

His Ser Phe Leu Cys Tyr Gly Lys Asp Gln Ala Leu Trp Gln Lys Leu
        115                 120                 125

Ala Lys Asp Ile Gln Val Ala Ser Asn Glu Ile Leu Arg Asp Pro Cys
    130                 135                 140

Phe His Pro Gly Tyr Lys Lys Val Val Asn Val Ser Asp Leu Tyr Lys
145                 150                 155                 160

Thr Pro Cys Thr Lys Arg Phe Glu Met Thr Leu Pro Phe Gln Gln Phe
                165                 170                 175

Glu Ile Gln Gly Ile Gly Asn Tyr Gln Gln Cys His Gln Ser Ile Leu
            180                 185                 190

Glu Leu Phe Asn Thr Ser Tyr Cys Pro Tyr Ser Gln Cys Ala Phe Asn
        195                 200                 205

Gly Ile Phe Leu Pro Pro Leu Gln Gly Asp Phe Gly Ala Phe Ser Ala
    210                 215                 220

Phe Tyr Phe Val Met Lys Phe Leu Asn Leu Thr Ser Glu Lys Val Ser
225                 230                 235                 240

Gln Glu Lys Val Thr Glu Met Met Lys Lys Phe Cys Ala Gln Pro Trp
                245                 250                 255

Glu Glu Ile Lys Thr Ser Tyr Ala Gly Val Lys Glu Lys Tyr Leu Ser
            260                 265                 270

Glu Tyr Cys Phe Ser Gly Thr Tyr Ile Leu Ser Leu Leu Leu Gln Gly
        275                 280                 285

Tyr His Phe Thr Ala Asp Ser Trp Glu His Ile His Phe Ile Gly Lys
    290                 295                 300

Ile Gln Gly Ser Asp Ala Gly Trp Thr Leu Gly Tyr Met Leu Asn Leu
305                 310                 315                 320

Thr Asn Met Ile Pro Ala Glu Gln Pro Leu Ser Thr Pro Leu Ser His
                325                 330                 335

Ser Thr Tyr Val Phe Leu Met Val Leu Phe Ser Leu Val Leu Phe Thr
            340                 345                 350

Val Ala Ile Ile Gly Leu Leu Ile Phe His Lys Pro Ser Tyr Phe Trp
        355                 360                 365

Lys Asp Met Val
    370
```

<210> SEQ ID NO 14
<211> LENGTH: 1533
<212> TYPE: DNA
<213> ORGANISM: Mus musculus

<400> SEQUENCE: 14

```
atggaagata taaaggattc taaggtgaag agattttgct ccaaaaatat tctgatcatc      60
cttggtttca cctctatctt ggctgtgata gctttgattg ctgtgggact gacccagaac     120
aaacctttgc cagaaaatgt taagtatggg attgtgttgg atgcggggtc atctcacacc     180
aacctgtaca tctacaagtg gccggccgag aaggagaatg acacaggggt ggtgcagcag     240
ttagaggaat gccaagtgaa aggtcctgga atctcaaaat atgctcagaa acagatgaa     300
atcggtgcgt acctggccga atgcatggaa ctgtccaccg aactgatacc aacatccaag     360
catcaccaga ctcctgtcta cctgggagcc acagcaggca tgcgcttgct tagaatggaa     420
agcgaacaat cggcagacga ggtcctggct gcagtgtcaa caagccttaa gagctacccc     480
tttgacttcc agggtgccaa gatcatcact ggacaagagg aaggtgccta tgggtggatt     540
actattaact atctgctggg cagattcact caggaacaga gttggctaag cctcatctca     600
gacagtcaga acaggaaac cttggcgct ttggatctcg gcggagcctc cacacagatc     660
accttcgtgc cccaaaacag cactatagag tccccagaaa actctctgca attccgtctc     720
tatggcgagg actatactgt gtacacacac agcttcctgt gctatgggaa ggatcaggct     780
ctctggcaga aactgccaa ggacattcag gtttcaagtg gtggcgtcct taaggaccca     840
tgctttaacc caggatacga gaaggttgtg aatgtaagtg agctctatgg cactccctgc     900
accaaaagat tcgaaaagaa gctaccattt gatcagtttc gaatccaggg cactggagac     960
tacgaacagt gccaccagag catccttgag ctcttcaaca cagccactg cccttactcc    1020
cagtgtgcct tcaatggcgt cttcctgcca cctctccatg ggagttttgg ggcgttttct    1080
gctttctact ttgtgatgga ttttttaag aaggtagcga aaacagtgt catctctcag    1140
gagaaaatga ccgagataac aaaaaatttt tgctcaaaat cttgggaaga gacaaagaca    1200
tcttatcctt cagtaaagga gaagtacctg agtgagtact gcttctcggg cgcctacatc    1260
ctctctctcc tgcaaggcta taacttcaca gacagctcct gggaacagat tcattttatg    1320
ggcaagatca aagacagcaa cgcggggtgg actttgggct acatgctgaa cttgaccaac    1380
atgatcccag ctgaacagcc gttgtccccg cctctccctc actccaccta catcggcctc    1440
atggttctct ctcccctgct cttggttgct gtggccatca caggcctgtt catctatagc    1500
aagccttcat atttctggaa agaggcagta tag                                 1533
```

<210> SEQ ID NO 15
<211> LENGTH: 510
<212> TYPE: PRT
<213> ORGANISM: Mus musculus

<400> SEQUENCE: 15

```
Met Glu Asp Ile Lys Asp Ser Lys Val Lys Arg Phe Cys Ser Lys Asn
1               5                   10                  15

Ile Leu Ile Ile Leu Gly Phe Thr Ser Ile Leu Ala Val Ile Ala Leu
            20                  25                  30

Ile Ala Val Gly Leu Thr Gln Asn Lys Pro Leu Pro Glu Asn Val Lys
        35                  40                  45

Tyr Gly Ile Val Leu Asp Ala Gly Ser Ser His Thr Asn Leu Tyr Ile
```

```
            50                  55                  60
Tyr Lys Trp Pro Ala Glu Lys Glu Asn Asp Thr Gly Val Val Gln Gln
 65                  70                  75                  80

Leu Glu Glu Cys Gln Val Lys Gly Pro Gly Ile Ser Lys Tyr Ala Gln
                     85                  90                  95

Lys Thr Asp Glu Ile Gly Ala Tyr Leu Ala Glu Cys Met Glu Leu Ser
                    100                 105                 110

Thr Glu Leu Ile Pro Thr Ser Lys His His Gln Thr Pro Val Tyr Leu
                115                 120                 125

Gly Ala Thr Ala Gly Met Arg Leu Leu Arg Met Glu Ser Glu Gln Ser
            130                 135                 140

Ala Asp Glu Val Leu Ala Val Ser Thr Ser Leu Lys Ser Tyr Pro
145                 150                 155                 160

Phe Asp Phe Gln Gly Ala Lys Ile Ile Thr Gly Gln Glu Glu Gly Ala
                    165                 170                 175

Tyr Gly Trp Ile Thr Ile Asn Tyr Leu Leu Gly Arg Phe Thr Gln Glu
                180                 185                 190

Gln Ser Trp Leu Ser Leu Ile Ser Asp Ser Gln Lys Gln Glu Thr Phe
            195                 200                 205

Gly Ala Leu Asp Leu Gly Gly Ala Ser Thr Gln Ile Thr Phe Val Pro
            210                 215                 220

Gln Asn Ser Thr Ile Glu Ser Pro Glu Asn Ser Leu Gln Phe Arg Leu
225                 230                 235                 240

Tyr Gly Glu Asp Tyr Thr Val Tyr Thr His Ser Phe Leu Cys Tyr Gly
                245                 250                 255

Lys Asp Gln Ala Leu Trp Gln Lys Leu Ala Lys Asp Ile Gln Val Ser
                260                 265                 270

Ser Gly Gly Val Leu Lys Asp Pro Cys Phe Asn Pro Gly Tyr Glu Lys
            275                 280                 285

Val Val Asn Val Ser Glu Leu Tyr Gly Thr Pro Cys Thr Lys Arg Phe
290                 295                 300

Glu Lys Lys Leu Pro Phe Asp Gln Phe Arg Ile Gln Gly Thr Gly Asp
305                 310                 315                 320

Tyr Glu Gln Cys His Gln Ser Ile Leu Glu Leu Phe Asn Asn Ser His
                325                 330                 335

Cys Pro Tyr Ser Gln Cys Ala Phe Asn Gly Val Phe Leu Pro Pro Leu
                340                 345                 350

His Gly Ser Phe Gly Ala Phe Ser Ala Phe Tyr Phe Val Met Asp Phe
            355                 360                 365

Phe Lys Lys Val Ala Lys Asn Ser Val Ile Ser Gln Glu Lys Met Thr
370                 375                 380

Glu Ile Thr Lys Asn Phe Cys Ser Lys Ser Trp Glu Glu Thr Lys Thr
385                 390                 395                 400

Ser Tyr Pro Ser Val Lys Glu Lys Tyr Leu Ser Glu Tyr Cys Phe Ser
                405                 410                 415

Gly Ala Tyr Ile Leu Ser Leu Leu Gln Gly Tyr Asn Phe Thr Asp Ser
                420                 425                 430

Ser Trp Glu Gln Ile His Phe Met Gly Lys Ile Lys Asp Ser Asn Ala
            435                 440                 445

Gly Trp Thr Leu Gly Tyr Met Leu Asn Leu Thr Asn Met Ile Pro Ala
            450                 455                 460

Glu Gln Pro Leu Ser Pro Pro Leu Pro His Ser Thr Tyr Ile Gly Leu
465                 470                 475                 480
```

```
Met Val Leu Phe Ser Leu Leu Leu Val Ala Val Ala Ile Thr Gly Leu
                485                 490                 495

Phe Ile Tyr Ser Lys Pro Ser Tyr Phe Trp Lys Glu Ala Val
            500                 505                 510
```

<210> SEQ ID NO 16
<211> LENGTH: 1536
<212> TYPE: DNA
<213> ORGANISM: Rattus norvegicus

<400> SEQUENCE: 16

| | | | | | |
|---|---|---|---|---|---|
| atggaagata | taaaggattc | taaggtgaag | agattttgct | ccaaaaatat | tctgatcatc | 60 |
| cttggtttct | cctctgtctt | ggctgtgata | gctttgattg | ctgtgggact | gacccacaac | 120 |
| aaaccattgc | cagaaaatgt | taagtatggg | attgtgctgg | atgccgggtc | gtctcacacc | 180 |
| aacctgtaca | tctacaagtg | gccggctgag | aaggagaatg | atacaggagt | ggtgcagctg | 240 |
| ttagaagaat | gccaagtgaa | aggtcccgga | atctcaaaat | acgctcagaa | aacagatgaa | 300 |
| atagctgcat | atctggctga | atgcatgaaa | atgtccactg | agcggatacc | agcgtccaaa | 360 |
| cagcaccaga | cacccgtgta | cctgggagcc | accgcgggca | tgcgcttgct | cagaatggaa | 420 |
| agcaagcaat | cggcagacga | agtcctggct | gcagtgtcta | ggagcctgaa | gagctacccc | 480 |
| tttgacttcc | agggcgccaa | gatcatcact | gggcaggagg | aaggggccta | tgggtggatt | 540 |
| actattaact | atctgctggg | cagattcact | caggaacaga | gttggctaaa | cttcatctca | 600 |
| gacagccaga | aacaggcaac | ctttggcgct | ttggatcttg | gcggcagttc | tacacaagtc | 660 |
| accttcgtgc | ccctaaatca | gactctagag | gccccagaaa | cctccctgca | gttccgtctc | 720 |
| tacggcacgg | actacaccgt | gtacacacac | agcttcctgt | gctatgggaa | ggatcaggca | 780 |
| ctctggcaga | aactggccca | ggacattcag | gttttcaagtg | gtgggattct | caaggacccg | 840 |
| tgctttttacc | caggatataa | gaaggttgtg | aatgtaagcg | aactctatgg | cactcccgtgc | 900 |
| accaagagat | tgagaagaa | gctaccgttt | aatcagtttc | aagttcaggg | cactggagat | 960 |
| tacgaacagt | gccaccagag | catcctcaag | ttcttcaaca | acagccactg | cccttactcc | 1020 |
| cagtgtgcct | tcaacggtgt | cttttttacca | cctctccagg | ggagttttgg | ggcattttct | 1080 |
| gctttctact | ttgtgatgga | cttttttaag | aagatggcga | acgacagtgt | ctcctctcag | 1140 |
| gagaaaatga | ctgagataac | aaaaaacttt | tgctcaaagc | cttgggagga | ggtaaaggca | 1200 |
| tcttatccta | cagtaaagga | gaagtacctg | agtgaatact | gtttctcggg | gacctacatc | 1260 |
| ctgtctctcc | ttctgcaagg | ctataacttc | acgggaacct | cctgggacca | gattcatttt | 1320 |
| atgggcaaga | tcaaagacag | caacgcaggg | tggactttgg | gctacatgct | gaacttgacc | 1380 |
| aacatgatcc | cagctgaaca | gccattatcc | ccgcctctcc | ctcactccac | ctacatcagc | 1440 |
| ctcatggttc | tcttctcccct | ggtcttggtc | gccatggtca | tcacagggct | gttcatcttt | 1500 |
| agcaagcctt | cgtatttctg | gaaagaggca | gtatag | | | 1536 |

<210> SEQ ID NO 17
<211> LENGTH: 511
<212> TYPE: PRT
<213> ORGANISM: Rattus norvegicus

<400> SEQUENCE: 17

```
Met Glu Asp Ile Lys Asp Ser Lys Val Lys Arg Phe Cys Ser Lys Asn
1               5                   10                  15

Ile Leu Ile Ile Leu Gly Phe Ser Ser Val Leu Ala Val Ile Ala Leu
```

```
            20                  25                  30
Ile Ala Val Gly Leu Thr His Asn Lys Pro Leu Pro Glu Asn Val Lys
            35                  40                  45

Tyr Gly Ile Val Leu Asp Ala Gly Ser Ser His Thr Asn Leu Tyr Ile
50                  55                  60

Tyr Lys Trp Pro Ala Glu Lys Glu Asn Asp Thr Gly Val Val Gln Leu
65                  70                  75                  80

Leu Glu Glu Cys Gln Val Lys Gly Pro Gly Ile Ser Lys Tyr Ala Gln
                    85                  90                  95

Lys Thr Asp Glu Ile Ala Ala Tyr Leu Ala Glu Cys Met Lys Met Ser
                    100                 105                 110

Thr Glu Arg Ile Pro Ala Ser Lys Gln His Gln Thr Pro Val Tyr Leu
            115                 120                 125

Gly Ala Thr Ala Gly Met Arg Leu Leu Arg Met Glu Ser Lys Gln Ser
            130                 135                 140

Ala Asp Glu Val Leu Ala Ala Val Ser Arg Ser Leu Lys Ser Tyr Pro
145                 150                 155                 160

Phe Asp Phe Gln Gly Ala Lys Ile Ile Thr Gly Gln Glu Glu Gly Ala
                    165                 170                 175

Tyr Gly Trp Ile Thr Ile Asn Tyr Leu Leu Gly Arg Phe Thr Gln Glu
                    180                 185                 190

Gln Ser Trp Leu Asn Phe Ile Ser Asp Ser Lys Gln Ala Thr Phe
            195                 200                 205

Gly Ala Leu Asp Leu Gly Gly Ser Ser Thr Gln Val Thr Phe Val Pro
            210                 215                 220

Leu Asn Gln Thr Leu Glu Ala Pro Glu Thr Ser Leu Gln Phe Arg Leu
225                 230                 235                 240

Tyr Gly Thr Asp Tyr Thr Val Tyr Thr His Ser Phe Leu Cys Tyr Gly
                    245                 250                 255

Lys Asp Gln Ala Leu Trp Gln Lys Leu Ala Gln Asp Ile Gln Val Ser
                    260                 265                 270

Ser Gly Gly Ile Leu Lys Asp Pro Cys Phe Tyr Pro Gly Tyr Lys Lys
            275                 280                 285

Val Val Asn Val Ser Glu Leu Tyr Gly Thr Pro Cys Thr Lys Arg Phe
290                 295                 300

Glu Lys Lys Leu Pro Phe Asn Gln Phe Gln Val Gln Gly Thr Gly Asp
305                 310                 315                 320

Tyr Glu Gln Cys His Gln Ser Ile Leu Lys Phe Phe Asn Asn Ser His
                    325                 330                 335

Cys Pro Tyr Ser Gln Cys Ala Phe Asn Gly Val Phe Leu Pro Pro Leu
                    340                 345                 350

Gln Gly Ser Phe Gly Ala Phe Ser Ala Phe Tyr Phe Val Met Asp Phe
            355                 360                 365

Phe Lys Lys Met Ala Asn Asp Ser Val Ser Ser Gln Glu Lys Met Thr
            370                 375                 380

Glu Ile Thr Lys Asn Phe Cys Ser Lys Pro Trp Glu Glu Val Lys Ala
385                 390                 395                 400

Ser Tyr Pro Thr Val Lys Glu Lys Tyr Leu Ser Glu Tyr Cys Phe Ser
                    405                 410                 415

Gly Thr Tyr Ile Leu Ser Leu Leu Gln Gly Tyr Asn Phe Thr Gly
                    420                 425                 430

Thr Ser Trp Asp Gln Ile His Phe Met Gly Lys Ile Lys Asp Ser Asn
            435                 440                 445
```

```
Ala Gly Trp Thr Leu Gly Tyr Met Leu Asn Leu Thr Asn Met Ile Pro
    450                 455                 460

Ala Glu Gln Pro Leu Ser Pro Pro Leu Pro His Ser Thr Tyr Ile Ser
465                 470                 475                 480

Leu Met Val Leu Phe Ser Leu Val Leu Val Ala Met Val Ile Thr Gly
                485                 490                 495

Leu Phe Ile Phe Ser Lys Pro Ser Tyr Phe Trp Lys Glu Ala Val
            500                 505                 510
```

<210> SEQ ID NO 18
<211> LENGTH: 1542
<212> TYPE: DNA
<213> ORGANISM: Bos taurus

<400> SEQUENCE: 18

| | |
|---|---|
| atggaagata aagggaatc tgaactgaag gtattttgct ctaaaaacat actgagcata | 60 |
| cttggtttct cctgcatcat cgctgtgata gcattgctcg ctctggggct gacccagaac | 120 |
| aaagcactgc cagaaaatgt taagtttggg attgtgctgg atgcgggctc ctctcatacg | 180 |
| agtttgtaca tctatagatg gccggcagag aaggagaatg cacgggggt ggtgactcag | 240 |
| atagaagaat cgaacgttaa aggtcccgga atctcaggct ttgctaaaaa agtaaatgaa | 300 |
| atcaatgttt atctgacggc atgcatgaaa agagcccaga agtgattcc gtcaatccag | 360 |
| cacatggaaa cacctgtgta cctgggagcc acggccggca tgcggttgct ccggatggaa | 420 |
| aataaacaga tggcagacaa gatcctggct gcagttgcaa gcagcatcag cgagtacccc | 480 |
| tttgacttcc aaggtgccag aatcatcagt ggccaggagg aaggtgccta tggctggatt | 540 |
| actgtcaact atttgctggg caaattcact cagaaattga gttggtttaa cctgaagcca | 600 |
| agcaaagacg cactcagga aacctatgga gctttagacc ttgggggagc ctctacacaa | 660 |
| atcacttttg tgccccaaaa tgaaacgacc gagtctccaa caacaaccct gtacttccgc | 720 |
| ctctatggca agaactacag tgtatacaca cacagcttcc tgtgctatgg gaaggaccaa | 780 |
| gcacttttgc agaaactggc cctgggactt cagggtacaa atggaatcat ccatgagcca | 840 |
| tgctttcact caagatacat gaggaaaata aagatgagcg tcttaaacga aggtttctgt | 900 |
| accaagagac atgagttgaa ttcttcattt tatccactcg ttgacattga aatccgtggc | 960 |
| gctgaaaact tccaacgatg tcggcaaagc atcattcaac tctttaacac cagttactgc | 1020 |
| ccttactcca gttgctcctt caatgggggtt ttcttgccgc cactccatgg gcagtttggg | 1080 |
| gcattttcag cttttttacta tgtgatggag ttttttaaacc ttacatcaga ggaatcagta | 1140 |
| tctgtggaac agttgactga aagttggaa gagttctgcg cacagcgttg ggaagaggtg | 1200 |
| cagaagaatt tggtgaagt gaaggagaaa tacctgagtg aatactgctt ttctggcacc | 1260 |
| tacatcctgg ttctcctcct gaatggctac cattttacag ctgagtcctg gaaaaatatt | 1320 |
| cacttcatga acaaggtccg gagcaccgac gttgggtgga cttttgggcta catgctgaac | 1380 |
| ctgaccaaca agattccagc tgaagagcca atgtccccac ccctccccca ctccacctat | 1440 |
| gtcttcctca tggtcctctt ctccctgatc ctgctcgcag tgatcatcgt aggcatagtt | 1500 |
| gtctttcaca agccttcgta tttctggaaa gacatggtat ag | 1542 |

<210> SEQ ID NO 19
<211> LENGTH: 513
<212> TYPE: PRT
<213> ORGANISM: Bos taurus

```
<400> SEQUENCE: 19

Met Glu Asp Arg Arg Glu Ser Glu Leu Lys Val Phe Cys Ser Lys Asn
1               5                   10                  15

Ile Leu Ser Ile Leu Gly Phe Ser Cys Ile Ala Val Ile Ala Leu
            20                  25                  30

Leu Ala Leu Gly Leu Thr Gln Asn Lys Ala Leu Pro Glu Asn Val Lys
        35                  40                  45

Phe Gly Ile Val Leu Asp Ala Gly Ser Ser His Thr Ser Leu Tyr Ile
    50                  55                  60

Tyr Arg Trp Pro Ala Glu Lys Glu Asn Asp Thr Gly Val Val Thr Gln
65                  70                  75                  80

Ile Glu Glu Ser Asn Val Lys Gly Pro Gly Ile Ser Gly Phe Ala Lys
                85                  90                  95

Lys Val Asn Glu Ile Asn Val Tyr Leu Thr Ala Cys Met Glu Arg Ala
            100                 105                 110

Gln Lys Val Ile Pro Ser Ile Gln His Met Glu Thr Pro Val Tyr Leu
        115                 120                 125

Gly Ala Thr Ala Gly Met Arg Leu Leu Arg Met Glu Asn Lys Gln Met
    130                 135                 140

Ala Asp Lys Ile Leu Ala Ala Val Ala Ser Ser Ile Ser Glu Tyr Pro
145                 150                 155                 160

Phe Asp Phe Gln Gly Ala Arg Ile Ile Ser Gly Gln Glu Glu Gly Ala
                165                 170                 175

Tyr Gly Trp Ile Thr Val Asn Tyr Leu Leu Gly Lys Phe Thr Gln Lys
            180                 185                 190

Leu Ser Trp Phe Asn Leu Lys Pro Ser Lys Asp Asp Thr Gln Glu Thr
        195                 200                 205

Tyr Gly Ala Leu Asp Leu Gly Gly Ala Ser Thr Gln Ile Thr Phe Val
    210                 215                 220

Pro Gln Asn Glu Thr Thr Glu Ser Pro Asn Asn Asn Leu Tyr Phe Arg
225                 230                 235                 240

Leu Tyr Gly Lys Asn Tyr Ser Val Tyr Thr His Ser Phe Leu Cys Tyr
                245                 250                 255

Gly Lys Asp Gln Ala Leu Leu Gln Lys Leu Ala Leu Gly Leu Gln Gly
            260                 265                 270

Thr Asn Gly Ile Ile His Glu Pro Cys Phe His Ser Arg Tyr Met Arg
        275                 280                 285

Lys Ile Lys Met Ser Val Leu Asn Glu Gly Phe Cys Thr Lys Arg His
    290                 295                 300

Glu Leu Asn Ser Ser Phe Tyr Pro Leu Val Asp Ile Glu Ile Arg Gly
305                 310                 315                 320

Ala Gly Asn Phe Gln Arg Cys Arg Gln Ser Ile Ile Gln Leu Phe Asn
                325                 330                 335

Thr Ser Tyr Cys Pro Tyr Ser Ser Cys Ser Phe Asn Gly Val Phe Leu
            340                 345                 350

Pro Pro Leu His Gly Gln Phe Gly Ala Phe Ser Ala Phe Tyr Tyr Val
        355                 360                 365

Met Glu Phe Leu Asn Leu Thr Ser Glu Glu Ser Val Ser Val Glu Gln
    370                 375                 380

Leu Thr Glu Lys Leu Glu Glu Phe Cys Ala Gln Arg Trp Glu Glu Val
385                 390                 395                 400

Gln Lys Asn Phe Gly Glu Val Lys Glu Lys Tyr Leu Ser Glu Tyr Cys
                405                 410                 415
```

```
Phe Ser Gly Thr Tyr Ile Leu Val Leu Leu Asn Gly Tyr His Phe
            420                 425                 430
Thr Ala Glu Ser Trp Lys Asn Ile His Phe Met Asn Lys Val Arg Ser
            435                 440                 445
Thr Asp Val Gly Trp Thr Leu Gly Tyr Met Leu Asn Leu Thr Asn Lys
            450                 455                 460
Ile Pro Ala Glu Glu Pro Met Ser Pro Pro Leu Pro His Ser Thr Tyr
465                 470                 475                 480
Val Phe Leu Met Val Leu Phe Ser Leu Ile Leu Leu Ala Val Ile Ile
                    485                 490                 495
Val Gly Ile Val Val Phe His Lys Pro Ser Tyr Phe Trp Lys Asp Met
            500                 505                 510
Val

<210> SEQ ID NO 20
<211> LENGTH: 1527
<212> TYPE: DNA
<213> ORGANISM: Xenopus laevis

<400> SEQUENCE: 20
atggacgaac caaaggctgc aaaacagaag aagacatggc acaaaaaagt cataatcttc      60
ctaggagctc tgtttgtctt gggtgttatc tctttagtcg caattgcagt agtgcagaat     120
aaacctcttc caaagaatat taagtatggc attgtgctgg acgctggttc gtcccatacc     180
agtgtgtata tatatgaatg gccggcagaa aaggaaaatg acaccggtgt tgtacagcag     240
ataaacgagt gcaaagttga aggcaacggt atatccagtt atggccacga gccactgaag     300
gccggtcttt ctctacagaa gtgtatgaat aaagcccgtc aggtcattcc tgagaagcag     360
caaagggaga caccagttta tttaggggcc acagcaggaa tgcgtttgct caggctaact     420
aatgcaacaa tggctgagga agtcctgtct tcagtggaaa atacgctgcg ttccttttcg     480
tttgattttc agggtgccag aataattaca ggacaagaag aaggcgctta tggatggatc     540
acaattaatt atctgcttgg aaactttatc caggattcag gttggttcaa atatatacca     600
aatttcaaac ccactgaaac ttccggtgca ctggatcttg gaggtgcctc aacacagatc     660
acctttgagt ccaaaagaga gattgaatcc aagaaaatt ccttgcactt ccgcctttat     720
ggtaaatcct atgatatcta tacacacagc tttctctgct atggaaagga ccaagctctg     780
cgccttcaga tagctaatag tataaaggat gcaacagatt ccatcctttt ggatccttgc     840
tttaactcag gatatagaag gaacgcaagc accaatgacc tctacagtag tccctgcata     900
tctaaactga ggataccaac agcacccagc accttagata ttagaggcac tggcaattat     960
cagctatgca agaaaatgt ccaggcaatc ttcaacagaa cacattgtac ttactcacat    1020
tgctcttta tggggttttt caaccaagt ttggatggca catttgggc attctcagca    1080
tattattttg ttatgaattt tttaaacctt accaatgagc aaatgtctct tgacaaagta    1140
aaagagacgg tagaaagaca ctgctccaga ccatgggacg aggtaaaaaa agactttcca    1200
aaaattaaag aaaaatacct gagtgaatac tgttttttctg aacatatat attaaatctt    1260
cttgaatatg gatacggctt tagctctgaa aactggaacg atatcagatt tttaggcaag    1320
atcaaagaca gtgatgcagg atggacactt ggttatatgc tgaacctgac caatatgatc    1380
cctgcagagc tgcctattc tcctccgctg tcccacgctg ttacactgg acttatggtc    1440
ttcttctcca ttttgttagt ctgcattatt ttgacttgct ggctgagttt ccggaaacca    1500
```

-continued aaatgtctac acaagggcat catctag 1527

<210> SEQ ID NO 21
<211> LENGTH: 508
<212> TYPE: PRT
<213> ORGANISM: Xenopus laevis

<400> SEQUENCE: 21

| | | | | | | | | | | | | | | | |
|---|---|---|---|---|---|---|---|---|---|---|---|---|---|---|---|
| Met | Asp | Glu | Pro | Lys | Ala | Ala | Lys | Gln | Lys | Lys | Thr | Trp | His | Lys | Lys |
| 1 | | | | 5 | | | | | 10 | | | | | 15 | |
| Val | Ile | Ile | Phe | Leu | Gly | Ala | Leu | Phe | Val | Leu | Gly | Val | Ile | Ser | Leu |
| | | | 20 | | | | | 25 | | | | | 30 | | |
| Val | Ala | Ile | Ala | Val | Val | Gln | Asn | Lys | Pro | Leu | Pro | Lys | Asn | Ile | Lys |
| | | 35 | | | | | 40 | | | | | 45 | | | |
| Tyr | Gly | Ile | Val | Leu | Asp | Ala | Gly | Ser | Ser | His | Thr | Ser | Val | Tyr | Ile |
| | 50 | | | | | 55 | | | | | 60 | | | | |
| Tyr | Glu | Trp | Pro | Ala | Glu | Lys | Glu | Asn | Asp | Thr | Gly | Val | Val | Gln | Gln |
| 65 | | | | | 70 | | | | | 75 | | | | | 80 |
| Ile | Asn | Glu | Cys | Lys | Val | Glu | Gly | Asn | Gly | Ile | Ser | Ser | Tyr | Gly | His |
| | | | | 85 | | | | | 90 | | | | | 95 | |
| Glu | Pro | Leu | Lys | Ala | Gly | Leu | Ser | Leu | Gln | Lys | Cys | Met | Asn | Lys | Ala |
| | | | | 100 | | | | | 105 | | | | | 110 | |
| Arg | Gln | Val | Ile | Pro | Glu | Lys | Gln | Gln | Arg | Glu | Thr | Pro | Val | Tyr | Leu |
| | | | 115 | | | | | 120 | | | | | 125 | | |
| Gly | Ala | Thr | Ala | Gly | Met | Arg | Leu | Leu | Arg | Leu | Thr | Asn | Ala | Thr | Met |
| 130 | | | | | 135 | | | | | 140 | | | | | |
| Ala | Glu | Glu | Val | Leu | Ser | Ser | Val | Glu | Asn | Thr | Leu | Arg | Ser | Phe | Pro |
| 145 | | | | | 150 | | | | | 155 | | | | | 160 |
| Phe | Asp | Phe | Gln | Gly | Ala | Arg | Ile | Ile | Thr | Gly | Gln | Glu | Glu | Gly | Ala |
| | | | | 165 | | | | | 170 | | | | | 175 | |
| Tyr | Gly | Trp | Ile | Thr | Ile | Asn | Tyr | Leu | Leu | Gly | Asn | Phe | Ile | Gln | Asp |
| | | | 180 | | | | | 185 | | | | | 190 | | |
| Ser | Gly | Trp | Phe | Lys | Tyr | Ile | Pro | Asn | Phe | Lys | Pro | Thr | Glu | Thr | Ser |
| | | 195 | | | | | 200 | | | | | 205 | | | |
| Gly | Ala | Leu | Asp | Leu | Gly | Gly | Ala | Ser | Thr | Gln | Ile | Thr | Phe | Glu | Ser |
| | 210 | | | | | 215 | | | | | 220 | | | | |
| Lys | Arg | Glu | Ile | Glu | Ser | Gln | Glu | Asn | Ser | Leu | His | Phe | Arg | Leu | Tyr |
| 225 | | | | | 230 | | | | | 235 | | | | | 240 |
| Gly | Lys | Ser | Tyr | Asp | Ile | Tyr | Thr | His | Ser | Phe | Leu | Cys | Tyr | Gly | Lys |
| | | | | 245 | | | | | 250 | | | | | 255 | |
| Asp | Gln | Ala | Leu | Arg | Leu | Gln | Ile | Ala | Asn | Ser | Ile | Lys | Asp | Ala | Thr |
| | | | 260 | | | | | 265 | | | | | 270 | | |
| Asp | Ser | Ile | Leu | Leu | Asp | Pro | Cys | Phe | Asn | Ser | Gly | Tyr | Arg | Arg | Asn |
| | | 275 | | | | | 280 | | | | | 285 | | | |
| Ala | Ser | Thr | Asn | Asp | Leu | Tyr | Ser | Ser | Pro | Cys | Ile | Ser | Lys | Leu | Arg |
| | 290 | | | | | 295 | | | | | 300 | | | | |
| Ile | Pro | Thr | Ala | Pro | Ser | Thr | Leu | Asp | Ile | Arg | Gly | Thr | Gly | Asn | Tyr |
| 305 | | | | | 310 | | | | | 315 | | | | | 320 |
| Gln | Leu | Cys | Lys | Arg | Asn | Val | Gln | Ala | Ile | Phe | Asn | Arg | Thr | His | Cys |
| | | | | 325 | | | | | 330 | | | | | 335 | |
| Thr | Tyr | Ser | His | Cys | Ser | Phe | Asn | Gly | Val | Phe | Gln | Pro | Ser | Leu | Asp |
| | | | 340 | | | | | 345 | | | | | 350 | | |
| Gly | Thr | Phe | Gly | Ala | Phe | Ser | Ala | Tyr | Tyr | Phe | Val | Met | Asn | Phe | Leu |
| | | 355 | | | | | 360 | | | | | 365 | | | |

```
Asn Leu Thr Asn Glu Gln Met Ser Leu Asp Lys Val Lys Glu Thr Val
        370                 375                 380

Glu Arg His Cys Ser Arg Pro Trp Asp Glu Val Lys Lys Asp Phe Pro
385                 390                 395                 400

Lys Ile Lys Glu Lys Tyr Leu Ser Glu Tyr Cys Phe Ser Gly Thr Tyr
                405                 410                 415

Ile Leu Asn Leu Leu Glu Tyr Tyr Gly Phe Ser Ser Glu Asn Trp
            420                 425                 430

Asn Asp Ile Arg Phe Leu Gly Lys Ile Lys Asp Ser Asp Ala Gly Trp
            435                 440                 445

Thr Leu Gly Tyr Met Leu Asn Leu Thr Asn Met Ile Pro Ala Glu Leu
450                 455                 460

Pro Tyr Ser Pro Pro Leu Ser His Ala Gly Tyr Thr Gly Leu Met Val
465                 470                 475                 480

Phe Phe Ser Ile Leu Leu Val Cys Ile Ile Leu Thr Cys Trp Leu Ser
                485                 490                 495

Phe Arg Lys Pro Lys Cys Leu His Lys Gly Ile Ile
                500                 505

<210> SEQ ID NO 22
<211> LENGTH: 1479
<212> TYPE: DNA
<213> ORGANISM: Danio rerio

<400> SEQUENCE: 22
atggaagtaa aagtcaaaaa cccatggcac aggccggttg tcatctttct gatggctgtt      60
gttgccgtgg ggattgtcat catggtatcc atttctgttg tccagcacaa gcctttaccc     120
caaaagtaca gtatggaat agtcctggat gccggctcct ctcacacctc tgtgtttatc     180
tataaatggc cagcagagaa agagaacaac acaggcatgg tacagcagca tcacacgtgc     240
aatgttaaag gcaaaggcat ctccagttac ttcgataaac acatggggc tggtgcatct     300 ctggaggagt gcatgaagga ggccaaggag aaaatacctg ctcacagaca cagcgaaacc     360
cctgtctacc tgggagccac ggctggcatg agactgctca agatggagga tgaaatggcc     420
tcagaaaaag tgcttacctc cgttgcacat tcactgaaga cgtaccccctt ctcctatcag     480 ggagctcgta tcctttcagg ccaagaggag ggagcttttg ggtggattac agtcaactac     540
cttagtgaaa acttgagaaa gcccgcaggc actcttggag ctctggacct tggtggagcc     600
tctactcaaa taaccttcgt acctcagcag attattgaat catctgacaa ttcgattgac     660
ttcagactgt atgaaatga ttatcatcta tacacccaca gctttctctg ttatgggaag     720
gaccaagctc tcaagcttgc tatggctgag aaattgcgct caacacctga aagacagat     780 gccattttgt taaggggatcc ttgttttcat cctggatata acaccaccaa gacgcttgaa     840
agtgtcaata caccatgtat gaaaccactg aaaatgccaa aggagcagtt ctcccatgtg     900
gggcttggaa attggtctca gtgccaagaa tcaatcagaa aggttttaa tactagccat     960 tgtccttatt caggctgctc attcaatggt gttttccaac ctactgttga aggaaaattt    1020
ggggcttttt ctgctttctt ttttgtaatg gacttttaa atctgaaaaa cgattcattg    1080
gacaaaacaa agcagaggct ggcaatgtac tgctctaccc catggcaaaa gattgtacaa    1140
gatcacccaa agtaaaaga aagtaccctt tctgaatact gcttctcagc aacatacatt    1200
ctcactctcc tggaacatgg atacaatttc acctcagaca actggaacga catcaagttt    1260
atcaagaaga ttggagacag tgatgcaggc tggactttag gttacatgct taacctgacc    1320
```

```
aacatgattc cggctgaaga tccagacaag ccactgatgc ctcatggagg atacgtcaca      1380
tttatgatcc tcttctcact tttgatactc gtcctcatca ttatggccta catttatttc      1440
cgtcgcttta ctaaaacagc ccagaaagac attatttag                              1479
```

<210> SEQ ID NO 23
<211> LENGTH: 492
<212> TYPE: PRT
<213> ORGANISM: Danio rerio

<400> SEQUENCE: 23

```
Met Glu Val Lys Val Lys Asn Pro Trp His Arg Pro Val Val Ile Phe
1               5                   10                  15

Leu Met Ala Val Val Ala Val Gly Ile Val Met Val Ser Ile Ser
            20                  25                  30

Val Val Gln His Lys Pro Leu Pro Gln Lys Tyr Lys Tyr Gly Ile Val
        35                  40                  45

Leu Asp Ala Gly Ser Ser His Thr Ser Val Phe Ile Tyr Lys Trp Pro
    50                  55                  60

Ala Glu Lys Glu Asn Asn Thr Gly Met Val Gln Gln His His Thr Cys
65                  70                  75                  80

Asn Val Lys Gly Lys Gly Ile Ser Ser Tyr Phe Asp Lys Pro His Gly
                85                  90                  95

Ala Gly Ala Ser Leu Glu Glu Cys Met Lys Glu Ala Lys Glu Lys Ile
            100                 105                 110

Pro Ala His Arg His Ser Glu Thr Pro Val Tyr Leu Gly Ala Thr Ala
        115                 120                 125

Gly Met Arg Leu Leu Lys Met Glu Asp Glu Met Ala Ser Glu Lys Val
    130                 135                 140

Leu Thr Ser Val Ala His Ser Leu Lys Thr Tyr Pro Phe Ser Tyr Gln
145                 150                 155                 160

Gly Ala Arg Ile Leu Ser Gly Gln Glu Glu Gly Ala Phe Gly Trp Ile
                165                 170                 175

Thr Val Asn Tyr Leu Ser Glu Asn Leu Arg Lys Pro Ala Gly Thr Leu
            180                 185                 190

Gly Ala Leu Asp Leu Gly Gly Ala Ser Thr Gln Ile Thr Phe Val Pro
        195                 200                 205

Gln Gln Ile Ile Glu Ser Ser Asp Asn Ser Ile Asp Phe Arg Leu Tyr
    210                 215                 220

Gly Asn Asp Tyr His Leu Tyr Thr His Ser Phe Leu Cys Tyr Gly Lys
225                 230                 235                 240

Asp Gln Ala Leu Lys Leu Ala Met Ala Glu Lys Leu Arg Ser Thr Pro
                245                 250                 255

Asp Lys Thr Asp Ala Ile Leu Leu Arg Asp Pro Cys Phe His Pro Gly
            260                 265                 270

Tyr Asn Thr Thr Lys Thr Leu Glu Ser Val Asn Thr Pro Cys Met Lys
        275                 280                 285

Pro Leu Lys Met Pro Lys Glu Gln Phe Ser His Val Gly Leu Gly Asn
    290                 295                 300

Trp Ser Gln Cys Gln Glu Ser Ile Arg Lys Val Phe Asn Thr Ser His
305                 310                 315                 320

Cys Pro Tyr Ser Gly Cys Ser Phe Asn Gly Val Phe Gln Pro Thr Val
                325                 330                 335

Glu Gly Lys Phe Gly Ala Phe Ser Ala Phe Phe Val Met Asp Phe
            340                 345                 350
```

Leu Asn Leu Lys Asn Asp Ser Leu Asp Lys Thr Lys Gln Arg Leu Ala
            355                 360                 365

Met Tyr Cys Ser Thr Pro Trp Gln Lys Ile Val Gln Asp His Pro Lys
    370                 375                 380

Val Lys Glu Lys Tyr Leu Ser Glu Tyr Cys Phe Ser Ala Thr Tyr Ile
385                 390                 395                 400

Leu Thr Leu Leu Glu His Gly Tyr Asn Phe Thr Ser Asp Asn Trp Asn
                405                 410                 415

Asp Ile Lys Phe Ile Lys Lys Ile Gly Asp Ser Asp Ala Gly Trp Thr
            420                 425                 430

Leu Gly Tyr Met Leu Asn Leu Thr Asn Met Ile Pro Ala Glu Asp Pro
            435                 440                 445

Asp Lys Pro Leu Met Pro His Gly Gly Tyr Val Thr Phe Met Ile Leu
            450                 455                 460

Phe Ser Leu Leu Ile Leu Val Leu Ile Ile Met Ala Tyr Ile Tyr Phe
465                 470                 475                 480

Arg Arg Phe Thr Lys Thr Ala Gln Lys Asp Ile Ile
                485                 490

<210> SEQ ID NO 24
<211> LENGTH: 10
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 24

Gly Ile Asp Pro Asn Ile Arg Thr Gly Val
1               5                   10

<210> SEQ ID NO 25
<211> LENGTH: 10
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 25

Lys Leu Val Ala Leu Gly Ile Asn Ala Val
1               5                   10

<210> SEQ ID NO 26
<211> LENGTH: 9
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 26

Ala Thr Asp Ala Leu Met Thr Gly Tyr
1               5

<210> SEQ ID NO 27
<211> LENGTH: 10
<212> TYPE: PRT
<213> ORGANISM: Artificial Sequence
<220> FEATURE:
<223> OTHER INFORMATION: /note="Description of Artificial Sequence: HLA
      Class I tetramer peptide"

```
<400> SEQUENCE: 27

Arg Glu Ile Ser Val Pro Ala Glu Ile Leu
1               5                   10

<210> SEQ ID NO 28
<211> LENGTH: 9
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 28

Gly Pro Arg Leu Gly Val Arg Ala Thr
1               5

<210> SEQ ID NO 29
<211> LENGTH: 9
<212> TYPE: PRT
<213> ORGANISM: Artificial Sequence
<220> FEATURE:
<223> OTHER INFORMATION: /note="Description of Artificial Sequence: HLA
      Class I tetramer
      peptide"

<400> SEQUENCE: 29

Val Leu Ser Asp Phe Lys Thr Trp Leu
1               5

<210> SEQ ID NO 30
<211> LENGTH: 10
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 30

Tyr Pro Tyr Arg Leu Trp His Tyr Pro Cys
1               5                   10

<210> SEQ ID NO 31
<211> LENGTH: 9
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 31

Ala Arg Met Ile Leu Met Thr His Phe
1               5

<210> SEQ ID NO 32
<211> LENGTH: 9
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 32

Cys Ile Asn Gly Val Cys Trp Thr Val
1               5

<210> SEQ ID NO 33
<211> LENGTH: 9
```

```
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 33

Asn Leu Val Pro Met Val Ala Thr Cys
1               5

<210> SEQ ID NO 34
<211> LENGTH: 9
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 34

Gly Leu Cys Thr Leu Val Ala Met Leu
1               5

<210> SEQ ID NO 35
<211> LENGTH: 8
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 35

Arg Tyr Pro Leu Thr Phe Gly Trp
1               5

<210> SEQ ID NO 36
<211> LENGTH: 11
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 36

Lys Ala Phe Ser Pro Glu Val Ile Pro Met Phe
1               5                   10

<210> SEQ ID NO 37
<211> LENGTH: 9
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 37

Asp Arg Phe Tyr Lys Thr Leu Arg Ala
1               5

<210> SEQ ID NO 38
<211> LENGTH: 9
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 38

His Pro Val His Ala Gly Pro Ile Ala
```

```
<210> SEQ ID NO 39
<211> LENGTH: 9
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 39

Asp Arg Phe Tyr Lys Thr Leu Arg Ala
1               5

<210> SEQ ID NO 40
<211> LENGTH: 9
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 40

Ser Leu Tyr Asn Thr Val Ala Thr Leu
1               5

<210> SEQ ID NO 41
<211> LENGTH: 9
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 41

Thr Pro Gln Asp Leu Asn Thr Met Leu
1               5

<210> SEQ ID NO 42
<211> LENGTH: 9
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 42

Ser Leu Tyr Asn Thr Val Ala Thr Leu
1               5

<210> SEQ ID NO 43
<211> LENGTH: 11
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 43

Lys Ala Phe Ser Pro Glu Val Ile Pro Met Phe
1               5                   10

<210> SEQ ID NO 44
<211> LENGTH: 8
<212> TYPE: PRT
<213> ORGANISM: Artificial Sequence
<220> FEATURE:
<223> OTHER INFORMATION: /note="Description of Artificial Sequence: HLA
```

```
              Class I tetramer peptide"

<400> SEQUENCE: 44

Glu Ile Tyr Lys Arg Trp Ile Ile
1               5

<210> SEQ ID NO 45
<211> LENGTH: 8
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 45

Val Pro Leu Arg Pro Met Thr Tyr
1               5

<210> SEQ ID NO 46
<211> LENGTH: 9
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 46

Gly Pro Gly His Lys Ala Arg Val Leu
1               5

<210> SEQ ID NO 47
<211> LENGTH: 11
<212> TYPE: PRT
<213> ORGANISM: Artificial Sequence
<220> FEATURE:
<223> OTHER INFORMATION: /note="Description of Artificial Sequence: HLA
      Class I tetramer peptide"

<400> SEQUENCE: 47

Ser Gly Val Glu Asn Pro Gly Gly Tyr Cys Leu
1               5                   10
```